US010233213B2

(12) United States Patent
Guichard et al.

(10) Patent No.: US 10,233,213 B2
(45) Date of Patent: Mar. 19, 2019

(54) FOLDAMER HELIX BUNDLE-BASED MOLECULAR ENCAPSULATION

(71) Applicants: UREKA SARL, Mulhouse (FR); Centre National De La Recherche Scientifique (CNRS), Paris (FR)

(72) Inventors: Gilles Guichard, Gradignan (FR); Gavin W. Collie, Aberdeenshire (GB); Karolina Pulka-Ziach, Warsaw (PL); Caterina Maria Lombardo, Sora (IT); Juliette Fremaux, Pessac (FR)

(73) Assignees: UREKA SARL, Mulhouse (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 0 days.

(21) Appl. No.: 15/756,513

(22) PCT Filed: Aug. 31, 2016

(86) PCT No.: PCT/EP2016/070556
§ 371 (c)(1),
(2) Date: Feb. 28, 2018

(87) PCT Pub. No.: WO2017/037142
PCT Pub. Date: Mar. 9, 2017

(65) Prior Publication Data
US 2018/0244718 A1    Aug. 30, 2018

Related U.S. Application Data

(60) Provisional application No. 62/212,583, filed on Aug. 31, 2015.

(51) Int. Cl.
*A61K 38/00*  (2006.01)
*C07K 7/02*  (2006.01)
*A61K 38/10*  (2006.01)
*A61K 47/59*  (2017.01)
*A61K 47/18*  (2017.01)
*C07C 275/16*  (2006.01)
*C07D 207/09*  (2006.01)
*C08L 75/02*  (2006.01)

(52) U.S. Cl.
CPC .......... *C07K 7/02* (2013.01); *A61K 38/10* (2013.01); *A61K 47/18* (2013.01); *A61K 47/59* (2017.08); *C07C 275/16* (2013.01); *C07D 207/09* (2013.01); *C08L 75/02* (2013.01)

(58) Field of Classification Search
None
See application file for complete search history.

(56) References Cited

U.S. PATENT DOCUMENTS

| 5,424,286 | A  | 6/1995  | Eng            |
|-----------|----|---------|----------------|
| 5,595,756 | A  | 1/1997  | Bally et al.   |
| 6,958,384 | B2 | 10/2005 | Gellman et al. |
| 7,060,845 | B2 | 6/2006  | Guichard       |
| 7,186,828 | B2 | 3/2007  | Guichard       |
| 7,691,807 | B2 | 4/2010  | Violette       |
| 7,858,737 | B2 | 12/2010 | Gellman et al. |
| 8,138,145 | B2 | 3/2012  | Violette et al.|
| 9,243,040 | B2 | 1/2016  | Cheng          |
| 2002/0143191 | A1 | 10/2002 | Guichard    |
| 2005/0038105 | A1 | 2/2005  | Guichard    |
| 2006/0211625 | A1 | 9/2006  | Violette    |
| 2010/0099185 | A1 | 4/2010  | Horne       |
| 2011/0118440 | A1 | 5/2011  | Gellman et al. |
| 2012/0021530 | A1 | 6/2012  | Gellman et al. |
| 2015/0141323 | A1 | 5/2015  | Guichard et al. |

FOREIGN PATENT DOCUMENTS

| EP | 1640361 A2        | 3/2006 |
|----|-------------------|--------|
| WO | WO 2003/029198 A1 | 4/2003 |
| WO | WO 2012/085479    | 6/2012 |
| WO | WO 2013/102209    | 7/2013 |
| WO | WO 2015/024955 A1 | 2/2015 |
| WO | WO 2017/037142    | 3/2017 |
| WO | WO 2017/037150    | 3/2017 |

OTHER PUBLICATIONS

Adams, P. D. et al. "PHENIX: a comprehensive Python-based system for macromolecular structure solution", Acta Crystallogr. D Biol. Crystallogr. 66, 213-221 (2010).
Aisenbrey, C., et al., "Solid state NMR studies of oligourea foldamers: interaction of 15N-labelled amphiphilic helices with oriented lipid membanes", Org. Biomol. Chem., 10, 1440-1447 (2012).
Arup Roy et al: "Diversifying the structural architecture of synthetic oligomers: the hetero foldamer approach", Chemical Communications, 47(42):11593-11611, Jan. 1, 2011.
Arvidsson, et al., On the Antimicrobial and Hemolytic Activities of Amphiphilic Beta-peptides. ChemBioChem, 2001, 10771-10773.
Ballaster, P., "Anion binding in covalent and self-assembled molecular capsule", Chem. Soc. Rev. 2010, 39 (10), 3810-3830.
Bathany, K., et al., "Sequencing of oligourea foldamers by tandem mass spectrometry", Journal of the American Society for Mass Spectrometry, Feb. 12, 2013, 24(3):458-462.
Beck, et al., "Construction of matryoshka-type structures from supercharged protein nanocages", Angew. Chem. Int. Engl. 2015, 54 (3), 937-940.

(Continued)

*Primary Examiner* — Jeanette M Lieb
(74) *Attorney, Agent, or Firm* — Bryan D. Zerhusen, Esq.; Cantor Colburn LLP

(57) ABSTRACT

The present description provides compositions and methods for producing therapeutic oligomeric compounds. In another aspect the description provides methods for administering the oligomeric compounds for the treatment and prevention of disease in a mammal. In particular, the disclosure relates to medicaments comprising various novel oligomeric compounds and pharmaceutically acceptable salts thereof. The compounds of the disclosure may optionally be administered with at least one of a pharmaceutically acceptable excipient, additional pharmacologically active agent or a combination thereof.

24 Claims, 64 Drawing Sheets
Specification includes a Sequence Listing.

(56) References Cited

OTHER PUBLICATIONS

Berkessel, A.; Roland, K.; Neudorfl, J. M. "Asymmetric Morita-Baylis-Hillman Reaction Catalyzed by Isophoronediamine-Derived Bis(thio)urea Organocatalysts", Org. Lett. 2006, 8, 4195-4198.
Biros, S. M., et al. "Structure and binding properties of water-soluble cavitands and capsules", Chem. Soc. Rev. 2007, 36 (1), 93-104.
Boeijen, A., et a., "Solid-Phase Synthesis of oligourea peptidomimetics employing the Fmoc protection strategy", J. Org. Chem, 2001, 66, 8454-8462.
Boeijen, et al., "Solid-Phase Synthesis of Oligourea Peptidomimetics", Eur. J. Org. Chem., 1999, 2127-2135.
Bouillere, F., et al., "Foldamers containing c-amino acid residues or their analogues: structural features and applications", Amino Acids, 41, 687-707 (2011).
Bromley, et al., "Peptide and protein building blocks for synthetic biology: from programming biomolecules to self-organized biomolecular systems", ACS Chem. Biol. 3, 38-50 (2008).
Brown, R.A., et al., "Induction of unexpected left-handed helicity by an N-Terminal L-Amino acid in an otherwise aciral peptide chain", Angew Chem Int Ed. 2012, 51, 1395-1399.
Burgess, et al., "Solid Phase Synthesis of Oligoureas", J. of American Chem. Soc. v119(7): 1556-1564 (1997).
Burgess, et al., "Solid-phase syntheses of unnatural biopolymers containing repeating urea units", Agnew. Chem. Int. Ed. Engl. 34, 907-909 (1995).
Castelletto, et al., Amyloid peptides incorporating a core sequence from the amyloid beta peptide and gamma amino acids: relating bioactivity to self-assembly, Chem. Commun., 2011, 47, 12470-12472.
Chandramouli, N., et al., Iterative design of a helically folded aromatic oligoamide sequence for the selective encapsulation of fructose, Nat. Chem. 2015, 7 (4), 334-341.
Chen, et al., "Determination of the Secondary Structures of Proteins by Circular Dichroism and Optical Rotatory Dispersion", Biochem. vol. 11, No. 22, 1972, pp. 4120-4131.
Chicchi, et al., "Alterations in receptor activation and divalent cation activation of agonist binding by deletion of intracellular domains of the glucagon receptor", J. Biol. Chem., 272: pp. 7765 (1997).
Cho, C., et al., "An unnatural Biopolymer", Science 1993, 261, 1303-1305.
Cho., C., et al., Synthesis and screening of linear and cyclic oligocarbamate libraries. Discovery of high affinity ligands for CPIIb/IIIa, J. Am. Chem. Soc. 1998, 120(31), 7706-7718.
Choi, Soo Hyuk, "Helical structures of unnatural peptides for biological applications", Biomedical Engineering Letters, vol. 3., No. 4, pp. 226-231, Dec. 1, 2013.
Claudon, P., et al., "Consequences of Isostructural Main-Chain modifications for the design of antimicrobial foldamers: Helical memics of host-defense peptides based on a heterogeneous amide/urea backbone", Angew. Chem. Int. Ed. Engl. 49, 333-336 (2010).
Collie, Gavin W., et al., "Shaping quaternary assemblies of water-soluable non-peptide helical goldamers by sequence manipulation", Nature Chemistry, vol. 7, No. 11, Sep. 28, 2015, pp. 871-878.
Conn, M. M., et al., Self-assembling capsules, Chem. Rev. 1997, 97 (5), 1647-1668.
Connon, S. J. "Organocatalysis mediated by (thio)urea derivatives", Chem. Eur. J. 2006, 12, 5418-5427.
Coward, "N-Me-pAB-Glu-gamma-Glu-gamma-Tyr(3-NO2): An Internally Quenched Fluorogenic Gamma-glutamyl Hudrolase Substrate", Bioorganic & Medicinal Chemistry Letters, Oxford GB, v11(12): 1561-1564 (2001).
Craig, et al., "Enhancing β3-peptide bundle stability by design", ChemBioChem 2011, 12 (7), 1035-1038.
Curran, D. P.; Kuo, L. H. "Altering the Stereochemistry of Allylation Reactions of Cyclic .alpha.-Sulfinyl Radicals with Diarylureas", J. Org. Chem. 1994, 59, 3259-3261.

Daniels, D. S., "High-resolution structure of a beta-peptide bundle", J. Am. Chem. Soc. 129, 1532-1533 (2007).
Delano, W.L., "The PyMOL molecular graphic system", DeLano Scientific, San Carols, CA (2002).
Der, et al., "The use of coiled coils could facilitate the modular, predictable design of protein nanocages", Nat. Biotechnol, 31 (9) 809-810 (2013).
Douat, Celine, et al., "A Cell-penetrating foldamer with a bioreducible linkage for intracellular delivery of DNA, "Agnew Chem Int Ed, 2015, 55, 11133-11137.
Douat-Casassus, et al., "Microwave-enhanced solid-phase synthesis of N,N'-linked aliphatic oligoureas and related hybrids", Org. Lett. 14,3130-3133 (2012).
Doyle, A. G.; Jacobsen, E. N. "Small-molecule H-bond donors in asymmetric catalysis", Chem. Rev. 2007, 107, 5713-43.
Ebalunode, et al., "Structure-based shape pharmacophore modeling for the discovery of novel anesthetic compounds", Bioorg. Med. Chem. 2009, 17 (14) 5133-5138.
Emsley, et al., "Features and development of Coot", Acta Crystallogr. D Biol. Crystallogr. 66, 486-501 (2010).
Evans, P. "Scaling and assessment of data quality", Acta Crystallogr. D Biol. Crystallogr.,D 62 (Pt 1) 72-82 (2006).
Faiella, M. et al. "An artificial di-iron oxo-protein with phenol oxidase activity", Nat. Chem. Biol. 5(12), 882-884 (2009) (Published in final form as Nat Chem Biol . Dec. 2009; 5(12): doi:10. 1038/nchembio.257.pp. 1-7).
Ferrand, Y., et al. "Diastereoselective Encapsulation of Tartaric Acid by a Helical Aromatic Oligoamide", J. Am. Chem. Soc., 132 (23), 7858-7859 (2010).
Fischer Lucile, "Succinimidyl carbamate derivatives from N-protected alpha-amino acids and dipeptides—Synthesis of Ureidopeptides and Oligourea/Peptide Hybrids", European Journal of Organic Chemistry, No. 15:2511-2525, May 1, 2007.
Fischer Lucile, et al., "Folding and self-assembly of aromatic and aliphatic urea oligomers: Towards connecting structure and function", Organic & Biomolecular Chemistry, 8(14):3101-3117, Jan. 1, 2010.
Fischer, L., "The Canonical Helix of Urea Oligomers at Atomic Resolution: Insights Into Folding-Induced Axial Organization", Angew. Chem. Int. Ed. Engl. 2010, 49, 1067-1070.
Fischer, L., et al., "The canonical helix of urea oligomers at atomic resolution: insights into folding-induced axial organization", Angew. Chem. Int. Ed. Engl. 2010, 122, 1085-1088.
Fletcher, et al., "Self-assembling cages from coiled-coil peptide modules", Science 340,595-599 (2013)—ScienceExpress http://www.sciencemag.org/content/early/recent/ Apr. 11, 2013 / p. 1 / 10.1126/science. 1233936.
Frackenpohl, et al., "The outstanding biological stability of beta- and gama-peptides toward proteylytic enzymes: an in vitro investigation with fifteen peptidases", Chembiochem 2, 445-455 (2001).
Fremaux, J. et al. "α-Peptide/Oligourea Chimeras: Stabilization of Short α-helices by Non Peptide Helical Foldamers", Angew. Chem. Int. Ed. Engl. , vol. 54, 2015, pp. 9816-9820 DOI: 10.1002/anie. 201500901R201500901.
Fremaux, J., et al., "Influence of archiral unites with gem-dimethy substituents on the helical charater of aliphatic oligourea foldamers", Chem Comm (Camb). Aug. 28, 2013, 49(67); 7415-7. Doi:10. 1039/c3cc40961a.
Fremaux, J., et al., G. "Condensation approach to aliphatic oligourea foldamers: helices with N-(pyrrolidin-2-ylmethyl)ureido junctions", Angew. Chem. Int. Ed Engl. 50, 11382-11385 (2011).
Gao, Yi et al., "Theoretical Study of the Secondary Structures of Unionized Poly(y-D-glutamic acid)", Molecular Physics (2004), 102(23-24), pp. 2491-2498.
Garric, J., et al. "Encapsulation of Small Polar Guests in Molecular Apple Peels", Chemical Eng. Journal, 13 (30), 8454-8462 (2007).
Garric, J., et al. "Molecular Apple Peels", Angew. Chem. Int. Ed. Engl., 44 (13), 1954-1958 (2005).
Gellman, et al., "Foldamers: A Manifesto", Acc. Chem. Res. 31, 173-180 (1998).
Gennari, C., et al., "Synthesis of sulfonamide-pseudopeptides: new chiral unnatural oligomers", Angew. Chem. Int. Ed. 1994, 33, 2067-2069.

(56) References Cited

OTHER PUBLICATIONS

Ghirlanda, G. et al. "Volatile anesthetic modulation of oligomerization equilibria in a hexameric model peptide", FEBS Lett. 578, 140-144 (2004).
Giuliano, M. W., et al. "An alpha/beta-peptide helix bundle with a pure beta3-amino acid core and a distinctive quaternary structure", J. Am. Chem. Soc. 131, 9860-9861 (2009).
Goodman, et al., "Biophysical and structural characterization of a robust octameric β-peptide bundle", J. Am. Chem. Soc. 2007, 129 (47), 14746-14751.
Goodman, et al., "Foldamers as versatile frameworks for the design and evolution of function", Nat. Chem Biol. 3, 252-262 (2007).
Gradišar, et al., "Design of a single-chain polypeptide tetrahedron assembled from coiled-coil segments", Nat. Chem. Biol. 9, 362-366 (2013).
Gradišar, et al., "Self-assembled bionanostructures: proteins following the lead of DNA nanostructures", J. Nanobiotechnology 12, 4, 1-9, (2014).
Guichard, et al., "Synthetic foldamers", Chem. Commun. 47, 5933-5941 (2011).
Guichard, G., et al., "Effective Preparation of O-succinimidyl-2(tert-butoxycarbonylamino) ethylcarbamate derivatives from B-amino Acids. Application to the synthesis of urea-containing pseudopeptides and oligoureas", J. Org. Chem. 1999, 64, 8702-8705.
Guichard, G., et al., "Solution structure determination of oligoureas using methylene spin state selective NMR at $^{13}$C natural abundance", Magn. Reson. Chem., 2008, 46, 918-924.
Gura, "Cancer Models: Systems for Identifying New Drugs are Often Faulty", Science vol. 278 (1997), 1041-1042.
Hamuro et al., "De Novo Design of Antibacterial B-Peptides", J. Am. Chem. Soc., 1999, 121, 12200-12201.
Harbury, P. B., et al., "High-resolution protein design with backbone freedom", Science 282, 1462-1467 (1998).
Hemmerlin C et al: "Helix-forming oligoureas: Temperature-dependent NMR, structure determination, and circular dichroism of a nonamer with functionalized side chains", Helvetica Chimica Acta, Verlag Helvetica Chimica Acta, CH, vol. 85, No. 11, Jan. 1, 2002 (Jan. 1, 2002), pp. 3692-3711, XP002417783, ISSN: 0018-019X, DOI: 10.1002/1522-2675(200211)85:11<3692::AID-HLCA3692>3.0.00;2-W oligoureas 1 and 2.
Hernandez, H., et al., "Determining the stoichiometry and interactions of macromolecular assemblies from mass spectrometry", Nat. Protoc. 2, 715-726 (2007).
Hill, R. et al, "De novo design of helical bundles as models for understanding protein folding and function", Acc. Chem. Res. 33, 745-754 (2000).
Hintermann, et al., "Gamma-Peptides Forming More Stable Secondary Structures Than Alpha-Peptides: Synthesis and Helical NMR-Solution Structure of the Hexapeptide Analong of H-(Val-Ala-Leu)2-0H", Helvetica Chimica Acta., v81: 983-1002 (1998).
Horne, et al. "Interplay among side chain sequence, backbone composition, and residue rigidification in polypeptide folding and assembly", Proc. Natl. Acad. Sci. U.S., 105 (27) 9151-9156 (2008).
Horne, et al., "Helix bundle quaternary structure from alpha/beta-peptide foldamers", J. Am. Chem. Soc. 129, 4178-4180 (2007).
Horne, W.S., et al., "Foldamers with Heterogeneous Backbones", Acc. Chem. Res., 41, 1399-1408 (2008).
Hua, Y., et al. "Hydrophobic Collapse of Foldamer Capsules Drives Picomolar-Level Chloride Binding in Aqueous Acetonitrile Solutions", J. Am. Chem. Soc., 135 (38), 14401-14412 (2013).
Inouye, M., et al. "Saccharide-Dependent Induction of Chiral Helicity in Achiral Synthetic Hydrogen-Bonding Oligomers", J. Am. Chem. Soc., 126 (7), 2022-2027 (2004).
Jakab, G.; Tancon, C.; Zhang, Z.; Lippert, K. M.; Schreiner, P. R. "(Thio)urea Organocatalyst Equilibrium Acidities in DMSO", Org. Lett., 14, 1724-1727 (2012).
Joh, N. H. et al., "De novo design of a transmembrane Zn2+-transporting four-helix bundle", Science 346, 1520-1524 (2014).
Johansson, et al., "A Designed Cavity in the Hydrophobic Core of a Four-α-Helix Bundle Improves Volatile Anesthetic Binding Affinity", Biochemistry 1998, 37 (5) 1421-1429.
Johnson, et al., "a-Helix mimicry with a/β-peptides", Methods Enzymol 523, 407-429 (2013).
Jones, C. R.; Pantos, G. D.; Morrison, A. J.; Smith, M. D. "Plagiarizing proteins: enhancing efficiency in asymmetric hydrogen-bonding catalysis through positive cooperativity", Angew. Chem. Int. Ed. Engl. 2009, 48, 7391-4.
Juwarker, H., et al., "Foldamers with helical cavities for binding complementary guests", Chem. Soc. Rev. 2009, 38 (12), 3316-3325.
Kabsch, W. "XDS", Acta Crystallogr. D Biol. Crystallogr. 66, 125-132 (2010)) and CCP4 (Winn, M. D. et al. Overview of the CCP4 suite and current developments. Acta Crystallogr. D Biol. Crystallogr. 67, 235-242 (2011).
Kichler, A., et al., "Histidine-rich amphipathic peptide antibiotics promote efficient delivery of DNA into mammalian cells", Proc. Natl. Acad. Sci. USA,100, 1564-1568 (2003).
Kim, J., et al., "The solid phase synthesis of oligoureas", Tetrahedron Letter., 1996, 37, 5305-5308.
King et al., "Computational design of self-assembling protein nanomaterials with atomic level accuracy", Science 336, 1171-1174 (2012).
King, et al., "Accurate design of co-assembling multi-component protein nanomaterials", Nature 510, 103-108 (2012).
Kodakek.T., et al., "The Rise, Fall and Reinvention of Combinatorial Chemistry", Chem. Commun., 47, 9757-9763 (2011).
Kofoed, J., et al., "A General Method for Designing Combinatorial Peptide Libraries Decodable by Amino Acid Analysis", J. Comb. Chem., 9, 1046-1052 (2007).
Koziara, K. B., et al., "Testing and validation of the automated topology builder (ATB) version 2.0: prediction of hydration free enthalpies", J. Comput. Aided Mol. Des. 2014, 28 (3), 221-223.
Lai, et al., "Principles for designing ordered protein assemblies"., Tends Cell Biol. 22, 653-661 (2012).
Lai, et al., "Structure of a 16-nm cage designed by using protein oligomers", Science 336, 1129 (2012).
Lai, et al., "Structure of a designed protein cage that self-assembles into a highly porous cube", Nat. Chem 6, 1065-1071 (2014).
Laskowski, R.A. "SURFNET: a program for visualizing molecular surfaces, cavities and intermolecular interactions", J. Mol. Graph. 13, 323-330 (1995).
Lear, J. D., et al., "Synthetic amphiphilic peptide models for protein ion channels", Science 240, 1177-1181 (1988).
Legrand, B., et al., "Robust helix formation in a new family of oligoureas based on a constrained bicyclic building block", Angew. Chem. Int. Ed., 2012, 51, 11267-11270.
Leplae et al. "Tolerance of Acyclic Residues in the Beta-Peptide 12-Helix: Access to Diverse Side-Chain Arrays for Biological Applications". J. Am. Chem. Soc., 2002, 124, 6820-1.
Li, X., et al., "Peptides of aminoxy acids as foldamers", Chem. Commun. 2006, 3367-3379.
Liu et al., "De Novo Design, Synthesis, and Characterization of Antimicrobial B-Peptides", J. Am Chem. Soc., 123, 7553-7559 (2001).
Liu, et al., "Atomic structure of a tryptophan-zipper pentamer", Proc. Natl. Sci. U.S.A. 2004, 101 (46) 16156-16161 (2004).
Liu, R., Loll, P. J. & Eckenhoff, R. G. "Structural basis for high-affinity volatile anesthetic binding in a natural 4-helix bundle protein", FASEB J. 19, 567-576 (2005).
Lombardo, C.M., et al., "Anatomy of an oligourea six-helix bundle", Journal of the American Chemical Society, Aug. 24, 2016, vol. 138, No. 33, pp. 10522-10530.
Maity, B., et al. "Use of the confined spaces of apo-ferritin and virus capsids as nanoreactors for catalytic reactions", Curr. Opin. Chem. Biol. 2015, 25, 88-97.
McCoy, A. J. et al. "Phaser crystallographic software", J. Appl. Crystallogr. 40, 658-674 (2007).
Mecozzi, S., et al., "The 55% solution: a formula for molecular recognition in the Liquid State", Chem. Eur. J. 1998, 4 (6), 1016-1022.

(56) References Cited

OTHER PUBLICATIONS

Murshudov, G. N. et al., "REFMAC5 for the refinement of macromolecular crystal structures", Acta Crystallogr. D Biol. Crystallogr. 67, 355-367 (2011).
Nelli, et al., "Structural characterization of short hybrid urea/carbamate (U/C) foldamers: a case of partial helix unwinding", Biopolymers 100, 687-697 (2013).
Nelli, Y. R.; "Isosteric Substitutions of Urea to Thiourea and Selenourea in Aliphatic Oligourea Foldamers: Site-Specific Perturbation of the Helix Geometry", Chem. Eur. J. 2015, 21, 2870-2880.
Nelli, Y.R., et al., "An activated building block for the introduction of the histidine side chain in aliphatic oligourea foldamers", Tetrahedron, 2012, 68, 4492-4500.
O'Shea, E.K., et al., "X-ray structure of the GCN4 leucine zipper, a two-stranded, parallel coiled coil", Science 254, 539-544 (1991).
Oh, et al., "Design, synthesis and characterization of antimicrobial pseudopeptides corresponding to membrane-active peptide", J. Peptide Res., 1999, 54, 129-136.
Okino, T.; Hoashi, Y.; Takemoto, Y. "Enantioselective Michael Reaction of Malonates to Nitroolefins Catalyzed by Bifunctional Organocatalysts", J. Am. Chem. Soc. 2003, 125, 12672-12673.
Oostenbrink, C., et al., "A biomolecular force field based on the free enthalpy of hydration and solvation: the GROMOS force-field parameter sets 53A5 and 53A6", J. Comput. Chem. 2004, 25 (13), 1656-1676.
Patch, et al., "Mimicry of bioactive peptides via non-natural, sequence-specific peptidomimetic oligomers", Curr. Op. Chem. Bio., 2002, 6, 872-877.
Pendem, N.; et al., "Helix-Forming Propensity of Aliphatic Urea Oligomers Incorporating Noncanonical Residue Substitution Patterns", J. Am. Chem. Soc. 2013, 135, 4884-4892.
Pendem, N. et al., "Controlling Helix Formation in the γ-Peptide Superfamily: Heterogeneous Foldamers with Urea/Amide and Urea/Carbamate Backbones", Angew. Chem. Int. Ed. 2013, 52, 4147-4151.
Pizzey, et al., "Characterization of nanofibers formed by self-assembly of beta-peptide oligomers using small angle x-ray scattering", J. Chem. Phys. 129, 095103 (2008).
Pomerantz, W. C. et al., "Nanofibers and lyotropic liquid crystals from a class of self-assembling beta-peptides", Angew. Chem. Int. Ed Engl. 47, 1241-1244 (2008).
Porter et al., "Mimicry of Host-Defense Peptides by Unnatural Oligomers: Antimicrobial Beta-Peptides", J. Am. Chem. Soc., 2002, 124, 7324-7330.
Porter et al., "Non-Haemolytic Beta-Amino-Acid Oligomers", Nature, 2000, 404, 565.
Pronk, S., et al., "Gromacs 4.5: a high-throughput and highly parallel open source molecular simulation toolkit", Bioinformatics, 29 (7), 845-854 (2013).
Rebilly, J.-N., et al., "Biomimetic cavity-based metal complexes", Chem. Soc. Rev., 44 (2), 467-489 (2015).
Reig, et al., "Altering the $O_2$-Dependent Reactivity of de novo due ferri proteins", Nat. Chem., 4 (11), 900-906 (2012).
Remington: The Science and Practice of Pharmacy, 20th Edition, A. R. Gennaro, Ed., Lippincott Williams & Wilkins, (2000), pp. 721-727.
Remington's Pharmaceutical Sciences, 1980, vol. 16, Mack Publishing Company, Easton, Pa., pp. 61 and 424.
Rufo, et al., "Short peptides self-assemble to produce catalytic amyloids", Nat. Chem. 6 (4), 303-309 (2014).
Runge, et al., "Different domains of the glucagon and glucagon-like peptide-1 receptors provide the critical determinants of ligand selectivity", Brit. J. Pharmacol., 138: pp. 787-794 (2003).
Schuttelkopf, et al., "PRODRG: a tool for high-throughput crystallography of protein-ligand complexes", Acta Crystallogr. D Biol. Crystallogr. 60, 1355-1363 (2004).
Seebach, D., et al., "The World of b- and g-Peptides Comprised of Homologated Proteinogenic Amino Acids and Other Components", Chem. Biodivers. 2004, 1, 1111-1239.
Semetey, V., et al., "Stable helical secondary structure in short-chain N,N-Linked oligoureas bearing proteininogenic side chains", Angew. Chem. Int. Ed., 41, 1893-1895 (2002).
Singleton, M. L., et al., "Increasing the size of an aromatic helical foldamer cavity by strand intercalation", Angew. Chem. Int. Ed. Engl. 2014, 53 (48), 13140-13144.
Smith, L.J., et al., "Analysis of main chain torsion angles in proteins: prediction of NMR coupling constants for native and random coil conformations", J. Mol. Biol., 255, 494-506 (1996).
Smrcina, et al., "Facile stereoselective synthesis of y-substituted y-amino acids from corresponding a-amino acids", Tetrahedron, 1997, 53, 12867-12874.
Sola, J., et al., "Nanometer-range communication of stereochemical information by reversible switching of molecular helicity", Angew. Chem. Int. Ed. 2010, 49, 6836-6839.
Soth and Nowick, "A peptide/Oligourea/Azapeptide Hybrid That Adopts a Hairpin Turn", J. Org. Chem. 1999, 64, 276-281.
Sporn et. al., "Chemoprevention of Cancer," Carcinogenesis, vol. 21 (2000), 525-530.
Suk, J.-M., et al., "Indolocarbazole-Based Foldamers Capable of Binding Halides in Water", J. Am. Chem. Soc. 2008, 130 (36), 11868-11869.
Takemoto, Y. "Recognition and activation by ureas and thioureas: stereoselective reactions using ureas and thioureas as hydrogen-bonding donors", Org. Biomol. Chem. 2005, 3, 4299-306.
Tamilarasu, et al., "Targeting RNA with peptidomimetic oligomers in human cells", Biorg. Med. Chem. Let., 2001, 11, 505-7.
Tamilarasu, "High Affinity and Specific Binding of HIV-1 TAR RNA by a Tat-Derived Oligourea", Journal of the American Chemical Society (1999), 121(7), 1597-1598.
Tamilarasu, "Supporting Information—High Affinity and Specific Binding of HIV-1 TAR RNA by a Tat-Derived Oligourea", Journal of the American Chemical Society (1999), 121(7), pp. S1-S12.
Tanatani, A., et al. "Foldamers as dynamic receptors: probing the mechanism of molecular association between helical oligomers and rodlike ligands", Angew. Chem. Int. Ed. Engl. 2002, 41 (2), 325.
Tebo, et al., "Artificial metalloenzymes derived from three-helix bundles", Curr. Opin. Chem. Biol. 25, 65-70 (2015).
Tegoni, M., et al., "Designing a functional type 2 copper center that has nitrite reductase activity within α-helical coiled coils", Proc. Natl. Acad. Sci. U. S. A. 109, 21234-21239 (2012).
Toniolo, C., et al., "The polypeptide 310-helix", Trends Biochem Sci. 1991, 16, 350-353.
Vallavoju, N. et al., "Supramolecular photocatalysis: combining confinement and non-covalent interactions to control light initiated reactions", J. Chem. Soc. Rev. 2014, 43 (12), 4084-4101.
Violette, et al., "Mimicking Helical Antibacterial Peptides with Nonpeptidic Folding Oligomers", Chemistry and Biology., vol. 13, No. 5, pp. 531-538, XP055307145, GB ISSN: 1074-5521, DOI: 10.1016/j.chembiol.2006.03.009 (2006).
Violette, A., et al., "Exploring helical folding of oligoureas during chain elongation by high-resolution magic-angle-spinning (HRMAS) NMR spectroscopy", Chem. Eur. J. 2008, 14, 3874-3882.
Violette, et al., "N,N'-Linked Oligoureas as Foldamers: Chain Length Requirements for Helix Formation in Protic Solvent Investigated by Circular Dichroism, NMR Spectroscopy, and Molecular Dynamics", Journal of the American Chemical Society, vol. 127, No. 7, pp. 2156-2164, XP055152097, ISSN: 0002-7863, DOI: 10.1021/ja044392b (2005).
Wang, P. S. P., et al., "Design and high-resolution structure of a β3-peptide bundle catalyst", J. Am. Chem. Soc. 136, 6810-6813 (2014).
Wechsel, Romina, et al., "Inducing archiral aliphatic oligoureas to fold into helical conformations", Chemical Communications, vol. 50, No. 95, Jan. 1, 2014, pp. 15006-15009.
Winn, M. D. et al., "Overview of the CCP4 suite and current developments", Acta Crystallogr. D Biol. Crystallogr. 67, 235-242 (2011).
Wiszniewska, Anna et al: "Synthesis of peptidomimetics: An evaluation of p-nitrophenyl carbamate of ethylenediamine", Letters in Peptide Science, Jan. 1, 2003 (Jan. 1, 2003), pp. 33-39, XP055307149, Dordrecht DOI: 10.1007/13F02443640 Retrieved from the Internet: URL:http://rd.springer.com/content/pdf/10.1023/B:LIPS.0000014027.84594.e6.pdf.
Wiszniewska, et al., "p-Nitrophenoxycarbonyl derivatives of Boc-protected diaminoalkanes in the synthesis of encephalin peptidomimetics", J. Peptide Sci. 11:579-583 (2005).

(56) References Cited

OTHER PUBLICATIONS

Woolfson, D. N. "The design of coiled-coil structures and assemblies", Adv. Protein Chem. 70, 79-112 (2005).
Wu, et al., "Chloride Coordination by Oligoureas: From Mononuclear Crescents to Dinuclear Foldamers", Org. Lett. 2012, 14 (3), 684-687.
Xu, Y.-X., et al. "Folding of Aromatic Amide-Based Oligomers Induced by Benzene-1,3,5-tricarboxylate Anion in DMSO", J. Org. Chem. 2009, 74 (19), 7267-7273.
Yadav, et al. "Structure-based engineering of internal cavities in coiled-coil peptides", Biochemistry 44, 9723-9732 (2005).
Zaccai, et al., "A de novo peptide hexamer with a mutable channel", Nat. Chem. Biol. 7, 935-941 (2011).
Zarra, et al., "Molecular containers in complex chemical systems", Chem. Soc. Rev. 2015, 44 (2), 419-432.
Zhang, et al., "Structural DNA nanotechnology: state of the art and future perspective", J. Am. Chem. Soc. 136, 11198-11211 (2014).
Zhang, Z. & Fan, E. "Solid-phase and solution-phase syntheses of oligomeric guanidines bearing peptide side chains", J. Org. Chem. 80, 8801-8810 (2005).
International Search Report and Written Opinion for PCT/162017/000528, dated Jan. 9, 2018.

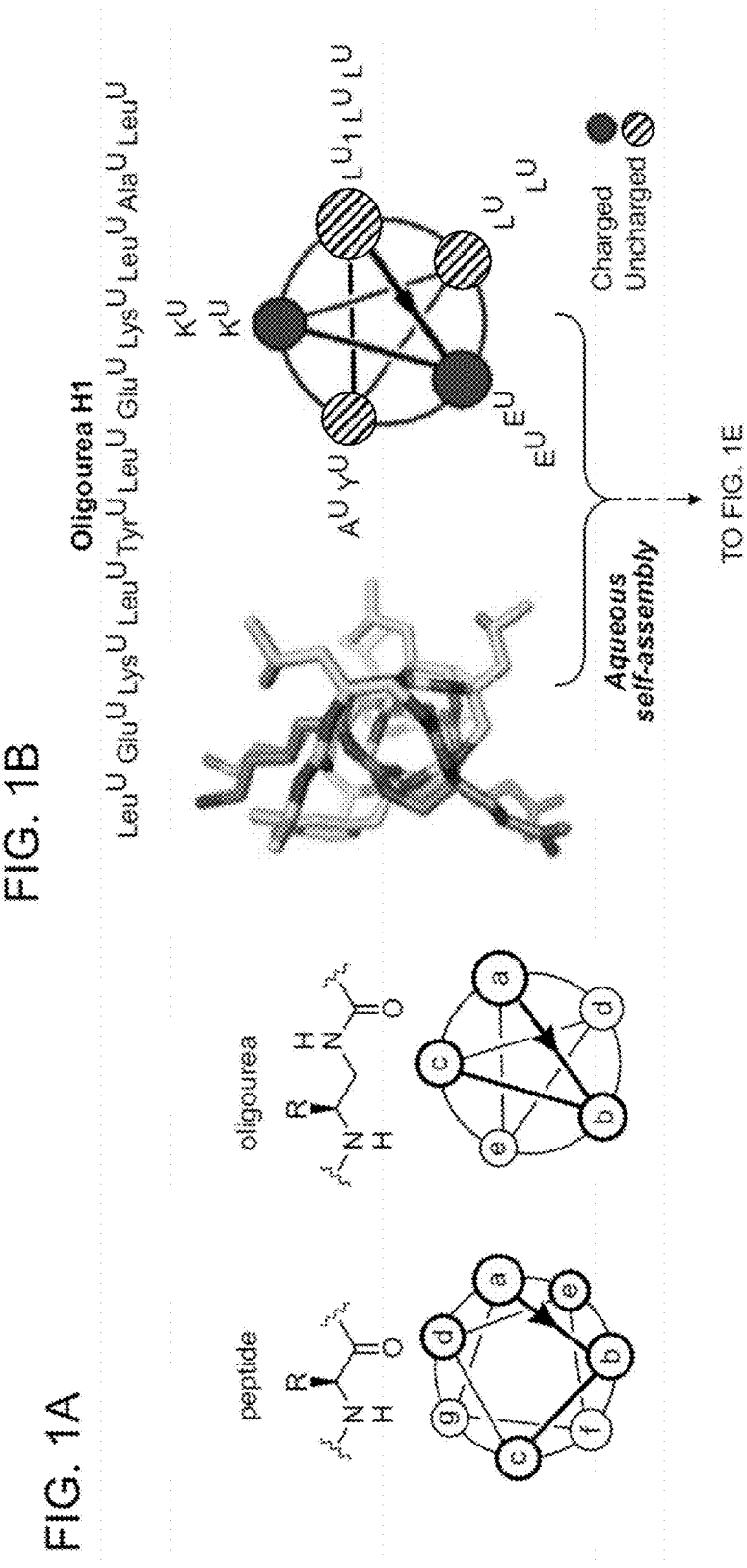

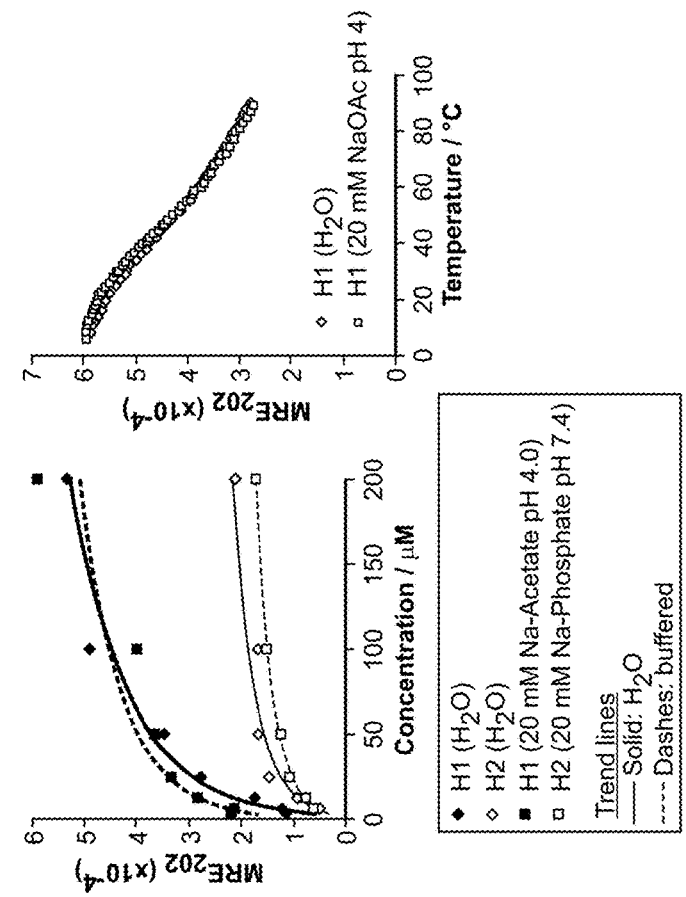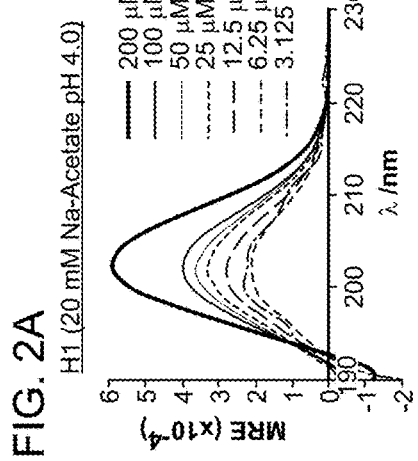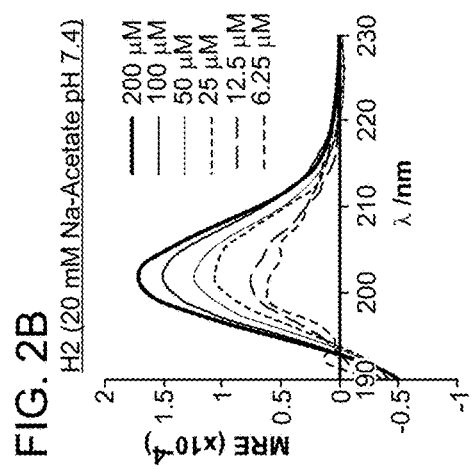

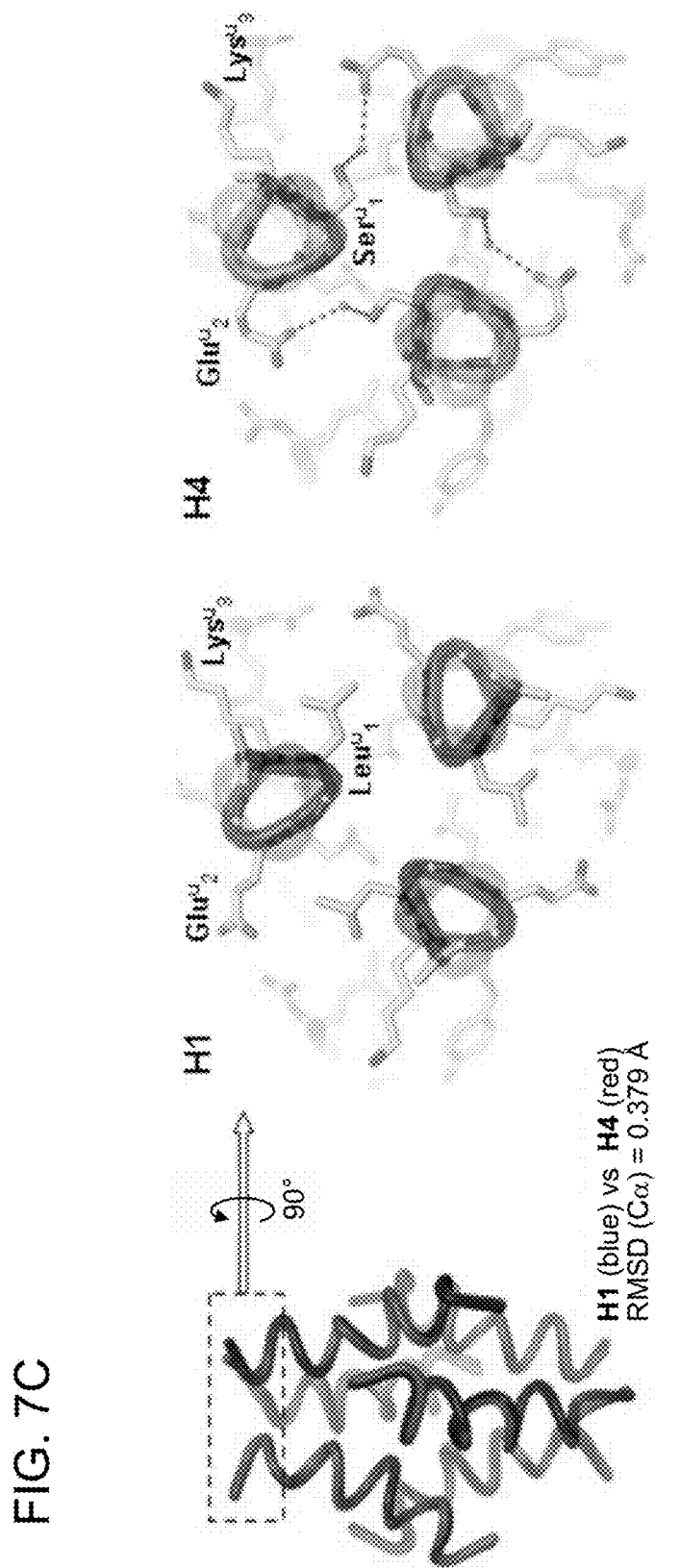

FIG. 18
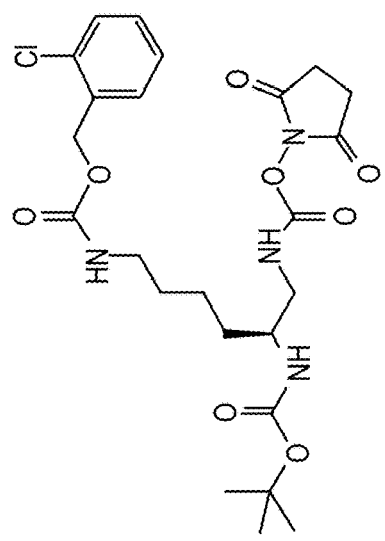
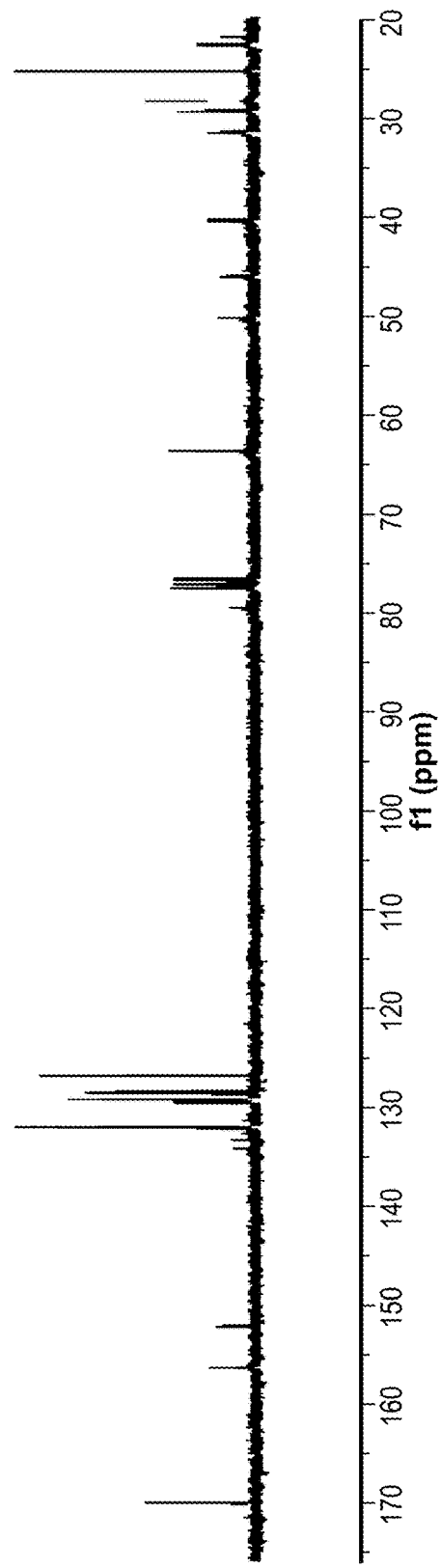

FIG. 23
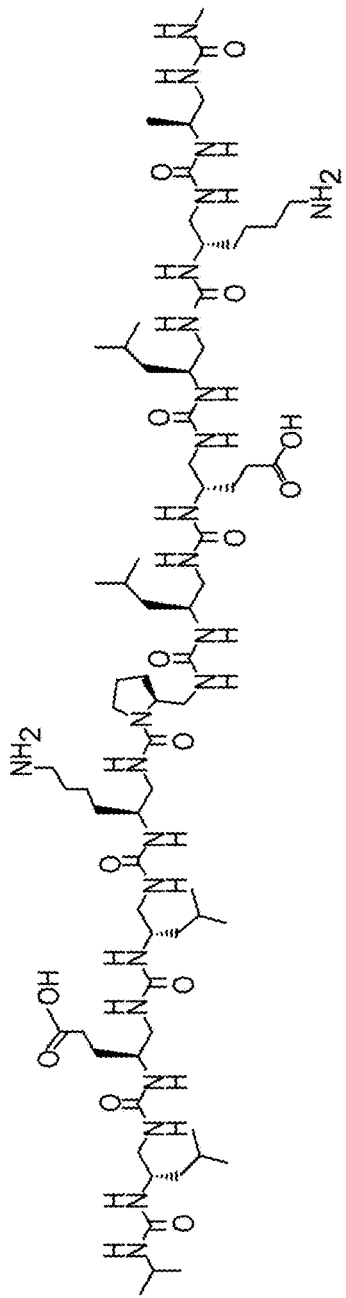
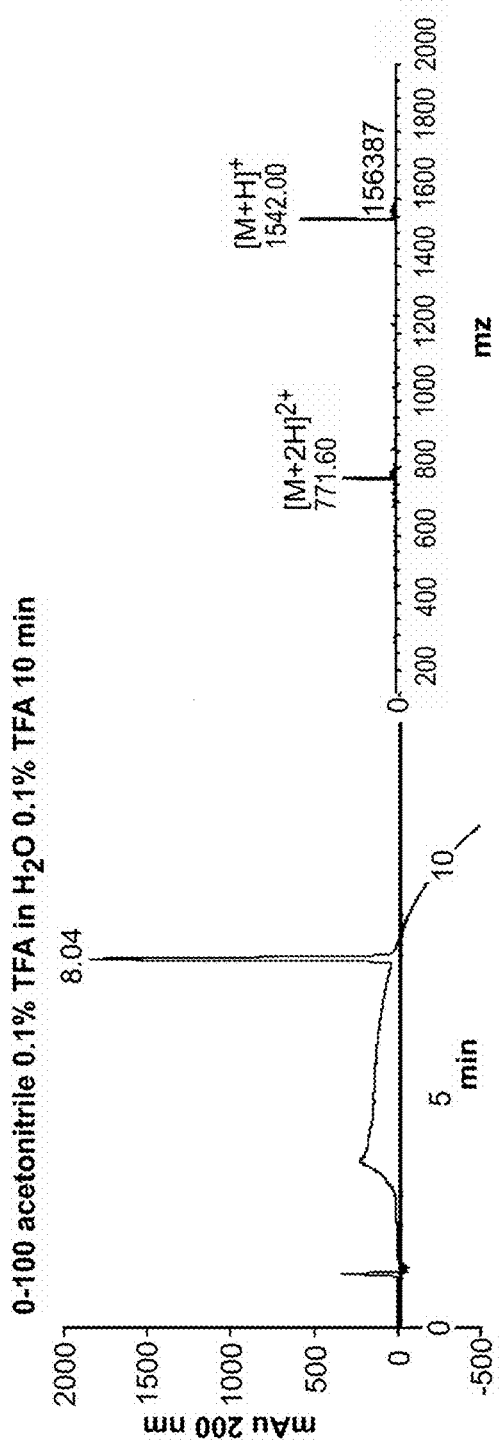

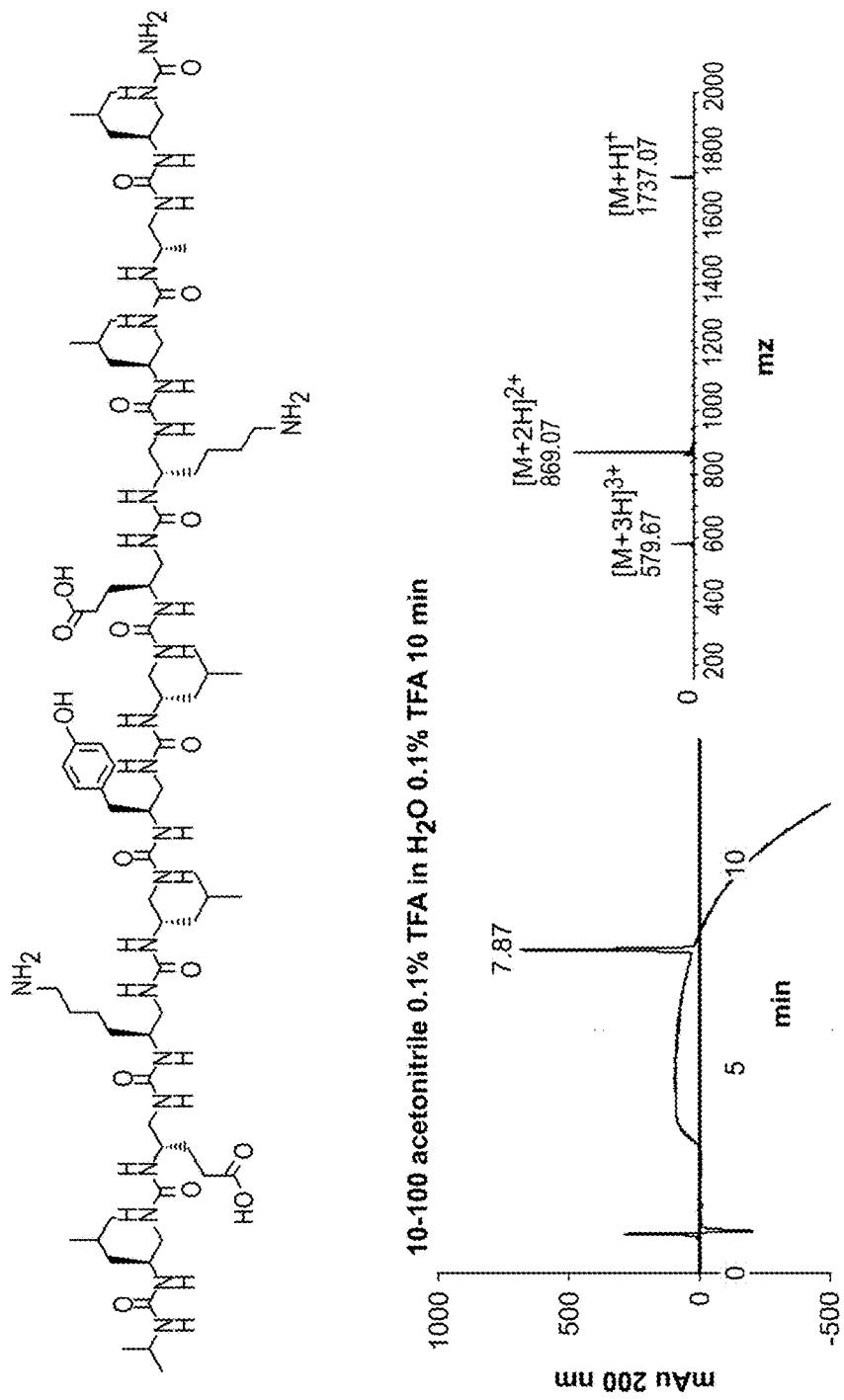
FIG. 32 H1

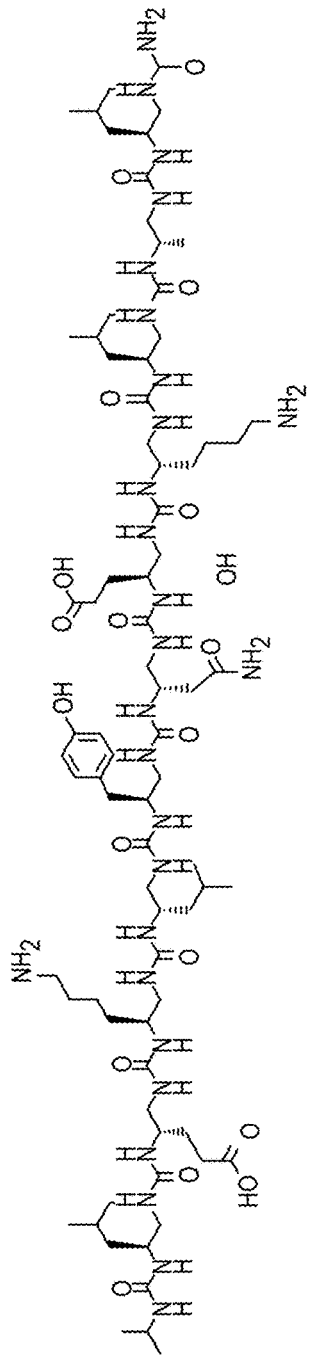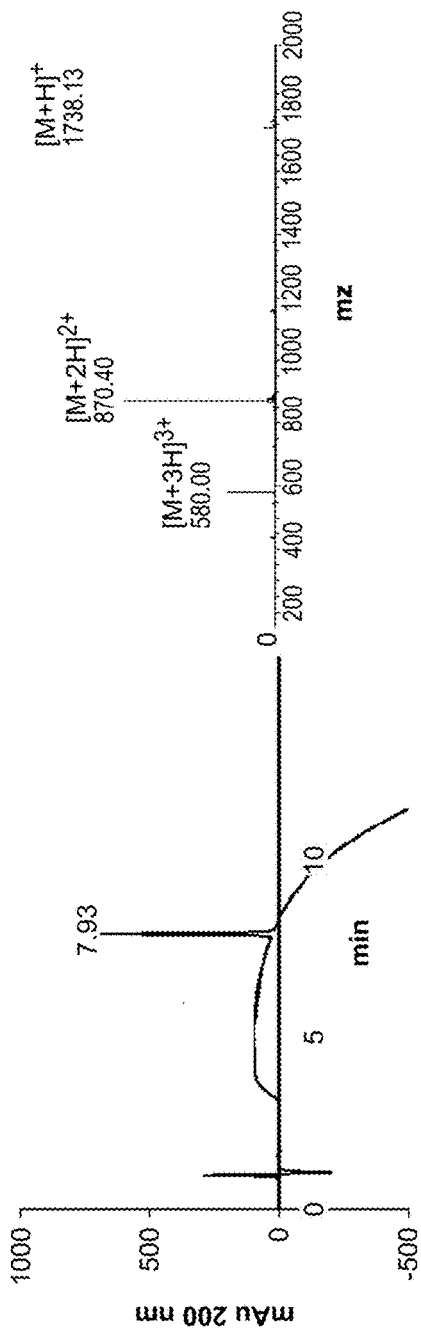
FIG. 33  H3
30-39 5 min 39-40 7.5 min acetonitrile 0.1% TFA in H₂O 0.1% TFA

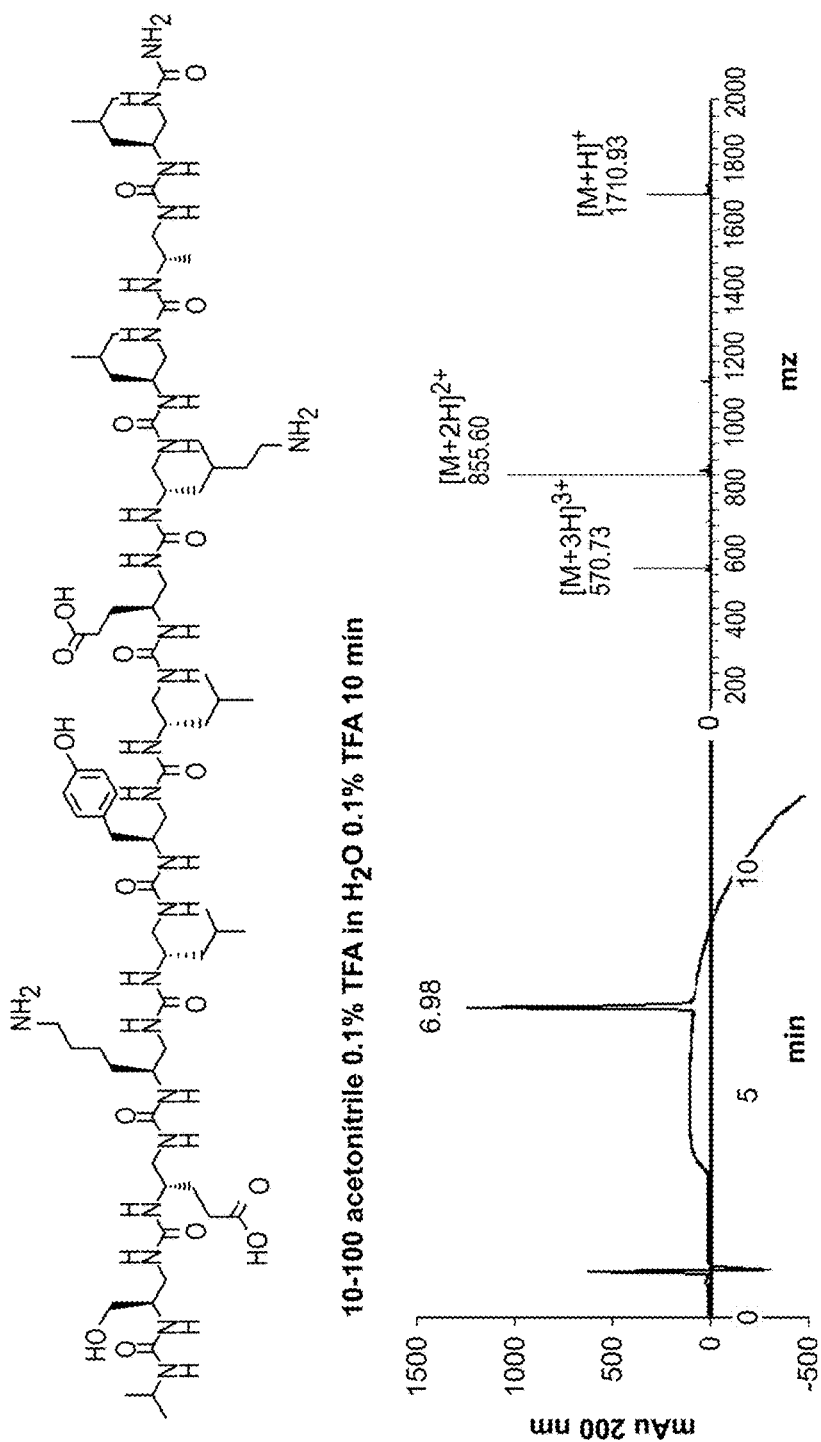
FIG. 34 H4

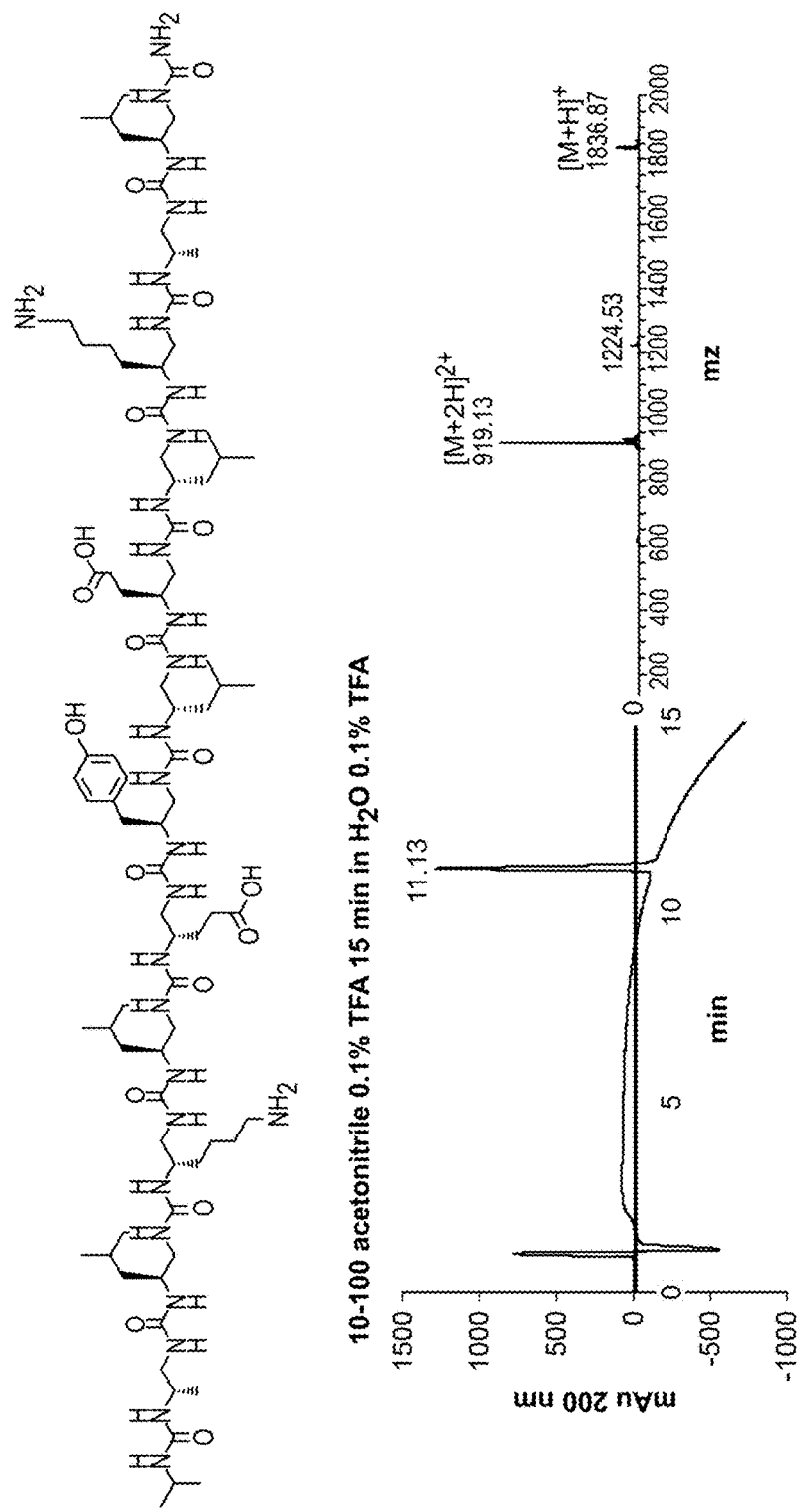
FIG. 35  H5

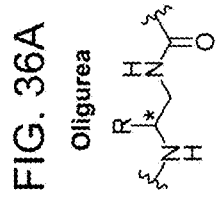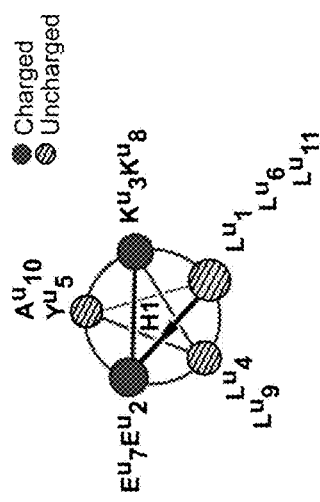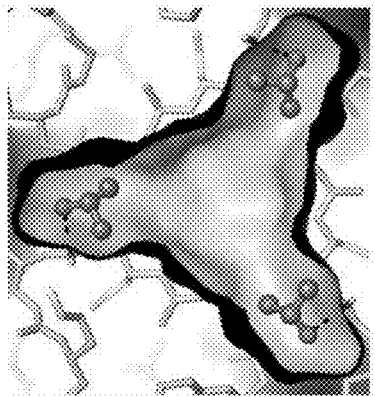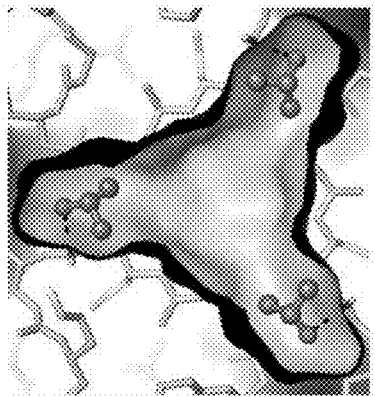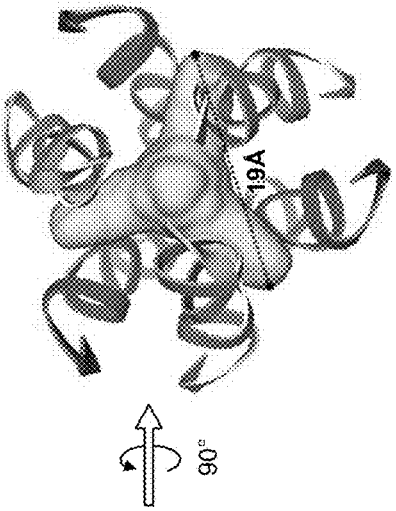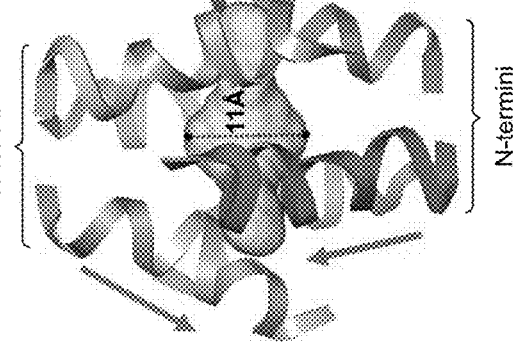
FIG. 36A
FIG. 36B
FIG. 36C
FIG. 36D
FIG. 36E
FIG. 36F

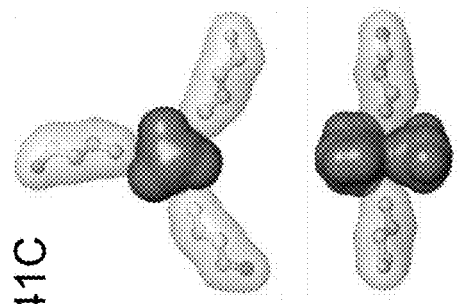
FIG. 41A
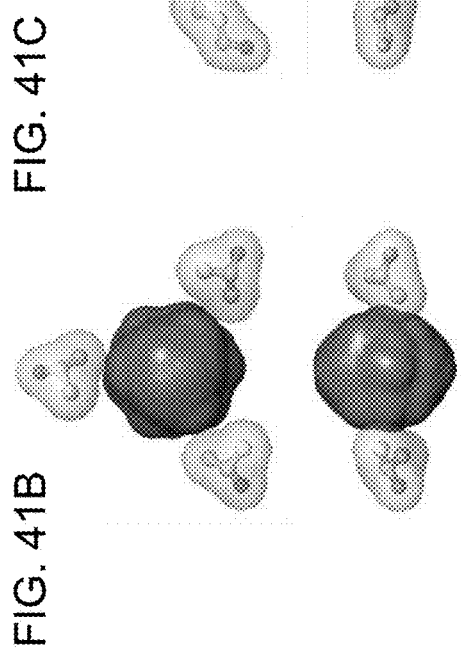
FIG. 41B
FIG. 41C
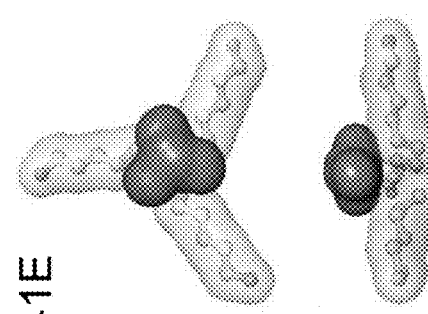
FIG. 41D
FIG. 41E
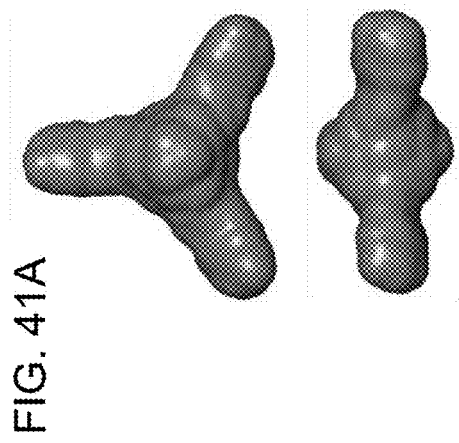
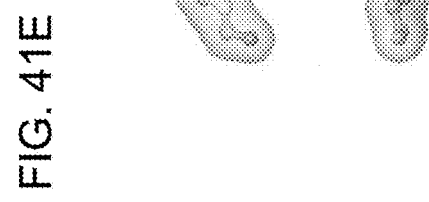

FIG. 45A

Table 4. X-ray diffraction data collection and refinement details for oligourea H1-alcohol co-crystal structures (structures 1-7).

| | Structure 1 | Structure 2 | Structure 3 | Structure 4 | Structure 5 | Structure 6 | Structure 7 |
|---|---|---|---|---|---|---|---|
| Oligourea | H1 | H1 | H1 | H1 | H1 | H1 | H1 |
| Guest alcohol | Isopropanol | 1-butanol | 1-pentanol | 1-hexanol | 2-ethoxyethanol | 2-propoxyethanol | 1,4-butanediol |
| Crystallisation conditions[a] | 15 % isopropanol | 8 % 1-butanol 15 % 1,4-dioxane | 2.5 % 1-pentanol 10 % 1,4-dioxane | 1.5 % 1-hexanol 25 % 1,4-dioxane | 5 % 2-ethoxyethanol 20 % 1,4-dioxane | 5 % 2-propoxyethanol 15 % 1,4-dioxane | 5 % 1,4-butanediol 20 % 1,4-dioxane |
| Data Collection | | | | | | | |
| Beam line | ID29 | PROXIMA 1 | ID23-2 | ID23-2 | PROXIMA 1 | PROXIMA 1 | PROXIMA 1 |
| Space group | $P6_3$ | $P6_3$ | $P6_3$ | $P6_3$ | $P6_3$ | $P6_3$ | $P6_3$ |
| Unit cell | | | | | | | |
| $a, b, c$ (Å) | 33.98, 33.98, 37.78 | 33.87, 33.87, 38.07 | 34.03, 34.03, 38.24 | 34.13, 34.13, 38.27 | 34.09, 34.09, 37.91 | 34.06, 34.06, 37.93 | 34.11, 34.11, 37.87 |
| $\alpha, \beta, \gamma$ (°) | 90.0, 90.0, 120.0 | 90.0, 90.0, 120.0 | 90.0, 90.0, 120.0 | 90.0, 90.0, 120.0 | 90.0, 90.0, 120.0 | 90.0, 90.0, 120.0 | 90.0, 90.0, 120.0 |
| Resolution (Å) | 29.43–1.18 (1.25–1.18)[b] | 38.07–1.35 (1.43–1.35) | 38.24–1.52 (1.61–1.52) | 38.27–1.15 (1.22–1.15) | 37.91–1.45 (1.54–1.45) | 37.93–1.62 (1.72–1.62) | 37.873–1.38 (1.46–1.38) |
| $R_{meas}^c$ (%) | 4.0 (62.0) | 4.1 (67.7) | 5.3 (66.2) | 13.5 (70.0) | 7.3 (73.6) | 5.8 (46.7) | 11.8 (38.6) |
| $I/\sigma$ | 23.12 (3.30) | 25.66 (3.24) | 19.22 (2.58) | 8.47 (2.14) | 20.10 (3.13) | 17.30 (3.82) | 10.75 (3.36) |
| Completeness (%) | 99.9 (99.2) | 99.6 (97.6) | 99.6 (99.4) | 100 (99.9) | 99.8 (99.2) | 99.9 (99.6) | 100 (100) |
| Reflections (total) | 65495 | 46031 | 30694 | 70121 | 43334 | 19317 | 30420 |
| Reflections (unique) | 8219 | 5457 | 3926 | 9101 | 4520 | 3212 | 5218 |
| Redundancy | 8.0 (7.1) | 8.4 (7.9) | 7.8 (7.7) | 7.7 (7.1) | 9.6 (9.1) | 6.0 (5.8) | 5.8 (5.3) |

FIG. 45B

| Refinement | | | | | | | |
|---|---|---|---|---|---|---|---|
| Resolution (Å) | 29.43 –1.18 | 29.33 –1.35 | 29.47 –1.52 | 29.55 –1.15 | 29.52 –1.45 | 29.49 –1.62 | 29.54 –1.38 |
| $R_{work}/R_{free}$ (%) | 16.38 / 20.09 | 15.83 / 24.47 | 18.96 / 20.76 | 18.72 / 21.31 | 21.24 / 25.94 | 22.97 / 26.82 | 23.05 / 28.34 |
| No. of atoms | 279 | 270 | 272 | 279 | 268 | 258 | 270 |
| Waters | 22 | 16 | 22 | 22 | 12 | 7 | 14 |
| Overall B-factor (Å$^2$) | 14.50 | 26.05 | 24.70 | 19.27 | 18.46 | 25.22 | 29.39 |
| R.M.S. deviations | | | | | | | |
| Bond lengths (Å) | 0.018 | 0.017 | 0.018 | 0.017 | 0.017 | 0.017 | 0.020 |
| Bond angles (°) | 2.185 | 1.799 | 1.868 | 2.015 | 1.840 | 1.967 | 2.018 |
| CCDC code | 1057613 | 1057611 | 1057614 | 1057612 | 1057608 | 1057609 | 1057610 |

[a] All crystallisation conditions also contained 200 mM calcium chloride and 100 mM sodium acetate buffer (pH 4.6).
[b] Values in brackets refer to highest resolution shell.
[c] See: Diederichs, K. & Karplus, P. A. Improved R-factors for diffraction data analysis in macromolecular crystallography. *Nat. Struct. Biol.* 4, 269-275 (1997).

SEQUENCE LISTING

<160> NUMBER OF SEQ ID NOS: 5

<210> SEQ ID NO 1
<211> LENGTH: 11
<212> TYPE: PRT
<213> ORGANISM: Artificial Sequence
<220> FEATURE:
<223> OTHER INFORMATION: Synthetic

```
<220> FEATURE:
<221> NAME/KEY: MISC_FEATURE
<222> LOCATION: (1)..(11)
<223> OTHER INFORMATION: At least one of 1-11 is an oligourea
      peptidomimetic residue

<400> SEQUENCE: 1

Leu Glu Lys Leu Tyr Leu Glu Lys Leu Ala Leu
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(10)
<223> OTHER INFORMATION: At least one of 1-10 is an oligourea
      peptidomimetic residue

<400> SEQUENCE: 2

Leu Glu Leu Lys Pro Leu Glu Leu Lys Ala
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(11)
<223> OTHER INFORMATION: At least one of 1-11 is an oligourea
      peptidomimetic residue

<400> SEQUENCE: 3

Leu Glu Lys Leu Tyr Asn Glu Lys Leu Ala Leu
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(11)
<223> OTHER INFORMATION: At least one of 1-11 is an oligourea
      peptidomimetic residue

<400> SEQUENCE: 4

Ser Glu Lys Leu Tyr Leu Glu Lys Leu Ala Leu
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(12)
<223> OTHER INFORMATION: At least one of 1-12 is an oligourea
      peptidomimetic residue
```

```
<400> SEQUENCE: 5

Ala Leu Lys Leu Glu Tyr Leu Glu Leu Lys Ala Leu
1               5                   10
```

FOLDAMER HELIX BUNDLE-BASED MOLECULAR ENCAPSULATION

CROSS-REFERENCE TO RELATED APPLICATIONS

This application is a National Stage of International Application No. PCT/EP2016/070556, filed Aug. 31, 2016, entitled "FOLDAMER HELIX BUNDLE-BASED MOLECULAR ENCAPSULATION", which claims priority to U.S. Provisional Application Ser. No. 62/212,583, file on Aug. 31, 2015, entitled "FOLDAMER HELIX BUNDLE-BASED MOLECULAR ENCAPSULATION", the entire contents of which are incorporated herein by reference in its entirety and for all purposes.

INCORPORATION BY REFERENCE

In compliance with 37 C.F.R. § 1.52(e)(5), the sequence information contained in electronic file name: 1513195_128WO2_Sequence_Listing_ST25.txt; size 1.87 KB; created on: 30 Aug. 2016; using Patent-In 3.5, and Checker 4.4.0 is hereby incorporated herein by reference in its entirety.

FIELD OF THE INVENTION

The present description relates to α-helicomimetic foldamers, and their synthesis. In particular, the description provides short amphiphlic α-helicomimetic foldamers bearing proteinaceous sidechains that can form a series of diverse quaternary arrangments, which can be controlled at the sequence level.

BACKGROUND

Interactions between proteins and/or their substrates or ligands are critical for normal cell function, physiologic signal transduction, as well as for therapeutic intervention in many pathophysiologic or disease-related processes. Proteins and peptides are capable of adopting compact, well-ordered conformations, and performing complex chemical operations, e.g., catalysis, highly selective recognition, etc. The three dimensional structure is the principal determinant that governs specificity in protein-protein and/or protein-substrate interactions. Thus, the conformation of peptides and proteins is central for their biological function, pharmaceutical efficacy, and their therapeutic preparation.

Protein folding is inextricably linked to function in both proteins and peptides because the creation of an "active site" requires proper positioning of reactive groups. Consequently, there has been a long-felt need to identify synthetic polymer or oligomers, which display discrete and predictable (i.e., stable) folding and oligomerizing propensities (hereinafter referred to as "foldamers") to mimic natural biological systems. Insofar as these unnatural backbones are resistant to the action of proteases and peptidases, they are useful as probes having constrained conformational flexibility or as therapeutics with improved pharmacological properties, e.g., pharmacokinetic (PK) and/or pharmacodynamics (PD) features, such as potency and/or half-life. Whereas a naturally occurring polypeptide comprised entirely of α-amino acid residues will be readily degraded by any number of proteases and peptidases, foldamers, including chimeras of natural peptides and synthetic amino acid derivatives, mimetics or pseudopeptides, are not.

As noted above, the interest in foldamers stems in part from their resistance to enzymatic degradation. They are also interesting molecules because of their conformational behavior. The elucidation of foldamers having discrete conformational propensities akin to those of natural proteins has led to explorations of peptides constructed from β, γ-, or δ-amino acids. γ-Peptides containing residues bearing γ-substitution or α, γ-disubstitution or α, β, γ-trisubstitution have been shown to adopt a helical conformation defined by a 14-member turn that is stabilized by $C=O_{(i)} \rightarrow NH_{(i+3)}$ hydrogen bonds. Both the $3_{14}$ and $2.5_{12}$ helical backbones have been found suitable for the design of stabilized helical peptides useful for therapeutic purposes. For example, in order to cluster polar residues on one face of the helix, amphiphilic $3_{14}$-helical β-peptides have been constructed from hydrophobic-cationic-hydrophobic- or hydrophobic-hydrophobic-cationic residue triads.

Considerable effort has been applied towards the development of artificial bio-inspired systems able to form predictable and homogeneous assemblies at the nanometer scale in aqueous conditions (Zhang, F., Nangreave, J., Liu, Y. & Yan, H. Structural DNA nanotechnology: state of the art and future perspective. *J. Am. Chem. Soc.* 136, 11198-11211 (2014); Lai, Y.-T., King, N. P. & Yeates, T. O. Principles for designing ordered protein assemblies. *Trends Cell Biol.* 22, 653-661 (2012); King, N. P. et al. Computational design of self-assembling protein nanomaterials with atomic level accuracy. *Science* 336, 1171-1174 (2012); Lai, Y.-T., Cascio, D. & Yeates, T. O. Structure of a 16-nm cage designed by using protein oligomers. *Science* 336, 1129 (2012); Gradišar, H. & Jerala, R. Self-assembled bionanostructures: proteins following the lead of DNA nanostructures. *J. Nanobiotechnology* 12, 4 (2014); Lai, Y.-T. et al. Structure of a designed protein cage that self-assembles into a highly porous cube. *Nat. Chem.* 6, 1065-1071 (2014); King, N. P. et al. Accurate design of co-assembling multicomponent protein nanomaterials. *Nature* 510, 103-108 (2014); Fletcher, J. M. et al. Self-assembling cages from coiled-coil peptide modules. *Science* 340, 595-599 (2013); Tebo, A. G. & Pecoraro, V. L. Artificial metalloenzymes derived from three-helix bundles. *Curr. Opin. Chem. Biol.* 25C, 65-70 (2015); Gradišar, H. et al. Design of a single-chain polypeptide tetrahedron assembled from coiled-coil segments. *Nat. Chem. Biol.* 9, 362-366 (2013); and Bromley, E. H. C., Channon, K., Moutevelis, E. & Woolfson, D. N. Peptide and protein building blocks for synthetic biology: from programming biomolecules to self-organized biomolecular systems. *ACS Chem. Biol.* 3, 38-50 (2008)). Although building units based on short peptides possess a number of advantages for nano-scale assembly—including synthetic availability, modularity and sequence diversity (Fletcher, J. M. et al. Self-assembling cages from coiled-coil peptide modules. *Science* 340, 595-599 (2013); Tebo, A. G. & Pecoraro, V. L. Artificial metalloenzymes derived from three-helix bundles. *Curr. Opin. Chem. Biol.* 25C, 65-70 (2015); Gradišar, H. et al. Design of a single-chain polypeptide tetrahedron assembled from coiled-coil segments. *Nat. Chem. Biol.* 9, 362-366 (2013); and Bromley, E. H. C., Channon, K., Moutevelis, E. & Woolfson, D. N. Peptide and protein building blocks for synthetic biology: from programming biomolecules to self-organized biomolecular systems. *ACS Chem. Biol.* 3, 38-50 (2008))—one limitation resides in the intimate connection between primary sequence and secondary structure. In this respect, non-natural synthetic oligomers designed to form predictable and well-defined secondary structures akin to those found in proteins—i.e. 'foldamers' (Gellman, S. H. Foldamers: A Manifesto. *Acc.*

Chem. Res. 31, 173-180 (1998); Goodman, C. M., Choi, S., Shandler, S. & DeGrado, W. F. Foldamers as versatile frameworks for the design and evolution of function. *Nat. Chem. Biol.* 3, 252-262 (2007); and Guichard, G. & Huc, I. Synthetic foldamers. *Chem. Commun.* 47, 5933-5941 (2011))—obey different folding rules and thus provide new opportunities for creating self-assembled architectures with topologies similar to and beyond those of natural polypeptides. Additionally, in contrast to α-peptides, fully non-natural biopolymer backbones are likely—and in some cases proven—to be resistant to naturally occurring proteases (Johnson, L. M. & Gellman, S. H. α-Helix mimicry with α/β-peptides. *Methods Enzymol.* 523, 407-429 (2013); and Frackenpohl, J., Arvidsson, P. I., Schreiber, J. V. & Seebach, D. The outstanding biological stability of beta- and gamma-peptides toward proteolytic enzymes: an in vitro investigation with fifteen peptidases. *Chembiochem* 2, 445-455 (2001)), a highly desirable characteristic for systems intended for bio-applications.

Advances in foldamer research have led to the discovery of a wide range of oligomeric backbones predisposed to adopt well-defined secondary structures, yet few reports have described the aqueous assembly of foldamers into homogeneous tertiary or quaternary arrangements—such examples being limited to the creation of de novo octameric helical bundles (Daniels, D. S., Petersson, E. J., Qiu, J. X. & Schepartz, A. High-resolution structure of a beta-peptide bundle. *J. Am. Chem. Soc.* 129, 1532-1533 (2007); and Wang, P. S. P., Nguyen, J. B. & Schepartz, A. Design and high-resolution structure of a β³-peptide bundle catalyst. *J. Am. Chem. Soc.* 136, 6810-6813 (2014)) and nanofibers (Pizzey, C. L. et al. Characterization of nanofibers formed by self-assembly of beta-peptide oligomers using small angle x-ray scattering. *J. Chem. Phys.* 129, 095103 (2008); and Pomerantz, W. C. et al. Nanofibers and lyotropic liquid crystals from a class of self-assembling beta-peptides. *Angew. Chem. Int. Ed Engl.* 47, 1241-1244 (2008)) formed from short amphiphilic helical β-peptides, and hybrid α/β-peptide tetrameric helical bundles obtained by reengineering the dimerization domain of the yeast GCN4 transcription factor (Horne, W. S., Price, J. L., Keck, J. L. & Gellman, S. H. Helix bundle quaternary structure from alpha/beta-peptide foldamers. *J. Am. Chem. Soc.* 129, 4178-4180 (2007); and Giuliano, M. W., Horne, W. S. & Gellman, S. H. An alpha/beta-peptide helix bundle with a pure beta3-amino acid core and a distinctive quaternary structure. *J. Am. Chem. Soc.* 131, 9860-9861 (2009)).

Sequence remodeling of these backbones to yield well-defined yet dissimilar topologies has not been documented, except a rearrangement from parallel to anti-parallel helix topology in the α/β peptide bundle series (Giuliano, M. W., Horne, W. S. & Gellman, S. H. An alpha/beta-peptide helix bundle with a pure beta3-amino acid core and a distinctive quaternary structure. *J. Am. Chem. Soc.* 131, 9860-9861 (2009)). Current aqueous foldamer quaternary assemblies are thus limited in terms of: 1) backbone diversity; 2) divergence from nature; 3) diversity of topology and, importantly; 4) control. An additional—more general—limitation is the paucity of high-resolution structural data available for aqueous foldamer quaternary assemblies (Daniels, D. S., Petersson, E. J., Qiu, J. X. & Schepartz, A. High-resolution structure of a beta-peptide bundle. *J. Am. Chem. Soc.* 129, 1532-1533 (2007); Wang, P. S. P., Nguyen, J. B. & Schepartz, A. Design and high-resolution structure of a β³-peptide bundle catalyst. *J. Am. Chem. Soc.* 136, 6810-6813 (2014); Horne, W. S., Price, J. L., Keck, J. L. & Gellman, S. H. Helix bundle quaternary structure from alpha/beta-peptide foldamers. *J. Am. Chem. Soc.* 129, 4178-4180 (2007); and Giuliano, M. W., Horne, W. S. & Gellman, S. H. An alpha/beta-peptide helix bundle with a pure beta3-amino acid core and a distinctive quaternary structure. *J. Am. Chem. Soc.* 131, 9860-9861 (2009))—and water-soluble foldamers in general. As such, there is a deficiency of pre-existing structures for use as templates for the design of new aqueous quaternary (and tertiary) assemblies.

Aliphatic oligoureas are a class of non-peptide α-helicomimetic foldamer which possess several features conducive for their use as self-organizing biomimetic building units. The chemical accessibility of the urea-based monomers permits the synthesis of urea oligomers bearing, yet not limited to, any of the 20 naturally occurring amino acid side-chains (Burgess, K., Shin, H. & Linthicum, D. S. Solid-Phase Syntheses of Unnatural Biopolymers Containing Repeating Urea Units. *Angew. Chem. Int. Ed. Engl.* 34, 907-909 (1995); and Douat-Casassus, C., Pulka, K., Claudon, P. & Guichard, G. Microwave-enhanced solid-phase synthesis of N,N'-linked aliphatic oligoureas and related hybrids. *Org. Lett.* 14, 3130-3133 (2012)). Importantly, the helicity of urea oligomers is largely unaffected by the nature of the side-chains used, making these foldamers highly robust and tunable (Fischer, L. et al. The canonical helix of urea oligomers at atomic resolution: insights into folding-induced axial organization. *Angew. Chem. Int. Ed Engl.* 49, 1067-1070 (2010); and Violette, A. et al. N,N'-linked oligoureas as foldamers: chain length requirements for helix formation in protic solvent investigated by circular dichroism, NMR spectroscopy, and molecular dynamics. *J. Am. Chem. Soc.* 127, 2156-2164 (2005)). In addition, oligoureas as short as 4-6 residues in length are able to adopt stable helical structures (Nelli, Y. R., Fischer, L., Collie, G. W., Kauffmann, B. & Guichard, G. Structural characterization of short hybrid urea/carbamate (U/C) foldamers: A case of partial helix unwinding. *Biopolymers* 100, 687-697 (2013)), bestowing an added dimension of versatility to these foldamers as self-assembling building blocks.

A key principle of foldamer research is to use biomolecules as inspiration for the design and development of molecules with functions and capabilities beyond those found in nature, such as catalysts or artificial bio-receptors with tailored ligand specificity. As function is intimately linked with structure, the creation of new and unique foldamer architectures is a necessary step towards the goal of developing foldamers with tailored/preternatural functions. However, the construction of novel foldamer structures can be challenging, particularly the creation of multi-component architectures, which require controlled, precise self-assembly. A seemingly even greater challenge than this is presented by the development of multimeric foldamer systems with the ability to self-assemble in aqueous conditions into precise, well-defined arrangements. The development of aqueous self-assembling foldamer systems is an important step towards the creation of foldamers with true bio-functions—such as bio-catalysis (Rufo, C. M., et al. *Nat. Chem.* 2014, 6 (4), 303; Wang, P. S. P., et al. *J. Am. Chem. Soc.* 2014, 136 (19), 6810; Tegoni, M., et al. *Proc. Natl. Acad. Sci.* U.S.A. 2012, 109 (52), 21234; and Reig, A. J., et al. *Nat. Chem.* 2012, 4 (11), 900).

Until recently, examples of atomic-level structural elucidation of water-soluble foldamer quaternary assemblies were largely limited to β-amino acid containing backbones (Craig, C. J.; et al. *ChemBioChem* 2011, 12 (7), 1035; Giuliano, M. W., et al. *J. Am. Chem. Soc.* 2009, 131 (29), 9860; Home, W. S., et al. *Proc. Natl. Acad. Sci.* U.S.A. 2008, 105 (27), 9151; Horne, W. S. et al. *J. Am. Chem. Soc.* 2007, 129 (14), 4178; Daniels, D. S., et al. *J. Am. Chem. Soc.* 2007, 129 (6), 1532, Goodman, J. L., et al. *J. Am. Chem. Soc.* 2007, 129 (47), 14746). However, the strong propensity of short aliphatic oligourea foldamers to self-assemble in aqueous conditions into unique, precise quaternary arrangements, encompassing discrete helical bundles and extended tubular structures with water-filled pores was recently reported by the Applicant. Of particular note was the surprise discovery of an isolated hydrophobic cavity with a volume of around 500 Å$^3$ within the helical bundle arrangements reported (FIG. 1). Although this volume is much smaller than that of nanocages built from the self-assembly of de novo designed proteins (Beck, T.; et al. *Angew. Chem. Int. Ed. Engl.* 2015, 54 (3), 937; Der, B. S.; et al. *Nat. Biotechnol.* 2013, 31 (9), 809; Lai, Y.-T., et al. *Science* 2012, 336 (6085), 1129; King, N. P., et al. *Science* 2012, 336 (6085), 1171.), it compares favourably with cavities engineered into peptide coiled-coils for small guest recognition (Ebalunode, J. O., et al. *Bioorg. Med. Chem.* 2009, 17 (14), 5133; Yadav, M. K., et al. *Biochemistry* 2005, 44 (28), 9723; Liu, J., et al. *Proc. Natl. Acad. Sci. U.S.A.* 2004, 101 (46), 16156; Johansson, J. S., et al. *Biochemistry* 1998, 37 (5), 1421). Cavities formed from water-soluble constructs represent a particularly enticing structural motif, as one could envisage the use of such a feature for, eventually, (drug) delivery, bio-sensing or catalysis. Over the last decade, supramolecular chemists have made remarkable progress towards the preparation of sophisticated organic and metal-organic containers—including covalent and self-assembled capsules—with a wide range of physicochemical properties (such as water solubility) and functions (such as dynamic systems able to adapt to the nature of the guest) (Rebilly, J.-N., et al. *Chem. Soc. Rev.* 2015, 44 (2), 467; Zarra, S., et al. *Chem. Soc. Rev.* 2015, 44 (2), 419; Biros, S. M., et al. *Chem. Soc. Rev.* 2007, 36 (1), 93; Ballester, P. *Chem. Soc. Rev.* 2010, 39 (10), 3810; and Conn, M. M., et al. *Chem. Rev.* 1997, 97 (5), 1647). Systems exploiting secondary structural folding have also been developed as capsules, and in particular, helical foldamers able to form internal cavities upon folding have emerged as a new and promising class of synthetic receptor (Singleton, M. L., et al. *Angew. Chem. Int. Ed. Engl.* 2014, 53 (48), 13140; Hua, Y., et al. *J. Am. Chem. Soc.* 2013, 135 (38), 14401; Wu, B. et al. *Org. Lett.* 2012, 14 (3), 684; Ferrand, Y., et al. *J. Am. Chem. Soc.* 2010, 132 (23), 7858; Juwarker, H., et al. *Chem. Soc. Rev.* 2009, 38 (12), 3316; Xu, Y.-X., et al. *J. Org. Chem.* 2009, 74 (19), 7267; Suk, J.-M., et al. *J. Am. Chem. Soc.* 2008, 130 (36), 11868; Garric, J., et al. *Chemistry* 2007, 13 (30), 8454; Garric, J., et al. *Angew. Chem. Int. Ed. Engl.* 2005, 44 (13), 1954; Inouye, M., et al. *J. Am. Chem. Soc.* 2004, 126 (7), 2022; and Tanatani, A., et al. *Angew. Chem. Int. Ed. Engl.* 2002, 41 (2), 325). Such capsule systems permit the optimisation of guest recognition to be achieved through rational sequence variation, allowing the volume and chemical nature of the cavity to be modified by the incorporation of appropriate residual building blocks. A recent example of such a fine tuning process describes the iterative design of helical foldamers with high selectivity for specific monosaccharides (Chandramouli, N., et al. *Nat. Chem.* 2015, 7 (4), 334). The vast majority of existing foldamer capsules, however, are restricted to monomeric helical foldamers with internal cavities, with few reports of foldamer capsules formed by the self-assembly of multimolecular components (Singleton, M. L., et al. *Angew. Chem. Int. Ed. Engl.* 2014, 53 (48), 13140). Furthermore, foldamer capsule systems have not generally been employed and studied in aqueous environments (Suk, J.-M., et al. *J. Am. Chem. Soc.* 2008, 130 (36), 11868), thus there is a need for further development and diversification of foldameric capsule systems.

The design and construction of biomimetic self-assembling systems is a challenging yet potentially highly rewarding endeavour, contributing to the development of new biomaterials, catalysts, drug-delivery systems and tools for the manipulation of biological processes. While much has been achieved by engineering self-assembling DNA-, protein- and peptide-based building units, the design of entirely new, fully non-natural folded architectures resembling biopolymers ("foldamers") with the ability to self-assemble into atomically precise nano-structures in aqueous conditions has proved exceptionally challenging. Furthermore, artificial synthetic molecules able to adopt well-defined stable secondary structures comparable to those found in nature ("foldamers") have considerable potential for use in a range of applications such as bio-materials, bio-recognition, nano-machines and as therapeutic agents. The development of foldamers with the ability to bind and encapsulate "guest" molecules is of particular interest, as such an ability is a key step towards the development of artificial sensors, receptors and drug-delivery vectors. While significant progress has been reported within this context, foldamer capsules reported thus far are largely restricted to organic solvent systems. Therefore, there exists a need for fully non-natural folded architectures resembling biopolymers ("foldamers") with the ability to self-assemble into atomically precise nano-structures in aqueous conditions, as well as a need for guest-encapsulation in aqueous conditions by a self-assembled foldameric capsule.

SUMMARY

The present disclosure relates to the surprising and unexpected discovery that de novo design and subsequent sequence manipulation of non-peptide oligourea helical foldamers results in the controllable formation of diverse protein-like higher-order structures in aqueous conditions, ranging from discrete helical bundles with isolated cavities to pH-responsive super-helical channels with water-filled channels. The quaternary arrangements of the present disclosure represent the first examples of molecular self-assembly of fully non-peptidic foldamers into three-dimensional nanostructures in aqueous conditions, and are unprecedented in terms of topological diversity and programmability. In particular, the description provides a modular design, formation and structural elucidation at the atomic level of a series of diverse quaternary arrangements formed by the self-assembly of short amphiphilic α-helicomimetic foldamers bearing proteinaceous side-chains. Furthermore, the final quaternary assembly can be controlled at the sequence level, permitting the programmed formation of, e.g., either discrete helical bundles containing isolated cavities or pH-responsive water-filled channels with controllable diameters. That is, the channel diameters can be altered by modifying the non-peptide oligourea peptidomimetic residues.

The present disclosure further relates to the surprising and unexpected discovery that host-agent complexes are possible involving a self-assembled oligourea helical bundle comprising agents bound at least partially within its internal cavity. In certain embodiments, the agent can be, e.g., primary alcohols. In certain additional embodiments, the oligourea helical bundles can at least partially encapsulate the agent in aqueous conditions through an artificial cavity formed by a self-assembled foldamer.

Oligoureas represent interesting classes of peptidomimetic foldamers that have previously received little attention. In one aspect, the description provides a compound that at least partially encapsulates an agent. The compound comprising aliphatic oligoureas. In certain embodiments, the aliphatic oligoureas form an oligourea helical bundle. In other embodiments, the aliphatic oligoureas are comprised of short amphiphilic α-helicomimetic foldamers with proteinaceous sidechains. In an embodiment, the short amphiphilic α-helicomimetic foldamers self-assemble into the oligourea helical bundle. In a particular embodiment, the foldamers self-assemble under aqueous conditions. Because the compounds as described herein can adopt desired secondary structures similar to native peptides, including, e.g., helicoidal structures, they can serve as, for example, receptor ligands, effector molecules, agonists, antagonists, modulators of protein-protein interactions, organocatalysts, or enzymes. The agent can be any substance that needs to be transported, e.g., a therapeutic agent, a drug, a catalyst, or any combination thereof. In an embodiment, the compound at least partially encapsulates an agent that has an atomic mass less than 600 Da.

In one aspect, the description provides oligourea compounds that comprise an oligourea helical bundle at least partially encapsulating an agent and attached to a peptide. The peptide can be a peptide α-helix. In certain embodiments, the peptide comprises an epitope that recognizes another compound, e.g. they can act as receptor ligands, effector molecules, agonists, antagonists, modulators of protein-protein interactions, organocatalysts, or enzymes. In an embodiment, the agent has an atomic mass in a range of about 10 Da to about 600 Da.

In additional aspects, the description provides peptide-oligourea chimeric compounds for encapsulating an agent. The chimeric compound comprises an oligourea helical bundle that at least partially encapsulates the agent and a peptide, which can be a peptide α-helix. In an embodiment, the oligourea helical bundle comprises a non-peptide oligourea helical foldamer. The oligourea helical bundle is coupled, joined to or contiguous with the peptide α-helix. In certain embodiments, the oligourea helical bundle is "fused" to a terminus, e.g., amino terminus, carboxy terminus or both, of an α-amino acid peptide.

In one aspect, the present disclose provides a quaternary assembly adapted to at least partially encapsulate an agent. The quaternary assembly comprising non-peptide helical foldamers. According to an embodiment, the quaternary assembly's final topology is directed by manipulation of the primary sequence. In a certain embodiment, the quaternary assembly is either a finite helical bundle or a super-helical water-filled channel. In a particular embodiment, the finite helical bundle or the super-helical water-filled channel has a tunable cavity size or diameter, respectively. According to an embodiment, the non-peptide helical foldamer is a catalyst with tailored substrate specificity. In a particular embodiment, non-peptide helical foldamers are formed from water-soluble foldamers. According to an embodiment, the quaternary assembly has an isolated internal cavity capable of at least partially encapsulating an agent. In an embodiment, the non-peptide helical foldamers encapsulate a drug or a substrate. In other embodiments, the quaternary assemblies are designed/configured for the conductance of an aqueous fluid (e.g., water) or (metal) ion cargo across a membrane. In a particular embodiment, the internal cavity of the oligourea helical bundle has a volume of about 500 $Å^3$. Furthermore, the oligourea helical bundle can encapsulate up to about 600 Da of the agent. In certain embodiments, the quaternary assembly further comprises a peptide. In certain embodiments, the non-peptide helical foldamer is "fused" to a terminus, e.g., amino terminus, carboxy terminus or both, of the peptide. The peptide can be a peptide α-helix.

In certain aspects, the description provides peptide-oligourea chimeras that at least partially encapsulates an agent and that adopts stable secondary structures, including, e.g., helicoidal, tertiary structure, and/or quaternary structures, wherein the chimeras comprise a peptide contiguous with or coupled to a sequence of non-peptide helical foldamers, and wherein the chimera can accept up to about 600 Da of the agent within the formed secondary structure.

In certain aspects, the description provides a non-peptide helical foldamer or a oligourea helical bundle capable of binding specifically to a target, e.g., a protein such as a receptor or other polypeptide or peptide, or small molecule, similar to the native or natural peptide, and at least partially encapsulating up to about 600 Da of the agent within the helical foldamer or helical bundle. In another aspect, the description provides a chimeric ligand compound for encapsulating an agent comprising oligourea helical bundle or a non-peptide helical foldamers and a peptide capable of binding specifically to a target, e.g., a protein such as a receptor or other polypeptide or peptide, or small molecule, similar to the native or natural peptide. The chimeric ligand compound can retain up to 600 Da of the agent. In an additional embodiments, the chimeric ligand compound peptide is contiguous with or coupled to a non-peptide helical foldamer.

In any of the embodiments described herein, the non-peptide helical foldamers are contiguous with or covalently linked or joined to at least one of the amino terminus (N'), the carboxyl terminus (C'), within the peptide sequence or a combination thereof, of the peptide. In a preferred embodiment, the peptide-oligourea chimeric compound comprises an oligourea portion covalently linked or joined to the C-terminus of the peptide portion.

In another aspect, the description provides a composition that includes an oligourea helical bundle comprising a non-peptide oligourea helical foldamer; and an agent at least partially encapsulated by the oligourea helical bundle. In an embodiment, the agent has an atomic mass less than about 600 Da.

In any aspect or embodiment described herein, the compounds can further comprise at least one additional chemical modification. In certain embodiments, the chemical modification includes at least one of, for example, acetylation, phosphorylation, methylation, glycosylation, prenylation, isoprenylation, farnesylation, geranylation, pegylation, a disulfide bond, or combination thereof.

In an additional aspect, the description provides pharmaceutically acceptable acid and base salt forms of the compounds described herein.

The oligourea foldamers and compounds as described herein, including pharmaceutically acceptable salts thereof, are useful for the preparation of a medicament and/or the treatment of disease in a subject. The compounds of the disclosure may optionally be administered with at least one of a pharmaceutically acceptable excipient, pharmacologically active agent or a combination thereof. As such, in an addition aspect the description provides compositions comprising an effective amount of a peptide-oligourea chimera or oligourea foldamers, or a oligourea helical bundle as described herein, and a pharmaceutically acceptable carrier or excipient.

The description also provides methods of treating a disease or disorder or ameliorating the effects of the same comprising the steps of administering to an individual in need thereof, a composition comprising: an effective amount of a peptide-oligourea chimera, oligourea foldamers, a oligourea compound, or salt form thereof as described herein; an agent at least partially encapsulated by the chimera, the foldamer(s), the compounds, or salt forms thereof; and a pharmaceutically acceptable carrier or excipient, wherein the composition is effective for treating, preventing or ameliorating the effects of the disease or disorder.

In another aspect, the present description provides methods of making and using the compounds, the chimeras, or the compositions as described herein. For example, the oligourea compounds or oligourea foldamers as described herein can be used as a diagnostic agent or a therapeutic agent for the treatment of a disease or condition.

In an additional aspect the present description provides methods of making oligourea compounds, oligourea foldamer compounds, or peptide-oligourea compounds as described herein. Thus, in one aspect, the present description provides for the synthesis of a non-peptide helical structure. In another aspect, the present description provides methods of making and using the compounds of the disclosure. For example, in one embodiment, the description provides a method of making an oligourea compound of the disclosure comprising fabricating a oligourea helical bundle with a non-peptide oligourea peptidomimetic residue sequence selected from the group consisting of: a helical pentad repeat (a, b, c, d, e): oligourea peptidomimetic residues with a hydrophobic side chain in positions a and d (e.g., Leu$^u$), oligourea peptidomimetic residues with a charged residue in position b and c (e.g. Glu$^u$ and Lys$^u$, respectively), and Tyr$^u$ and Ala$^u$ in position e; and a helical pentad repeat (a, b, c, d, e): oligourea peptidomimetic residues with a hydrophobic side chain in positions a and c (e.g. Leu$^u$), oligourea peptidomimetic residues with a hydrophobic side chain in position e (e.g., Ala$^u$ and Pro$^u$ residues at the e position), and oligourea peptidomimetic residues with a charged side chain in positions b and d (e.g., Glu$^u$ and Lys$^u$, respectively). In another embodiment, the non-peptide oliguria peptiomimetic residue sequence is selected from the group consisting of: Leu$^U$ Glu$^U$ Lys$^U$ Leu$^U$ Tyr$^U$ Leu$^U$ Glu$^U$ Lys$^U$ Leu$^U$ Ala$^U$ Leu$^U$ (H1); Leu$^U$ Glu$^U$ Leu$^U$ Lys$^U$ Pro$^U$ Leu$^U$ Glu$^U$ Leu$^U$ Lys$^U$ Ala$^U$ (H2); Leu$^U$ Glu$^U$ Lys$^U$ Leu$^U$ Tyr$^U$ Asn$^U$ Glu$^U$ Lys$^U$ Leu$^U$ Ala$^U$ Leu$^U$ (H3); Ser$^U$ Glu$^U$ Leu$^U$ Lys$^U$ Leu$^U$ Tyr$^U$ Leu$^U$ Glu$^U$ Lys$^U$ Leu$^U$ Ala$^U$ Leu$^U$ (H4); and Ala$^U$ Leu$^U$ Lys$^U$ Leu$^U$ Glu$^U$ Tyr$^U$ Leu$^U$ Glu$^U$ Leu$^U$ Lys$^U$ Ala$^U$ Leu$^U$ (H5). Furthermore, the method includes supplying the agent when the oligourea helical bundle self-assembles in an aqueous environment.

The preceding general areas of utility are given by way of example only and are not intended to be limiting on the scope of the present disclosure and appended claims. Additional objects and advantages associated with the compositions, methods, and processes of the present disclosure will be appreciated by one of ordinary skill in the art in light of the instant claims, description, and examples. For example, the various aspects and embodiments of the disclosure may be utilized in numerous combinations, all of which are expressly contemplated by the present description. These additional advantages objects and embodiments are expressly included within the scope of the present disclosure. The publications and other materials used herein to illuminate the background of the disclosure, and in particular cases, to provide additional details respecting the practice, are incorporated by reference, and for convenience are listed in the appended bibliography.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating an embodiment of the disclosure and are not to be construed as limiting the disclosure. Further objects, features and advantages of the disclosure will become apparent from the following detailed description taken in conjunction with the accompanying figures showing illustrative embodiments of the disclosure, in which:

FIGS. 1A, 1B, 1C, 1D, and 1F. Quaternary assemblies formed from short water-soluble oligourea foldamers: FIG. 1A. Helical-wheel representations of α-peptides and aliphatic oligoureas. FIG. 1B. Primary sequence of H1 (top), view down helical axis of the crystal structure of H1 (bottom left) and helical wheel showing side-chain distribution of H1 (bottom right). Superscript 'u' denotes urea-based residue. FIG. 1C Equivalent information as in B for oligourea H2. FIG. 1D Variable-concentration circular dichroism (CD) analysis of oligoureas H1 and H2 (in pure water) (MRE: molar residual ellipticity [deg.cm$^2$.dmol$^{-1}$.residue$^{-1}$], MRE$_{202}$: molar residual ellipticity at 202 nm). Trend lines are shown to guide the eye only, and are not fit to mathematical models. Equivalent CD studies of H1 and H2 performed in suitable buffered conditions yield data highly similar to data collected in pure water (See FIG. 2).

FIGS. 2A, 2B, 2C, and 2D. Circular dichroism (CD) analysis of oligoureas H1 and H2 in buffered conditions. FIG. 1A. Variable concentration CD spectra of H1 in 20 mM sodium acetate (Na-acetate) pH 4.0. Concentration range measured: 3.125 μM to 200 μM. MRE: molar residual ellipticity (deg.cm$^2$.dmol$^{-1}$.residue$^{-1}$). FIG. 1B. Equivalent experiments as (a) performed on H2 in 20 mM sodium phosphate (Na-Phosphate) at pH 7.4 (3.125 μM not measured due to weak signal intensity). FIG. 1C. Plots of oligourea concentration vs MRE$_{202}$ (molar residual ellipticity at 202 nm) for oligoureas H1 (blue markers) and H2 (green markers) measured in pure water (solid lines) and buffered conditions (dashed lines). Trend lines are not fit to specific mathematical models, and are shown to guide the eye only. FIG. 1D. Comparison of CD-monitored thermal melting profiles of H1 in pure water (black) and 20 mM sodium acetate (NaOAc) pH 4.0 (grey). Fitting these melting curves to a simple two-state Boltzmann unfolding model provides T$_m$ values of 45.9° C. and 48.9° C. for H1 measure in pure water and 20 mM sodium acetate (pH 4), respectively (adjusted R-square values: 0.99943 [pure water] and 0.99871 [sodium acetate buffer]).

FIG. 3A. Hexameric helical bundle formed from oligourea H1. Helices colored according to common helix orientation. FIG. 3B. Helix-dimer building block of helical bundle. The hexameric helical bundle is formed from three identical helical dimers. FIG. 3B. shows the hydrophilic dimer interface. Key inter-helical hydrogen bonds between the amine of Lys$^u{}_8$ and the free carbonyl group of Leu$^u{}_{11}$ are indicated (dashes). FIG. 3C. Hydrophobic Leu$^u$-rich interface of the helical dimer, highlighting the knobs-into-holes type packing of the Leu$^u$ side-chains (shown as spheres).

FIGS. 7A, 7B, and 7C. Solution and solid-state studies of oligourea helical-bundle formation. FIG. 7A Top: sequences of oligoureas H1, H3 and H4. Superscript 'u' denotes urea-based residue. Bottom: circular dichroism (CD) monitored thermal melting of oligoureas H1 (blue) and H4 (negative control—green), and accompanying native electrospray ionization mass spectrometry (ESI-MS) analysis. The major isotopic distribution at m/z=2083.4 for H1 shows isotope spacing of 0.2 m/z (inset), and therefore corresponds unambiguously to a hexameric species ([H1$_6$]$^{5+}$). Ion counts for these spectra are normalized (to 1000 counts) to permit comparison between H1 and H3. Foldamers were analyzed at a concentration of 200 µM in pure water for CD studies and 100 µM in 20 mM ammonium acetate for ESI-MS studies. MRE$_{202}$: molar residual ellipticity at 202 nm (with units of deg.cm$^2$.dmol$^{-1}$.residue$^{-1}$). FIG. 7B. NOESY spectra (200 ms mixing time) of H1 and H3 (measured at 200 µM foldamer concentration in 100% D$_2$O at 20° C.), showing strong evidence of intermolecular interactions for H1, and an absence of intermolecular interactions for H3. Red labels indicate unambiguous intermolecular interactions. The intermolecular interactions of H1 correlate excellently with the crystal structure (insets, NOE peaks shown as dashes). Note slight difference in Glu$^u{}_2$ rotamer conformation between NMR and X-ray data. NOESY experiments performed on H1 and H3 in buffered conditions (20 mM sodium acetate pH 4.0, 98% D$_2$O) yield spectra almost identical to spectra recorded in pure water (see FIGS. 8A and 8B). FIG. 7C. Structural alignment of crystal structures of helical bundles formed from H1 (blue) and H4 (red), plus separate views onto N-terminal junctions of each bundle (middle and right panels).

FIG. 9A. Variable concentration CD spectra of H3 in double-distilled H$_2$O. Concentration range measured: 3.125 µM to 200 µM. MRE: molar residual ellipticity (deg.cm$^2$.dmol$^{-1}$.residue$^{-1}$). FIG. 9B. Plots of oligourea concentration vs MRE$_{202}$ (molar residual ellipticity at 202 nm) for oligoureas H1 (blue diamonds) and H3 (red squares). FIG. 9C. Comparison of the effect of buffer on the variable-concentration CD profile of H3. Square symbols plus solid line corresponds to spectra of H3 recorded in water only, triangles plus dashed line corresponds to spectra of H3 recorded in 20 mM sodium acetate (NaOAc) at pH 4.0. As with H1 and H2, the variable-concentration CD profile of H3 in pure water is very similar to that of H3 obtained from buffered conditions. FIG. 9D. DOSY NMR analysis of 200 µM H1 or H3 in 20 mM sodium acetate (pH 4.0), 98% D$_2$O, and at a temperature of 293 K. The two spectra were collected under identical conditions and used a diffusion time of 250 ms and a diffusion gradient strength of 3 ms with a linear distribution of 16 points using gradient powers from 2% to 95%. The average diffusion for each molecule is illustrated with a dotted line, and the numerical values are from a curve fit using TopSpin 2.1 (Bruker) of the methyl region at ~0.8 ppm for H1 and H3, or the main peak of acetate at 2.08 ppm. The acetate exhibited the same diffusion rate in both samples.

FIG. 11A. Variable concentration circular dichroism (CD) spectra of H4 in double-distilled $H_2O$. Concentration range measured: 6.25 μM to 200 μM. MRE: molar residual ellipticity (deg.cm$^2$.dmol$^{-1}$.residue$^{-1}$). FIG. 11B. Plots of oligourea concentration vs MRE$_{202}$ (molar residual ellipticity at 202 nm) for oligoureas H1 (blue diamonds) and H4 (green squares). FIG. 11C. Comparison of CD-monitored thermal melting of oligoureas H1 (blue) and H4 (green). Foldamers were analyzed at a concentration of 200 μM in double-distilled $H_2O$. The CD signal at a wavelength of 202 nm was monitored for these experiments. FIG. 11D. NOESY NMR spectra of H4 (200 μM at 20° C. in 100% $D_2O$): a weak peak corresponding to intermolecular interactions between the δ2 proton of Leu$^u{}_{11}$ and the δ proton of Tyr$^u{}_5$ can be seen (red label), providing some, albeit weak, evidence of the presence of specific intermolecular interactions for this foldamer. FIG. 11E. Native electrospray ionization mass spectrometric analysis of a 100 μM solution of H4 in 20 mM aqueous ammonium acetate: the predominant multimer peak (with a stoichiometry greater than dimer) corresponds to a hexameric species (m/z=2050.8 Da, with a charge state of 5$^+$).

FIG. 12A. Native electrospray ionization (ESI) mass spectrum of H2 at 100 μM in 20 mM aqueous ammonium acetate. The ESI mass spectrum reveals extremely low levels of multimeric species (note the ion count on the Y axis, which is normalized to 60 to permit comparison to H5) with a concomitant high level of background 'noise'. MS-MS analysis of an m/z arbitrarily selected in the noisy region (indicated by arrow and diamond) reveals this background signal to be composed of H2 monomers FIG. 12B, suggesting that H2 exists predominantly in a multimerized/aggregated yet polydisperse form in these conditions. FIG. 12C. TOCSY NMR spectra of oligoureas H2, H3 and H5 at pH 4. At pH values above 5.5, the NMR spectra of H2 show no clear signals, consistent with the severe line-broadening due to the large size of the assembled channels. In contrast, NMR spectra of H2 at pH 4.0 (left TOCSY spectra) reveals the presence of small multimers or monomers with properties more similar to the monomeric H3 (middle). The spectra of H5 at pH 4.0 (right) also shows the presence of small multimers that appear to be on average larger than for H2. FIG. 12D. Using natural abundance 1H,13C-HSQC spectra for H3 at both pH 4.0 and pH 5.5, the only chemical shift differences are observed for the glutamate-urea side-chains, consistent with a change in protonation state of the carboxylate group. We would anticipate the protonation state of the glutamate-urea side-chains of oligoureas H2 and H5 to respond in a similar manner to equivalent changes in pH. FIG. 12E. Variable concentration circular dichroism (CD) spectra of H5 in double-distilled $H_2O$. Concentration range measured: 3.125 μM to 200 μM. MRE: molar residual ellipticity (deg.cm$^2$.dmol$^{-1}$.residue$^{-1}$). FIG. 12F. Plot of oligourea concentration vs MRE$_{202}$ (molar residual ellipticity at 202 nm) of oligourea H5. FIG. 12G. Comparison of CD-monitored thermal melting of H2 (blue data points) and H5 (magenta data points) (foldamers analysed at a concentration of 200 μM in double-distilled $H_2O$). FIG. 12H. ESI-MS analysis of H5 under the same conditions as H2 (i.e. as in [a]) reveals a total absence of discrete multimeric species with stoichiometries above dimer. In addition, there is a high level of background 'noise'. The corresponding MS-MS spectrum of a arbitrarily selected m/z (indicated by arrow and diamond) is shown in FIG. 12I, indicating that the background signal in 12H is composed of aggregated H5 monomers.

FIG. 13A. Negative staining electron microscopy (EM) and cryo-EM analysis of H2 (at a concentration of 200 μM in 50 mM sodium HEPES buffer, pH 7.5). Left: wide-field negative staining EM image of H2 revealing the presence of extended tubule structures (scale bar: 50 nm). Middle: magnification of a single tubule from the left panel with accompanying density analysis. Right: cryo-EM analysis of H2 (at 200 μM in 50 mM sodium HEPES buffer, pH 7.5) plus accompanying density analysis revealing the presence of tubule structures comparable to those seen by negative staining EM. Scale bars for middle and right panels: 10 nm. Y axes of plots denote average density. For additional EM images see FIGS. 14 and 15. FIG. 13B. Primary sequence and crystal structure of a 12-mer oligourea foldamer (H5) bearing a distribution of charged and uncharged side-chains analogous to oligourea H2 (superscript 'u' denotes urea-based residue). The crystal structure of H5 reveals a channel-type assembly constructed from six super-helices (individual super-helix chains colored separately)—comparable yet somewhat larger than the H2-channel. FIG. 13C. Crystal packing of H2 showing the mechanism by which multiple channels interact in the crystal state: individual channels pack into extended arrays via their hydrophobic exterior surfaces. The cross-section shows the dimensions and overall water structure of the internal pore. Residues are colored according to the helical wheel diagram in FIG. 1c. Waters shown as red spheres. FIG. 13D. Equivalent crystal packing of H5, highlighting the increased internal and external channel dimensions compared to H2. Color scheme as for helical wheel diagram in panel 13B. Additional details of channel packing interactions can be found in FIGS. 4 and 5.

FIG. 18. $^{13}$C NMR (75 MHz) of compound (3).
FIG. 23. Chemical structure, HPLC profile and electrospray ionization mass spectrum of oligourea H2.
FIG. 32. Chemical structure, HPLC profile and electrospray ionization mass spectrum of oligourea H1.

FIG. 33. Chemical structure, HPLC profile and electrospray ionization mass spectrum of oligourea H3.

FIG. 34. Chemical structure, HPLC profile and electrospray ionization mass spectrum of oligourea H4.

FIG. 35. Chemical structure, HPLC profile and electrospray ionization mass spectrum of oligourea H5.

FIGS. 36A, 36B, 36C, 36D, 36E, and 36F. Details of oligourea H1. (36C, 36D, and 36E) Details of the isolated cavity present in the crystal structure of the hexameric helical bundle formed from the self-assembly of oligourea H1 (H1-bundle). Black arrows in (36E) indicate the carbonyl groups of $Leu^u_6$ residues which are available for hydrogen bonding within the otherwise hydrophobic cavity. (36F) 1.18 Å crystal structure of H1 with three isopropanol guest molecules bound within the hydrophobic cavity of the helical bundle (structure 1). Each isopropanol molecule is hydrogen bonded to a carbonyl group of a $Leu^u_6$ residue. All hydrogen bonds shown here are 2.9 Å.

FIGS. 38A and 28B. (38A) Structural alignment of crystal structures 1-7. Green carbons: H1-isopropanol complex; cyan carbons: H1-1-butanol complex; magenta carbons: H1-1-pentanol complex; yellow carbons: H1-1-hexanol complex; pink carbons: H1-2-ethoxyethanol complex; white carbons: H1-2-propoxyethanol complex; and blue carbons: H1-1,4-butanediol complex. (38B) Close up of $Leu^u$ residues within internal cavity, highlighting the subtle structural differences in side-chain positions. Structural alignments were performed using PyMOL, with 732 to 732 atoms (corresponding to atoms of the H1-bundle only) aligned in all cases.

FIGS. 41A, 41B, 41C, 41D, and 41E. Axial (top row) and side views (bottom row) of the H1-bundle cavity bound by increasingly larger alcohol guests (unoccupied cavity, isopropanol, 1-butanol, 1-pentanol, and 1-hexanol). Blue surface corresponds to unoccupied cavity volume. Cavity analysis performed using SURFNET using a 1.4 Å probe radius. Occupation of >80% of the cavity volume as in the case of (41D) and (41E) results in noticeable stabilisation of the H1-bundle as measured by CD (FIG. 37A).

FIGS. 45A and 45B. Table 4. X-ray diffraction data collection and refinement details for oligourea H1-alcohol co-crystal structures (structures 1-7).

DETAILED DESCRIPTION

Figure 1C:
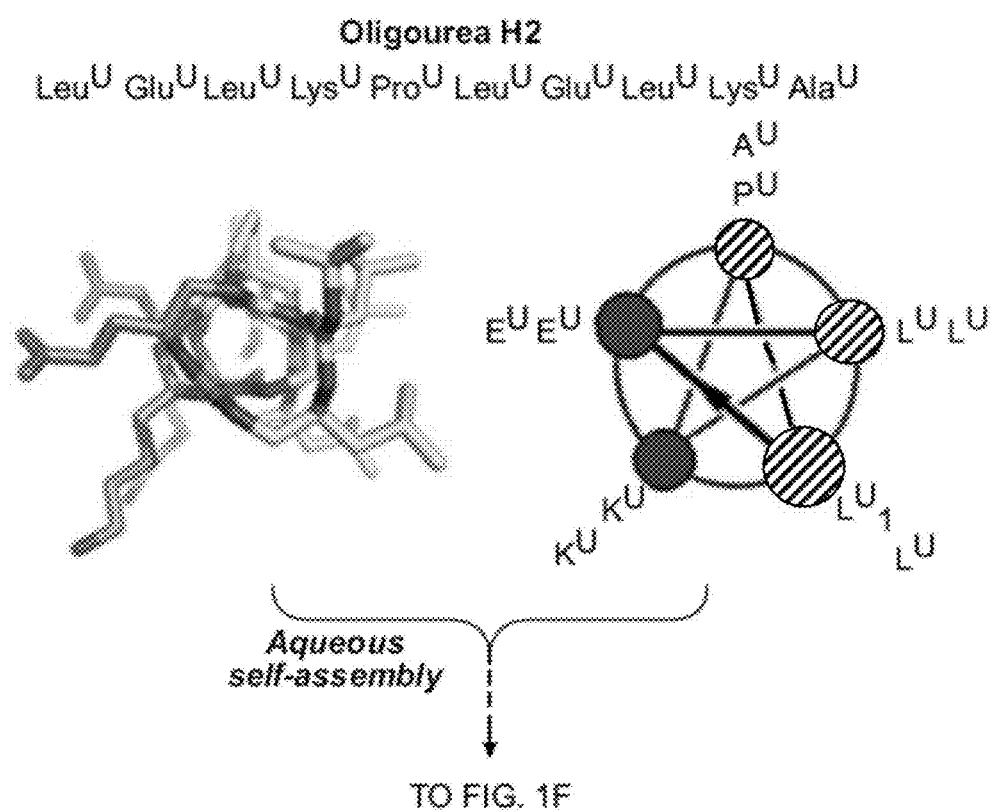

The following is a detailed description of the invention provided to aid those skilled in the art in practicing the present disclosure. Those of ordinary skill in the art may make modifications and variations in the embodiments described herein without departing from the spirit or scope of the present disclosure. Unless otherwise defined, all technical and scientific terms used herein have the same meaning as commonly understood by one of ordinary skill in the art to which this disclosure belongs. The terminology used in the description of the invention herein is for describing particular embodiments only and is not intended to be limiting of the disclosure. All publications, patent applications, patents, figures and other references mentioned herein are expressly incorporated by reference in their entirety.

U.S. Provisional Patent Application No. 61/868,128 filed 21 Aug. 2013 titled: Oligourea Foldamer Organocatalysts and Methods of Their Use; U.S. Provisional Patent Application No. 61/887,651 filed 7 Oct. 2013 titled: Peptide-Oligourea Chimeric Compounds and Methods of Their Use; U.S. patent application Ser. No. 14/465,680 filed 21 Aug. 2014 titled: Peptide-oligourea Chimeric Compounds and Methods of their Use; U.S. Provisional Patent Application No. 62/212,590 filed 1 Sep. 2015 entitled: Quaternary Assemblies of Water-Soluble Non-Peptide Helical Foldamers, their Use and Production Thereof, are hereby incorporated by reference in their entirety for all purposes. Furthermore, the disclosures of each and every patent, patent application, and publication cited herein are hereby incorporated herein by reference in their entirety.

The present disclosure related to non-peptide helical foldamers with the ability to self-assemble to an oligourea helical bundle and at least partially encapsulating an agent. According to an embodiment, the final topology of a quaternary assembly is directed by manipulation of the primary sequence. In a certain embodiment, the quaternary assembly is either finite helical bundles or super-helical water-filled channels.

In a particular embodiment, the finite helical bundles or super-helical water-filled channels have a tunable size, volume and/or diameter. According to an embodiment, the foldamer is a catalyst with tailored substrate specificity. As structure and function are intimately linked, the creation of new and unique foldamer architectures is an important step towards this goal. The higher-order assemblies described herein are unique in terms of backbone composition and quaternary topology. The channel-type assemblies described here represent the first examples of such entities formed from water-soluble foldamers to be characterized at atomic resolution. The stoichiometry (and topology) of the helical bundle reported herein (hexameric) is rare among both natural and non-natural helical bundles (Zaccai, N. R. et al. A de novo peptide hexamer with a mutable channel. *Nat. Chem. Biol.* 7, 935-941 (2011)). Importantly, these unique quaternary assemblies are accompanied by unique structural characteristics (isolated internal cavities and large water-filled pores) which could conceivably lead to tailored function(s) with future development. For example, in an embodiment, the non-peptide helical foldamers encapsulate an agent, e.g., a drug or a substrate (Yadav, M. K. et al. Structure-based engineering of internal cavities in coiled-coil peptides. *Biochemistry* 44, 9723-9732 (2005); Liu, R., Loll, P. J. & Eckenhoff, R. G. Structural basis for high-affinity volatile anesthetic binding in a natural 4-helix bundle protein. *FASEB J.* 19, 567-576 (2005); and Ghirlanda, G. et al. Volatile anesthetic modulation of oligomerization equilibria in a hexameric model peptide. *FEBS Lett.* 578, 140-144 (2004)), and/or are designed/configured for the conductance of a substance, e.g., water or (metal) ion cargo, across a membrane (Joh, N. H. et al. De novo design of a transmembrane $Zn^{2+}$-transporting four-helix bundle. *Science* 346, 1520-1524 (2014)). Several examples of internal cavities engineered into peptide coiled-coils have been reported, with cavity volumes in the range of 200-300 $Å^3$ for the few structures for which high-resolution data is available (Yadav, M. K. et al. Structure-based engineering of internal cavities in coiled-coil peptides. *Biochemistry* 44, 9723-9732 (2005); and Liu, R., Loll, P. J. & Eckenhoff, R. G. Structural basis for high-affinity volatile anesthetic binding in a natural 4-helix bundle protein. *FASEB J.* 19, 567-576 (2005)). With volumes of about 500 $Å^3$, the cavities observed in the crystal structures of H1 and H4 reported here are significantly larger and thus, more amenable to future development for various applications, such as the design of selective catalysts (Tegoni, M., et al. Designing a functional type 2 copper center that has nitrite reductase activity within α-helical coiled coils. *Proc. Natl. Acad. Sci.* U.S.A. 109, 21234-21239 (2012); and Faiella, M. et al. An artificial di-iron oxo-protein with phenol oxidase activity. *Nat. Chem. Biol.* 5, 882-884 (2009)).

Unlike previously reported aqueous self-assembling foldamers (Daniels, D. S., et al. High-resolution structure of a beta-peptide bundle. *J. Am. Chem. Soc.* 129, 1532-1533 (2007); Wang, P. S. P., et al. Design and high-resolution structure of a $β^3$-peptide bundle catalyst. *J. Am. Chem. Soc.* 136, 6810-6813 (2014); Pizzey, C. L. et al. Characterization of nanofibers formed by self-assembly of beta-peptide oligomers using small angle x-ray scattering. *J. Chem. Phys.* 129, 095103 (2008); Pomerantz, W. C. et al. Nanofibers and lyotropic liquid crystals from a class of self-assembling beta-peptides. *Angew. Chem. Int. Ed Engl.* 47, 1241-1244 (2008); Horne, W. S., et al. Helix bundle quaternary structure from alpha/beta-peptide foldamers. *J. Am. Chem. Soc.* 129, 4178-4180 (2007); and Giuliano, M. W., et al. An alpha/beta-peptide helix bundle with a pure beta3-amino acid core and a distinctive quaternary structure. *J. Am. Chem. Soc.* 131, 9860-9861 (2009)), the presently described system allows for the control of the final quaternary assembly by manipulating the primary sequence, permitting the creation of dramatically different yet equally unique three-dimensional structures (discrete helical bundles or extended channel-type assemblies of defined pore diameter) with a high degree of precision. Due to: 1) the simplicity of the design; 2) the short length of the helical components; and 3) the tunability of the reported assemblies (a result of the independence of oligourea helicity on primary sequence), the approach described herein can be easily implemented for the creation of structures with a broader range of topologies (and stoichiometries), functional properties and, consequently, applications. In addition, the similarity in screw-sense, pitch and polarity between peptide α-helices and oligourea 2.5-helices allow these two backbones to be combined, permitting key beneficial features of both species, such as natural epitope recognition of α-peptides and the innate helical stability of oligoureas, to be exploited in a single chimeric construct (Fremaux, J. et al. α-Peptide/Oligourea Chimeras: Stabilization of Short α-helices by Non Peptide Helical Foldamers. *Angew. Chem. Int. Ed. Engl.* (2015). DOI: 10.1002/anie.201500901R201500901). These goals will be aided significantly by the wealth of high-resolution structural information (X-ray and high-field NMR) generated for the assemblies reported herein, permitting a rational as well as directed approach for the development of new aqueous quaternary assemblies of equal potential utility.

Furthermore, the present disclosure relates to the ability of self-assembled foldamer helical bundle to at least partially encapsulate an agent or agents within an internal cavity in aqueous conditions. Seven exemplary high-resolution crystal structures reported below provide valuable atomic-level insight into the mode and precise details of host-agent binding, i.e., the agent encapsulated by a foldamer helical bundle. The helical bundle is able to expand or contract in response to specific (agent) chemical stimuli. The structural flexibility of the bundle indicates that the cavity can adapt to some degree in order to accommodate suboptimal agents (e.g., 1-hexanol). Agent-binding within the H1 cavity is an energetically feasible and dynamic process, in which the helical bundle transiently unfolds, exposing the central cavity to the bulk solvent and resulting in agent ejection. Considering the relatively low $T_m$ values of H1 both in the absence and presence of potential agents (as measured by CD), the results of these molecular dynamics simulations are to be expected. In certain applications, there can be a high guest turnover (e.g. in the context of catalysis) or ready agent release (e.g. for the purposes of cargo delivery).

Although the agent molecules studied here are relatively simple, the multiplicity in binding observed for all seven host-agent complexes has two important consequences: 1) three copies of the largest agent studied here equates to 312.45 Da, which theoretically permits the encapsulation of a agent large enough to be functionally interesting (e.g. a pharmaceutically active compound or a bio-substrate), and 2) multiple agent-binding results in a surprisingly high percentages of cavity occupation. These occupancy levels are far higher than those described for optimal encapsulation of agents by molecular containers in organic solvent conditions (Mecozzi, S., et al. *Chem. Eur. J.* 1998, 4 (6), 1016), and thus implies that the rules governing the encapsulation of relatively large.

The foldamer helical bundle described here is a potential capsule or carrier for agent, e.g., drug/cargo, delivery. A cavity provides an ideal isolated compartment for (catalytic) reactions to take place. The H1-1,4-butanediol crystal structure reported below demonstrate that multiple polar groups may be introduced within the helical bundle core. Furthermore, the H1-bundle hydrophobic cavity may be used as an enclosed environment for "confined reactions" (Maity, B., et al. *Curr. Opin. Chem. Biol.* 2015, 25, 88; and Vallavoju, N.; Sivaguru, *J. Chem. Soc. Rev.* 2014, 43 (12), 4084).

In one aspect, the description provides short oligourea sequences that result in amphiphilic structures with well-defined and distinct hydrophobic and charged regions when folded as canonical 2.5-helices. In certain embodiments, the sequestration of hydrophobic side-chains provide the driving force for self-assembly in aqueous conditions and the complementary charged side-chains facilitate inter-helical interactions. These self-assembled short oligourea sequences can at least partially encapsulate an agent. In a particular embodiment, the oligourea has a primary sequence selected from H1 or H2, as shown in FIG. 1B or FIG. 1C.

In additional aspects, the description provides oligourea compounds comprising an oligourea helical bundle that at least partially encapsulates an agent. In an embodiment, the oligourea helical bundle comprises non-peptide oligourea peptidomimetic residues. In a particular embodiment, the oligourea residues are coupled, joined to or contiguous with a peptide. In certain embodiments, the oligourea residues are "fused" to a terminus, e.g., amino terminus, carboxy terminus or both, of an α-amino acid peptide. In an embodiment, the peptide is a peptide α-helix.

The present description relates to the surprising and unexpected discovery that short amphiphilic α-helicomimetic foldamers with proteinaceous side-chains can self-assemble under aqueous conditions to form oligourea helical bundles. These foldamers can at least partially encapsulate an agent.

In another aspect, the description provides peptide-oligourea chimeric foldamer compounds comprising an oligourea helical bundle comprising non-peptide oligourea peptidomimetic residues that at least partially encapsulate an agent, and a peptide. In a certain embodiment, the non-peptide oligourea foldamers include non-peptide oligourea peptidomimetic residues. In a particular embodiment, the peptide includes a peptide α-helix. The chimeric compounds described herein improve at least one of potency, specificity, stability, pharmacokinetic (PK) and/or pharmacodynamics (PD) profile or combinations thereof, of the peptide precursor, e.g., alpha peptide precursor. The peptidomimetics as described herein are resistant or wholly immune to peptidase and protease degradation and are conformationally restrained. Thus, they are useful as tools to model peptide and protein conformations in aqueous solutions. The compounds are also useful as non-enzymatically degradable probes to mimic protein behavior in solution.

In one aspect, the description provides oligourea compounds and peptide-oligourea compounds at least partially encapsulating an agent synthesized using the methods of the disclosure. The description also provides pharmaceutical compositions comprising effective amounts of said compounds. In other aspects, the description provides therapeutic methods comprising the administration of an effective amount of the compounds of the disclosure to a mammal in need thereof.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either both of those included limits are also included in the disclosure.

The following terms are used to describe the present disclosure. In instances where a term is not specifically defined herein, that term is given an art-recognized meaning by those of ordinary skill applying that term in context to its use in describing the present invention.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the 10 United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects of the present disclosure, one or more of the present compounds described herein, are coadministered in combination with at least one additional bioactive agent. In particularly preferred aspects of the disclosure, the co-administration of compounds results in synergistic activity and/or therapy.

"Peptides" are typically short chains of amino acid monomers linked by peptide (amide) bonds, the covalent chemical bonds formed when the carboxyl group of one amino acid reacts with the amino group of another. The shortest peptides are dipeptides, consisting of 2 amino acids joined by a single peptide bond, followed by tripeptides, tetrapeptides, etc. A polypeptide is a long, continuous, and unbranched peptide chain.

The term "amino" or "amine" as used herein refers to —NH2 and substituted derivatives thereof wherein one or both of the hydrogens are independently replaced with 20 substituents selected from the group consisting of alkyl, haloalkyl, fluoro alkyl, alkenyl, alkynyl, carbocyclyl, heterocyclyl, aryl, aralkyl, hetero aryl, hetero aralkyl, alkylcarbonyl, haloalkylcarbonyl, carbocyclylcarbonyl, fluoroalkylcarbonyl, alkenylcarbonyl, heterocyclylcarbonyl, arylcarbonyl, alkynylcarbonyl, aralkylcarbonyl, heteroarylcarbonyl, heteroaralkylcarbonyl and the sulfonyl and sulfinyl groups defined above; or when both hydrogens together are replaced with an alkylene group (to form a ring which contains the nitrogen). Representative examples include, but are not limited to methylamino, acetylamino, and dimethylamino.

"Amino acid" refers to any molecule that contains both amino and carboxylic acid functional groups, and includes any of the naturally occurring amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D, L, or DL form. The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), alkaryl (e.g., as in phenylalanine and tryptophan), substituted arylalkyl (e.g., as in tyrosine), and heteroarylalkyl (e.g., as in histidine). The term is inclusive of various types of amino acids including α-, β-, γ-, or δ-amino acids, analogs and derivatives of the same, unless the context clearly indicates otherwise.

The term "amino acid sidechain" or "amino acid residue" shall mean, within context, a radical of a D- or L-amino acid sidechain (derived from an amino acid) which functions as a substituent on another group, often an alkylene (usually a methylene) group on R2' or R3' as otherwise described herein. Preferred amino acid sidechains for use in the present disclosure are derived from the sidechains of both natural and unnatural amino acids, preferably including, for example, alanine, β-alanine, arginine, asparagine, aspartic acid, cyclohexylalanine, cysteine, cystine, glutamic acid, glutamine, glycine, phenylalanine, histidine, isoleucine, lysine, leucine, methionine, naphthylalanine, norleucine, norvaline, proline, serine, threonine, valine, tryptophan or tyrosine, among others.

Unless the context clearly indicates otherwise, the term "any amino acid" can mean any natural or synthetic amino acid, including α-, β-, γ-, or δ-amino acids, possibly modified by the presence of one or more substituents, or combinations thereof, including analogs, derivatives, mimetics, and peptoid versions of the same. More precisely the term α-amino acid means an alpha aminated amino acid with the following general structure:

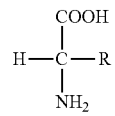

where R represents the side chain of the amino acid. In the context of the present disclosure, R therefore represents the side chain of a side or non-side amino acid. The term "natural amino acid" means any amino acid which is found naturally in vivo in a living being. Natural amino acids therefore include amino acids coded by mRNA incorporated into proteins during translation but also other amino acids found naturally in vivo which are a product or by-product of a metabolic process, such as for example ornithine which is generated by the urea production process by arginase from L-arginine. In the present disclosure, the amino acids used can therefore be natural or not. Namely, natural amino acids generally have the L configuration but also, according to the disclosure, an amino acid can have the L or D configuration. Moreover, R is of course not limited to the side chains of natural amino acid but can be freely chosen.

As used herein, "urea" or carbamide is an organic compound with the chemical formula $CO(NH_2)_2$. The molecule has two —$NH_2$ groups joined by a carbonyl (C=O) functional group.

Unless indicated otherwise, the term "peptide precursor" or "parental peptide" refers, but is in no way limited to, a parental α-peptide sequence that is coupled with oligourea pseudopeptide or peptidomimetic subunits or substituting oligourea pseudopeptide subunits (i.e., exchanging one or more α-amino acids for one or more oligourea pseudopeptide subunits).

Unless indicated otherwise, the term "oligourea" refers, but is in no way limited to, a residue containing N,N'-linked urea residues including oligomers of substituted or unsubstituted N-2-ethylaminocarbamoyl or 1, 2-ethylene diamine residues.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives (including prodrug forms) thereof where applicable, in context. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond is shown, both a double bond and single bond are represented within the context of the compound shown.

The term "hydrocarbyl" shall mean a compound which contains carbon and hydrogen and which may be fully saturated, partially unsaturated or aromatic and includes aryl groups, alkyl groups, alkenyl groups and alkynyl groups.

The term "amido" as used herein means an ammo group, as defined herein, appended to the parent molecular moiety through a carbonyl.

The term "cyano" as used herein means a —C≡N group.
The term "nitro" as used herein means a —N02 group.
The term "azido" as used herein means a —N3 group.

The abbreviations Me, Et, Ph, Tf, Nf, Ts, Ms, Cbz, and Boc represent methyl, ethyl, phenyl, trifluoromethanesulfonyl, nonafluorobutanesulfonyl, p-toluenesulfonyl, methanesulfonyl, carbobenzyloxy, and tert-butyloxycarbonyl, respectively.

A more comprehensive list of the abbreviations utilized by organic chemists of ordinary skill in the art appears in the first issue of each volume of the *Journal of Organic Chemistry*; this list is typically presented in a table entitled Standard List of Abbreviations, and is incorporated herein by reference.

"Alkyl" refers to a branched or unbranched alkyl group having 1-6 carbon atoms, a branched or unbranched alkenyl group having 1-6 carbon atoms, a branched or unbranched alkinyl group having 1-6 carbon atoms. The term "alkyl" shall mean within its context a linear, branch-chained or cyclic fully saturated hydrocarbon radical or alkyl group, preferably a C1-C10, more preferably a C1-C6, alternatively a C1-C3 alkyl group, which may be optionally substituted. Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopentylethyl, cyclohexylethyl and cyclohexyl, among others. In certain preferred embodiments, compounds according to the present disclosure which may be used to covalently bind to dehalogenase enzymes. These compounds generally contain a side chain (often linked through a polyethylene glycol group) which terminates in an alkyl group which has a halogen substituent (often chlorine or bromine) on its distil end which results in covalent binding of the compound containing such a moiety to the protein.

The term "Alkenyl" refers to linear, branch-chained or cyclic C2-C10 (preferably C2-C6) hydrocarbon radicals containing at least one C═C bond. The term "Alkynyl" refers to linear, branchchained or cyclic C2-C10 (preferably C2-C6) hydrocarbon radicals containing at least one C≡C bond.

The term "alkylene" when used, refers to a —(CH2)n-group (n is an integer generally from 0-6), which may be optionally substituted. When substituted, the alkylene group preferably is substituted on one or more of the methylene groups with a C1-C6 alkyl group (including a cyclopropyl group or a t-butyl group), more preferably a methyl group, but may also be substituted with one or more halo groups, preferably from 1 to 3 halo groups or one or two hydroxyl groups or O—(C1-C6 alkyl) groups. In certain embodiments, an alkylene group may be substituted with a urethane or alkoxy group (or other group) which is further substituted with a polyethylene glycol chain (of from 1 to 10, preferably 1 to 6, often 1 to 4 ethylene glycol units) to which is substituted (preferably, but not exclusively on the distal end of the polyethylene glycol chain) an alkyl chain substituted with a single halogen group, preferably a chlorine group. In still other embodiments, the alkylene group may be substituted with an amino acid side chain such as group obtained from an amino acid (a natural or unnatural amino acid) such as, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine.

The term "unsubstituted" shall mean substituted only with hydrogen atoms. A range of carbon atoms which includes C0 means that carbon is absent and is replaced with H. Thus, a range of carbon atoms which is C0-C6 includes carbons atoms of 1, 2, 3, 4, 5 and 6 and for C0, H stands in place of carbon. The term "substituted" or "optionally substituted" shall mean independently (i.e., where more than substituent occurs, each substituent is independent of another substituent), one or more substituents (independently, up to five substitutents, preferably up to three substituents, often 1 or 2 substituents on a moiety in a compound according to the present disclosure and may include substituents which themselves may be further substituted) at a carbon (or nitrogen) position anywhere on a molecule within context, and independently includes as substituents hydroxyl, thiol, carboxyl, cyano (C≡N), nitro (NO2), halogen (preferably, 1, 2 or 3 halogens, especially on an alkyl, especially a methyl group such as a trifluoromethyl), an alkyl group (preferably, C1-C10, more preferably, C1-C6), aryl (especially phenyl and substituted phenyl for example benzyl or benzoyl), alkoxy group (preferably, C1-C6 alkyl or aryl, including phenyl and substituted phenyl), thioether (C1-C6 alkyl or aryl), acyl (preferably, C1-C6 acyl), ester or thioester (preferably, C1-C6 alkyl or aryl) including alkylene ester (such that attachment is on the alkylene group, rather than at the ester function which is preferably substituted with a C1-C6 alkyl or aryl group), preferably, C1-C6 alkyl or aryl, halogen (preferably, F or Cl), amine (including a five- or six-membered cyclic alkylene amine, further including a C1-C6 alkyl amine or a C1-C6 dialkyl amine which alkyl groups may be substituted with one or two hydroxyl groups) or an optionally substituted —N(C0-C6 alkyl)C(O)(O—C1-C6 alkyl) group (which may be optionally substituted with a polyethylene glycol chain to which is further bound an alkyl group containing a single halogen, preferably chlorine substituent), hydrazine, amido, which is preferably substituted with one or two C1-C6 alkyl groups (including a carboxamide which is optionally substituted with one or two C1-C6 alkyl groups), alkanol (preferably, C1-C6 alkyl or aryl), or alkanoic acid (preferably, C1-C6 alkyl or aryl).

The term "substituted" (each substituent being independent of another substituent) shall also mean within its context of use C1-C6 alkyl, C1-C6 alkoxy, halogen, amido, carboxamido, sulfone, including sulfonamide, keto, carboxy, C1-C6 ester (oxyester or carbonylester), C1-C6 keto, urethane —O—C(O)—NR1R2 or —N(R1)-C(O)—O—R1, nitro, cyano and amine (especially including a C1-C6 alkylene-NR1R2, a mono- or di-C1-C6 alkyl substituted amines which may be optionally substituted with one or two hydroxyl groups). Each of these groups contain unless otherwise indicated, within context, between 1 and 6 carbon atoms. In certain embodiments, preferred substituents will include for example, —NH—, —NHC(O)—, —O—, =O, —(CH2)m- (here, m and n are in context, 1, 2, 3, 4, 5 or 6), —S—, —S(O)—, SO2- or —NH—C(O)—NH—, —(CH2)nOH, —(CH2)nSH, —(CH2)nCOOH, C1-C6 alkyl, —(CH2)nO—(C1-C6 alkyl), —(CH2)nC(O)—(C1-C6 alkyl), —(CH2)nOC(O)—(C1-C6 alkyl), —(CH2)nC(O)O—(C1-C6 alkyl), —(CH2)nNHC(O)—R1, —(CH2)nC(O)—NR1R2, —(OCH2)nOH, —(CH2O)nCOOH, C1-C6 alkyl, —(OCH2)nO—(C1-C6 alkyl), —(CH2O)nC(O)—(C1-C6 alkyl), —(OCH2)nNHC(O)—R1, —(CH2O)nC(O)—NR1R2, —S(O)2-RS, —S(O)—RS (RS is C1-C6 alkyl or a —(CH2)m-NR1R2 group), NO2, CN or halogen (F, Cl, Br, I, preferably F or Cl), depending on the context of the use of the substituent. R1 and R2 are each, within context, H or a C1-C6 alkyl group (which may be optionally substituted with one or two hydroxyl groups or up to three halogen groups, preferably fluorine). The term "substituted" shall also mean, within the chemical context of the compound defined and substituent used, an optionally substituted aryl or heteroaryl group or an optionally substituted heterocyclic group as otherwise described herein. Alkylene groups may also be substituted as otherwise disclosed herein, preferably with optionally substituted C1-C6 alkyl groups (methyl, ethyl or hydroxymethyl or hydroxyethyl is preferred, thus providing a chiral center), an amido group as described hereinabove, or a urethane group O—C(O)—NR1R2 group where R1 and R2 are as otherwise described herein, although numerous other groups may also be used as substituents. Various optionally substituted moieties may be substituted independently with 3 or more substituents, preferably no more than 3 substituents and preferably with 1 or 2 substituents. It is noted that in instances where, in a compound at a particular position of the molecule substitution is required (principally, because of valency), but no substitution is indicated, then that substituent is construed or understood to be H, unless the context of the substitution suggests otherwise.

"Hydroxyl" refers the functional group —OH when it is a substituent in an organic compound.

"Heterocycle" refers to a heterocyclic group having from 4 to 9 carbon atoms and at least one heteroatom selected from the group consisting of N, O or S, and may be aromatic (heteroaryl) or non-aromatic. Thus, the heteroaryl moieties are subsumed under the definition of heterocycle, depending on the context of its use. Exemplary heteroaryl groups are described hereinabove. Exemplary nonaromatic heterocyclic groups for use in the present disclosure include, for example, pyrrolidinyl, pyrrolinyl, piperidinyl, piperazinyl, N-methylpiperazinyl, imidazolinyl, pyrazolidinyl, imidazolidinyl, morpholinyl, tetrahydropyranyl, azetidinyl, oxetanyl, oxathiolanyl, pyridone, 2-pyrrolidone, ethyleneurea, 1,3-dioxolane, 1,3-dioxane, 1,4-dioxane, phthalimide and succinimide, among others.

Heterocyclic groups can be optionally substituted with 1 to 5, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO2-alkyl, —SO2-substituted alkyl, —SO2-aryl, oxo (=O), and —SO2-heteroaryl. Such heterocyclic groups can have a single ring or multiple condensed rings. Preferred heterocyclics include morpholino, piperidinyl, and the like.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxynitrogen containing heterocycles.

"Heteroaryl" refers to a heterocyclic group having from 4 to 9 carbon atoms and at least one heteroatom selected from the group consisting of N, O or S with at least one ring of this group being aromatic. Heteroaryl groups having one or more nitrogen, oxygen, or sulfur atoms in the ring (moncyclic) such as imidazole, furyl, pyrrole, furanyl, thiene, thiazole, pyridine, pyrimidine, pyrazine, triazole, oxazole or fused ring systems such as indole, quinoline, indolizine, azaindolizine, benzofurazan, etc., among others, which may be optionally substituted as described above. Among the heteroaryl groups which may be mentioned include nitrogen containing heteroaryl groups such as pyrrole, pyridine, pyridone, pyridazine, pyrimidine, pyrazine, pyrazole, imidazole, triazole, triazine, tetrazole, indole, isoindole, indolizine, azaindolizine, purine, indazole, quinoline, dihydroquinoline, tetrahydroquinoline, isoquinoline, dihydroisoquinoline, tetrahydroisoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, perimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

"Substituted heteroaryl" refers to a heterocyclic group having from 4 to 9 carbon atoms and at least one heteroatom selected from the group consisting of N, O or S with at least one ring of this group being aromatic and this group being substituted with one or more substituents selected from the group consisting of halogen, alkyl, carbyloxy, carbylmercapto, alkylamino, amido, carboxyl, hydroxyl, nitro, mercapto or sulfo, whereas these generic substituent group have meanings which are identical with definitions of the corresponding groups as defined in this legend.

The term "thiol" refers to the group —SH.

The term "thioalkoxy" refers to the group —S-alkyl.

"Amidine" refers to a functional group that has two amine groups attached to the same carbon atom with one carbon-nitrogen double bond: HN=CR'—NH"2.

"Alkoxyl" refers to an alkyl group linked to oxygen thus: R—O—, where R is an alkyl.

"Substituted alkyl" refers to a branched or unbranched alkyl, alkenyl or alkinyl group having 1-10 carbon atoms and having substituted by one or more substituents selected from the group consisting of hydroxyl, mercapto, carbylmercapto, halogen, carbyloxy, amino, amido, carboxyl, cycloalkyl, sulfo or acyl. These substituent generic groups having the meanings being identical with the definitions of the corresponding groups as defined herein.

"Halogen" refers to fluorine, bromine, chlorine, and iodine atoms.

"Acyl" denotes the group —C(O)$R_e$, where $R_e$ is hydrogen, alkyl, substituted alkyl, aryl, substituted aryl, arylalkyl, substituted arylalkyl, cycloalkyl, substituted cycloalkyl whereas these generic groups have meanings which are identical with definitions of the corresponding groups as defined in this legend.

"Acloxy" denotes the group —OAc, where Ac is an acyl, substituted acyl, heteroacyl or substituted heteroacyl whereas these generic groups have meanings which are identical with definitions of the corresponding groups as defined in this legend.

"Alkylamino" denotes the group —$NR_fR_g$, where $R_f$ and $R_g$, that are independent of one another, represent hydrogen, alkyl, substituted alkyl, aryl, substituted aryl, heteroaryl or substituted heteroaryl, whereas these generic substituents have meanings which are identical with definitions of the corresponding groups defined herein.

"Aryl" refers to an aromatic carbocyclic group having from 1 to 18 carbon atoms and being a substituted (as otherwise described herein) or unsubstituted monovalent aromatic radical having a single ring (e.g., benzene, phenyl, benzyl) or condensed (fused) rings, wherein at least one ring is aromatic (e.g., naphthyl, anthracenyl, phenanthrenyl, etc.) and can be bound to the compound according to the present disclosure at any available stable position on the ring(s) or as otherwise indicated in the chemical structure presented. Other examples of aryl groups, in context, may include heterocyclic aromatic ring systems.

"Substituted aryl" refers to an aromatic carbocyclic group having from 1 to 18 carbon atoms and being composed of at least one aromatic ring or of multiple condensed rings at least one of which being aromatic. The ring(s) are optionally substituted with one or more substituents selected from the group consisting of halogen, alkyl, hydroxyl, carbylmercapto, alkylamino, carbyloxy, amino, amido, carboxyl, nitro, mercapto or sulfo, whereas these generic substituent group have meanings which are identical with definitions of the corresponding groups as defined in this legend.

"Carboxyl" denotes the group —C(O)OR, where R is hydrogen, alkyl, substituted alkyl, aryl, substituted aryl, heteroaryl or substituted heteroaryl, whereas these generic substituents have meanings which are identical with definitions of the corresponding groups defined herein.

"Cycloalkyl" refers to a monocyclic or polycyclic alkyl group containing 3 to 15 carbon atoms.

"Substituted cycloalkyl" refers to a monocyclic or polycyclic alkyl group containing 3 to 15 carbon atoms and being substituted by one or more substituents selected from the group consisting of halogen, alkyl, substituted alkyl, carbyloxy, carbylmercapto, aryl, nitro, mercapto or sulfo, whereas these generic substituent groups have meanings which are identical with definitions of the corresponding groups as defined in this legend.

"Heterocycloalkyl" refers to a monocyclic or polycyclic alkyl group containing 3 to 15 carbon atoms which at least one ring carbon atom of its cyclic structure being replaced with a heteroatom selected from the group consisting of N, O, S or P.

"Substituted heterocycloalkyl" refers to a monocyclic or polycyclic alkyl group containing 3 to 15 carbon atoms which at least one ring carbon atom of its cyclic structure being replaced with a heteroatom selected from the group consisting of N, O, S or P and the group is containing one or more substituents selected from the group consisting of halogen, alkyl, substituted alkyl, carbyloxy, carbylmercapto, aryl, nitro, mercapto or sulfo, whereas these generic substituent group have meanings which are identical with definitions of the corresponding groups as defined in this legend.

The term "alkenyl" refers to a monoradical of a branched or unbranched unsaturated hydrocarbon group preferably having from 2 to 40 carbon atoms, more preferably 2 to 10 carbon atoms and even more preferably 2 to 6 carbon atoms. Preferred alkenyl groups include ethenyl (—CH=CH2), n-propenyl (—CH2CH=CH2), iso-propenyl (—C(CH3)=CH2), and the like.

"Imidazole" refers to a heterocyclic base of the general formula: $C_3H_4N_2$.

"Aralkyl group" refers to, for example, a C1-C6 alkyl group which is attached to 1 or 2 aromatic hydrocarbon rings having from 6 to 10 carbon atoms and which has a total of 7 to 14 carbon atoms, such as the benzyl, alpha-naphthylmethyl, indenylmethyl, diphenylmethyl, 2-phenethyl, 2-alpha-naphthylethyl, 3-phenylpropyl, 3-alpha-naphthylpropyl, phenylbutyl, 4-alpha-naphthylbutyl or 5-phenylpentyl groups.

"Guanidine" refers generally to the amidine of amidocarbonic acid and has the general formula of: $C(NH_2)_3$.

The terms "aralkyl" and "heteroarylalkyl" refer to groups that comprise both aryl or, respectively, heteroaryl as well as alkyl and/or heteroalkyl and/or carbocyclic and/or heterocycloalkyl ring systems according to the above definitions.

In one aspect, the description provides for oligourea compounds comprising aliphatic oligoureas at least partially encapsulating an agent. In certain embodiments, the aliphatic oligoureas form a oligourea helical bundle. In another embodiment, the aliphatic oligoureas are comprised of short amphiphilic α-helicomimetic foldamers with proteinaceous sidechains. In an embodiment, the short amphiphilic α-helicomimetic foldamers self-assemble into the oligourea helical bundle. Furthermore, the foldamers can self-assemble under aqueous conditions. Because the compounds as described herein can adopt desired secondary structures similar to native peptides, including, e.g., helicoidal structures, they can serve as, for example, receptor ligands, effector molecules, agonists, antagonists, modulators of protein-protein interactions, organocatalysts, or enzymes.

Oligourea Compounds

In certain aspects, the present description provides foldamer compounds comprising non-peptide oligourea helices at least partially encapsulating an agent. In particular, the non-peptide oligourea helical foldamers self-assemble under aqueous conditions to form oligourea helical bundles. In an embodiment, the oligourea helical bundle has an isolated cavity within the hydrophobic core of the bundle. In another embodiment, the oligourea helical bundle has a pH-responsive water-filled channel within the hydrophobic core of the bundle. Furthermore, the diameter of the pores can be controlled through the modification of the non-peptide oligourea peptidomimetic residue sequence, which is described in greater detail with regard to the figures. In an alternative embodiment, the oligourea helical bundle or super-helical channel has a pH-responsive water-filled cavity or channel, respectively, within the hydrophobic core.

In an embodiment, there is at least one agent (e.g., 1, 2, 3, 4, 5, 6, 7, 8, 9, 10, 11, 12, 13, 14, 15, 16, etc.) in the cavity or channel of a foldamer as described herein. Furthermore, in an embodiment, the oligourea helical bundle can at least partially encapsulate up to about 600 Da of agent. In another embodiment, the oligourea helical bundle can at least partially encapsulate in a range of about 5 Da to about 600 Da of agent. Alternatively, the oligourea helical bundle can at least partially encapsulate about 5 Da to about 550 Da, about 5 Da to about 500 Da, about 5 Da to about 475 Da, about 5 Da to about 450 Da, about 5 Da to about 425 Da, about 5 Da to about 400 Da, about 5 Da to about 375 Da, about 5 Da to about 350 Da, about 5 Da to about 325 Da, about 5 Da to about 300 Da, about 5 Da to about 275 Da, about 5 Da to about 250 Da, about 5 Da to about 225 Da, about 5 Da to about 200 Da, about 5 Da to about 175 Da, about 5 Da to about 150 Da, about 5 Da to about 125 Da, about 5 Da to about 100 Da, about 5 Da to about 75 Da, about 5 Da to about 50 Da, about 5 Da to about 25 Da, about 25 Da to about 600 Da, about 25 Da to about 550 Da, about 25 Da to about 500 Da, about 25 Da to about 475 Da, about 25 Da to about 450 Da, about 25 Da to about 425 Da, about 25 Da to about 400 Da, about 25 Da to about 375 Da, about 25 Da to about 350 Da, about 25 Da to about 325 Da, about 25 Da to about 300 Da, about 25 Da to about 275 Da, about 25 Da to about 250 Da, about 25 Da to about 225 Da, about 25 Da to about 200 Da, about 25 Da to about 175 Da, about 25 Da to about 150 Da, about 25 Da to about 125 Da, about 25 Da to about 100 Da, about 25 Da to about 75 Da, about 25 Da to about 50 Da, about 50 Da to about 600 Da, about 50 Da to about 550 Da, about 50 Da to about 500 Da, about 50 Da to about 475 Da, about 50 Da to about 450 Da, about 50 Da to about 425 Da, about 50 Da to about 400 Da, about 50 Da to about 375 Da, about 50 Da to about 350 Da, about 50 Da to about 325 Da, about 50 Da to about 300 Da, about 50 Da to about 275 Da, about 50 Da to about 250 Da, about 50 Da to about 225 Da, about 50 Da to about 200 Da, about 50 Da to about 175 Da, about 50 Da to about 150 Da, about 50 Da to about 125 Da, about 50 Da to about 100 Da, about 50 Da to about 75 Da, about 75 Da to about 600 Da, about 75 Da to about 550 Da, about 75 Da to about 500 Da, about 75 Da to about 475 Da, about 75 Da to about 450 Da, about 75 Da to about 425 Da, about 75 Da to about 400 Da, about 75 Da to about 375 Da, about 75 Da to about 350 Da, about 75 Da to about 325 Da, about 75 Da to about 300 Da, about 75 Da to about 275 Da, about 75 Da to about 250 Da, about 75 Da to about 225 Da, about 75 Da to about 200 Da, about 75 Da to about 175 Da, about 75 Da to about 150 Da, about 75 Da to about 125 Da, about 75 Da to about 100 Da, about 100 Da to about 600 Da, about 100 Da to about 550 Da, about 100 Da to about 500 Da, about 100 Da to about 475 Da, about 100 Da to about 450 Da, about 100 Da to about 425 Da, about 100 Da to about 400 Da, about 100 Da to about 375 Da, about 100 Da to about 350 Da, about 100 Da to about 325 Da, about 100 Da to about 300 Da, about 100 Da to about 275 Da, about 100 Da to about 250 Da, about 100 Da to about 225 Da, about 100 Da to about 200 Da, about 100 Da to about 175 Da, about 100 Da to about 150 Da, about 100 Da to about 125 Da, about 125 Da to about 600 Da, about 125 Da to about 550 Da, about 125 Da to about 500 Da, about 125 Da to about 475 Da, about 125 Da to about 450 Da, about 125 Da to about 425 Da, about 125 Da to about 400 Da, about 125 Da to about 375 Da, about 125 Da to about 350 Da, about 125 Da to about 325 Da, about 125 Da to about 300 Da, about 125 Da to about 275 Da, about 125 Da to about 250 Da, about 125 Da to about 225 Da, about 125 Da to about 200 Da, about 125 Da to about 175 Da, about 125 Da to about 150 Da, about 150 Da to about 600 Da, about 150 Da to about 550 Da, about 150 Da to about 500 Da, about 150 Da to about 475 Da, about 150 Da to about 450 Da, about 150 Da to about 425 Da, about 150 Da to about 400 Da, about 150 Da to about 375 Da, about 150 Da to about 350 Da, about 150 Da to about 325 Da, about 150 Da to about 300 Da, about 150 Da to about 275 Da, about 150 Da to about 250 Da, about 150 Da to about 225 Da, about 150 Da to about 200 Da, about 150 Da to about 175 Da, about 175 Da to about 600 Da, about 175 Da to about 550 Da, about 175 Da to about 500 Da, about 175 Da to about 475 Da, about 175 Da to about 450 Da, about 175 Da to about 425 Da, about 175 Da to about 400 Da, about 175 Da to about 375 Da, about 175 Da to about 350 Da, about 175 Da to about 325 Da, about 175 Da to about 300 Da, about 175 Da to about 275 Da, about 175 Da to about 250 Da, about 175 Da to about 225 Da, about 175 Da to about 200 Da, about 200 Da to about 600 Da, about 200 Da to about 550 Da, about 200 Da to about 500 Da, about 200 Da to about 475 Da, about 200 Da to about 450 Da, about 200 Da to about 425 Da, about 200 Da to about 400 Da, about 200 Da to about 375 Da, about 200 Da to about 350 Da, about 200 Da to about 325 Da, about 200 Da to about 300 Da, about 200 Da to about 275 Da, about 200 Da to about 250 Da, about 200 Da to about 225 Da, about 225 Da to about 600 Da, about 225 Da to about 550 Da, about 225 Da to about 500 Da, about 225 Da to about 475 Da, about 225 Da to about 450 Da, about 225 Da to about 425 Da, about 225 Da to about 400 Da, about 225 Da to about 375 Da, about 225 Da to about 350 Da, about 225 Da to about 325 Da, about 225 Da to about 300 Da, about 225 Da to about 275 Da, about 225 Da to about 250 Da, about 250 Da to about 600 Da, about 250 Da to about 550 Da, about 250 Da to about 500 Da, about 250 Da to about 475 Da, about 250 Da to about 450 Da, about 250 Da to about 425 Da, about 250 Da to about 400 Da, about 250 Da to about 375 Da, about 250 Da to about 350 Da, about 250 Da to about 325 Da, about 250 Da to about 300 Da, about 250 Da to about 275 Da, about 275 Da to about 600 Da, about 275 Da to about 550 Da, about 275 Da to about 500 Da, about 275 Da to about 475 Da, about 275 Da to about 450 Da, about 275 Da to about 425 Da, about 275 Da to about 400 Da, about 275 Da to about 375 Da, about 275 Da to about 350 Da, about 275 Da to about 325 Da, about 275 Da to about 300 Da, about 300 Da to about 600 Da, about 300 Da to about 550 Da, about 300 Da to about 500 Da, about 300 Da to about 475 Da, about 300 Da to about 450 Da, about 300 Da to about 425 Da, about 300 Da to about 400 Da, about 300 Da to about 375 Da, about 300 Da to about 350 Da, about 300 Da to about 325 Da, about 325 Da to about 600 Da, about 325 Da to about 550 Da, about 325 Da to about 500 Da, about 325 Da to about 475 Da, about 325 Da to about 450 Da, about 325 Da to about 425 Da, about 325 Da to about 400 Da, about 325 Da to about 375 Da, about 325 Da to about 350 Da, about 350 Da to about 600 Da, about 350 Da to about 550 Da, about 350 Da to about 500 Da, about 350 Da to about 475 Da, about 350 Da to about 450 Da, about 350 Da to about 425 Da, about 350 Da to about 400 Da, about 350 Da to about 375 Da, about 375 Da to about 600 Da, about 375 Da to about 550 Da, about 375

Da to about 500 Da, about 375 Da to about 475 Da, about 375 Da to about 450 Da, about 375 Da to about 425 Da, about 375 Da to about 400 Da, about 400 Da to about 600 Da, about 400 Da to about 550 Da, about 400 Da to about 500 Da, about 400 Da to about 475 Da, about 400 Da to about 450 Da, about 400 Da to about 425 Da, about 450 Da to about 600 Da, about 450 Da to about 550 Da, about 450 Da to about 500 Da, about 450 Da to about 475 Da, about 475 Da to about 600 Da, about 475 Da to about 550 Da, about 475 Da to about 500 Da, about 500 Da to about 600 Da, about 500 Da to about 550 Da, or about 550 Da to about 600 Da.

In an embodiment, the agent is selected from the group consisting of: a hydrophobic molecule, a primary alcohol, an alcohol with a polar group, a pharmaceutically active compound, a bio-substrate, or a compound with one or more hydrogen binding groups (e.g., 1, 2, 3, 4, 5, 6, 7, etc.). The alcohol with a polar group can comprise a multiple primary alcohol (e.g., 1,4-butanediol) or an alcohol with an ether group (e.g., 2-ethoxyethanol or 2-propoxyethanol). In an embodiment, the primary alcohol is selected from isopropanol, 1-butanol, 1-pentanol, and 1-hexanol. In another embodiment, the primary alcohol is selected from isopropanol, 1-butanol, and 1-pentanol. In certain embodiments, the oligourea helical bundle at least partially encapsulates more than one agent (e.g., 1, 2, 3, 4, 5, 6, 7, 8, 9, 10, 11, 12, 13, 14, 15, 16, 17, 18, 19, 20, etc.).

According to an embodiment, the agent is selected from the group comprising anti-cancer agents, antiviral agents (especially including anti-HIV agents and anti-HCV agents), antimicrobial agents, and antifungal agents. The anti-cancer agents can include, e.g., everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitor, an AKT inhibitor, an mTORC1/2 inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

The "anti-HIV agent" can includes, for example, nucleoside reverse transcriptase inhibitors (NRTI), other non-nucleoeoside reverse transcriptase inhibitors (i.e., those which are not representative of the present disclosure), protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development.

Other anti-HIV agents include, for example, NNRTI's selected from the group consisting of nevirapine (BI-R6-587), delavirdine (U-90152S/T), efavirenz (DMP-266), UC-781 (N-[4-chloro-3-(3-methyl-2-butenyloxy)phenyl]-2methyl3-furancarbothiamide), etravirine (TMC125), Trovirdine (Ly300046.HCl), MKC-442 (emivirine, coactinon), HI-236, HI-240, HI-280, HI-281, rilpivirine (TMC-278), MSC-127, HBY 097, DMP266, Baicalin (TJN-151) ADAM-II (Methyl 3',3'-dichloro-4',4"-dimethoxy-5',5"-bis(methoxycarbonyl)-6,6-diphenylhexenoate), Methyl 3-Bromo-5-(1-5-bromo-4-methoxy-3-(methoxycarbonyl)phenyl)hept-1-enyl)-2-methoxybenzoate (Alkenyldiarylmethane analog, Adam analog), (5-chloro-3-(phenylsulfinyl)-2'-indolecarboxamide), AAP-BHAP (U-104489 or PNU-104489), Capravirine (AG-1549, S-1153), atevirdine (U-87201E), aurin tricarboxylic acid (SD-095345), 1-[(6-cyano-2-indolyl)carbonyl]-4-[3-(isopropylamino)-2-pyridinyl]piperazine, 1-[5-[[N-(methyl)methylsulfonylamino]-2-indolylcarbonyl-4-[3-(isopropylamino)-2-pyridinyl]piperazine, 1-[3-(Ethylamino)-2-[pyridinyl]-4-[(5-hydroxy-2-indolyl)carbonyl]piperazine, 1-[(6-Formyl-2-indolyl)carbonyl]-4-[3-(isopropylamino)-2-pyridinyl]piperazine, 1-[[5-(Methylsulfonyloxy)-2-indoyly)carbonyl]-4-[3-(isopropylamino)-2-pyridinyl]piperazine, U88204E, Bis(2-nitrophenyl)sulfone (NSC 633001), Calanolide A (NSC675451), Calanolide B, 6-Benzyl-5-methyl-2-(cyclohexyloxy)pyrimidin-4-one (DABO-546), DPC 961, E-EBU, E-EBU-dm, E-EPSeU, E-EPU, Foscarnet (Foscavir), HEPT (1-[(2-Hydroxyethoxy)methyl]-6-(phenylthio)thymine), HEPT-M (1-[(2-Hydroxyethoxy)methyl]-6-(3-methylphenyl)thio)thymine), HEPT-S (1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethyoxymethyl)-5-isopropyluracil, NPPS, E-BPTU (NSC 648400), Oltipraz (4-Methyl-5-(pyrazinyl)-3H-1,2-dithiole-3-thione), N-{2-(2-Chloro-6-fluorophenethyl]-N'-(2-thiazolyl)thiourea (PETT Cl, F derivative), N-{2-(2,6-Difluorophenethyl]-N'-[2-(5-bromopyridyl)]thiourea {PETT derivative), N-{2-(2,6-Difluorophenethyl]-N'-[2-(5-methylpyridyl)]thiourea {PETT Pyridyl derivative), N-[2-(3-Fluorofuranyl)ethyl]-N'-[2-(5-chloropyridyl)]thiourea, N-[2-(2-Fluoro-6-ethoxyphenethyl)]-N'-[2-(5-bromopyridyl)]thiourea, N-(2-Phenethyl)-N'-(2-thiazolyl)thiourea (LY-73497), L-697,639, L-697,593, L-697,661, 3-[2-(4,7-Difluorobenzoxazol-2-yl)ethyl}-5-ethyl-6-methyl (pypridin-2(1H)-thione (2-Pyridinone Derivative), 3-[[(2-Methoxy-5,6-dimethyl-3-pyridyl)methyl]amine]-5-ethyl-6-methyl(pypridin-2(1H)-thione, R82150, R82913, R87232, R88703, R89439 (Loviride), R90385, S-2720, Suramin Sodium, TBZ (Thiazolobenzimidazole, NSC 625487), Thiazoloisoindol-5-one, (+)(R)-9b-(3,5-Dimethylphenyl-2,3-dihydrothiazolo [2,3-a]isoindol-5(9bH)-one, Tivirapine (R86183), UC-38 and UC-84, among others.

The term "disease state or condition" is used to describe any disease state or condition wherein protein dysregulation (i.e., the amount of protein expressed in a patient is elevated) occurs and where degradation of one or more proteins in a patient may provide beneficial therapy or relief of symptoms to a patient in need thereof. In certain instances, the disease state or condition may be cured.

Disease states of conditions which may be treated using compounds or compositions according to the present disclosure include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease, (PKD1) or 4 (PKD2) Prader-Willi syndrome, Sickle-cell disease, Tay-Sachs disease, Turner syndrome.

Further disease states or conditions which may be treated by compounds or compositions according to the present disclosure include Alzheimer's disease, Amyotrophic lateral sclerosis (Lou Gehrig's disease), Anorexia nervosa, Anxiety disorder, Atherosclerosis, Attention deficit hyperactivity disorder, Autism, Bipolar disorder, Chronic fatigue syndrome, Chronic obstructive pulmonary disease, Crohn's disease, Coronary heart disease, Dementia, Depression, Diabetes mellitus type 1, Diabetes mellitus type 2, Epilepsy, Guillain-Barré syndrome, Irritable bowel syndrome, Lupus, Metabolic syndrome, Multiple sclerosis, Myocardial infarction, Obesity, Obsessive-compulsive disorder, Panic disorder, Parkinson's disease, Psoriasis, Rheumatoid arthritis, Sarcoidosis, Schizophrenia, Stroke, Thromboangiitis obliterans, Tourette syndrome, Vasculitis.

Still additional disease states or conditions which can be treated by compounds or compositions according to the present disclosure include aceruloplasminemia, Achondrogenesis type II, achondroplasia, Acrocephaly, Gaucher disease type 2, acute intermittent porphyria, Canavan disease, Adenomatous Polyposis Coli, ALA dehydratase deficiency, adenylosuccinate lyase deficiency, Adrenogenital syndrome, Adrenoleukodystrophy, ALA-D porphyria, ALA dehydratase deficiency, Alkaptonuria, Alexander disease, Alkaptonuric ochronosis, alpha 1-antitrypsin deficiency, alpha-1 proteinase inhibitor, emphysema, amyotrophic lateral sclerosis Alström syndrome, Alexander disease, Amelogenesis imperfecta, ALA dehydratase deficiency, Anderson-Fabry disease, androgen insensitivity syndrome, Anemia Angiokeratoma Corporis Diffusum, Angiomatosis retinae (von Hippel-Lindau disease) Apert syndrome, Arachnodactyly (Marfan syndrome), Stickler syndrome, Arthrochalasis multiplex congenital (Ehlers-Danlos syndrome#arthrochalasia type) ataxia telangiectasia, Rett syndrome, primary pulmonary hypertension, Sandhoff disease, neurofibromatosis type II, Beare-Stevenson cutis gyrata syndrome, Mediterranean fever, familial, Benjamin syndrome, beta-thalassemia, Bilateral Acoustic Neurofibromatosis (neurofibromatosis type II), factor V Leiden thrombophilia, Bloch-Sulzberger syndrome (incontinentia pigmenti), Bloom syndrome, X-linked sideroblastic anemia, Bonnevie-Ullrich syndrome (Turner syndrome), Bourneville disease (tuberous sclerosis), prion disease, Birt-Hogg-Dubé syndrome, Brittle bone disease (osteogenesis imperfecta), Broad Thumb-Hallux syndrome (Rubinstein-Taybi syndrome), Bronze Diabetes/Bronzed Cirrhosis (hemochromatosis), Bulbospinal muscular atrophy (Kennedy's disease), Burger-Grutz syndrome (lipoprotein lipase deficiency), CGD Chronic granulomatous disorder, Campomelic dysplasia, biotinidase deficiency, Cardiomyopathy (Noonan syndrome), Cri du chat, CAVD (congenital absence of the vas deferens), Caylor cardiofacial syndrome (CBAVD), CEP (congenital erythropoietic porphyria), cystic fibrosis, congenital hypothyroidism, Chondrodystrophy syndrome (achondroplasia), otospondylomegaepiphyseal dysplasia, Lesch-Nyhan syndrome, galactosemia, Ehlers-Danlos syndrome, Thanatophoric dysplasia, Coffin-Lowry syndrome, Cockayne syndrome, (familial adenomatous polyposis), Congenital erythropoietic porphyria, Congenital heart disease, Methemoglobinemia/Congenital methaemoglobinaemia, achondroplasia, X-linked sideroblastic anemia, Connective tissue disease, Conotruncal anomaly face syndrome, Cooley's Anemia (beta-thalassemia), Copper storage disease (Wilson's disease), Copper transport disease (Menkes disease), hereditary coproporphyria, Cowden syndrome, Craniofacial dysarthrosis (Crouzon syndrome), Creutzfeldt-Jakob disease (prion disease), Cockayne syndrome, Cowden syndrome, Curschmann-Batten-Steinert syndrome (myotonic dystrophy), Beare-Stevenson cutis gyrata syndrome, primary hyperoxaluria, spondyloepimetaphyseal dysplasia (Strudwick type), muscular dystrophy, Duchenne and Becker types (DBMD), Usher syndrome, Degenerative nerve diseases including de Grouchy syndrome and Dejerine-Sottas syndrome, developmental disabilities, distal spinal muscular atrophy, type V, androgen insensitivity syndrome, Diffuse Globoid Body Sclerosis (Krabbe disease), Di George's syndrome, Dihydrotestosterone receptor deficiency, androgen insensitivity syndrome, Down syndrome, Dwarfism, erythropoietic protoporphyria Erythroid 5-aminolevulinate synthetase deficiency, Erythropoietic porphyria, erythropoietic protoporphyria, erythropoietic uroporphyria, Friedreich's ataxia, familial paroxysmal polyserositis, porphyria cutanea tarda, familial pressure sensitive neuropathy, primary pulmonary hypertension (PPH), Fibrocystic disease of the pancreas, fragile X syndrome, galactosemia, genetic brain disorders, Giant cell hepatitis (Neonatal hemochromatosis), Gronblad-Strandberg syndrome (pseudoxanthoma elasticum), Gunther disease (congenital erythropoietic porphyria), haemochromatosis, Hallgren syndrome, sickle cell anemia, hemophilia, hepatoerythropoietic porphyria (HEP), Hippel-Lindau disease (von Hippel-Lindau disease), Huntington's disease, Hutchinson-Gilford progeria syndrome (progeria), Hyperandrogenism, Hypochondroplasia, Hypochromic anemia, Immune system disorders, including X-linked severe combined immunodeficiency, Insley-Astley syndrome, Jackson-Weiss syndrome, Joubert syndrome, Lesch-Nyhan syndrome, Jackson-Weiss syndrome, Kidney diseases, including hyperoxaluria, Klinefelter's syndrome, Kniest dysplasia, Lacunar dementia, Langer-Saldino achondrogenesis, ataxia telangiectasia, Lynch syndrome, Lysyl-hydroxylase deficiency, Machado-Joseph disease, Metabolic disorders, including Kniest dysplasia, Marfan syndrome, Movement disorders, Mowat-Wilson syndrome, cystic fibrosis, Muenke syndrome, Multiple neurofibromatosis, Nance-Insley syndrome, Nance-Sweeney chondrodysplasia, Niemann-Pick disease, Noack syndrome (Pfeiffer syndrome), Osler-Weber-Rendu disease, Peutz-Jeghers syndrome, Polycystic kidney disease, polyostotic fibrous dysplasia (McCune-Albright syndrome), Peutz-Jeghers syndrome, Prader-Labhart-Willi syndrome, hemochromatosis, primary hyperuricemia syndrome (Lesch-Nyhan syndrome), primary pulmonary hypertension, primary senile degenerative dementia, prion disease, progeria (Hutchinson Gilford Progeria Syndrome), progressive chorea, chronic hereditary (Huntington) (Huntington's disease), progressive muscular atrophy, spinal muscular atrophy, propionic acidemia, protoporphyria, proximal myotonic dystrophy, pulmonary arterial hypertension, PXE (pseudoxanthoma elasticum), Rb (retinoblastoma), Recklinghausen disease (neurofibromatosis type I), Recurrent polyserositis, Retinal disorders, Retinoblastoma, Rett syndrome, RFALS type 3, Ricker syndrome, Riley-Day syndrome, Roussy-Levy syndrome, severe achondroplasia with developmental delay and acanthosis nigricans (SADDAN), Li-Fraumeni syndrome, sarcoma, breast, leukemia, and adrenal gland (SBLA) syndrome, sclerosis tuberose (tuberous sclerosis), SDAT, SED congenital (spondyloepiphyseal dysplasia congenita), SED Strudwick (spondyloepimetaphyseal dysplasia, Strudwick type), SEDc (spondyloepiphyseal dysplasia congenita) SEMD, Strudwick type (spondyloepimetaphyseal dysplasia, Strudwick type), Shprintzen syndrome, Skin pigmentation disorders, Smith-Lemli-Opitz syndrome, South-African genetic porphyria (variegate porphyria), infantile-onset ascending hereditary spastic paralysis, Speech and communication disorders, sphingolipidosis, Tay-Sachs disease, spinocerebellar ataxia, Stickler syndrome, stroke, androgen insensitivity syndrome, tetrahydrobiopterin deficiency, beta-thalassemia, Thyroid disease, Tomaculous neuropathy (hereditary neuropathy with liability to pressure palsies), Treacher Collins syndrome, Triplo X syndrome (triple X syndrome), Trisomy 21 (Down syndrome), Trisomy X, VHL syndrome (von Hippel-Lindau disease), Vision impairment and blindness (Alström syndrome), Vrolik disease, Waardenburg syndrome, Warburg Sjo Fledelius Syndrome, Weissenbacher-Zweymüller syndrome, Wolf-Hirschhorn syndrome, Wolff Periodic disease, Weissenbacher-Zweymüller syndrome and Xeroderma pigmentosum, among others.

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present disclosure include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

In certain embodiments, the oligourea helical bundle comprises an internal cavity or interior pore. In a preferred embodiment, the cavity or interior pore is sufficient to at least partially encapsulate one or more agents. In additional embodiments, the cavity or interior pore of the oligourea helical bundle has an internal diameter of in a range of about 10 Å to about 30 Å. Alternatively, an interior pore internal diameter is in a range of about 12.5 Å to about 30 Å, about 12.5 Å to about 27.5 Å, about 12.5 Å to about 25 Å, about 12.5 Å to about 22.5 Å. About 12.5 Å to about 20 Å, about 12.5 Å to about 17.5 Å, about 12.5 Å to about 15 Å, about 15 Å to about 30 Å, about 15 Å to about 27.5 Å, about 15 Å to about 25 Å, about 15 Å to about 22.5 Å, about 15 Å to about 20 Å, about 15 Å to about 17.5 Å, about 17.5 Å to about 30 Å, about 17.5 Å to about 27.5 Å, about 17.5 Å to about 25 Å, about 20 Å to about 25 Å, about 20 Å to about 30 Å, about 20 Å to about 27.5 Å, to about 20 Å to about 25 Å, about 20 Å to about 22.5 Å, about 22.5 Å to about 30 Å, about 22.5 Å to about 27.5 Å, or about 22.5 Å to about 25 Å. In particular embodiments, the internal diameter of the internal pore of the oligourea helical bundle is 10 Å, 11 Å, 12 Å, 13 Å, 14 Å, 15 Å, 16 Å, 17 Å, 18 Å, 19 Å, 20 Å, 21 Å, 22 Å, 23 Å, 24 Å, 25 Å, 26 Å, 27 Å, 28 Å, 29 Å, or 30 Å.

In particular embodiments, the oligourea helical bundle has a diameter in a range of about 2 nm to about 12 nm. Alternatively, the diameter can be in a range of about 2 nm to about 11 nm, about 2 nm to about 10 nm, about 2 nm to about 9 nm, about 2 nm to about 8 nm, about 2 nm to about 7 nm, about 2 nm to about 6 nm, about 2 nm to about 5 nm, about 3 nm to about 12 nm, about 3 nm to about 11 nm, about 3 nm to about 10 nm, about 3 nm to about 9 nm, about 3 nm to about 8 nm, about 3 nm to about 7 nm, about 3 nm to about 4 nm, about 4 nm to about 12 nm, about 4 nm to about 11 nm, about 4 nm to about 10 nm, about 4 nm to about 9 nm, about 4 nm to about 8 nm, about 4 nm to about 7 nm, about 4 nm to about 6 nm, about 4 nm to about 5 nm, about 5 nm to about 12 nm, about 5 nm to about 11 nm, about 5 nm to about 10 nm, about 5 nm to about 9 nm, about 5 nm to about 8 nm, about 5 nm to about 7 nm, about 5 nm to about 6 nm, about 6 nm to about 12 nm, about 6 nm to about 11 nm, about 6 nm to about 10 nm, about 6 nm to about 9 nm, about 6 nm to about 8 nm, about 6 nm to about 7 nm, about 7 nm to about 12 nm, about 7 nm to about 11 nm, about 7 nm to about 10 nm, about 7 nm to about 9 nm, about 7 nm to about 8 nm, about 8 nm to about 12 nm, about 8 nm to about 11 nm, about 8 nm to about 10 nm, about 8 nm to about 9 nm, about 9 nm to about 12 nm, about 9 nm to about 11 nm, about 9 nm to about 10 nm, about 10 nm to about 12 nm, about 10 nm to about 11 nm, or about 11 nm to about 12 nm. In certain embodiments, the diameter of the oligourea helical bundle is about 2 nm, about 3 nm, about 4 nm, about 5 nm, about 6 nm, about 7 nm, about 8 nm, about 9 nm, about 10 nm, about 11 nm, or about 12 nm.

In certain embodiments, the non-peptide oligourea helical foldamer is an aliphatic oligourea. In a particular embodiment, the non-peptide oligourea helical foldamer is a short amphiphilic α-helicomimetic foldamer with proteinaceous side-chains.

In a particular embodiment, the oligourea helical bundle has a non-peptide oligourea peptidomimetic residue sequence selected from the group consisting of: Leu$^u$ Glu$^u$ Lys$^u$ Leu$^u$ Tyr$^u$ Leu$^u$ Glu$^u$ Lys$^u$ Leu$^u$ Ala$^u$ Leu$^u$ (H1) (SEQ ID NO: 1); Leu$^u$ Glu$^u$ Leu$^u$ Lys$^u$ Pro$^u$ Leu$^u$ Glu$^u$ Leu$^u$ Lys$^u$ Ala$^u$ (H2) (SEQ ID NO: 2); Leu$^u$ Glu$^u$ Lys$^u$ Leu$^u$ Tyr$^u$ Asn$^u$ Glu$^u$ Lys$^u$ Leu$^u$ Ala$^u$ Leu$^u$ (H3) (SEQ ID NO: 3); Ser$^u$ Glu$^u$ Lys$^u$ Leu$^u$ Tyr$^u$ Leu$^u$ Glu$^u$ Lys$^u$ Leu$^u$ Ala$^u$ Leu$^u$ (H4) (SEQ ID NO: 4); and Ala$^u$ Leu$^u$ Lys$^u$ Leu$^u$ Glu$^u$ Tyr$^u$ Leu$^u$ Glu$^u$ Leu$^u$ Lys$^u$ Ala$^u$ Leu$^u$ (H5) (SEQ ID NO: 5). Alternatively, the oligourea helical bundle has a non-peptide peptidomimetic residue sequence that follows one of the following two helical pentad repeat sequences. Helical pentad repeat sequence 1: oligourea peptidomimetic residues with a hydrophobic side chain in positions a and d (e.g., Leu$^u$); oligourea peptidomimetic residues with a charged residue in position b and c (e.g. Glu$^u$ and Lys$^u$, respectively); and Tyr$^u$ and Ala$^u$ in position e. Helical pentad repeat sequence 2: oligourea peptidomimetic residues with a hydrophobic side chain in positions a and c (e.g. Leu$^u$); oligourea peptidomimetic residues with a hydrophobic side chain in position c (e.g., Ala$^u$ and Pro$^u$ residues at the e position); and oligourea peptidomimetic residues with a charged side chain in positions b and d (e.g., Glu$^u$ and Lys$^u$, respectively).

In additional embodiments, the oligourea compound includes at least one of: a plurality of oligourea helical bundles (e.g., two, three, four, etc.); a plurality of non-peptide oligourea helical foldamers (e.g., two, three, four, etc.); and a plurality of peptides (e.g., two, three, four, etc.). In certain embodiments, the oligourea compound includes two oligourea helical bundles. In another embodiment, the oligourea helical bundle comprises one or more non-peptide oligourea helical foldamer (e.g., one foldamer, two foldamers, three foldamers, 4 foldamers, etc.).

In a particular embodiment, the non-peptide oligourea peptidomimetic residue sequence is selected from the group consisting of: Leu$^u$ Glu$^u$ Lys$^u$ Leu$^u$ Tyr$^u$ Leu$^u$ Glu$^u$ Lys$^u$ Leu$^u$ Ala$^u$ Leu$^u$ (H1); Leu$^u$ Glu$^u$ Leu$^u$ Lys$^u$ Pro$^u$ Leu$^u$ Glu$^u$ Leu$^u$ Lys$^u$ Ala$^u$ (H2); Leu$^u$ Glu$^u$ Lys$^u$ Leu$^u$ Tyr$^u$ Asn$^u$ Glu$^u$ Lys$^u$ Leu$^u$ Ala$^u$ Leu$^u$ (H3); Ser$^u$ Glu$^u$ Lys$^u$ Leu$^u$ Tyr$^u$ Leu$^u$ Glu$^u$ Lys$^u$ Leu$^u$ Ala$^u$ Leu$^u$ (H4); and Ala$^u$ Leu$^u$ Lys$^u$ Leu$^u$ Glu$^u$ Tyr$^u$ Leu$^u$ Glu$^u$ Leu$^u$ Lys$^u$ Ala$^u$ Leu$^u$ (H5). Alternatively, the non-peptide oligourea helical foldamer has a non-peptide peptidomimetic residue sequence that follows one of the following two helical pentad repeat sequences. Helical pentad repeat sequence 1: oligourea peptidomimetic residues with a hydrophobic side chain in positions a and d (e.g., Leu$^u$); oligourea peptidomimetic residues with a charged residue in position b and c (e.g. Glu$^u$ and Lys$^u$, respectively); and Tyr$^u$ and Ala$^u$ in position e. Helical pentad repeat sequence 2: oligourea peptidomimetic residues with a hydrophobic side chain in positions a and c (e.g. Leu$^u$); oligourea peptidomimetic residues with a hydrophobic side chain in position e (e.g., Ala$^u$ and Pro$^u$ residues at the e position); and oligourea peptidomimetic residues with a charged side chain in positions b and d (e.g., Glu$^u$ and Lys$^u$, respectively).

In a certain embodiment, the oligourea helical bundle has an internal cavity with a volume in a range of about 300 to about 1000 Å$^3$. In another embodiment, the volume of the internal cavity is in a range of 300 to about 650 Å$^3$, about 300 to about 600 Å$^3$, about 300 to about 575 Å$^3$, about 300 to about 550 Å$^3$, about 300 to about 500 Å$^3$, about 300 to about 475 Å$^3$, about 300 to about 450 Å$^3$, about 300 to about 425 Å$^3$, about 350 to about 700 Å$^3$, about 350 to about 650 Å$^3$, about 350 to about 600 Å$^3$, about 350 to about 575 Å$^3$, about 350 to about 550 Å$^3$, about 350 to about 525 Å$^3$, about 350 to about 500 Å$^3$, about 350 to about 475 Å$^3$, about 350 to about 450 Å$^3$, about 350 to about 425 Å$^3$, about 350 to about 400 Å$^3$, about 375 to about 700 Å$^3$, about 375 to about 650 Å$^3$, about 375 to about 600 Å$^3$, about 375 to about 575 Å$^3$, about 375 to about 550 Å$^3$, about 375 to about 525 Å$^3$, about 375 to about 500 Å$^3$, about 375 to about 400 Å$^3$, about 400 to about 700 Å$^3$, about 400 to about 650 Å$^3$, about 400 to about 600 Å$^3$, about 400 to about 575 Å$^3$, about 400 to about 550 Å$^3$, about 400 to about 525 Å$^3$, about 400 to about 500 Å$^3$, about 400 to about 475 Å$^3$, about 425 to about 700 Å$^3$, about 425 to about 650 Å$^3$, about 425 to about 600 Å$^3$, about 425 to about 575 Å$^3$, about 425 to about 550 Å$^3$, about 425 to about 525 Å$^3$, about 500 to about 700 Å$^3$, about 425 to about 475 Å$^3$, about 450 to about 700 Å$^3$, about 450 to about 650 Å$^3$, about 450 to about 600 Å$^3$, about 450 to about 575 Å$^3$, about 450 to about 550 Å$^3$, about 450 to about 525 Å$^3$, about 450 to about 500 Å$^3$, about 475 to about 700 Å$^3$, about 475 to about 650 Å$^3$, about 475 to about 600 Å$^3$, about 475 to about 550 Å$^3$, about 475 to about 525 Å$^3$, about 500 to about 700 Å$^3$, about 500 to about 650 Å$^3$, about 500 to about 625 Å$^3$, about 500 to about 600 Å$^3$, about 500 to about 575 Å$^3$, or about 500 to about 575 Å$^3$. In particular embodiments, the volume of the internal cavity is 300 Å$^3$, 325 Å$^3$, 350 Å$^3$, 375 Å$^3$, 400 Å$^3$, 425 Å$^3$, 450 Å$^3$, 475 Å$^3$, 500 Å$^3$, 525 Å$^3$, 550 Å$^3$, 575 Å$^3$, 600 Å$^3$, 625 Å$^3$, 650 Å$^3$, 675 Å$^3$, 600 Å$^3$, 625 Å$^3$, 650 Å$^3$, 675 Å$^3$, or 700 Å$^3$.

In certain embodiments, the oligourea compound has a secondary structure similar to a native peptide. As such, the secondary structure can act in a fashion similar to that of the native peptide. For example, the secondary structure of the oligourea compound can be biologically active. By way of another example, the secondary structure can act as a receptor ligand, an effector molecule, an agonist, an antagonist, a modulator of protein-protein interactions, an organocatalyst, or an enzyme.

Alternatively, the oligourea compound may have a secondary structure that provides a function not found in nature. For example, the oligourea compound may be a catalyst with tailored substrate specificity.

The present description describes the surprising and unexpected discovery that non-peptide oligourea foldamers comprising non-peptide oligourea peptidomimetic residues demonstrate the ability to self-assemble oligourea helical bundles to at least partially encapsulate an agent under aqueous conditions. Furthermore, in another aspect, peptide-oligourea chimeric compounds that at least partially encapsulate an agent are described herein. The chimeric compound comprises an oligourea helical bundle, a peptide, and the agent at least partially encapsulated by the oligourea helical bundle. In a particular embodiment, the peptide is fused to, contiguous with, or conjugated to the oligourea helical bundle. In a particular embodiment, the peptide is a peptide α-helix. The chimeric compounds as described herein improve at least one PK and/or PD characteristic of the natural peptide. Because the chimeric compounds as described herein can adopt desired secondary structures similar to native peptides, including, e.g., helicoidal structures, they can serve as, for example, receptor ligands, effector molecules, agonists, antagonists, modulators of protein-protein interactions, organocatalysts or enzymes. Therefore, in certain aspects, the present description provides chimeric compounds, methods of making, and using the same. These aspects will be discussed next.

Peptide-Oligourea Chimeric Compounds

In certain aspects, the present description provides compounds comprising peptide/oligourea chimeras (herein, "chimeras" or "chimeric compounds"). In particular, the description provides chimeric compounds comprising a portion or sequence of amino acids (i.e., a peptide) covalently coupled to a oligourea helix bundle that at least partially encapsulates an agent. In an embodiment, the oligourea helical bundle self-assembles into its three-dimensional nanostructure under aqueous conditions. In a particular embodiment, the peptide is a peptide α-helix. In a certain embodiment, the peptide is a α-peptide (i.e., the peptide is made of alpha amino acids). In certain embodiments, the non-peptide oligourea helical foldamer is an aliphatic oligourea. In a particular embodiment, the non-peptide oligourea helical foldamer is a short amphiphilic α-helicomimetic foldamer with proteinaceous side-chains.

In an embodiment, the oligourea helical bundle has an isolated cavity within the hydrophobic core of the bundle, which at least partially encapsulates an agent (i.e., at least part of the agent is within the isolated cavity). In another embodiment, the oligourea helical bundle has a pH-responsive aqueous-fluid-filled channel within the hydrophobic core of the bundle. In an embodiment, the fluid is an aqueous agent (i.e., an agent in aqueous form). Furthermore, the size and/or diameter of the pore, i.e., cavity and/or channel, can be controlled through the modification of the non-peptide oligourea peptidomimetic residue sequence, which is described in greater detail below. In an alternative embodiment, the oligourea helical bundle has a pH-responsive super-helical channel with acquire fluid-filled pores within the hydrophobic core of the bundle.

In a particular embodiment, the oligourea helical bundle has a non-peptide oligourea peptidomimetic residue sequence selected from the group consisting of: Leu$^u$ Glu$^u$ Lys$^u$ Leu$^u$ Tyr$^u$ Leu$^u$ Glu$^u$ Lys$^u$ Leu$^u$ Ala$^u$ Leu$^u$ (H1); Leu$^u$ Glu$^u$ Leu$^u$ Lys$^u$ Pro$^u$ Leu$^u$ Glu$^u$ Leu$^u$ Lys$^u$ Ala$^u$ (H2); Leu$^u$ Glu$^u$ Lys$^u$ Leu$^u$ Tyr$^u$ Asn$^u$ Glu$^u$ Lys$^u$ Leu$^u$ Ala$^u$ Leu$^u$ (H3); Ser$^u$ Glu$^u$ Lys$^u$ Leu$^u$ Tyr$^u$ Leu$^u$ Glu$^u$ Lys$^u$ Leu$^u$ Ala$^u$ Leu$^u$ (H4); and Ala$^u$ Leu$^u$ Lys$^u$ Leu$^u$ Glu$^u$ Tyr$^u$ Leu$^u$ Glu$^u$ Leu$^u$ Lys$^u$ Ala$^u$ Leu$^u$ (H5). Alternatively, the oligourea helical bundle has a non-peptide peptidomimetic residue sequence that follows one of the following two helical pentad repeat sequences. Helical pentad repeat sequence 1: oligourea peptidomimetic residues with a hydrophobic side chain in positions a and d (e.g., Leu$^u$); oligourea peptidomimetic residues with a charged residue in position b and c (e.g. Glu$^u$ and Lys$^u$, respectively); and Tyr$^u$ and Ala$^u$ in position e. Helical pentad repeat sequence 2: oligourea peptidomimetic residues with a hydrophobic side chain in positions a and c (e.g. Leu$^u$); oligourea peptidomimetic residues with a hydrophobic side chain in position e (e.g., Ala$^u$ and Pro$^u$ residues at the e position); and oligourea peptidomimetic residues with a charged side chain in positions b and d (e.g., Glu$^u$ and Lys$^u$, respectively).

In a particular embodiment, the non-peptide oligourea peptidomimetic residue sequence is selected from the group consisting of: Leu$^u$ Glu$^u$ Lys$^u$ Leu$^u$ Tyr$^u$ Leu$^u$ Glu$^u$ Lys$^u$ Leu$^u$ Ala$^u$ Leu$^u$ (H1); Leu$^u$ Glu$^u$ Leu$^u$ Lys$^u$ Pro$^u$ Leu$^u$ Glu$^u$ Leu$^u$ Lys$^u$ Ala$^u$ (H2); Leu$^u$ Glu$^u$ Lys$^u$ Leu$^u$ Tyr$^u$ Asn$^u$ Glu$^u$ Lys$^u$ Leu$^u$ Ala$^u$ Leu$^u$ (H3); Ser$^u$ Glu$^u$ Lys$^u$ Leu$^u$ Tyr$^u$ Leu$^u$ Glu$^u$ Lys$^u$ Leu$^u$ Ala$^u$ Leu$^u$ (H4); and Ala$^u$ Leu$^u$ Lys$^u$ Leu$^u$ Glu$^u$ Tyr$^u$ Leu$^u$ Glu$^u$ Leu$^u$ Lys$^u$ Ala$^u$ Leu$^u$ (H5). Alternatively, the non-peptide oligourea helical foldamer has a non-peptide peptidomimetic residue sequence that follows one of the following two helical pentad repeat sequences. Helical pentad repeat sequence 1: oligourea peptidomimetic residues with a hydrophobic side chain in positions a and d (e.g., Leu$^u$); oligourea peptidomimetic residues with a charged residue in position b and c (e.g. Glu$^u$ and Lys$^u$, respectively); and Tyr$^u$ and Ala$^u$ in position e. Helical pentad repeat sequence 2: oligourea peptidomimetic residues with a hydrophobic side chain in positions a and c (e.g. Leu$^u$); oligourea peptidomimetic residues with a hydrophobic side chain in position e (e.g., Ala$^u$ and Pro$^u$ residues at the e position); and oligourea peptidomimetic residues with a charged side chain in positions b and d (e.g., Glu$^u$ and Lys$^u$, respectively).

In a certain embodiment, the oligourea helical bundle has an internal cavity with a volume in a range of about 300 to about 1000 Å$^3$. In another embodiment, the volume of the internal cavity is in a range of 400 to about 600 Å$^3$. In a particular embodiment, the volume of the internal cavity is about 500 Å$^3$.

In certain embodiments, the oligourea compound has a secondary structure similar to a native peptide. As such, the secondary structure can act in a fashion similar to that of the native peptide. For example, the secondary structure of the oligourea compound can be biologically active. By way of further example, the secondary structure can act as a receptor ligand, an effector molecule, an agonist, an antagonist, a modulator of protein-protein interactions, an organocatalyst, or an enzyme. Alternatively, the oligourea compound may have a secondary structure that provides a function not found in nature. For example, the oligourea compound may be a catalyst with tailored substrate specificity not known in nature.

In certain embodiments, the peptide is capable of binding specifically to a target, e.g., a protein such as a receptor or other polypeptide or peptide, or small molecule. In particular, the peptide may comprise an epitope that recognizes another compound, e.g. they can act as receptor ligands, effector molecules, agonists, antagonists, modulators of protein-protein interactions, organocatalysts, or enzymes.

In certain embodiments, the chimeric compounds comprise a peptide portion (i.e., a sequence of α-amino acid residues) contiguous with or coupled to an oligourea portion (i.e., a sequence of oligourea residues) that at least partially encapsulates an agent. In certain embodiments, the peptide portion comprises at least 2 α-amino acids. In certain additional embodiments, the oligourea portion comprises a non-peptide oligourea helical foldamer, for example, non-peptide oligourea peptidomimetic residues. The non-peptide oligourea helical foldamer can be an aliphatic oligourea. The non-peptide oligourea helical foldamer can be a short amphiphilic α-helicomimetic foldamer, which may include proteinaceous side chains.

In further embodiments, the oligourea compounds comprise at least one non-peptide oligourea peptidomimetic residue of the formula I and oligomers thereof:

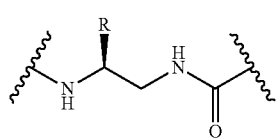

(I)

wherein R is independently selected from the group consisting of a hydrogen atom, an amino acid side chain, a (C1-C10) alkyl, (C1-C10) alkenyl, (C1-C10) alkynyl, (C5-C12) monocyclic or bicyclic aryl, (C5-C14) monocyclic or bicyclic aralkyl, (C5-C14) monocyclic or bicyclic heteroalkyl and (C1-C10) monocyclic or bicyclic heteroaryl group comprising up to 5 heteroatoms selected from N, O, and S, said groups being able to be non-substituted or substituted by 1 to 6 substituents further selected from the group consisting of: a halogen atom, an NO$_2$, OH, amidine, benzamidine, imidazole, alkoxy, (C1-C4) alkyl, NH2, CN, trihalomethyl, (C1-C4) acyloxy, (C1-C4) monoalkylamino, (C1-C4) dialkylamino, guanidino group, bis alkylated and bis acylated guanido group.

In any of the chimeric compound embodiments described herein, the peptide portion may comprise an α-amino acid sequence corresponding to a biologically active peptide or a fragment thereof.

In still additional embodiments, the chimeric compound as described herein is biologically active. The biological activity can stem from the peptide or the oligourea helical bundle. For example, in certain embodiments, the chimeric compounds as described herein are enzymatically active. In still additional embodiments, the chimeric compounds as described herein are configured to bind target proteins. In certain embodiments the target protein is a cytosolic protein. In certain embodiments, the target protein is a membrane protein. In certain embodiments, the membrane protein is a receptor. In still additional embodiments, the receptor is a growth factor receptor or a G-Protein Coupled Receptor (GPCR) or a fragment thereof. In an embodiment, the peptide is biologically active. Alternatively, in another embodiment, the oligourea helical bundle or the non-peptide oligourea helical foldamer is biologically active.

In certain aspects, the description provides chimeric compounds comprising a peptide portion coupled to an oligourea portion comprising a non-peptide oligourea helical foldamers which forms a helical bundle that at least partially encapsulates an agent. Surprisingly and unexpectedly non-peptide oligourea helical foldamers as described herein adopt well-defined helical secondary structures akin to that of α-polypeptides, can enhance or improve the beneficial properties of the cognate or parental "natural" peptide, and at least partially encapsulates an agent.

In certain aspects, the description provides peptide-oligourea chimeras that adopt stable secondary structures, including, e.g., linear, cyclic, or helicoidal, tertiary structure, and/or quaternary structures, wherein the chimeras comprise a sequence of amino acids (i.e., a polypeptide) contiguous with or coupled to an oligourea sequence of peptidomimetic or amino acid analog residues that at least partially encapsulate an agent. In certain embodiments, the amino acid sequence comprises α-amino acids. In an additional embodiments, the chimeric compound comprises an amino acid sequence contiguous with or coupled to one or more oligourea peptidomimetic residues, wherein the peptidomimetic residue includes at least one non-peptide oligourea helical foldamer. In certain embodiments, the chimera comprises two or more non-peptide oligourea helical foldamers.

In certain aspects, the description provides a chimeric ligand compound capable of binding specifically to a target, e.g., a protein such as a receptor or other polypeptide or peptide, or small molecule, similar to the native or natural peptide, and at least partially encapsulates an agent. In certain embodiments, the chimeric ligand compound comprises a peptide portion coupled to an oligourea portion. In certain embodiments, the peptide portion comprises α-amino acids. In an additional embodiments, the chimeric ligand compound comprises an amino acid sequence contiguous with or coupled to an oligourea portion including one or more oligourea peptidomimetic residues. In certain embodiments the chimeric ligand compound comprises two or more oligourea peptidomimetic residues. In a certain embodiment, the chimeric ligand compound comprises a non-peptide oligourea helical foldamer.

In any of the embodiments described herein, the peptide-oligourea chimeric compound comprises a polypeptide portion including at least one α-, γ-, δ-amino acid, derivative or combination thereof, which is contiguous with or coupled to one or more oligourea peptidomimetic residues. In a preferred embodiment, the peptide-oligourea chimeric compound comprises a non-peptide oligourea helical foldamer. In a particular embodiment, the peptide-oligourea chimeric compound comprises at least one non-peptide oligourea helical foldamer (e.g., one, two, three, four, five, etc.) and/or at least one peptide (e.g., one, two, three, four, five, etc.)

In any of the embodiments described herein, the peptide-oligourea chimeric compound comprises an oligourea portion contiguous with or covalently linked or joined to at least one of the amino terminus (N'), the carboxyl terminus (C'), within the peptide sequence or a combination thereof. In a preferred embodiment, the peptide-oligourea chimeric compound comprises an oligourea portion covalently linked or joined to the C-terminus of the peptide portion.

In any of the embodiments described herein, the peptide-oligourea chimeric compound or the oligourea compound comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more oligourea residues.

In any of the embodiments described herein, the peptide-oligourea chimeric compound or the oligourea compound encapsulates 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more agents.

In another aspect, the description provides oligourea compounds and peptide-oligourea chimeric compounds as described herein further comprising at least one additional chemical modification. In certain embodiments, the chemical modification includes at least one of, for example, acetylation, phosphorylation, methylation, glycosylation, prenylation, isoprenylation, farnesylation, geranylation, pegylation, a disulfide bond, or combination thereof.

In any of the embodiments described herein, the peptide-oligourea chimeric compound comprises a polypeptide portion including at least one α-, γ-, δ-amino acid, derivative or combination thereof, which is contiguous with or coupled to one or more non-peptide oligourea peptidomimetic residues. In a preferred embodiment, the peptide-oligourea chimeric compound comprises a non-peptide oligourea helical foldamer.

In any of the embodiments described herein, the peptide-oligourea chimeric compound comprises an oligourea portion contiguous with or covalently linked or joined to at least one of the amino terminus (N'), the carboxyl terminus (C'), within the peptide sequence or a combination thereof. In a preferred embodiment, the peptide-oligourea chimeric compound comprises an oligourea portion covalently linked or joined to the C-terminus of the peptide portion.

Pharmaceutical Forms

The compounds or compositions as described herein including pharmaceutically acceptable salts thereof are useful for the preparation of a medicament and/or the treatment of disease in a subject. In the case where a salt of a compound is desired and the compound/composition is produced in the form of the desired salt, it can be subjected to purification as such. In the case where a compound/composition is produced in the free state and its salt is desired, the compound/composition is dissolved or suspended in a suitable organic solvent, followed by addition of an acid or a base to form a salt. As such, in an addition aspect the description provides compositions comprising an effective amount of a peptide-oligourea chimera as described herein, and a pharmaceutically acceptable carrier or excipient.

The compounds or compositions of the description may optionally be administered with at least one of a pharmaceutically acceptable excipient, pharmacologically active agent or a combination thereof. These novel, unnatural peptidomimetics are resistant or wholly immune to peptidase and protease degradation and are conformationally restrained. Thus, they are useful as tools to model peptide and protein conformations in aqueous solutions. The compounds are also useful as non-enzymatically degradable probes to mimic protein behavior in solution. As such, the description further provides the compositions comprising an effective amount of a chimeric compound as described herein, and a pharmaceutically acceptable carrier or excipient.

Certain compounds or composition of the description and their salts may exist in more than one crystal form and the present disclosure includes each crystal form and mixtures thereof. Certain compounds/compositions of the disclosure and their salts may also exist in the form of solvates, for example hydrates, and the present disclosure includes each solvate and mixtures thereof.

Certain compounds/compositions of the disclosure may contain one or more chiral centers, and exist in different optically active forms. When compounds/compositions of the disclosure contain one chiral center, the compounds/compositions exist in two enantiomeric forms and the present disclosure includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step may be used to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound or composition of the description contains more than one chiral center, it may exist in diastereoisomeric forms. The diastereoisomeric compounds may be separated by methods known to those skilled in the art, for example chromatography or crystallization and the individual enantiomers may be separated as described above. The present disclosure includes each diastereoisomer of compounds of the disclosure and mixtures thereof.

Certain compounds of the disclosure may exist in different tautomeric forms or as different geometric isomers, and the present disclosure includes each tautomer and/or geometric isomer of compounds of the disclosure and mixtures thereof.

Certain compounds or compositions of the disclosure may exist in different stable conformational forms which may be separable. Torsional asymmetry due to restricted rotation about an asymmetric single bond, for example because of steric hindrance or ring strain, may permit separation of different conformers. The present disclosure includes each conformational isomer of compounds of the disclosure and mixtures thereof.

Certain compounds of the disclosure may exist in zwitterionic form and the present disclosure includes each zwitterionic form of compounds of the disclosure and mixtures thereof.

The present disclosure encompasses all possible isomers including tautomers and mixtures thereof. Where chiral carbons lend themselves to two different enantiomers, both enantiomers are contemplated as well as procedures for separating the two enantiomers.

The present disclosure also relates to pharmaceutically acceptable salts, racemates, and optical isomers thereof. The compounds of this disclosure typically contain one or more chiral centers. Accordingly, this disclosure is intended to include racemic mixtures, diastereomers, enantiomers and mixture enriched in one or more stereoisomer. The scope of the disclosure as described and claimed encompasses the racemic forms of the compounds as well as the individual enantiomers and non-racemic mixtures thereof.

Many of the compounds of the disclosure may be provided as salts with pharmaceutically compatible counterions (i.e., pharmaceutically acceptable salts).

The term "pharmaceutically acceptable salt" is used throughout the specification to describe, where applicable, a salt form of one or more of the compounds or prodrugs described herein which are presented to increase the solubility of the compound in the gastric juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present disclosure. In a preferred embodiment, the description provides pharmaceutically acceptable salts of the modified peptides as described herein, which retain the biological effectiveness and properties of the parent compounds and which are not biologically or otherwise harmful as the dosage administered. The compounds of this disclosure are capable of forming both acid and base salts by virtue of the presence of amino and carboxy groups respectively.

A "pharmaceutically acceptable counterion" is an ionic portion of a salt that is not toxic when released from the salt upon administration to a recipient. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, parabromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, sub erate, sebacate, fumarate, maleate, butyne-I,4-dioate, hexyne-I,6-dioate, benzoate, chlorobenzoate, methylbenzoate, dinitrobenzoate, hydroxybenzoate, methoxybenzoate, phthalate, terephthalate, sulfonate, xylenesulfonate, phenylacetate, phenylpropionate, phenylbutyrate, citrate, lactate, ~-hydroxybutyrate, glycolate, maleate, tartrate, methanesulfonate, propanesulfonate, naphthalene-I-sulfonate, naphthalene-2-sulfonate, mandelate and the like salts.

Preferred pharmaceutically acceptable acid addition salts include those formed with mineral acids such as hydrochloric acid and hydrobromic acid, and especially those formed with organic acids such as maleic acid. Suitable bases for forming pharmaceutically acceptable salts with acidic functional groups include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-Iower alkyl amines), such as mono-, bis-, or tris-(2-hydroxyethyl)amine, 2-hydroxy-tert-butylamine, or tris-(hydroxymethyl)methylamine, N,N-di-lower alkyl-N (hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

Prodrugs

The description also provides prodrug forms of the above described oligourea compounds, wherein the prodrug is metabolized in vivo to produce an analog or derivative as set forth above. Indeed, some of the described compounds may be a prodrug for another analog or derivative. The term "prodrug" is well understood in the art and refers to an agent which is converted into the parent drug in vivo by some physiological chemical process (e.g., a prodrug on being brought to the physiological pH is converted to the desired drug form). For example, see *Remington's Pharmaceutical Sciences,* 1980, vol. 16, Mack Publishing Company, Easton, Pa., 61 and 424.

Pro-drugs are often useful because, in some situations, they may be easier to administer than the parent drug. They may, for instance, be bioavailable by oral administration whereas the parent drug is not. The prodrug may also have improved solubility in pharmacological compositions over the parent drug. An example, without limitation, of a pro-drug would be a compound of the present disclosure wherein it is administered as an ester (the "pro-drug") to facilitate transmittal across a cell membrane where water solubility is not beneficial, but then it is metabolically hydrolyzed to the carboxylic acid once inside the cell where water solubility is beneficial. Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue.

Exemplary pro-drugs upon cleavage release the corresponding free acid, and such hydrolyzable ester-forming residues of the compounds of this disclosure include but are not limited to carboxylic acid substituents (e.g., —C(O)2H or a moiety that contains a carboxylic acid) wherein the free hydrogen is replaced by (C1-C4)alkyl, (Cz-C12)alkanoyloxymethyl, (C4-C9)1-(alkanoyloxy)ethyl, I-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, I-methyl-1-10 (alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N, N—(C1-C2)alkylamino(C2-C3)alkyl (such as ~-dimethylaminoethyl), carbamoyl-(C1-C2)alkyl, N,N-die C1-C2)-alkylcarbamoyl-(C1-15 C2)alkyl and piperidino-, pyrrolidino- or morpholino(C2-C3)alkyl.

Other exemplary pro-drugs release an alcohol or amine of a compound of the disclosure wherein the free hydrogen of a hydroxyl or amine substituent is replaced by (C1-C6) alkanoyloxymethyl, 1-((C1-C6)alkanoyloxy)ethyl, I-methyl-1-((C1-C6)alkanoyloxy)ethyl, (C1-C6)alkoxycarbonyl-oxymethyl, N—(C1-C6)alkoxycarbonylamino-20 methyl, succinoyl, (C1-C6)alkanoyl, a-amino(C1-C4)alkanoyl, arylactyl and a-aminoacyl, or a-aminoacyl-a-aminoacyl wherein said a-aminoacyl moieties are independently any of the naturally occurring L-amino acids found in proteins, —P(O)(OH)2'—P(O)(O(C1-C6)alkyl)2 or glycosyl (the radical resulting from detachment of the hydroxyl of the hemiacetal of a carbohydrate).

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. Protective 30 Groups in Organic Synthesis, 2nd ed.; Wiley: N.Y., 1991). Protected forms of the inventive compounds are included within the scope of this disclosure.

The term "chemically protected form," as used herein, pertains to a compound in which one or more reactive functional groups are protected from undesirable chemical reactions, that is, are in the form of a protected or protecting group (also known as a masked or masking group). It may be convenient or desirable to prepare, purify, and/or handle the active compound in a chemically protected form.

By protecting a reactive functional group, reactions involving other unprotected reactive functional groups can be performed, without affecting the protected group; the protecting group may be removed, usually in a subsequent step, without substantially affecting the remainder of the molecule. See, for example, Protective Groups in Organic Synthesis (T. Green and P. Wuts, Wiley, 1991), and Protective Groups in Organic Synthesis (T. Green and P. Wuts; 3rd Edition; John Wiley and Sons, 1999).

For example, a hydroxy group may be protected as an ether (—OR) or an ester (—OC(═O)R), for example, as: a t-butyl ether; a benzyl, benzhydryl (diphenylmethyl); a trityl (triphenylmethyl) ether; a trimethylsilyl or t-butyldimethylsilyl ether; or an acetyl ester (—OC(═O)CH3,—OAc).

For example, an aldehyde or ketone group may be protected as an acetal or ketal, respectively, in which the carbonyl group (C(═O)) is converted to a diether (C(OR)2), by reaction with, for example, a primary alcohol. The aldehyde or ketone group is readily regenerated by hydrolysis using a large excess of water in the presence of acid. For example, an amine group may be protected, for example, as an amide (NRC(═O)R) or a urethane (—NRC(═O)OR), for example, as: a methyl amide (—NHC(═O)CH3); a benzyloxy amide (—NHC(═O)OCH2C6HsNHCbz); as a t-butoxy amide (NHC═(═O)OC(CH3)3,-NHBoc); a 2-biphenyl-2-propoxy amide (NHC(═O)OC(CH3) 2C6H4C6HsNHBoc), as a 9-fluorenylmethoxy amide (—NHFmoc), as a 6-nitroveratryloxy amide (—NHNvoc), as a 2-trimethylsilylethyloxy amide (—NHTeoc), as a 2,2, 2-trichloroethyloxy amide (—NHTroc), as an allyloxy amide (—NHAlloc), as a 2-(phenylsulfonyl)ethyloxy amide (—NHPsec); or, in suitable cases (e.g., cyclic amines), as a nitroxide radical.

For example, a carboxylic acid group may be protected as an ester or an amide, for example, as: a benzyl ester; a t-butyl ester; a methyl ester; or a methyl amide. For example, a thiol group may be protected as a thioether (—SR), for example, as: a benzyl thioether; or an acetamidomethyl ether (—SCH2NHC(═O)CH3). In at least certain examples, the compounds disclosed herein can be used in the treatment of disorders associated with pathogen infection. Disorders associated with infection by pathogens include, but are not limited to, infection by viruses (DNA viruses, RNA viruses, animal viruses, and the like), bacteria (e.g., gram positive bacteria, gram negative bacteria, acid-fast bacteria, and the like), fungi, parasitic microbes, nematodes, and the like.

The term "pharmaceutically acceptable derivative" is used throughout the specification to describe any pharmaceutically acceptable prodrug form (such as an ester, amide other prodrug group) which, upon administration to a patient, provides directly or indirectly the present compound or an active metabolite of the present compound. The term "independently" is used herein to indicate that the variable, which is independently applied, varies independently from application to application.

The term "treatment" as used herein includes any treatment of a condition or disease in an animal, particularly a mammal, more particularly a human, and includes: (i) preventing the disease or condition from occurring in a subject which may be predisposed to the disease but has not yet been diagnosed as having it; (ii) inhibiting the disease or condition, i.e. arresting its development; relieving the disease or condition, i.e. causing regression of the condition; or (iii) ameliorating or relieving the conditions caused by the disease, i.e. symptoms of the disease.

The term "effective" is used to describe an amount of a compound, composition or component which, when used within the context of its intended use, effects an intended result.

The term "therapeutically effective amount" refers to that amount which is sufficient to effect treatment, as defined herein, when administered to a mammal in need of such treatment. The therapeutically effective amount will vary depending on the subject and disease state being treated, the severity of the affliction and the manner of administration, and may be determined routinely by one of ordinary skill in the art.

Suitable routes for administration include oral, peroral, rectal, vassal, topical (including ocular, buccal and sublingual), vaginal and parental (including subcutaneous, intramuscular, intravitreous, intravenous, intradermal, intrathecal and epidural). The preferred route of administration will depend upon the condition of the patient, the toxicity of the compound and the site of infection, among other considerations known to the clinician.

The therapeutic composition of the disclosure comprises about 1% to about 95% of the active ingredient, single-dose forms of administration preferably comprising about 20% to about 90% of the active ingredient and administration forms which are not single-dose preferably comprising about 5% to about 20% of the active ingredient. Unit dose forms are, for example, coated tablets, tablets, ampoules, vials, suppositories or capsules. Other forms of administration are, for example, ointments, creams, pastes, foams, tinctures, lipsticks, drops, sprays, dispersions and the like. Examples are capsules containing from about 0.05 g to about 1.0 g of the active ingredient.

The pharmaceutical compositions of the present disclosure are prepared in a manner known per se, for example by means of convential mixing, granulating, coating, dissolving or lyophilizing processes.

Preferably, solutions of the active ingredient, and in addition also suspensions or dispersions, especially isotonic aqueous solutions, dispersions or suspensions, are used, it being possible for these to be prepared before use, for example in the case of lyophilized compositions which comprise the active substance by itself or together with a carrier, for example mannitol. The pharmaceutical compositions can be sterilized and/or comprise excipients, for example preservatives, stabilizers, wetting agents and/or emulsifiers, solubilizing agents, salts for regulating the osmotic pressure and/or buffers, and they are prepared in a manner known per se, for example by means of convential dissolving or lyophilizing processes. The solutions or suspensions mentioned can comprise viscosity-increasing substances, such as sodium carboxymethylcellulose, carboxymethylcellulose, dextran, polyvinylpyrrolidone or gelatin.

Pharmaceutically acceptable forms include, for example, a gel, lotion, spray, powder, pill, tablet, controlled release tablet, sustained release tablet, rate controlling release tablet, enteric coating, emulsion, liquid, salts, pastes, jellies, aerosols, ointments, capsules, gel caps, or any other suitable form that will be obvious to one of ordinary skill in the art.

Suspensions in oil comprise, as the oily component, the vegetable, synthetic or semi-synthetic oils customary for injection purposes. Oils which may be mentioned are, in particular, liquid fatty acid esters which contain, as the acid component, a long-chain fatty acid having 8-22, in particular 12-22, carbon atoms, for example lauric acid, tridecylic acid, myristic acid, pentadecylic acid, palmitic acid, margaric acid, stearic acid, arachidinic acid, behenic acid or corresponding unsaturated acids, for example oleic acid, elaidic acid, euric acid, brasidic acid or linoleic acid, if appropriate with the addition of antioxidants, for example vitamin E, .beta.-carotene or 3,5-di-tert-butyl-4-hydroxytoluene. The alcohol component of these fatty acid esters has not more than 6 carbon atoms and is mono- or polyhydric, for example mono-, di- or trihydric alcohol, for example methanol, ethanol, propanol, butanol, or pentanol, or isomers thereof, but in particular glycol and glycerol. Fatty acid esters are therefore, for example: ethyl oleate, isopropyl myristate, isopropyl palmitate, "Labrafil M 2375" (polyoxyethylene glycerol trioleate from Gattefosee, Paris), "Labrafil M 1944 CS" (unsaturated polyglycolated glycerides prepared by an alcoholysis of apricot kernel oil and made up of glycerides and polyethylene glycol esters; from Gattefosee, Paris), "Labrasol" (saturated polyglycolated glycerides prepared by an alcoholysis of TCM and made up of glycerides and polyethylene glycol esters; from Gattefosee, Paris) and/or "Miglyol 812" (triglyceride of saturated fatty acids of chain length C8 to C12 from Huls AG, Germany), and in particular vegetable oils, such as cottonseed oil, almond oil, olive oil, castor oil, sesame oil, soybean oil and, in particular, groundnut oil.

The preparation of the injection compositions is carried out in the customary manner under sterile conditions, as are bottling, for example in ampoules or vials, and closing of the containers.

For example, pharmaceutical compositions for oral use can be obtained by combining the active ingredient with one or more solid carriers, if appropriate granulating the resulting mixture, and, if desired, processing the mixture or granules to tablets or coated tablet cores, if appropriate by addition of additional excipients.

Suitable carriers are, in particular, fillers, such as sugars, for example lactose, sucrose, mannitol or sorbitol cellulose preparations and/or calcium phosphates, for example tricalcium phosphate, or calcium hydrogen phosphate, and furthermore binders, such as starches, for example maize, wheat, rice or potato starch, methylcellulose, hydroxypropylmethylcellulose, sodium carboxymethylcellulose and/or polyvinyl-pyrrolidine, and/or, if desired, desintegrators, such as the above mentioned starches, and furthermore carboxymethyl-starch, cross-linked polyvinylpyrrolidone, alginic acid or a salt thereof, such as sodium alginate. Additional excipients are, in particular, flow regulators and lubricants, for example salicylic acid, talc, stearic acid or salts thereof, such as magnesium stearate or calcium stearate, and/or polyethylene glycol, or derivatives thereof.

Coated tablet cores can be provided with suitable coatings which, if appropriate, are resistant to gastric juice, the coatings used being, inter alia, concentrated sugar solutions, which, if appropriate, comprise gum arabic, talc, polyvinylpyrrolidine, polyethylene glycol and/or titanium dioxide, coating solutions in suitable organic solvents or solvent mixtures or, for the preparation of coatings which are resistant to gastric juice, solutions of suitable cellulose preparations, such as acetylcellulose phthalate or hydroxypropylmethylcellulose phthalate.

By "controlled release" it is meant for purposes of the present disclosure that therapeutically active compound is released from the preparation at a controlled rate or at a specific site, for example, the intestine, or both such that therapeutically beneficial blood levels (but below toxic levels) are maintained over an extended period of time, e.g., providing a 12 hour or a 24 hour dosage form.

The term "rate controlling polymer" as used herein includes hydrophilic polymers, hydrophobic polymers or mixtures of hydrophilic and/or hydrophobic polymers that are capable of retarding the release of the compounds in vivo. In addition, many of the same polymers can be utilized to create an enteric coating of a drug, drug suspension, or drug matrix. It is within the skill of those in the art to modify the coating thickness, permeability, and dissolution characteristics to provide the desired controlled release profile (e.g., drug release rate and locus) without undue experimentation.

Examples of suitable controlled release polymers to be used in this disclosure include hydroxyalkylcellulose, such as hydroxypropylcellulose and hydroxypropylmethyl-cellulose; poly(ethylene)oxide; alkylcellulose such as ethycellulose and methylcellulose; carboxymethylcellulose; hydrophilic cellulose derivatives; polyethylene glycol; polyvinylpyrrolidone; cellulose acetate; cellulose acetate butyrate; cellulose acetate phthalate; cellulose acetate trimellitate; polyvinylacetate phthalate; hydroxypropylmethylcellulose phthalate; hydroxypropylmethylcellulose acetate succinate; poly(alkyl methacrylate); and poly (vinyl acetate). Other suitable hydrophobic polymers include polymers or copolymers derived from acrylic or methacrylic acid esters, copolymers of acrylic and methacrylic acid esters, zein, waxes, shellac and hydrogenated vegetable oils.

To ensure correct release kinetics, the controlled release preparation of this disclosure contains about 5 and 75% by weight, preferably about 20 and 50% by weight, more preferably about 30 to 45% by weight controlled release polymer(s) and about 1 to 40% by weight, preferably about 3 to 25% by weight active compounds. The controlled release preparation according to the disclosure can preferably include auxiliary agents, such as diluents, lubricants and/or melting binders. Preferably, the excipients are selected to minimize the water content of the preparation. Preferably, the preparation includes an antioxidant. Suitable diluents include pharmaceutically acceptable inert fillers such as microcrystalline cellulose, lactose, dibasic calcium phosphate, saccharides, and/or mixtures of any of the foregoing. The diluent is suitably a water soluble diluent. Examples of diluents include microcrystalline cellulose such as Avicel ph112, Avicel pH101 and Avicel pH102; lactose such as lactose monohydrate, lactose anhydrous, and Pharmatose DCL 21; dibasic calcium phosphate such as Emcompress; mannitol; starch; sorbitol; sucrose; and glucose. Diluents are carefully selected to match the specific formulation with attention paid to the compression properties. Suitable lubricants, including agents that act on the flowability of the powder to be compressed are, for example, colloidal silicon dioxide such as Aerosil 200; talc; stearic acid, magnesium stearate, and calcium stearate. Suitable low temperature melting binders include polyethylene glycols such as PEG 6000; cetostearyl alcohol; cetyl alcohol; polyoxyethylene alkyl ethers; polyoxyethylene castor oil derivatives; polyoxyethylene sorbitan fatty acid esters; polyoxyethylene stearates; poloxamers; and waxes.

To improve the stability in the controlled release preparation, an antioxidant compound can be included. Suitable antioxidants include sodium metabisulfite; tocopherols such as alpha, beta, or delta-tocopherol tocopherol esters and alpha-tocopherol acetate; ascorbic acid or a pharmaceutically acceptable salt thereof; ascorbyl palmitate; alkyl gallates such as propyl gallate, Tenox PG, Tenox s-1; sulphites or a pharmaceutically acceptable salt thereof; BHA; BHT; and monothioglycerol.

The controlled release preparation according to the disclosure preferably can be manufactured by blending the compounds with the controlled release polymer(s) and auxiliary excipients followed by direct compression. Other methods for manufacturing the preparation include melt granulation. Preferred melt granulation techniques include melt granulation together with the rate controlling polymer(s) and diluent(s) followed by compression of the granules and melt granulation with subsequent blending with the rate controlling polymer(s) and diluents followed by compression of the blend. As desired prior to compression, the blend and/or granulate can be screened and/or mixed with auxiliary agents until an easily flowable homogeneous mixture is obtained.

Oral dosage forms of the controlled release preparation according to the disclosure can be in the form of tablets, coated tablets, enterically coated tablets or can be multiparticulate, such as in the form of pellets or mini-tablets. If desired, capsules such as hard or soft gelatin capsules, can contain the multiparticulates. If desired, the multiparticulate oral dosage forms can comprise a blend of at least two populations of pellets or mini-tablets having different controlled-release in vitro and/or in vivo release profiles. If desired, one of the pellet or mini-tablet populations can comprise immediate release multiparticulate, such as multiparticulates formed by conventional means.

If desired, the controlled release matrix tablets or multiparticulates of this disclosure can be coated with a controlled release polymer layer so as to provide additional controlled release properties. Suitable polymers that can be used to form this controlled release layer include the rate controlling polymers listed above.

As desired, the tablets, pellets or mini-tablets according to the disclosure can be provided with a light-protective and/or cosmetic film coating, for example, film-formers, pigments, anti-adhesive agents and plasticizers. Such a film former may consist of fast-dissolving constituents, such as low-viscosity hydroxypropylmethylcelluose, for example Methocel E5 or D14 or Pharmacoat 606 (Shin-Etsu). The film coating may also contain excipients customary in film-coating procedures, such as light-protective pigments, for example iron oxide, or titanium dioxide, anti-adhesive agents, for example talc, and also suitable plasticizers such as PEG 400, PEG 6000, and diethyl phthalate or triethyl citrate.

The controlled release polymer of this disclosure may consist of a hydrogel matrix. For instance, the compounds can be compressed into a dosage form containing a rate controlling polymer, such as HPMC, or mixture of polymers which when wet will swell to form a hydrogel. The rate of release from this dosage form is controlled both by diffusion from the swollen tablet mass and by erosion of the tablet surface over time. The rate of release may be controlled both by the amount of polymer per tablet and by the inherent viscosities of the polymers used.

Dyes or pigments can be admixed to the tablets or coated tablet coatings, for example for identification or characterization of different doses of active ingredient.

Pharmaceutical compositions, which can be used orally, are also hard capsules of gelatin and soft, closed capsules of gelatin and a plasticizer, such as glycerol or sorbitol. The hard capsules can contain the active ingredient in the form of granules, mixed for example with fillers, such as maize starch, binders and/or lubricants, such as talc or magnesium stearate, and stabilizers if appropriate. In soft capsules, the active ingredient is preferably dissolved or suspended in suitable liquid excipients, such as greasy oils, paraffin oil or liquid polyethylene glycols or fatty acid esters of ethylene glycol or propylene glycol, it being likewise possible to add stabilizers and detergents, for example of the polyethylene sorbitan fatty acid ester type.

Other oral forms of administration are, for example, syrups prepared in the customary manner, which comprise the active ingredient, for example, in suspended form and in a concentration of about 5% to 20%, preferably about 10% or in a similar concentration which results in a suitable individual dose, for example, when 5 or 10 ml are measured out. Other forms are, for example, also pulverulent or liquid concentrates for preparing of shakes, for example in milk. Such concentrates can also be packed in unit dose quantities.

Pharmaceutical compositions, which can be used rectally, are, for example, suppositories that comprise a combination of the active ingredient with a suppository base. Suitable suppository bases are, for example, naturally occurring or synthetic triglycerides, paraffin hydrocarbons, polyethylene glycols or higher alkanols.

Compositions which are suitable for parenteral administration are aqueous solutions of an active ingredient in water-soluble form, for example of water-soluble salt, or aqueous injection suspensions, which comprise viscosity-increasing substances, for example sodium carboxymethylcellulose, sorbitol and/or dextran, and if appropriate stabilizers. The active ingredient can also be present here in the form of a lyophilisate, if appropriate together with excipients, and be dissolved before parenteral administration by addition of suitable solvents. Solutions such as are used, for example, for parental administration can also be used as infusion solutions. Preferred preservatives are, for example. Antioxidants, such as ascorbic acid, or microbicides, such as sorbic or benzoic acid.

Ointments are oil-in-water emulsions, which comprise not more than 70%, but preferably 20-50% of water or aqueous phase. The fatty phase consists, in particular, hydrocarbons, for example vaseline, paraffin oil or hard paraffin's, which preferably comprise suitable hydroxy compounds, such as fatty alcohol's or esters thereof, for example cetyl alcohol or wool wax alcohols, such as wool wax, to improve the water-binding capacity. Emulsifiers are corresponding lipophilic substances, such as sorbitan fatty acid esters (Spans), for example sorbitan oleate and/or sorbitan isostearate. Additives to the aqueous phase are, for example, humectants, such as polyalcohols, for example glycerol, propylene glycol, sorbitol and/or polyethylene glycol, or preservatives and odoriferous substances.

Fatty ointments are anhydrous and comprise, as the base, in particular, hydrocarbons, for example paraffin, vaseline or paraffin oil, and furthermore naturally occurring or semi-synthetic fats, for example hydrogenated coconut-fatty acid triglycerides, or, preferably, hydrogenated oils, for example hydrogenated groundnut or castor oil, and furthermore fatty acid partial esters of glycerol, for example glycerol mono- and/or distearate, and for example, the fatty alcohols. They also contain emulsifiers and/or additives mentioned in connection with the ointments which increase uptake of water.

Creams are oil-in-water emulsions, which comprise more than 50% of water. Oily bases used are, in particular, fatty alcohols, for example lauryl, cetyl or stearyl alcohols, fatty acids, for example palmitic or stearic acid, liquid to solid waxes, for example isopropyl myristate, wool wax or beeswax, and/or hydrocarbons, for example vaseline (petrolatum) or paraffin oil. Emulsifiers are surface-active substances with predominantly hydrophilic properties, such as corresponding nonionic emulsifiers, for example fatty acid esters of polyalcohols or ethyleneoxy adducts thereof, such as polyglyceric acid fatty acid esters or polyethylene sorbitan fatty esters (Tweens), and furthermore polyoxyethylene fatty alcohol ethers or polyoxyethylene fatty acid esters, or corresponding ionic emulsifiers, such as alkali metal salts of fatty alcohol sulfates, for example sodium lauryl sulfate, sodium cetyl sulfate or sodium stearyl sulfate, which are usually used in the presence of fatty alcohols, for example cetyl stearyl alcohol or stearyl alcohol. Additives to the aqueous phase are, inter alia, agents which prevent the creams from drying out, for example polyalcohols, such as glycerol, sorbitol, propylene glycol and/or polyethylene glycols, and furthermore preservatives and odoriferous substances.

Pastes are creams and ointments having secretion-absorbing powder constituents, such as metal oxides, for example titanium oxide or zinc oxide, and furthermore talc and/or aluminum silicates, which have the task of binding the moisture or secretions present.

Foams are administered from pressurized containers and they are liquid oil-in-water emulsions present in aerosol for. As the propellant gases, halogenated hydrocarbons, such as chlorofluoro-lower alkanes, for example dichlorofluoromethane and dichlorotetrafluoroethane, or, preferably, non-halogenated gaseous hydrocarbons, air, $N_2O$, or carbon dioxide are used. The oily phases used are, inter alia, those mentioned above for ointments and creams, and the additives mentioned there are likewise used.

Tinctures and solutions usually comprise an aqueous-ethanolic base to which, humectants for reducing evaporation, such as polyalcohols, for example glycerol, glycols and/or polyethylene glycol, and re-oiling substances, such as fatty acid esters with lower polyethylene glycols, i.e. lipophilic substances soluble in the aqueous mixture to substitute the fatty substances removed from the skin with the ethanol, and, if necessary, other excipients and additives, are admixed.

Methods of Treatment

The disclosure also relates to a process or method for treatment of disease states. The oligourea compounds or chimeric compounds can be administered prophylactically or therapeutically as such or in the form of pharmaceutical compositions, preferably in an amount, which is effective against the diseases mentioned. With a warm-blooded animal, for example a human, requiring such treatment, the compounds are used, in particular, in the form of pharmaceutical composition. A daily dose of about 0.1 to about 5 g, preferably 0.5 g to about 2 g, of a compound of the present disclosure is administered here for a body weight of about 70 kg.

The description provides methods of treating a disease or disorder or ameliorating the effects of the same comprising the steps of administering to an individual in need thereof, a composition comprising an effective amount of a chimeric compound or a oligourea compound as described herein, and a pharmaceutically acceptable carrier or excipient, wherein the composition is effective for treating, preventing or ameliorating the effects of the disease or disorder.

The compounds or compositions described above are used for the manufacture of a medication for use in the treatment of a disease, disorder or condition. The term "disease involving deregulation of cell proliferation and/or angiogenesis" means, in the context of the disclosure, any human or animal disease affecting one or more organs. Exemplary diseases include, but are not limited to, rheumatoid arthritis, osteoarthritis, juvenile chronic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, atopic dermatitis, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpura, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia areata, seronegative arthopathy, arthropathy, Reiter's disease, psoriatic arthropathy, ulcerative colitic arthropathy, enteropathic synovitis, chlamydia, yersinia and salmonella associated arthropathy, spondyloarthopathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjodgren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycemia, type B insulin resistance with acanthosis nigricans, hypoparathyroidism, acute immune disease associated with organ transplantation, chronic immune disease associated with organ transplantation, osteoarthrosis, primary sclerosing cholangitis, idiopathic leucopenia, autoimmune neutropenia, renal disease NOS, glomerulonephritides, microscopic vasulitis of the kidneys, lyme disease, discoid lupus erythematosus, male infertility idiopathic or NOS, sperm autoimmunity, multiple sclerosis (all subtypes), insulin-dependent diabetes mellitus, sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Takayasu's disease/arteritis, autoimmune thrombocytopenia, idiopathic thrombocytopenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis and vitiligo. The human antibodies, and antibody portions of the disclosure can be used to treat autoimmune diseases, in particular those associated with inflammation, including, rheumatoid spondylitis, allergy, autoimmune diabetes, autoimmune uveitis.

The methods herein include administering to the subject (including a subject identified as in need of such treatment) an effective amount of a compound described herein, or a composition described herein to produce a desired effect. Identifying a subject in need of such treatment can be in the judgment of the subject or a health care professional and can be subjective (e.g., opinion) or objective (e.g., measurable by a test or diagnostic method). The therapeutic methods of the disclosure, which include prophylactic treatment, in general comprise administration of a therapeutically effective amount of at least one of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like).

In another aspect, the present description provides methods of making and using the peptide-oligourea chimeric compounds or the oligourea compounds as described herein. For example, the peptide-oligourea chimeric compounds or the oligourea compound as described herein can be used as a diagnostic agent or a therapeutic agent for the treatment of a disease or condition.

In one embodiment, the disclosure provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with protein-expression related disease (including misfolding), in which the subject has been administered a therapeutic amount of a compound or a composition herein sufficient to treat the disease or symptoms thereof. The level of Marker determined in the method can be compared to known levels of Marker in either healthy normal controls or in other afflicted patients to establish the subject's disease status. In certain embodiments, a second level of Marker in the subject is determined at a time point later than the determination of the first level, and the two levels are compared to monitor the course of disease or the efficacy of the therapy. In certain embodiments, a pre-treatment level of Marker in the subject is determined prior to beginning treatment according to this disclosure; this pre-treatment level of Marker can then be compared to the level of Marker in the subject after the treatment commences, to determine the efficacy of the treatment.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier. The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient. The active ingredient is preferably administered to achieve peak plasma concentrations of the active compound of about 0.00001-30 mM, preferably about 0.1-30 µM.

This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent. The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Methods of Preparation

In another aspect, the present description provides methods of making and using the compounds or compositions of the description. For example, in one embodiment, the description provides a method of making an oligourea compound composition of the description comprising fabricating a oligourea helical bundle with a non-peptide oligourea peptidomimetic residue sequence selected from the group consisting of: a helical pentad repeat (a, b, c, d, e): oligourea peptidomimetic residues with a hydrophobic side chain in positions a and d (e.g., Leu$^u$), oligourea peptidomimetic residues with a charged residue in position b and c (e.g. Glu$^u$ and Lys$^u$, respectively), and Tyr$^u$ and Ala$^u$ in position e; and a helical pentad repeat (a, b, c, d, e): oligourea peptidomimetic residues with a hydrophobic side chain in positions a and c (e.g. Leu$^u$), oligourea peptidomimetic residues with a hydrophobic side chain in position e (e.g., Ala$^u$ and Pro$^u$ residues at the e position), and oligourea peptidomimetic residues with a charged side chain in positions b and d (e.g., Glu$^u$ and Lys$^u$, respectively). In another embodiment, the oligourea helical bundle with a non-peptide oligourea peptidomimetic residue sequence selected from the group consisting of: Leu$^U$ Glu$^U$ Lys$^U$ Leu$^U$ Tyr$^U$ Leu$^U$ Glu$^U$ Lys$^U$ Leu$^U$ Ala$^U$ Leu$^U$ (H1); Leu$^U$ Glu$^U$ Leu$^U$ Lys$^U$ Pro$^U$ Leu$^U$ Glu$^U$ Leu$^U$ Lys$^U$ Ala$^U$ (H2); Leu$^U$ Glu$^U$ Lys$^U$ Leu$^U$ Tyr$^U$ Asn$^U$ Glu$^U$ Lys$^U$ Leu$^U$ Ala$^U$ Leu$^U$ (H3); Ser$^U$ Glu$^U$ Lys$^U$ Leu$^U$ Tyr$^U$ Leu$^U$ Glu$^U$ Lys$^U$ Leu$^U$ Ala$^U$ Leu$^U$ (H4); and Ala$^U$ Leu$^U$ Lys$^U$ Leu$^U$ Glu$^U$ Tyr$^U$ Leu$^U$ Glu$^U$ Leu$^U$ Lys$^U$ Ala$^U$ Leu$^U$ (H5).

Additional, exemplary methods for performing the synthesis of chimeric compounds as described herein are provided below.

It is understood that the examples and embodiments described herein are for illustrative purposes only and that various substitutions, modifications or changes in light thereof will be suggested to persons skilled in the art and are included within the spirit and purview of this application and are considered within the scope of the appended claims. The following examples are given by way of example of the preferred embodiments, and are in no way considered to be limiting to the disclosure. For example, the relative quantities of the ingredients may be varied to achieve different desired effects, additional ingredients may be added, and/or similar ingredients may be substituted for one or more of the ingredients described. All publications, patents, and patent applications cited herein are hereby incorporated by reference in their entirety for all purposes.

EXAMPLES

Design of Amphiphilic Oligourea Foldamers for Aqueous Self-Assembly.

Two short oligourea sequences that result in amphiphilic structures with well-defined and distinct hydrophobic and charged regions when folded as canonical 2.5-helices were designed. In certain embodiments, the sequestration of hydrophobic side-chains provide the driving force for self-assembly in aqueous conditions and the complementary charged side-chains facilitate inter-helical interactions. The primary sequences of oligoureas H1 or H2 are shown in FIG. 1B or FIG. 1C. H1 and H2 of FIGS. 1C and 1B primarily differ in their distribution of the charged and non-charged side-chains. By analogy to α-peptides known to form helical bundles (Hill, R. B., Raleigh, D. P., Lombardi, A. & DeGrado, W. F. De novo design of helical bundles as models for understanding protein folding and function. Acc. Chem. Res. 33, 745-754 (2000); and Woolfson, D. N. The design of coiled-coil structures and assemblies. Adv. Protein Chem. 70, 79-112 (2005)), the helix of H1 contains a hydrophobic face formed from two contiguous position so the helical pentad repeat (a and d) composed entirely of leucine-type urea residues (Leu$^u$-superscript 'u' denotes urea residue), flanked on either side by charged residues: glutamate-type urea residues (Glu$^u$) at position b, and lysine-type urea residues (Lys$^u$) at position c (FIGS. 1A and B). The fifth and final helical pentad position (e)—situated opposite the hydrophobic face—is composed of tyrosine-type (Tyr$^u$) and alanine-type (Ala$^u$) urea residues. In contrast, the helix of H2 contains a more extended hydrophobic face formed from three contiguous non-charged helical positions, composed of Leu$^u$ residues at the a and c positions, and Ala$^u$ and Pro$^u$ residues at the e position (FIG. 1C) (in contrast to proline amino acid residues, urea proline-type [Pro$^u$] residues have been shown to be helico-compatible in Fremaux, J., et al., G. Condensation approach to aliphatic oligourea foldamers: helices with N-(pyrrolidin-2-ylmethyl)ureido junctions. Angew. Chem. Int. Ed Engl. 50, 11382-11385 (2011)). The remaining two contiguous helical positions—b and d—are composed of charged Glu$^u$ and Lys$^u$ residues, respectively. Oligoureas H1 and H2 were synthesized chemically following previously reported procedures (Douat-Casassus, C., et al. Microwave-enhanced solid-phase synthesis of N,N'-linked aliphatic oligoureas and related hybrids. Org. Lett. 14, 3130-3133 (2012); and Fremaux, J., et al. Condensation approach to aliphatic oligourea foldamers: helices with N-(pyrrolidin-2-ylmethyl)ureido junctions. Angew. Chem. Int. Ed Engl. 50, 11382-11385 (2011)).

Circular dichroism (CD) experiments showed both molecules to be moderately helical in aqueous conditions at relatively low concentrations (<10 µM), and revealed a clear stabilizing influence of increasing foldamer concentration (from 3.125 µM to 200 µM) on the molar ellipticity of both molecules (FIG. 1D and FIG. 2)—a strong indicator of the existence of quaternary assemblies (Daniels, D. S., Petersson, E. J., Qiu, J. X. & Schepartz, A. High-resolution structure of a beta-peptide bundle. J. Am. Chem. Soc. 129, 1532-1533 (2007)). Next, crystals of oligoureas H1 and H2 were grown from aqueous crystallisation conditions and X-ray structures determined with resolutions of 1.25 Å and 1.4 Å for H1 and H2, respectively.

High-Resolution Crystallographic Studies of Oligoureas H1 and H2.

Figure 1D:
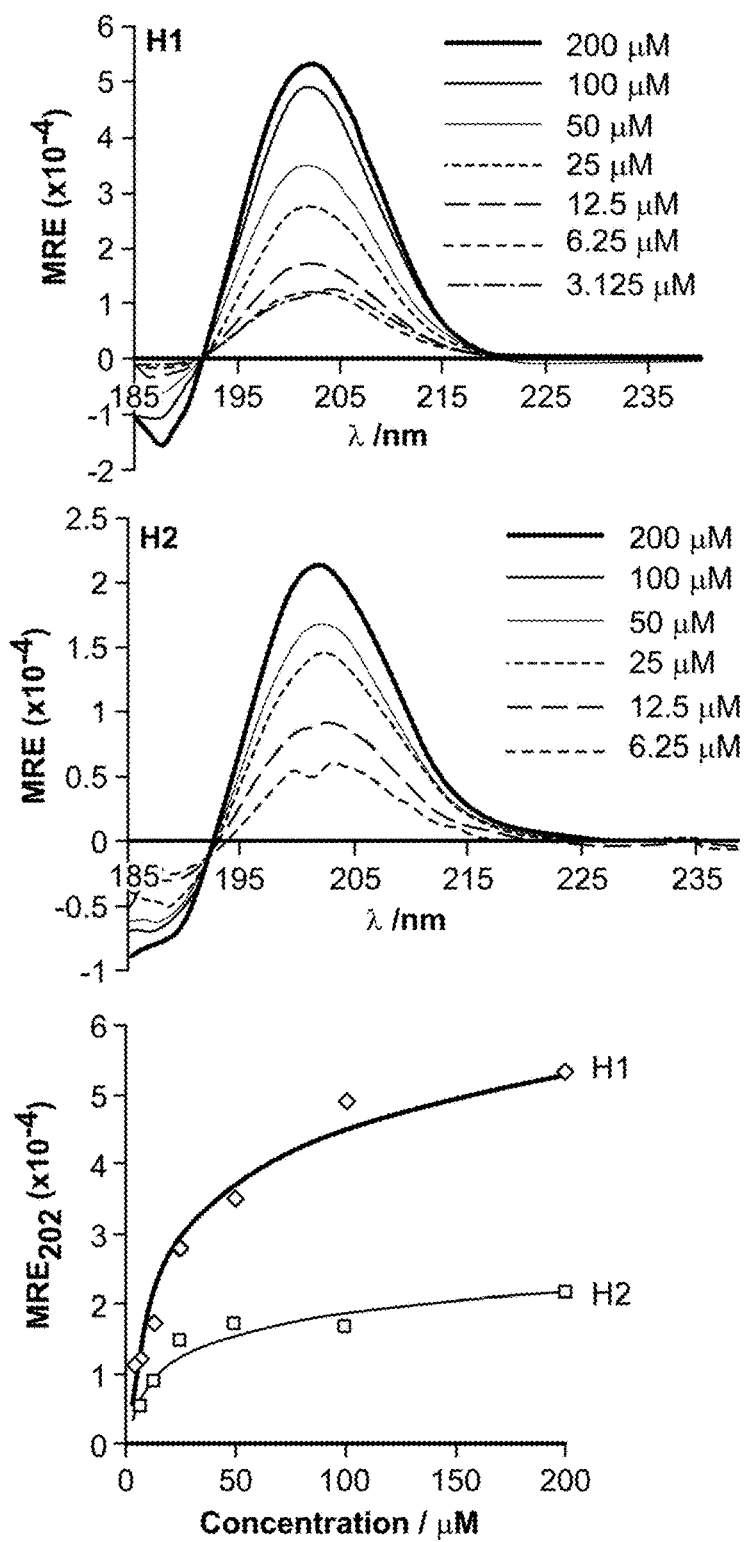
Figure 1E:
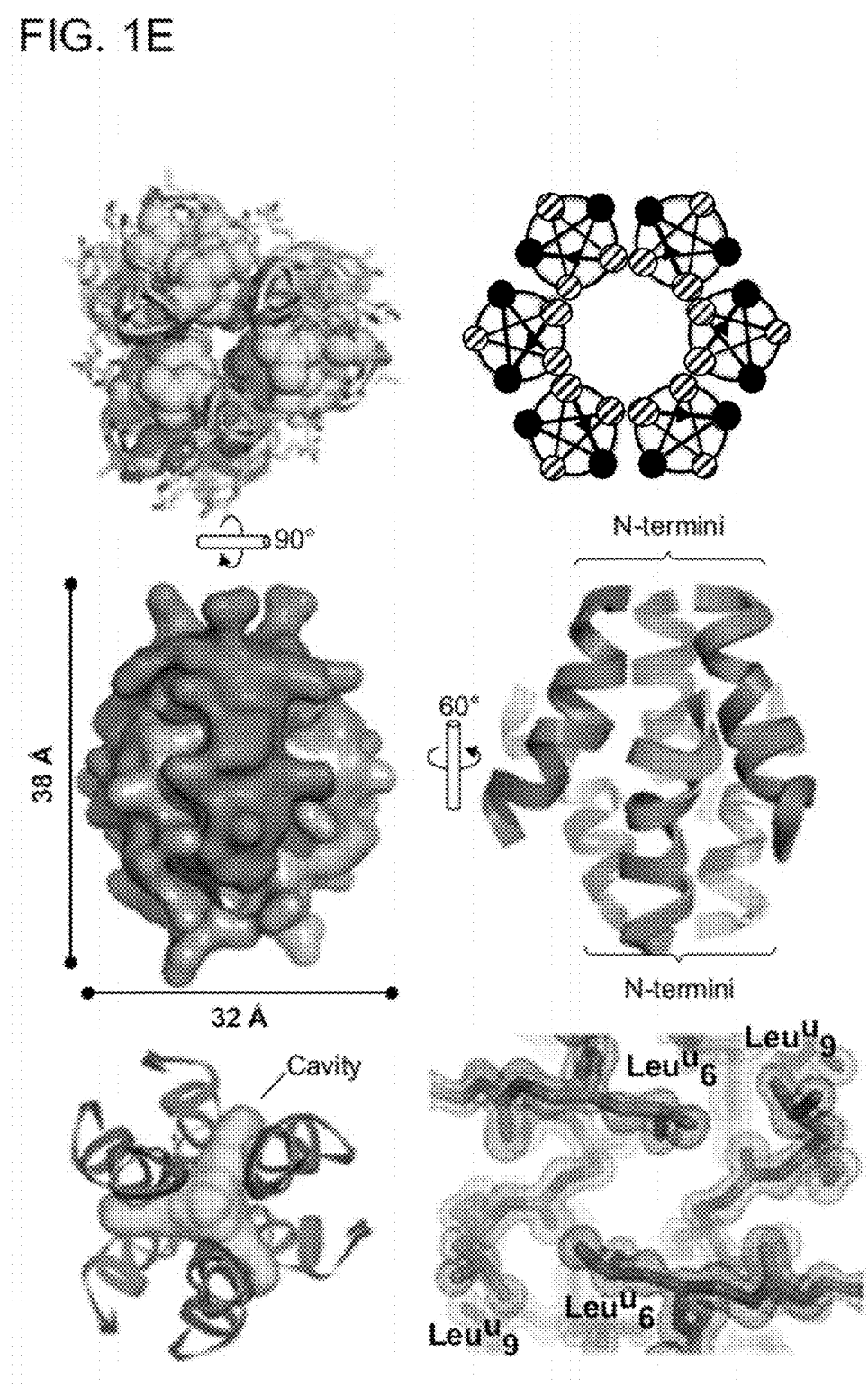
FIG. 1E. Crystal structure of a hexameric helical bundle formed from H1. Leu-type side-chains are shown as green spheres (top left). Middle panels: helices colored according to common chain orientation. Bottom left: internal cavity delineated in green (volume, 491.3 Å$^3$, calculated using SURFNET). Bottom right: electron density surrounding interlocked Leu-type (Leu$^u$) side-chains of hydrophobic core (2F$_o$-F$_c$, map, σ level: 1.4, resolution: 1.25 Å). (F) Crystal structure of channel-type assembly formed from oligourea H2. The two individual super-helix chains of the channel are colored separately. Inset: electron density surrounding a single mobile water molecule (red spheres) within the pore region of H2 channel (2F$_o$-F$_c$ map, σ level: 1.4, resolution: 1.40 Å).
Figure 3A:
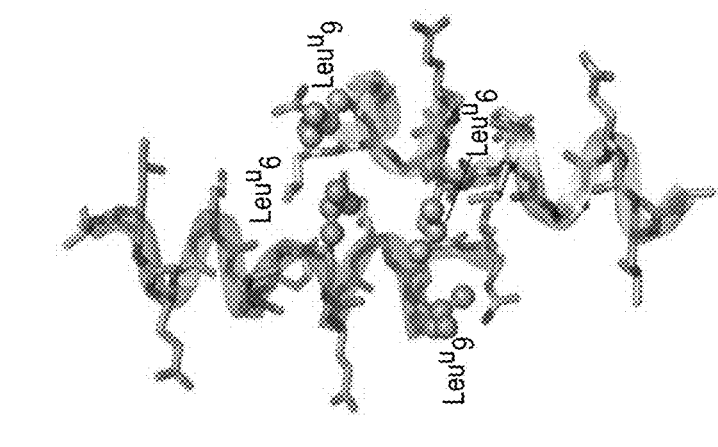
FIGS. 3A, 3B, and 3C. Crystal structure of oligourea H1: intermolecular interactions of hexameric helical-bundle formation.
Figure 3B:
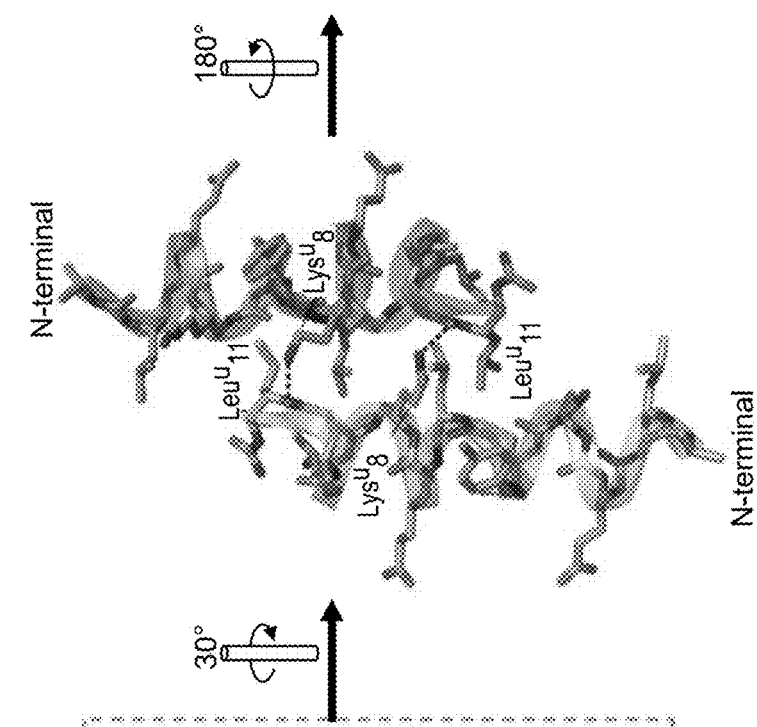
Figure 3C:
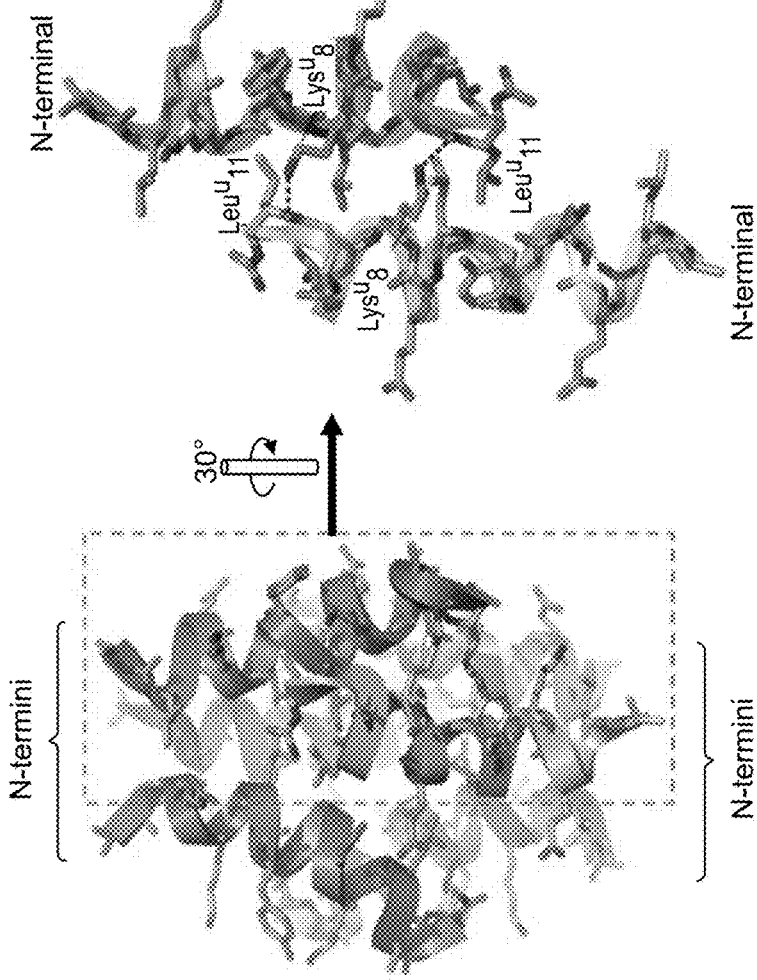
Figure 4A:
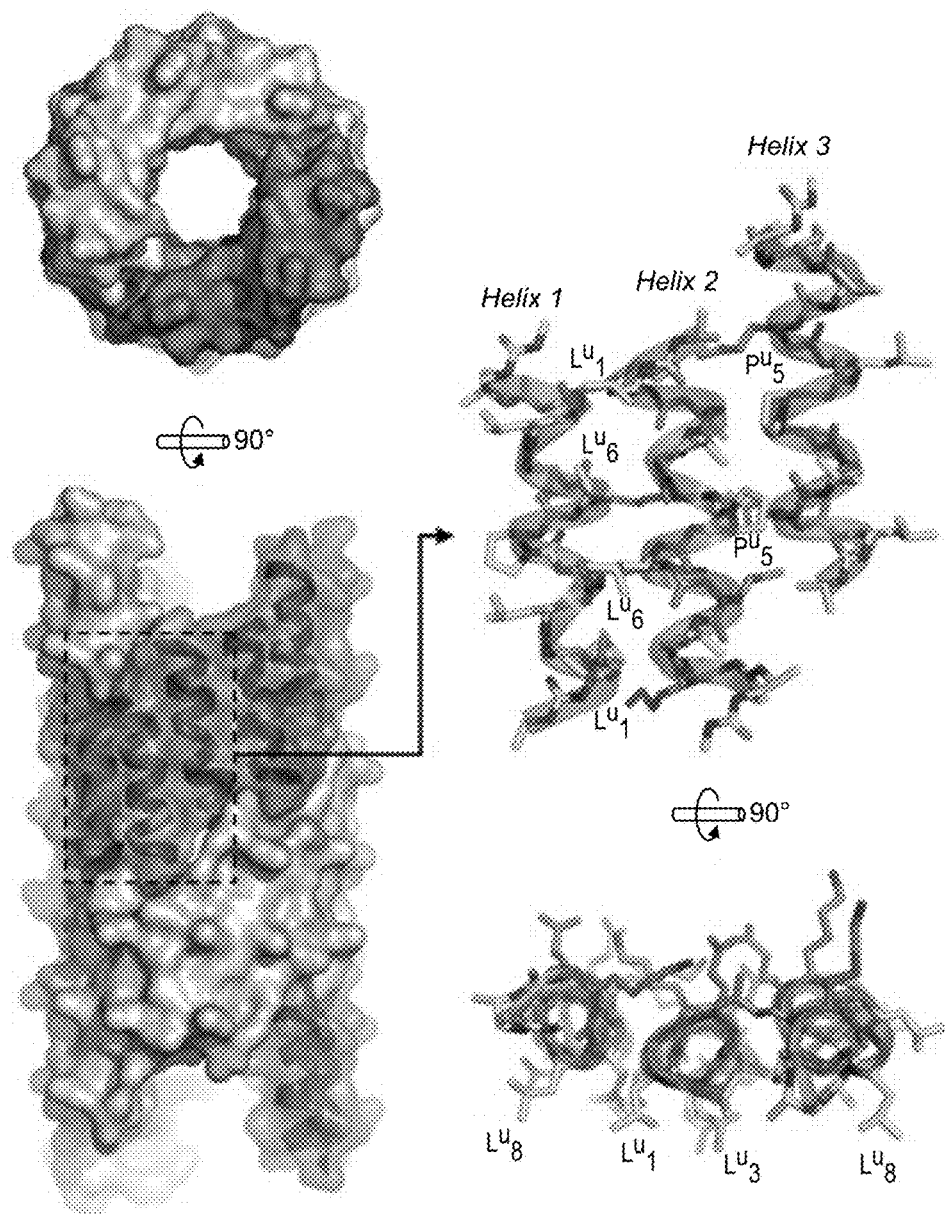
FIGS. 4A and 4B. Crystal structures of H2 and H5: comparison of the construction of channel-type assemblies formed from oligoureas H2 FIGS. 4A and H5 4B. Despite differing considerably in sequence, the common distribution of charged and uncharged residues around the helical circumferences of oligoureas H2 and H5 results in a surprisingly similar mechanism of inter-helical interactions for channels H2 and H5, involving helices packing laterally in an anti-parallel staggered fashion through hydrophobic interactions, creating extended super-helices. Super-helix chains are colored separately in FIGS. 4A and 4B. Inter-channel hydrophobic packing interactions are illustrated and discussed in FIG. 5.
Figure 4B:
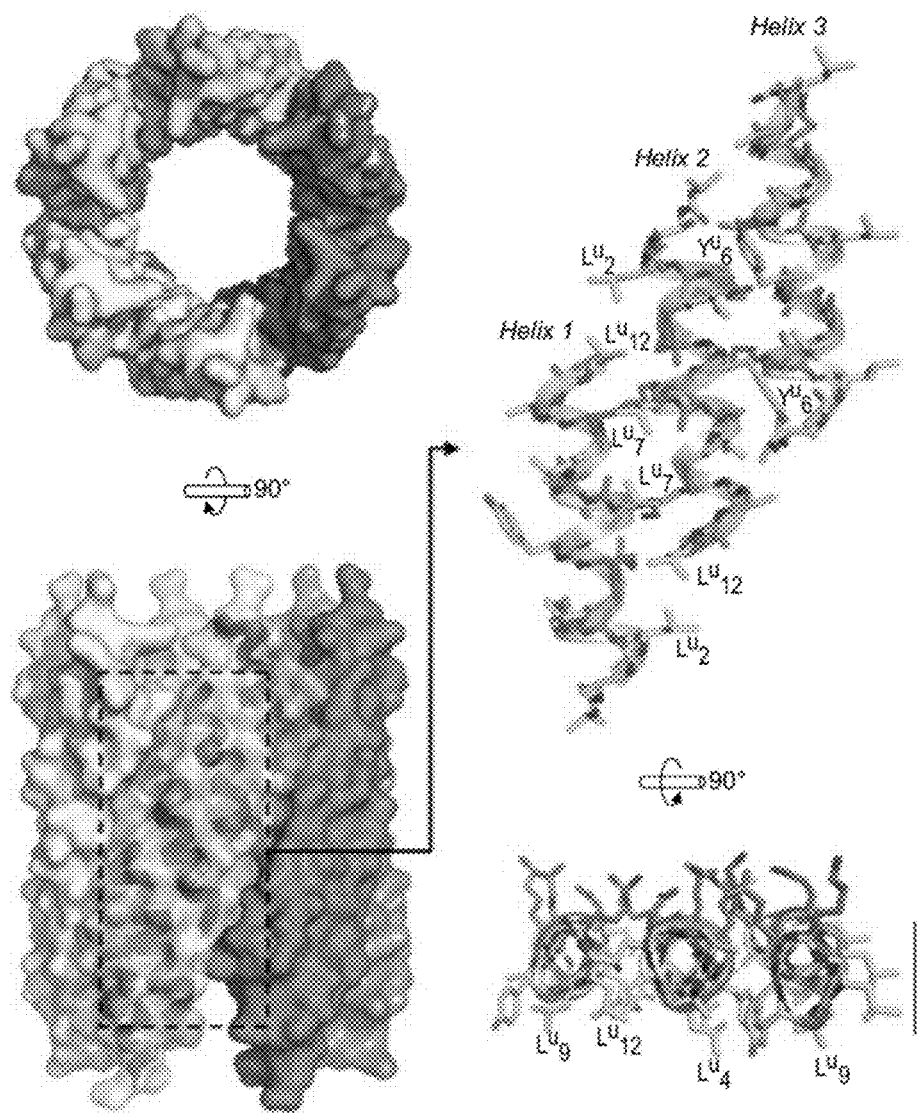
Figure 5A:
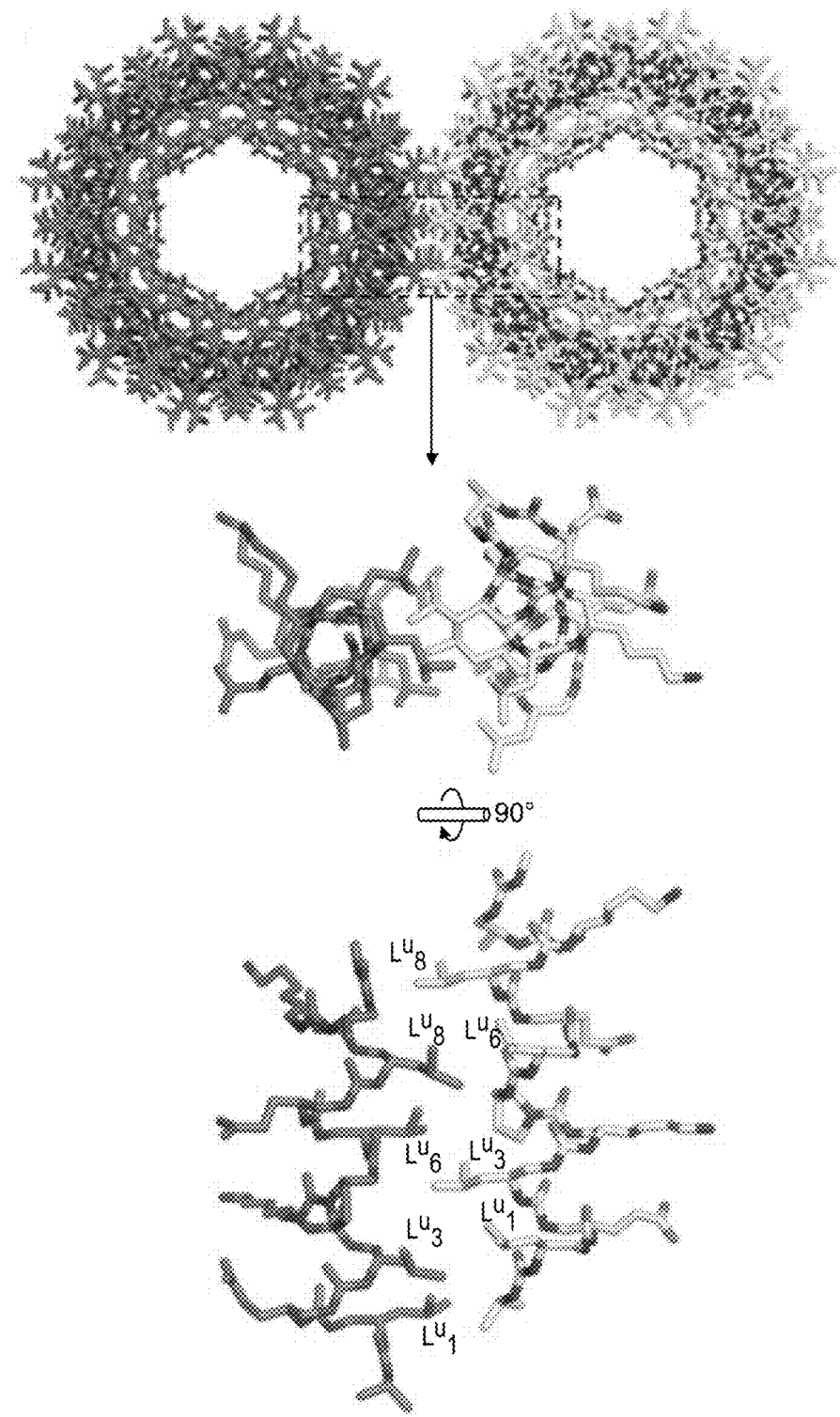
FIGS. 5A and 5B. Crystal structures of H2 (5A) and H5 (5B) showing details of inter-channel hydrophobic packing interactions. Individual neighboring channels of both channel-type arrangements (i.e. H2 and H5) interact through dense hydrophobic packing contacts primarily involving the precise inter-locking of Leucine-type (L$^u$) side-chains.
Figure 5B:
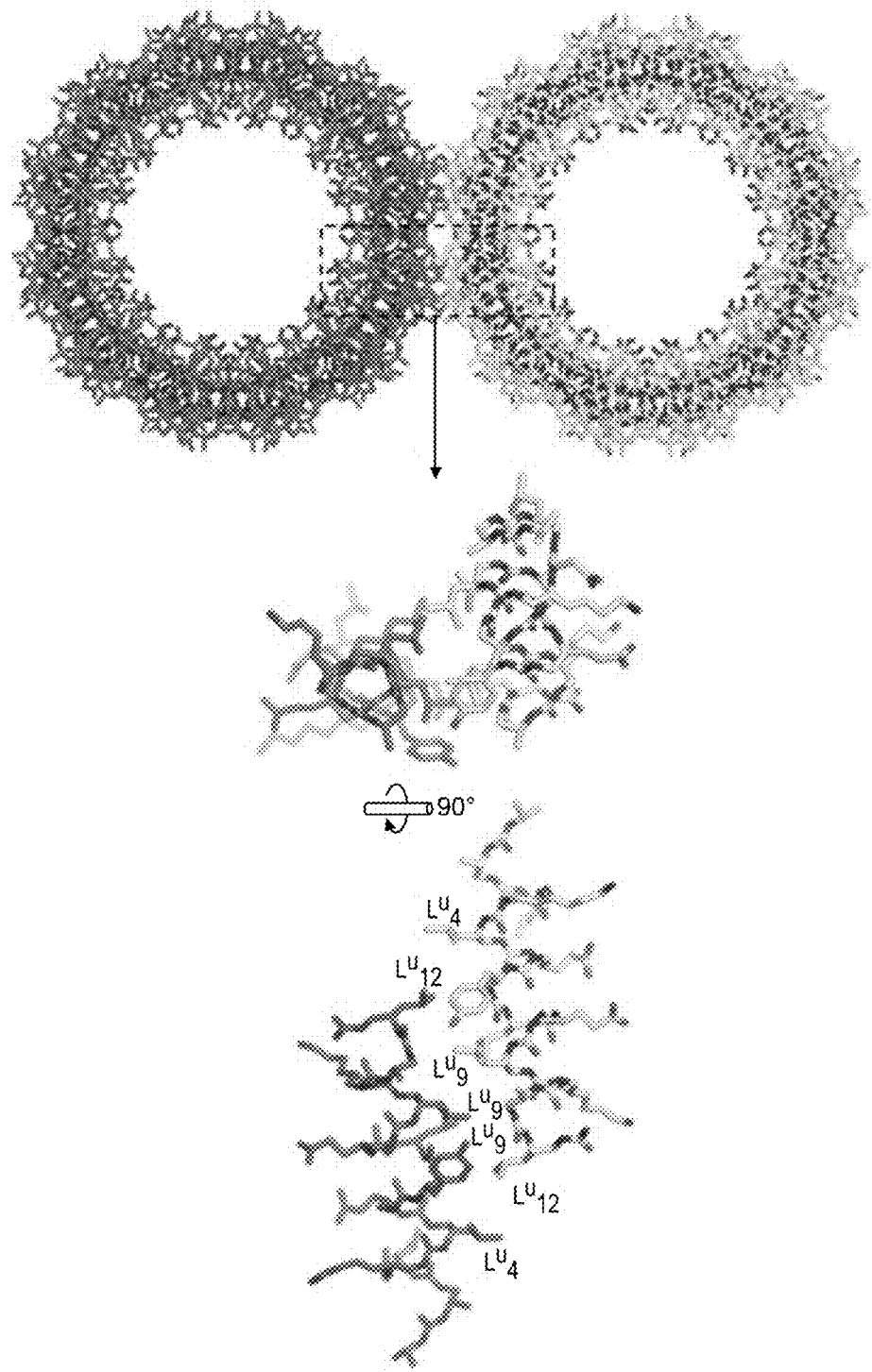

The crystal structure of H1 reveals a non-cylindrical helical-bundle formed from the assembly of six well-defined canonical oligourea helices, with a hydrophobic Leu$^u$-rich core and a charged, hydrated exterior (FIGS. 1B and E). As anticipated, hydrophobic interactions appear to play a key role in helical bundle assembly, with all of the leucine-type side-chains orientated towards the central hydrophobic core of the bundle, the majority of them interlocking in a manner highly reminiscent of the 'knobs-into-holes' (KIH) type packing of natural α-helical bundles (Hill, R. B., et al. De novo design of helical bundles as models for understanding protein folding and function. *Acc. Chem. Res.* 33, 745-754 (2000); Woolfson, D. N. The design of coiled-coil structures and assemblies. *Adv. Protein Chem.* 70, 79-112 (2005); Harbury, P. B., et al. High-resolution protein design with backbone freedom. *Science* 282, 1462-1467 (1998); and O'Shea, E. K., et al. X-ray structure of the GCN4 leucine zipper, a two-stranded, parallel coiled coil. *Science* 254, 539-544 (1991)) (FIG. 1D and FIG. 3). The helical bundle is formed from three H1 dimers, each dimer being composed of two anti-parallel helices held together by: 1) $Leu^u$-$Leu^u$ packing interactions and 2) a mirrored hydrogen bond between the amine of the $Lys^u_8$ side-chain and the free carbonyl group of the C-terminal $Leu^u_{11}$ residue (FIG. 3). Three such dimers interact primarily through further hydrophobic $Leu^u$-$Leu^u$ interactions to form a complete discrete hexameric helical bundle—a stoichiometry which is rare among α-peptide helical bundles (Zaccai, N. R. et al. A de novo peptide hexamer with a mutable channel. *Nat. Chem. Biol.* 7, 935-941 (2011)), and unheard of amongst foldamer helical bundles. No salt-bridges are observed within the oligourea helical bundle—despite the inclusion of four chargeable residues per helix—highlighting the significant role played by hydrophobic forces in bundle assembly. Also unexpected was the discovery of an isolated cavity within the hydrophobic core of the bundle (FIG. 1E). The cavity has a volume of 491.3 Å$^3$ and is therefore theoretically well-suited for the encapsulation of guest molecules in the size-range of, for example, pharmaceutical compounds.

Figure 1F:
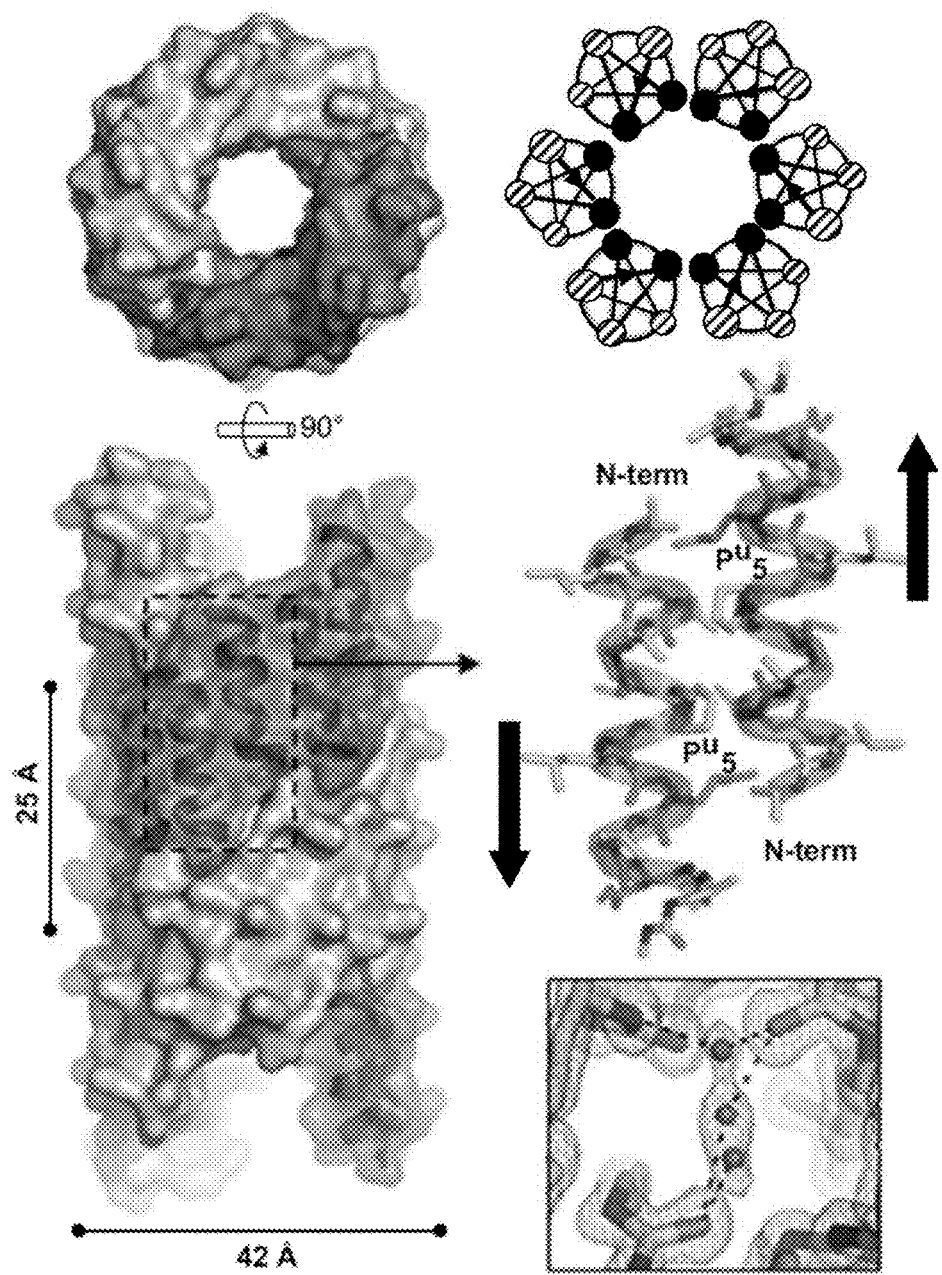
Figure 6A:
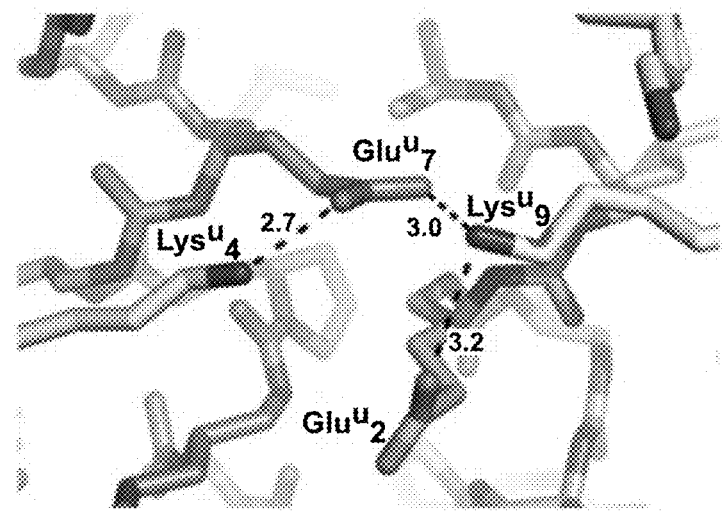
FIGS. 6A and 6B. Crystal structures of H2 (6A) and H5 (6B) illustrating electrostatic contacts within the charged pores of the channel-type quaternary assemblies. Inter-helical salt-bridges within the interior channel pores of both channel crystals structures link adjacent as well as distant helices forming 'zipper-type' salt-bridge networks of electrostatic contacts. Distinct oligourea molecules are distinguished by carbon color.
Figure 6B:
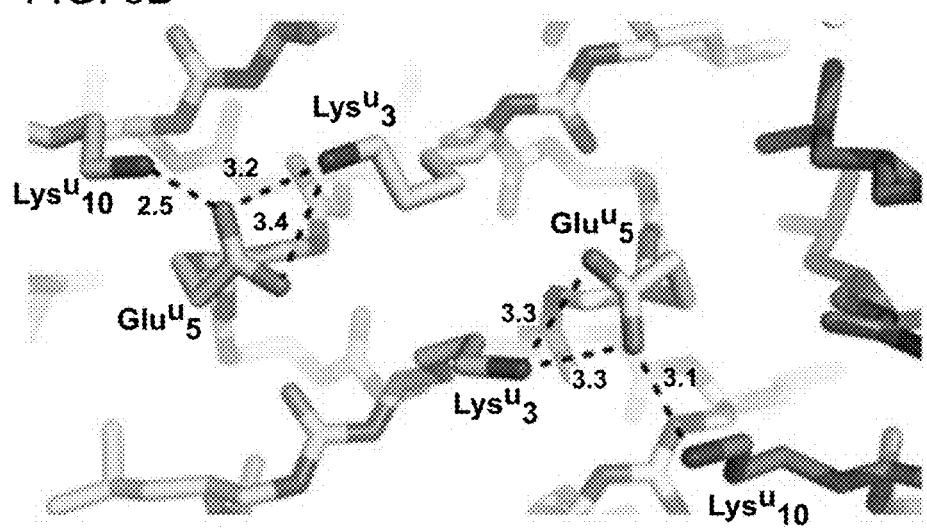

In contrast to oligourea H1, the crystal structure of H2 reveals higher-order assemblies of a dramatically different arrangement, with the H2 oligourea helices organizing to create an extended channel-type assembly with a highly charged, water-filled interior pore with an internal diameter of 17 Å (FIGS. 1C and 1F). The exterior surface is composed entirely of hydrophobic $Leu^u$, $Ala^u$ and $Pro^u$ residues, which pack in a dense and precise manner, with the interior pore composed entirely of charged $Lys^u$ and $Glu^u$ residues. The channel-type assembly is composed of two intertwined right-handed super-helices, with each super-helix composed of individual canonical oligourea helices packed in a staggered side-by-side manner (with 12 oligourea helices per super-helical turn), locked together by a combination of hydrophobic packing interactions and extensive inter-helical salt-bridges (FIG. 1F and FIGS. 4A, 4B, 5A, and 5B). Indeed, salt-bridges appear to play a major role in stabilizing the channel structure, as the majority of the chargeable side-chains are involved in intermolecular electrostatic contacts, forming intricate networks of salt-bridges linking adjacent and distal oligourea molecules (FIGS. 6A and 6B). The hydrophilic pore of the channel is heavily hydrated, and analysis of the electron density maps reveals the presence of both well-ordered and mobile water molecules (FIG. 1F, inset). This evidence of molecular mobility within the pore raises the possibility that such channels could potentially be of use within the context of, for example, ion conductance (Lear, J. D., et al. Synthetic amphiphilic peptide models for protein ion channels. *Science* 240, 1177-1181 (1988)). In order to more fully understand the nature of the assemblies observed crystallographically, a series of biophysical and solution analyses on molecules H1 and H2.

Biophysical Characterization and Molecular Basis of Bundle Formation of Oligourea H1.

Figure 7A:
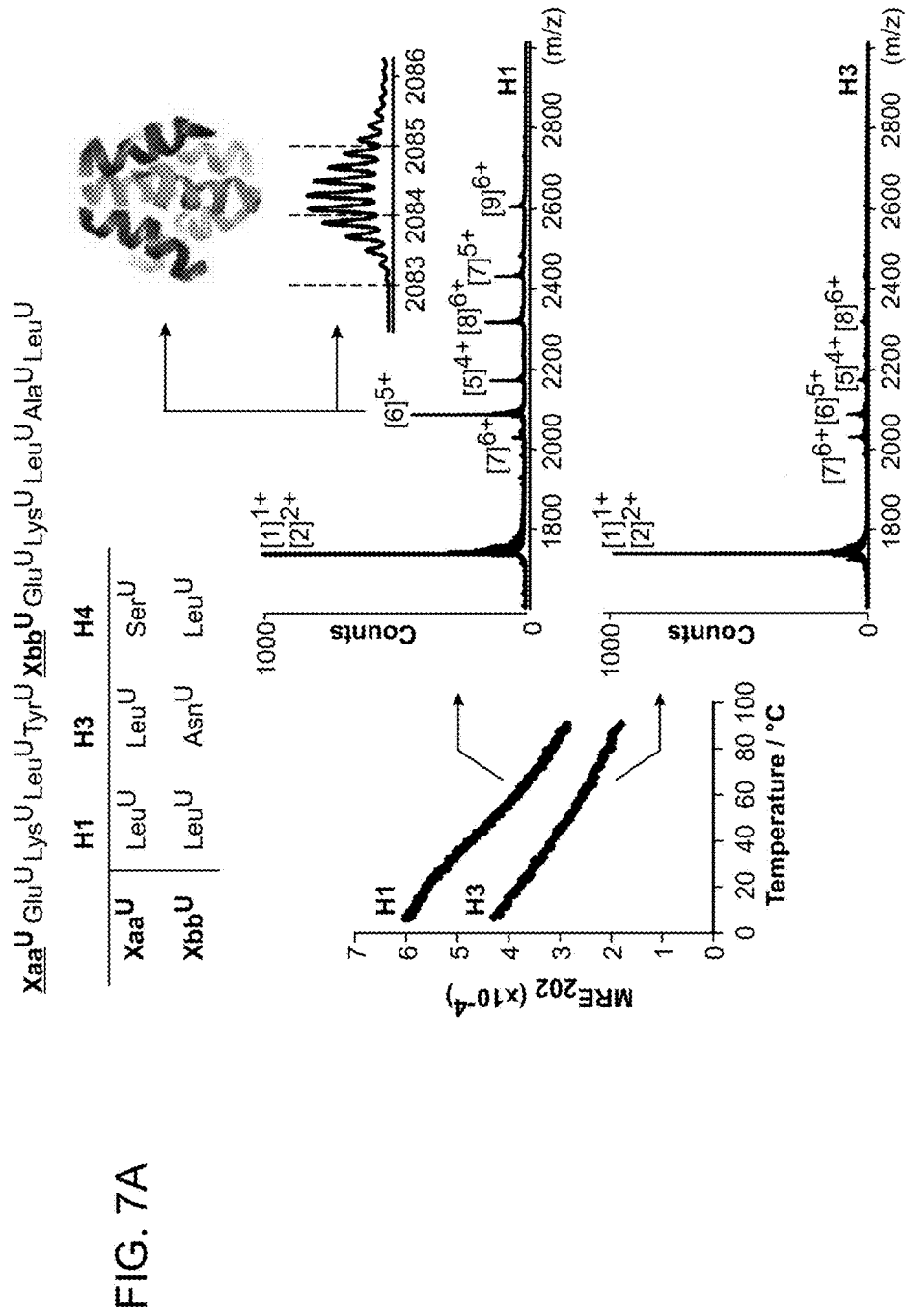

The stoichiometry of the H1 helical bundle evidenced by the crystal structure was investigated by native electrospray ionization mass spectrometry (ESI-MS), a technique well-suited for the detection and investigation of non-covalent assemblies (Lai, Y.-T. et al. Structure of a designed protein cage that self-assembles into a highly porous cube. *Nat. Chem.* 6, 1065-1071 (2014); and Hernandez, H. & Robinson, C. V. Determining the stoichiometry and interactions of macromolecular assemblies from mass spectrometry. *Nat. Protoc.* 2, 715-726 (2007)). Native ESI-MS analysis of a 100 µM solution of H1 (in 20 mM aqueous ammonium acetate) reveals a predominant multimer species with an m/z of 2083.4—attributed unambiguously to a hexameric species ($[H1_6]^{5+}$), and therefore in excellent agreement with the crystal structure (FIG. 7A). In order to corroborate this result, a third oligourea (H3) was synthesized as a negative control. H3 is analogous to H1, but bears an asparagine-type residue ($Asn^u$) at position six (FIG. 7A, top). This mutation results in the insertion of a highly hydrophilic residue ($Asn^u$) within an otherwise fully hydrophobic helical face, and was believed it would impair the ability of this foldamer to self-assemble. The analysis of H3 by ESI-MS under the same conditions as H1 revealed no such predominant hexameric species (FIG. 7A), suggesting the hexameric species present in the H1 spectrum to be significant. CD-monitored thermal melting experiments support the ESI-MS data, with H3 revealing a significantly reduced thermal melting profile compared to H1 (FIG. 7A). A $T_m$, of 45.9° C. can be derived from the melting profile of H1 shown in FIG. 7A, suggesting that the helical bundle formed by H1 has a certain degree of molten-globule-like character, which may be explained by the absence of salt-bridges evident from the crystal structure.

Figure 7B:
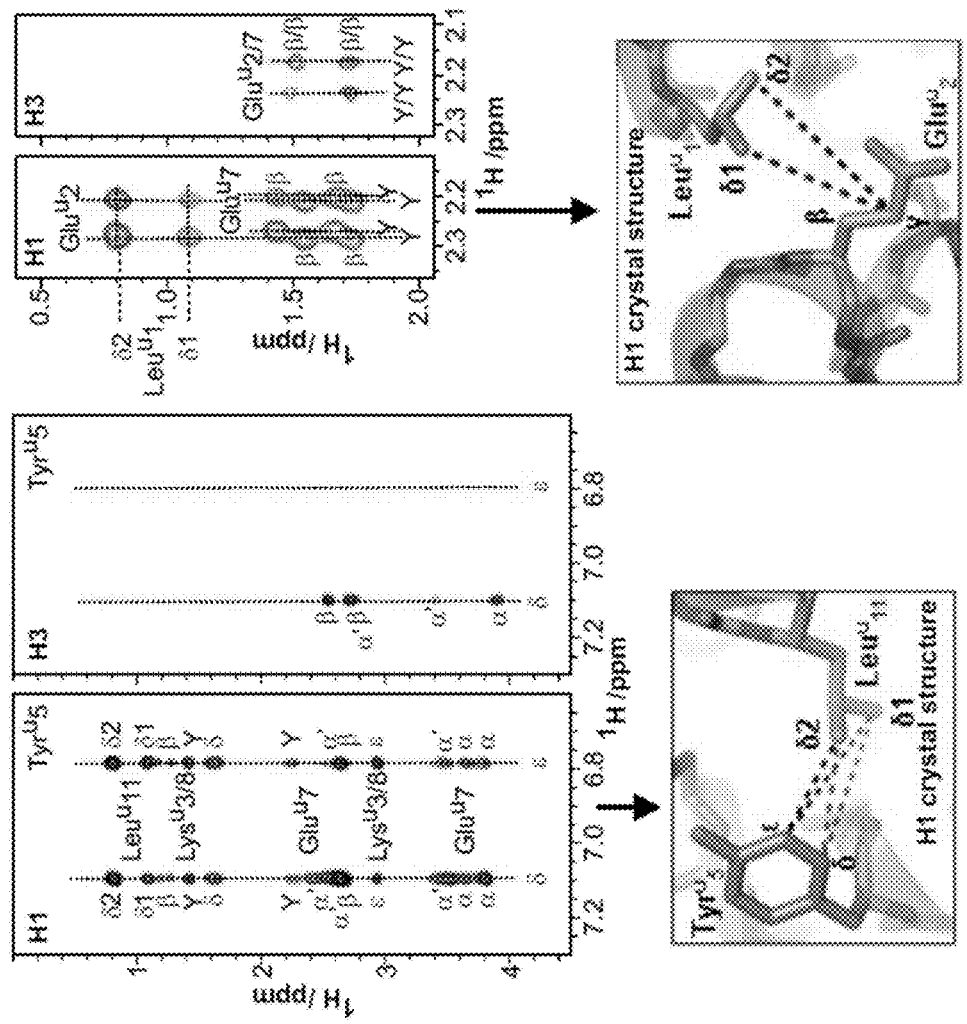
Figure 8A:
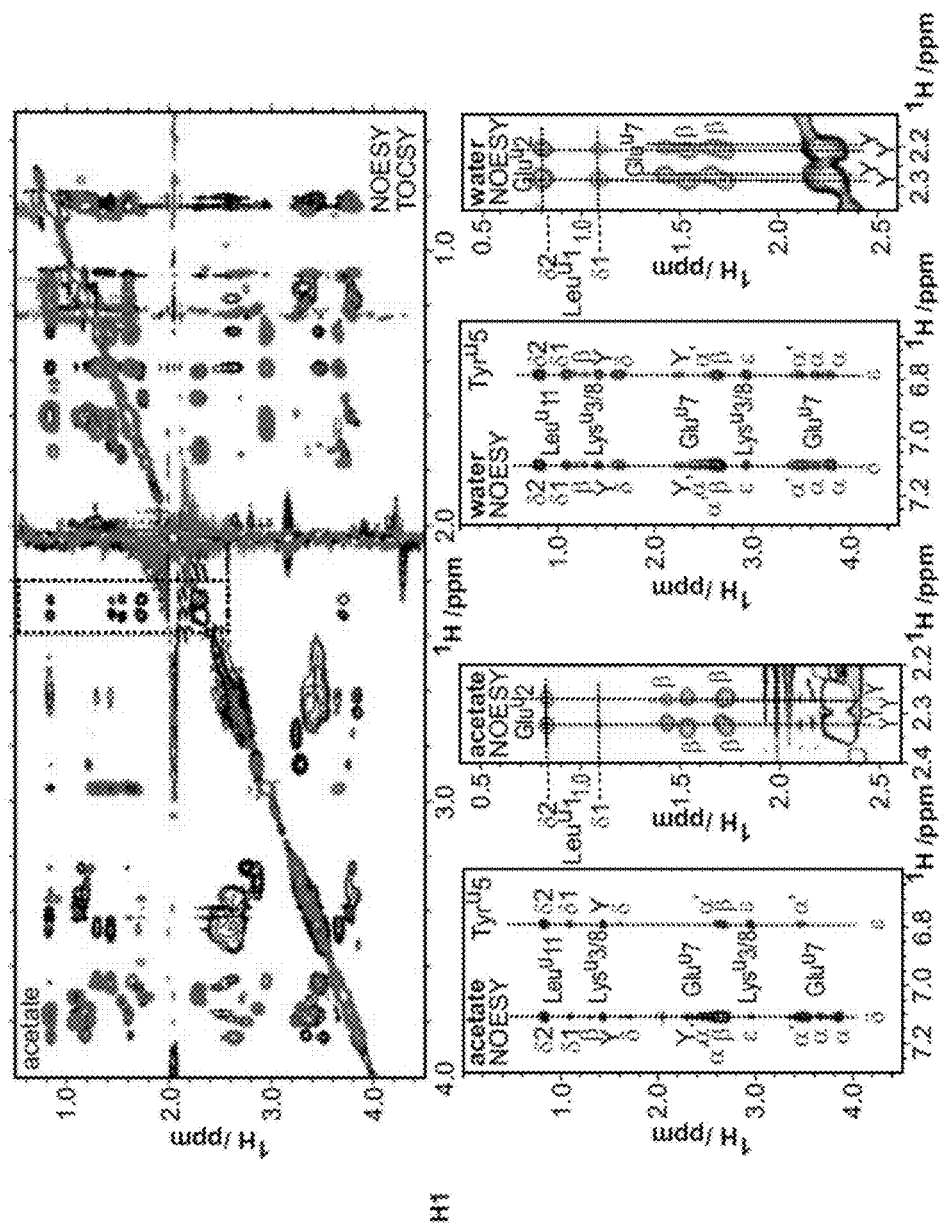
FIGS. 8A and 8B. Through-bond ($^1$H,$^1$H-TOCSY) and through-space ($^1$H,$^1$H-NOESY) spectra for the characterization of H1 (8A) and H3 (8B) in solution. Overlay of the NOESY (200 ms mixing time, black spectra) and TOCSY (80 ms mixing time, red spectra) demonstrate that only H1 has NOE crosspeaks between $^1$H nuclei that are long-range and not simply constrained by one or two bonds. For H3 only the geminal $^1$Hα' nuclei bound to the backbone urea Cα' show significant NOE crosspeaks (~2.8 ppm and ~3.2 ppm). Close-up views of the NOESY spectra for the Tyr$^u$5 $^1$Hδ and $^1$Hε aromatic protons and the Glu$^u$ $^1$Hγ aliphatic protons show a similar behavior for H1 and H3 in sodium acetate buffer (20 mM sodium acetate, pH 4.0, 98% $^2$H$_2$O) as compared to water (100% $^2$H$_2$O). The water spectra are the same as those in FIG. 2b. Note: side-chain atomic nomenclature here follows that of natural amino acid side-chains.
Figure 8B:
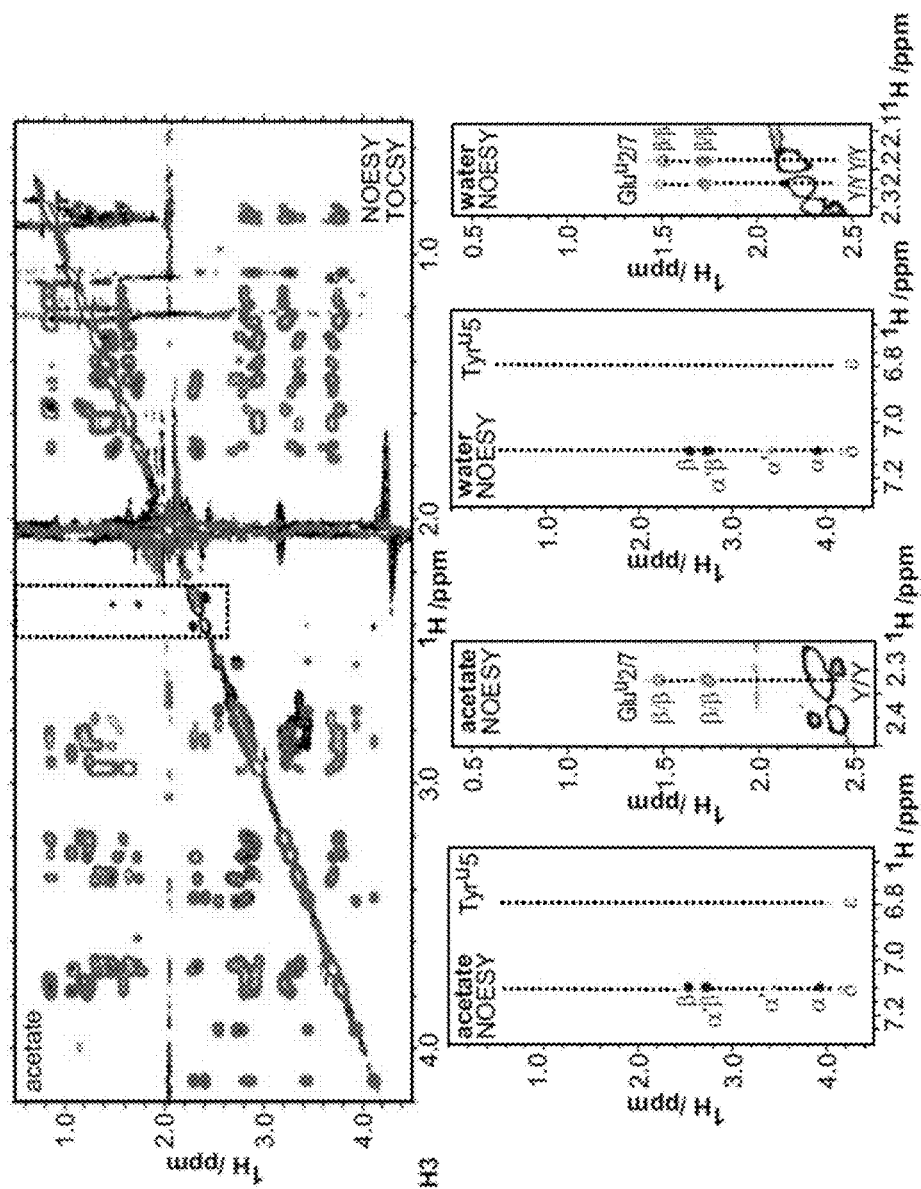
Figure 9A:
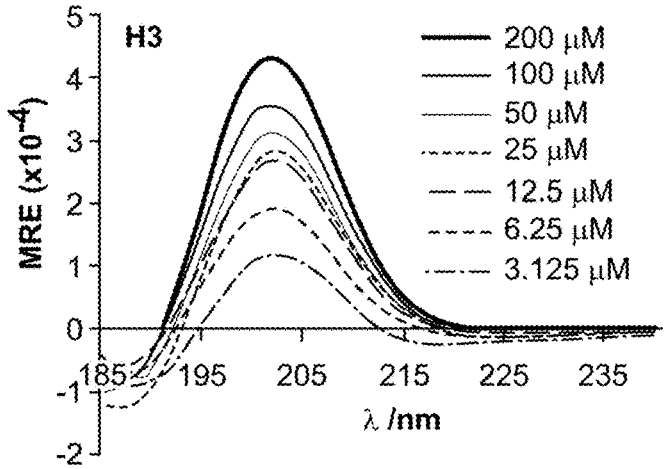
FIGS. 9A, 9B, 9C, and 9D. Circular dichroism (CD) and DOSY analysis of oligourea H3 and comparison to H1.
Figure 9B:
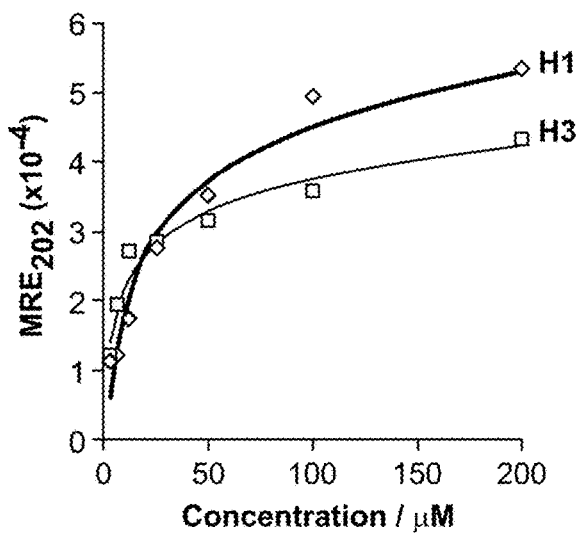
Figure 9C:
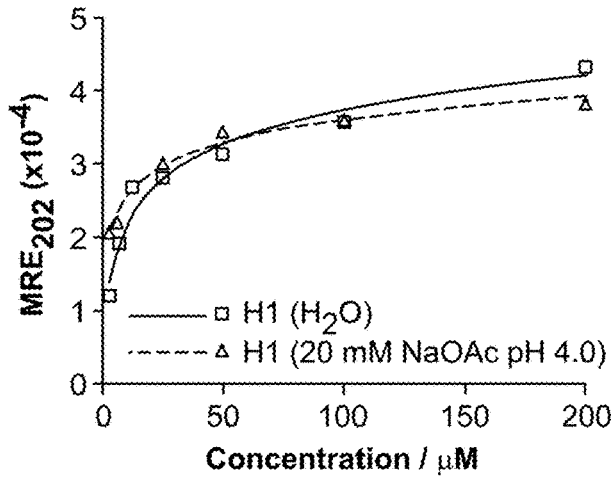
Figure 9D:
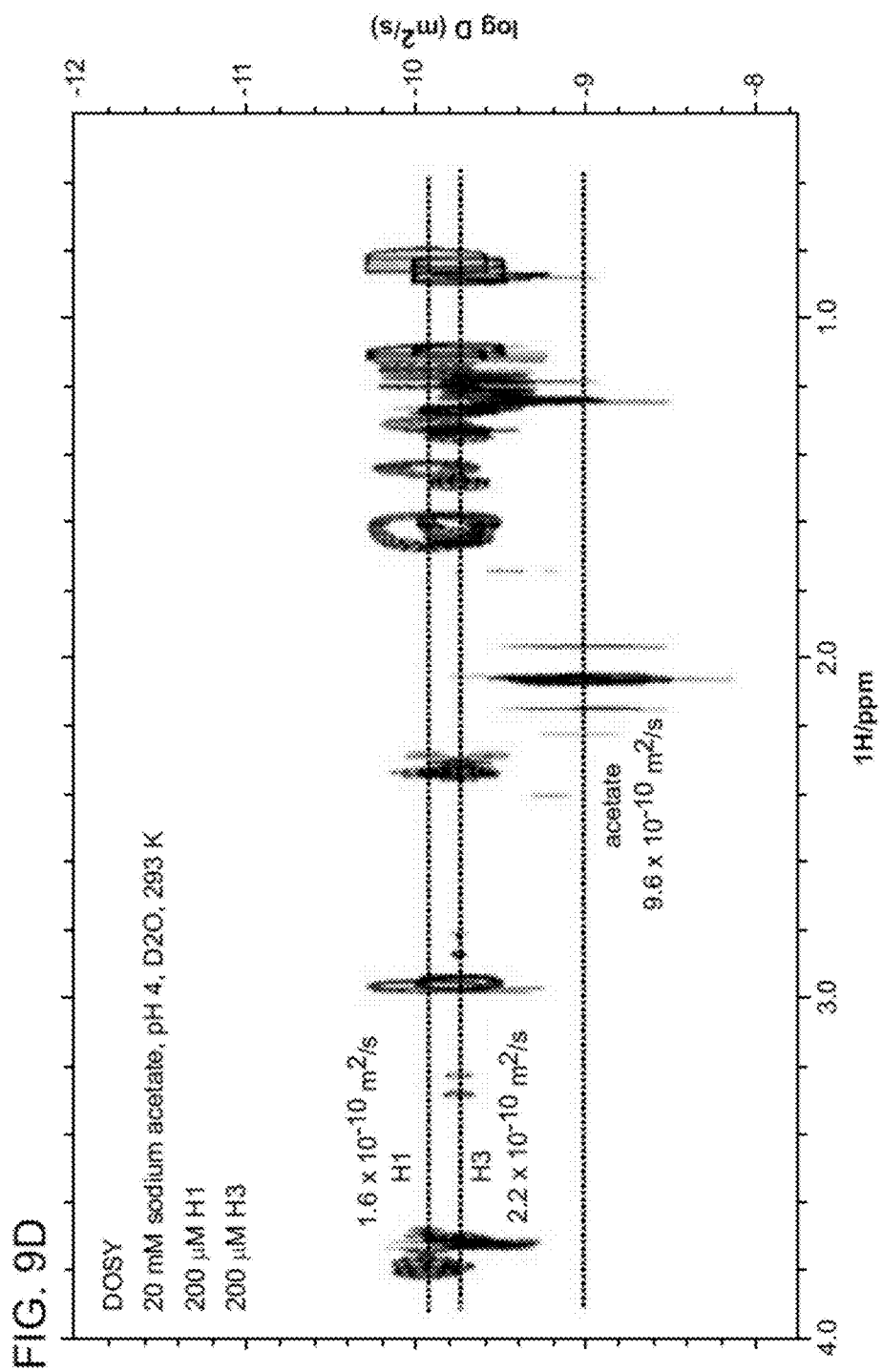
Figure 10A:
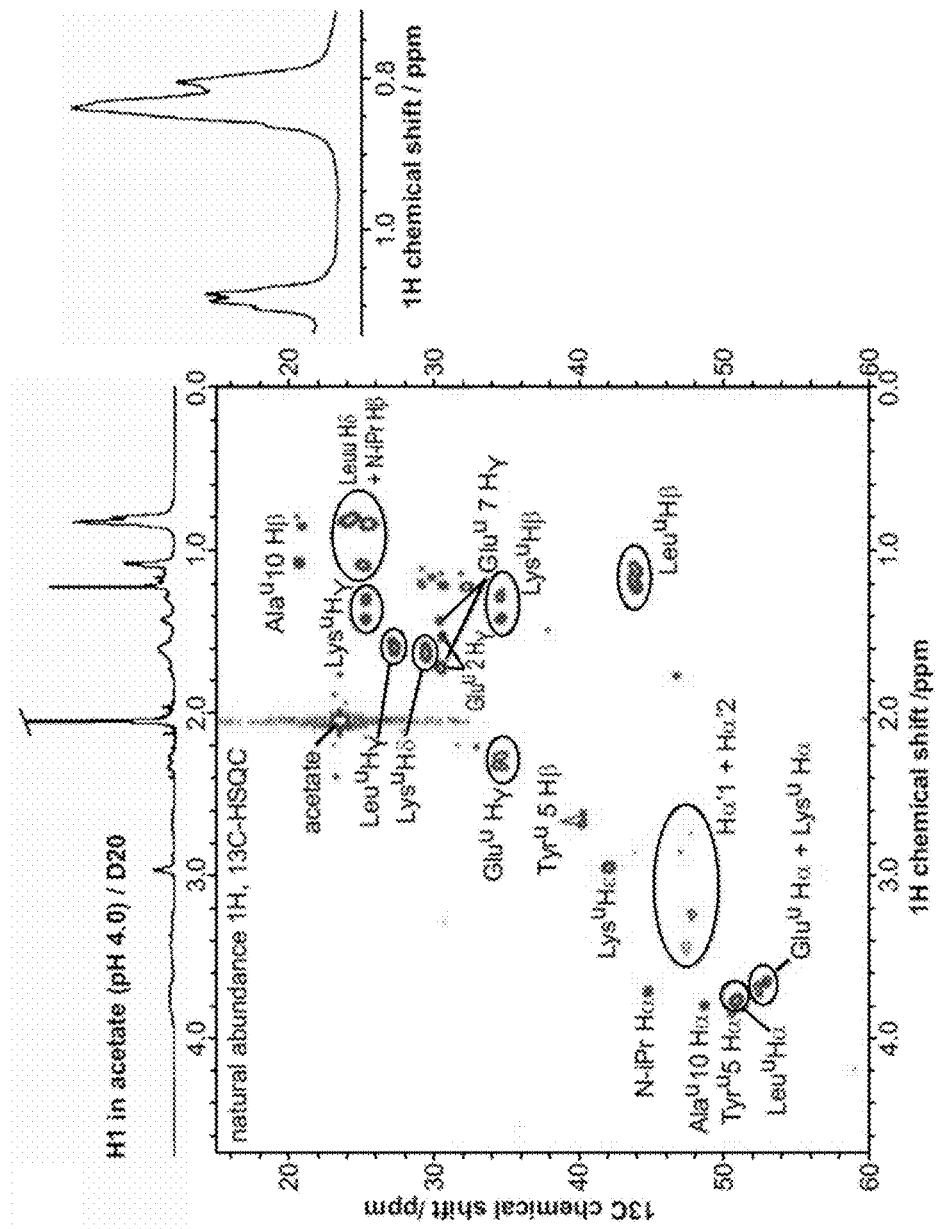
FIGS. 10A and 10B. Annotated natural abundance $^1$H,$^{13}$C-HSQC spectra for H1 (10A) and H3 (10B). Each sample contains 200 µM oligourea monomers resuspended in 20 mM sodium acetate buffer, pH 4.0, with 98% $^2$H$_2$O. The spectra were collected at 800 MHz at a temperature of 293 K. Chemical shift assignments were based on $^1$H,$^1$H-TOCSY (80 ms mixing time) and $^1$H,$^1$H-NOESY (200 ms mixing time) spectra. Above each HSQC is a representative $^1$H one-dimensional spectrum, with a closeup view of the $^1$H methyl region shown to the right. Note that the line-widths of the methyl groups in H1 are significantly broadened as compared to H3, which is consistent with the formation of an assembled multimeric complex with H1, whereas H3 has narrow line-widths as expected for a monomeric species. There is a high degree of degeneracy in most residues, as noted for example by the narrow range of the backbone Leu$^u$ $^1$Hα-$^{13}$Cα chemical shifts as well as the remaining Leu$^u$ aliphatic nuclei for the five Leu$^u$ sidechains in H1 and the four Leu$^u$ in H3. Peaks with an asterisk derive from impurities in the sodium acetate buffer. Side-chain atomic nomenclature here follows that of natural amino acid side-chains.
Figure 10B:
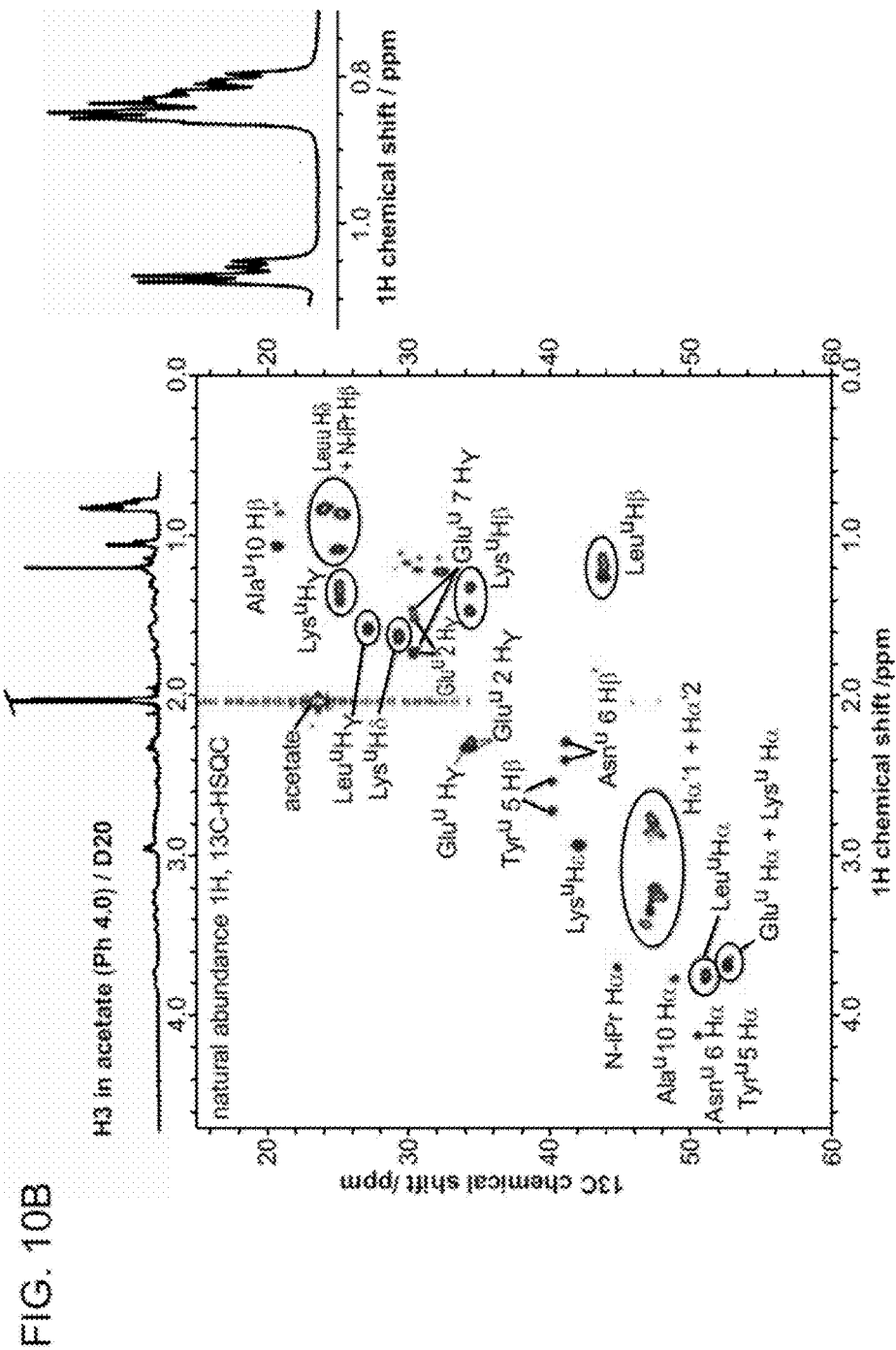

With the aim of investigating atomic-scale details of intermolecular interactions in solution, H1 and H3 were studied by high-field NMR. NOESY analysis of H3 (at a concentration of 200 µM in either 100% D$_2$O or in 98% D$_2$O, 20 mM sodium acetate, pH 4.0) indicates a predominantly monomeric species, with no evidence of specific intermolecular interactions (FIG. 7B and FIG. 8). Variable-concentration CD analysis of oligourea H3 (from 3.125 µM to 200 µM) shows this molecule unexpectedly displays a propensity to self-assemble only slightly lower than that of H1 (FIG. 9A-9C), suggesting that H3 may still self-associate to some degree in aqueous conditions, albeit into highly-dynamic and unstable assemblies of low stoichiometry. The relative size of H3 compared to H1 in aqueous conditions was investigated further by DOSY analysis, which indeed indicates—albeit qualitatively—that H3 is noticeably smaller than H1 in aqueous conditions (FIG. 9D). In contrast to H3, NOESY analysis of H1 under the same conditions provides clear evidence of specific, stable helix-helix intermolecular interactions—for example, strong NOE cross-peaks can be seen corresponding to interactions between the aromatic δ or ε protons of $Tyr^u_5$ side-chains and the aliphatic δ1 or δ2 protons of $Leu^u_{11}$ side-chains (FIG. 7B, left and FIGS. 8A and 8B). As $Tyr^u_5$ and $Leu^u_{11}$ are positioned on opposite faces of the helix (FIG. 1B), these NOE signals necessarily correspond to specific intermolecular interactions. Similarly strong intermolecular NOEs can also be seen between the aliphatic protons of $Leu^u_1$ side-chains and those of Glu$^u_2$ side-chains from a different chain (FIG. 7B, right and FIG. 8). Importantly, these intermolecular NOEs correlate remarkably well with the crystal structure of H1 (FIG. 7B, insets), and provide strong evidence that the helical bundle of H1 observed in the crystal state is indeed representative of the quaternary structure of this foldamer in solution. Additional NMR data (including detailed peak assignments for H1 and H3) is shown in FIGS. 8A, 8B, 10A, and 10B).

Figure 11A:
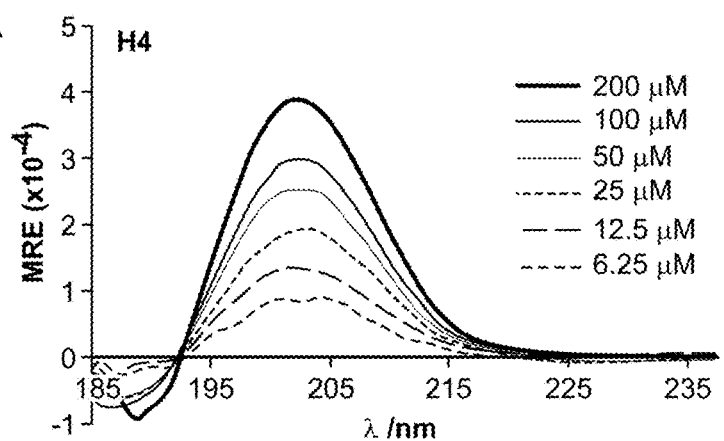
FIGS. 11A, 11B, 11C, 11D, and 11E. Solution studies of oligourea H4.
Figure 11B:
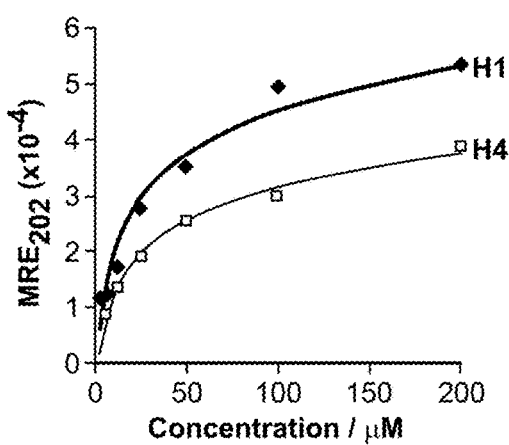
Figure 11C:
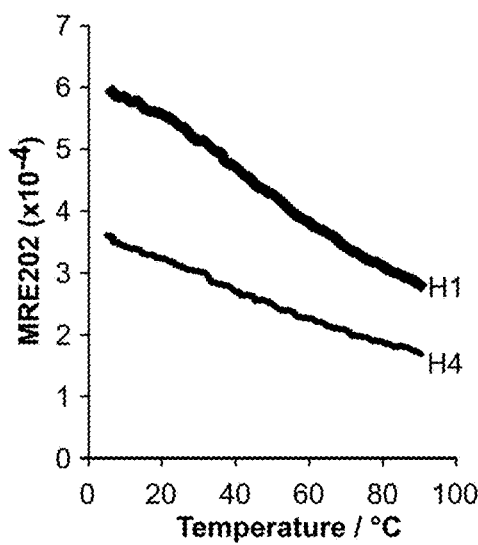
Figure 11D:
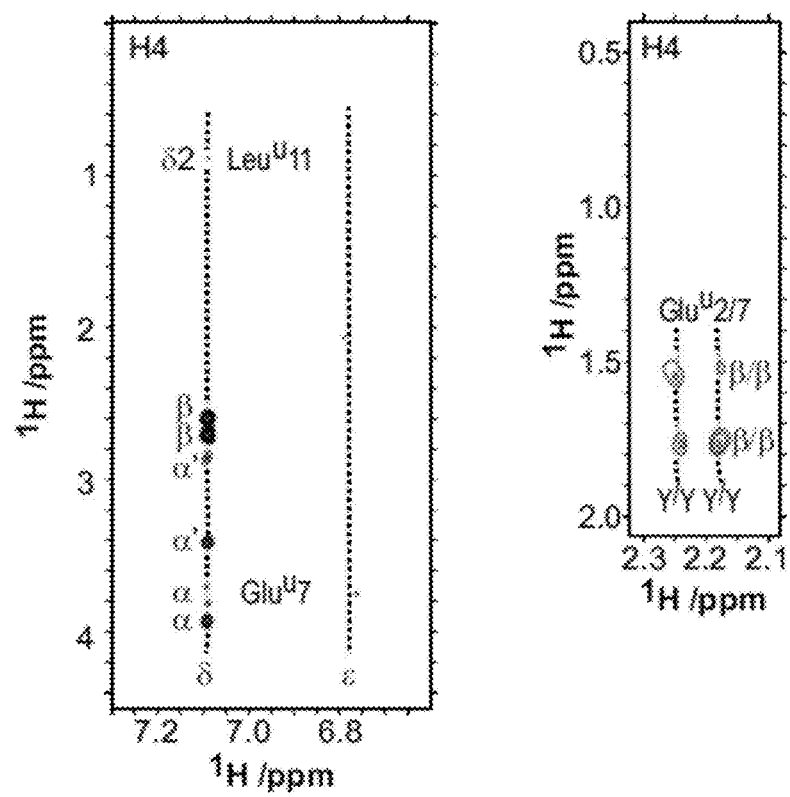
Figure 11E:
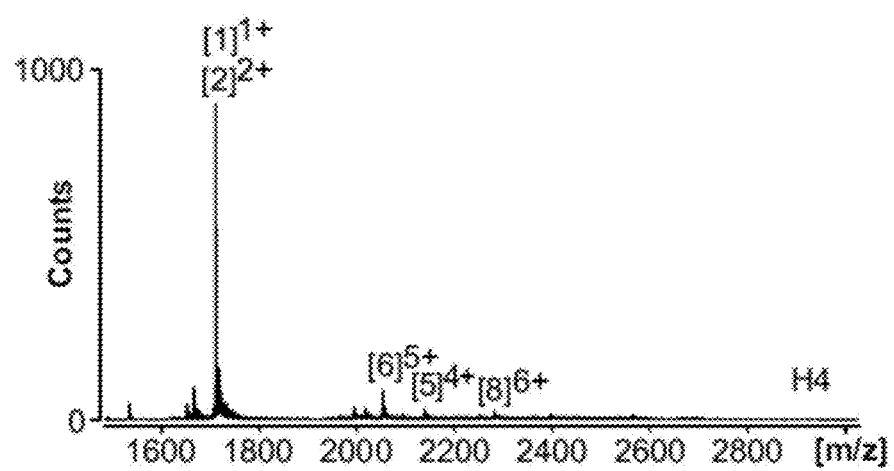

In order to test whether the hexameric helical bundle arrangement formed by oligourea H1 was structurally robust, we designed and synthesized an analogue of H1 bearing a serine-type urea residue (Ser$^u$) in place of Leu$^u_1$ (oligourea H4) (FIG. 7A). Leu$^u_1$ was chosen for modification for at least the following reasons: 1) from the crystal structure of H1 it is clear that, although this residue is orientated towards the hydrophobic core of the bundle, it does not appear to contribute extensively to the KIH-like packing of the remaining Leu$^u$ residues (FIG. 3A), and 2) as a means to corroborate the intermolecular NOE Leu$^u_1$-Glu$^u_2$ interactions of H1 described above. As with oligourea H1, a crystal structure was determined for H4 (refined to 1.69 Å), revealing a hexameric helical bundle almost identical to that formed from H1 (Cα r.m.s.d., 0.379 Å) (FIG. 7C). The incorporation of six Ser$^u$ urea residues within the hexameric H4 helical bundle results in the formation of water-bridged networks at the three-way N-terminal helix junctions, thereby increasing the number of indirect inter-helical contacts compared to the H1 bundle (FIG. 7C, right). As with the H1-bundle, the H4-bundle also contains an isolated hydrophobic cavity, with a comparable yet slightly larger volume of 519.5 Å$^3$. Variable-concentration CD experiments, CD-monitored thermal melting, native ESI-MS, and NMR studies all demonstrate H4 to possess a tendency to self-assemble similar yet noticeably reduced compared to H1, suggesting an important, but non-essential role, played by Leu$^u_1$ in bundle formation (FIGS. 11A, 11B, and 11C). In addition, the NOE peak corresponding to intermolecular Leu$^u_1$-Glu$^u_2$ interactions is absent in the H4 NOESY spectra, confirming the assignment of this interaction in the H1 spectra.

Solution and Imaging Studies of Oligourea H2.

Figure 12A:
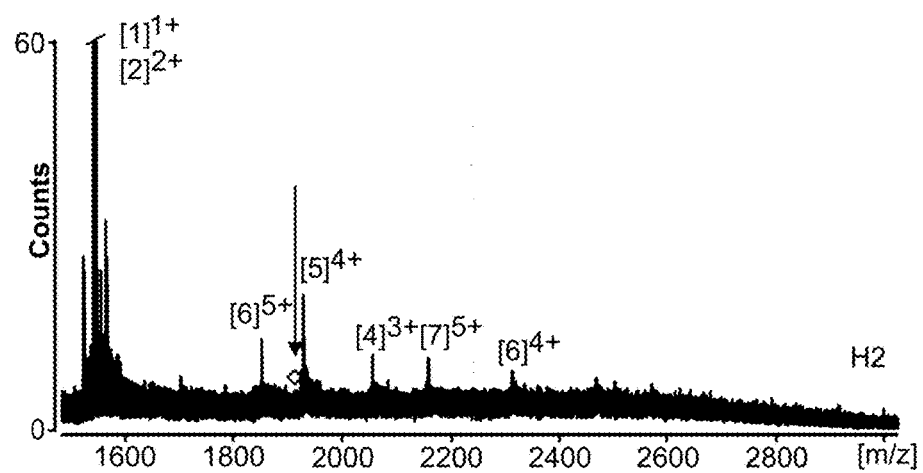
FIGS. 12A, 12B, 12C, 12D, 12E, 12F, 12G, 12H, and 12I. Solution studies of channel-forming oligoureas H2 and H5.
Figure 12B:
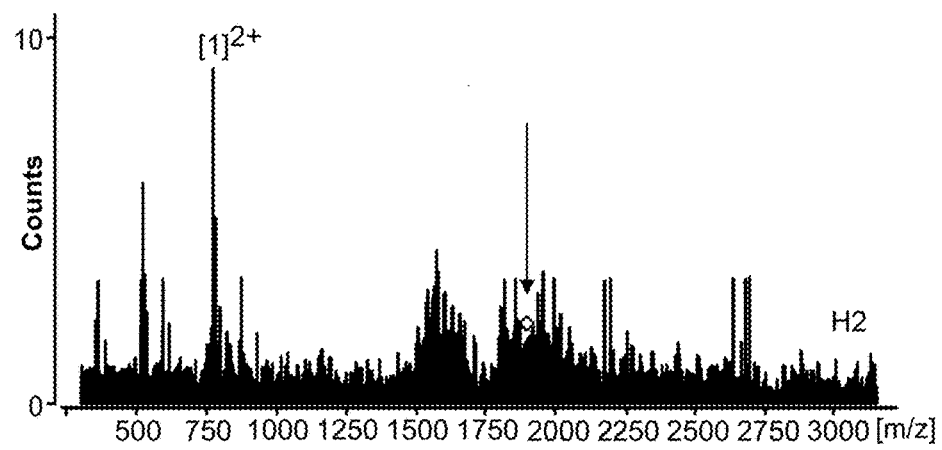
Figure 12C:
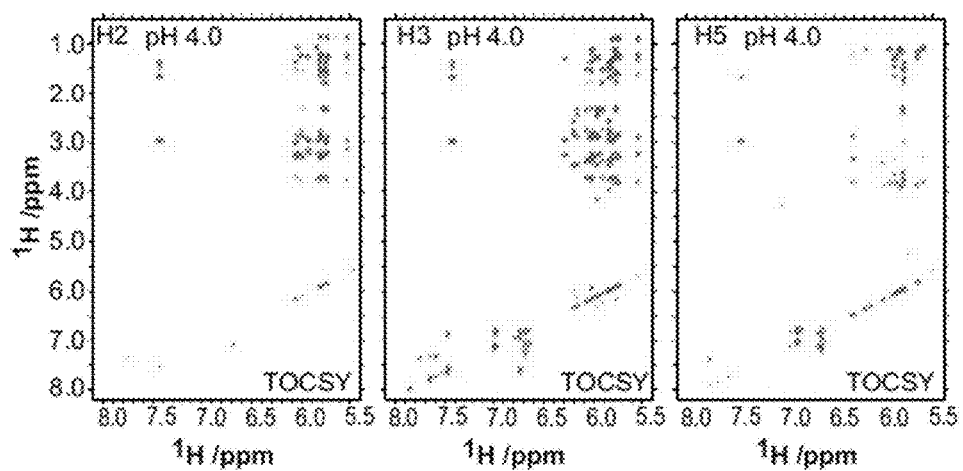
Figure 12D:
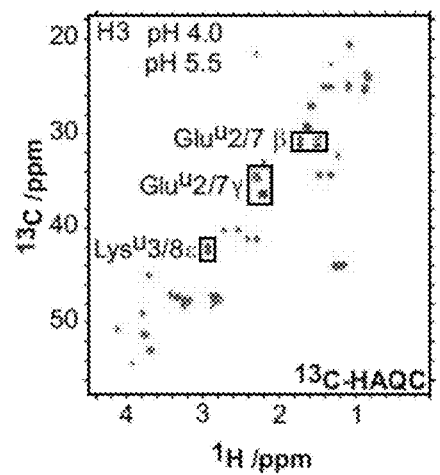
Figure 13A:
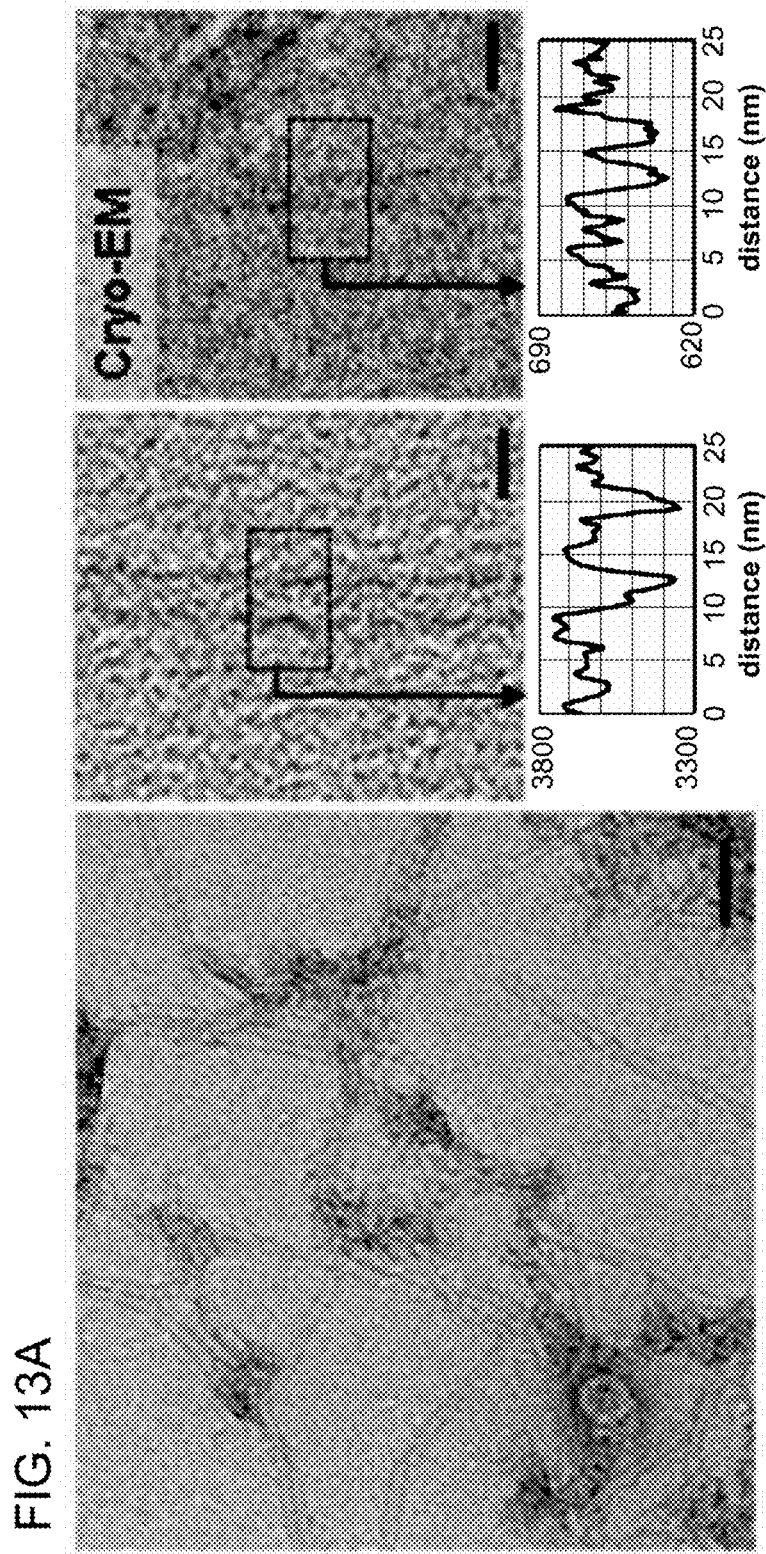
FIGS. 13A, 13B, 13C, and 13D. Solution and solid-state studies of channel-forming oligourea foldamers H2 and H5.
Figure 14:
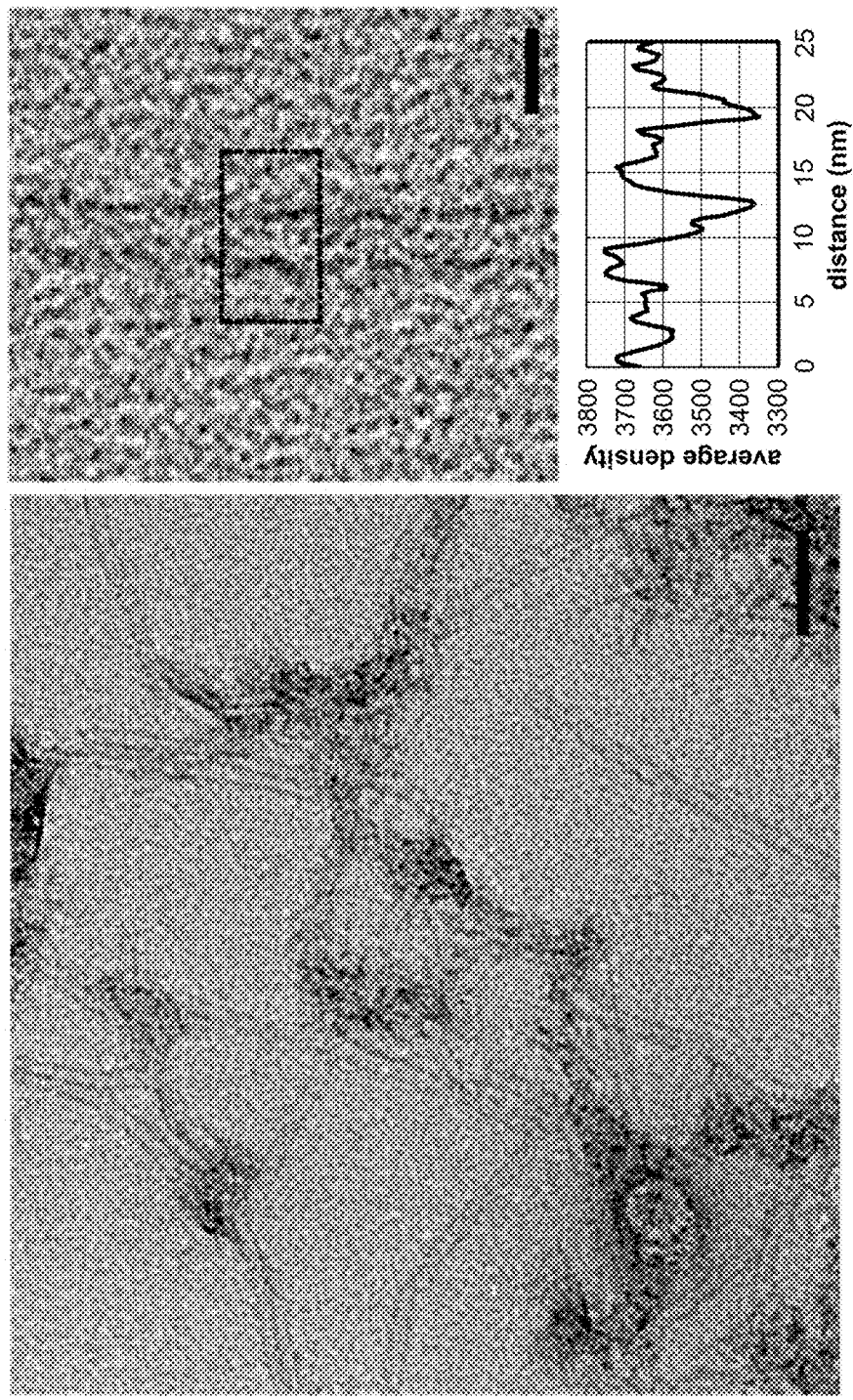
FIG. 14. Negative staining electron microscopy analysis of H2: enlarged view of FIG. 3a, left and middle panels. H2 analyzed at a concentration of 200 μM in a buffer composed of 50 mM sodium HEPES, pH 7.5.
Figure 15:
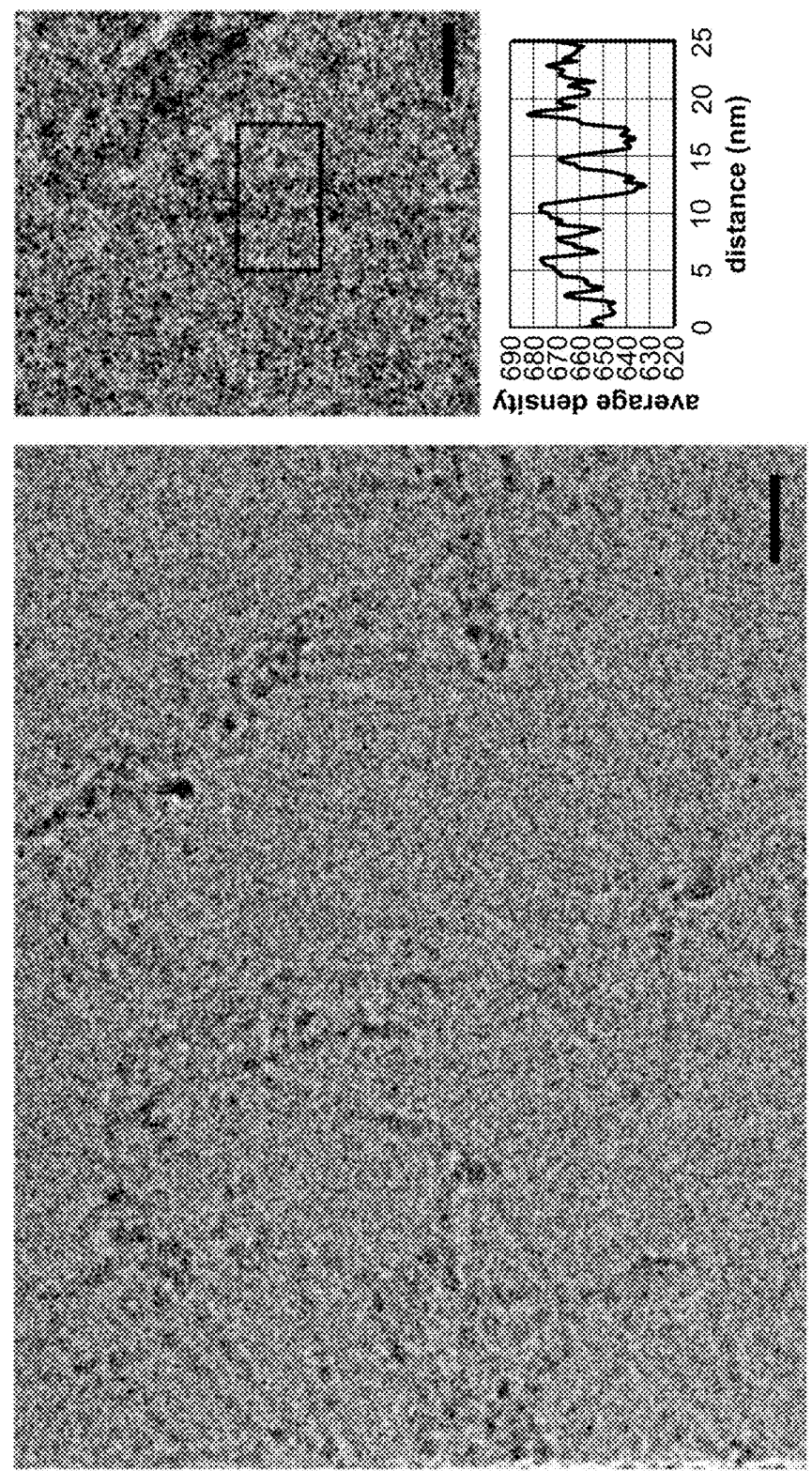
FIG. 15. Cryo-electron microscopy analysis of H2: enlarged view of FIG. 3a, right panel. H2 analyzed at a concentration of 200 μM in a buffer composed of 50 mM sodium HEPES, pH 7.5.

The dramatically different quaternary assembly formed by H2 compared to H1 in the crystal state was corroborated by solution and biophysical studies. Native ESI-MS analysis of H2 (in 20 mM aqueous ammonium acetate) revealed a significant reduction in discrete multimeric species in the spectra as compared to H1 (FIG. 12A—cf. ion counts in FIG. 7A, recorded in identical conditions). MS/MS analysis indicates that this background noise is composed of H2 monomers (FIG. 12B)—in good agreement with the presence of non-discrete assemblies. Analysis of H2 by negative staining electron microscopy (EM) and cryo-EM under similar buffered sample conditions revealed the presence of extended homogeneous hollow tubular nanostructures with diameters of 7 and 4.6 nm, respectively (FIG. 13A and FIGS. 14 and 15). These observations by EM are fully consistent with the molecular arrangement observed in the crystal. The detection of tubular structures by cryo-EM—a true solution technique—provides particularly strong evidence in support of the ability of H2 to self-assemble into channel-type structures in aqueous conditions. NMR analysis of H2 (in 100% D$_2$O at pH 5.5) revealed an absence of distinct peaks within NOESY spectra, suggesting H2 to be almost fully multimeric/aggregated in these conditions. The equivalent NMR analysis of H2 performed at a lower pH of 4—a pH at which the Glu$^u$ side-chains would be expected to be protonated (and hence unable to form salt-bridges)— showed H2 to be predominantly monomeric (Supplementary FIG. 12C), further demonstrating the importance of electrostatic contacts in H2 self-assembly as evidenced by the crystal structure (see FIGS. 12C and 12D and legend for further details and discussion). By regulating the formation of intermolecular salt-bridges, pH may act as a control mechanism for channel/tubule formation.

Principles of Control of Oligourea Aqueous Self-Assembly and Channel Pore Diameter.

Figure 12E:
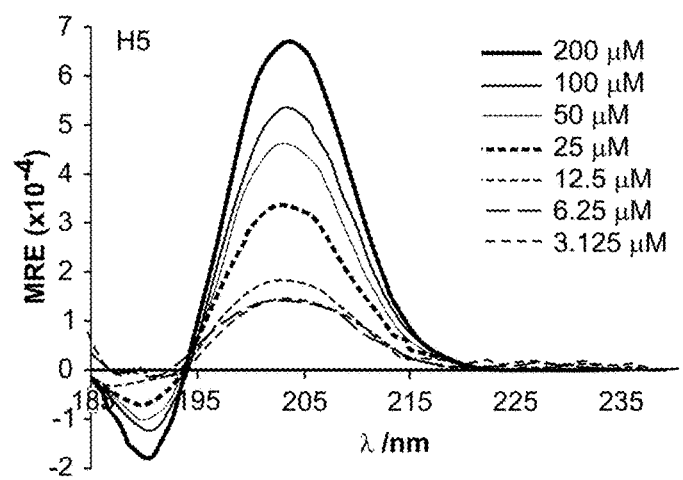
Figure 12F:
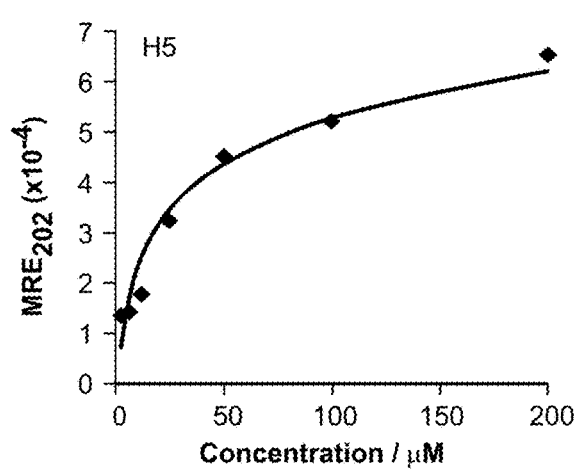
Figure 12G:
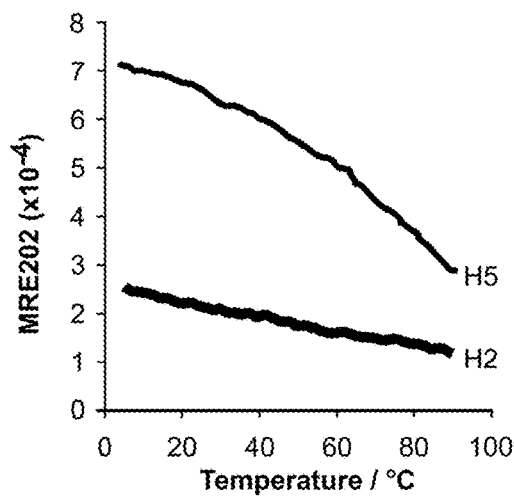
Figure 12H:
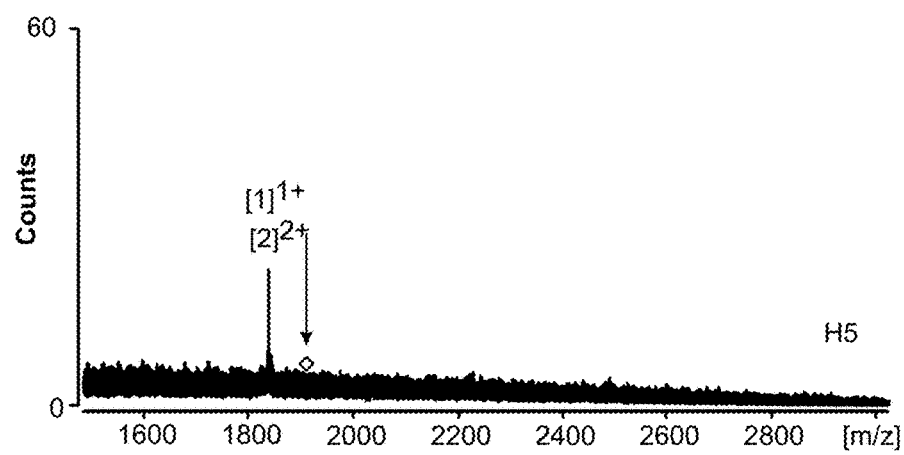
Figure 12I:
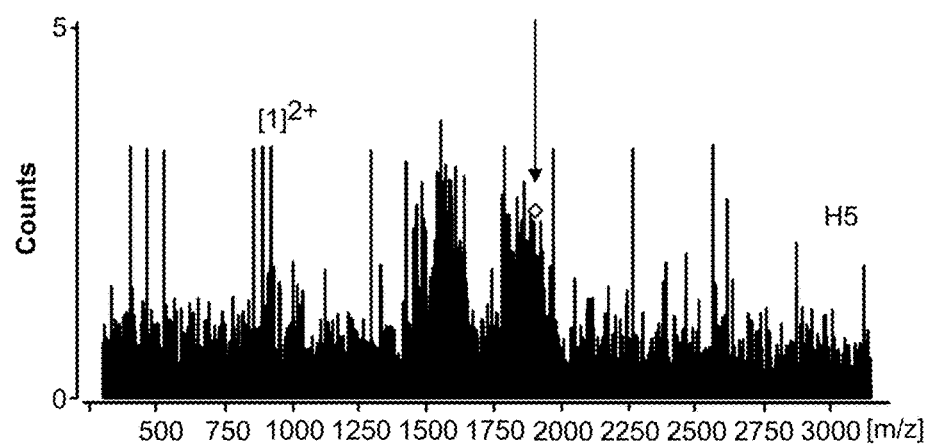
Figure 13B:
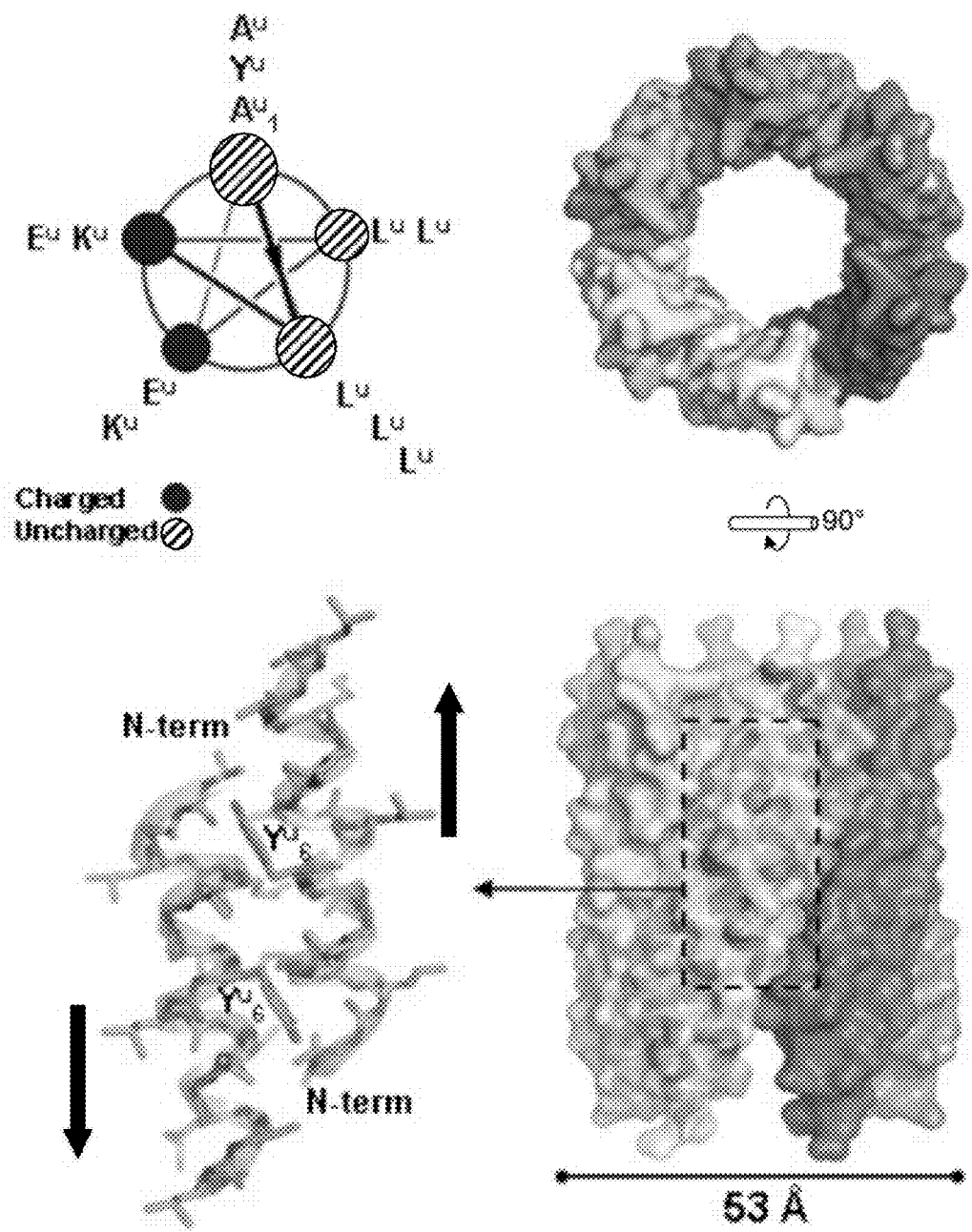
Figure 13C:
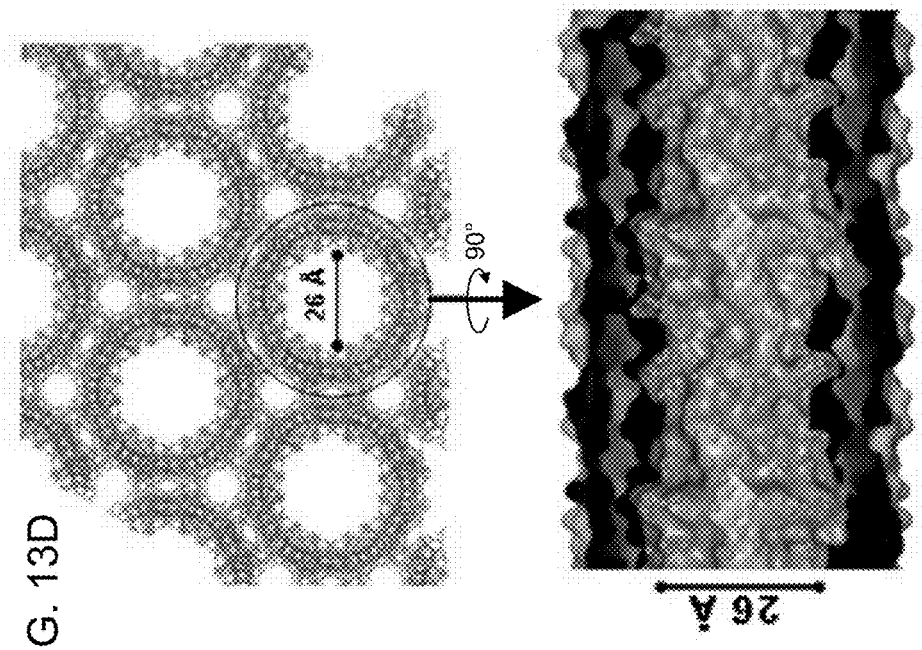
Figure 13D:
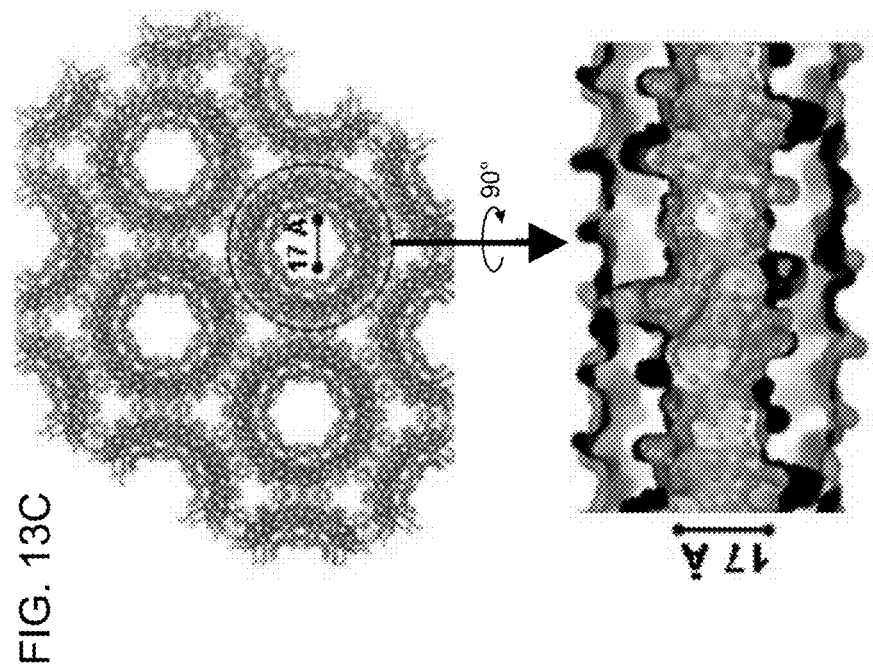
Figure 16:
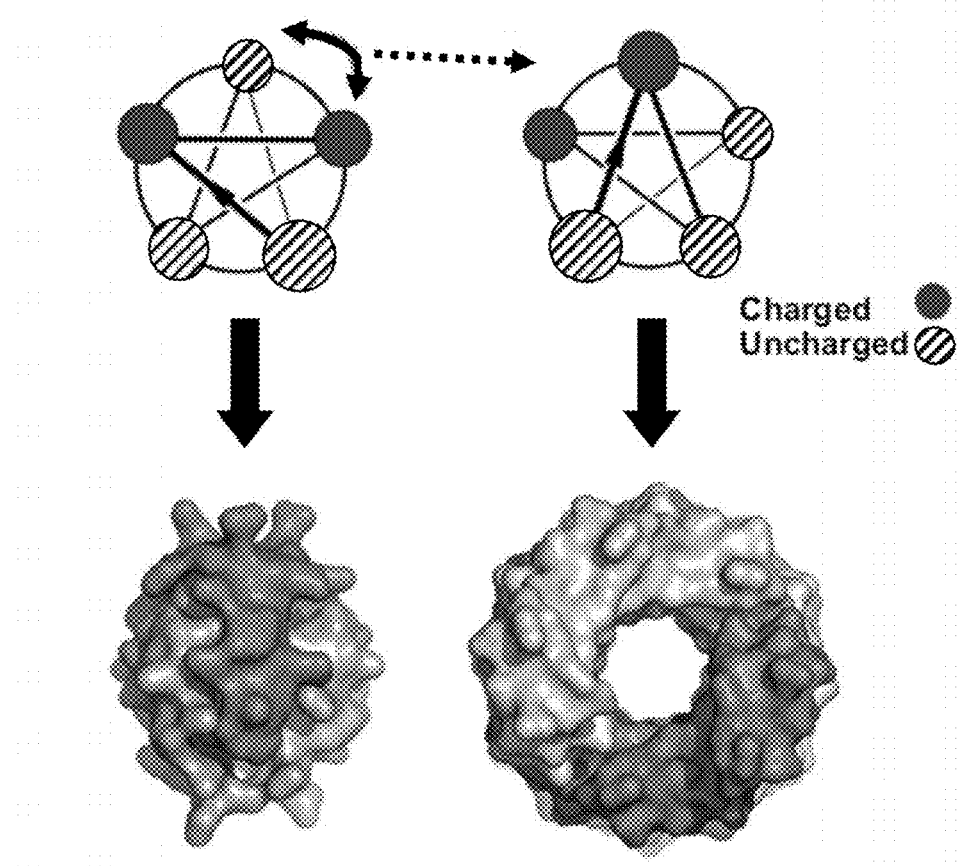
FIG. 16. Control of quaternary arrangement of oligourea foldamers through manipulation of primary sequence.

The key difference between oligoureas H1 and H2 relates to the distribution of the charged and uncharged residues, thus, the continuous charged helical face and the extended uncharged helical face of H2 appear to be critical design elements that shift the self-assemblies from discrete helical bundles to tubular nano-structures (e.g., compare FIG. 1E and FIG. 1F). In order to test this hypothesis, an additional oligourea—H5—was synthesized, bearing uncharged residues at three contiguous helical pentad positions (two composed of Leu$^u$ residues [b and d] and a third composed of Ala$^u$ and Tyr$^u$ residues [a]) and a continuous charged helical face composed of charged Lys$^u$ and Glu$^u$ residues (positions e and c) (FIG. 13B). Variable-concentration CD analysis revealed H5 to possess a strong tendency to self-assemble in solution (FIGS. 12E-12G), whilst native ESI-MS spectra revealed a clear absence of distinct multimeric species, accompanied by a significant level of high-mass background noise composed of H5 monomers (as shown by MS/MS analysis) (FIGS. 12H and 12I). Atomic-scale details of the assemblies indicated by the CD and native ESI-MS data were provided by a 1.47 Å crystal structure of H5, revealing a multi-stranded super-helical channel fundamentally similar to that formed from H2, yet differing noticeably in super-helix chain stoichiometry, with the H5 channel formed from six intertwined right-handed super-helices (FIG. 13B). Each super-helix of the H5 channel requires 24 oligourea molecules per complete super-helical turn. This, coupled with the increased super-helical chain stoichiometry, leads to an increase in the internal pore diameter of the H5 channel— from 17 Å (channel H2) to 25 Å (channel H5) (FIGS. 13C and 13D). Despite significant differences in the sequences of H2 and H5, the individual super-helix chains of channels H2 and H5 are constructed in remarkably similar fashions, involving the staggered side-by-side packing of oligourea helices, locked together by a combination of hydrophobic interactions and extensive salt-bridge networks (FIGS. 4, 5, 6, and 13B). As with the H2 channel, the H5 channel also has a densely packed, hydrophobic exterior (composed of Leu$^u$, Ala$^u$ and Tyr$^u$ residues) and a highly charged and hydrated interior pore. Oligourea H5 therefore not only supports the proposition that uniting the charged and uncharged helical positions through sequence modification to form continuous charged and uncharged helical faces results in the formation of non-discrete channel-type structures (FIG. 16), but also indicates that the diameter of the channel pores can be modulated through the length and sequence of the foldamer building unit.

TABLE 1

Data collection and refinement statistics for X-ray crystal structures of oligoureas H1, H2, H4 and H5.

| | Oligourea | | | |
|---|---|---|---|---|
| | H1 | H2 | H4 | H5 |
| Sequence | $L^uE^uK^uL^uY^uL^uE^uK^uL^uA^uL^u$ | $L^uE^uL^uK^uP^uL^uE^uL^uK^uA^u$ | $S^uE^uK^uL^uY^uL^uE^uK^uL^uA^uL^u$ | $A^uL^uK^uL^uE^uY^uL^uE^uL^uK^uA^uL^u$ |
| | Data Collection | | | |
| Space group | P 6$_3$ | P 6$_1$22 | P 6$_3$ | P 622 |
| a, b, c (Å) | 34.00, 34.00, 37.69 | 38.12, 38.12, 54.98 | 33.52, 33.2, 38.02 | 50.36, 50.36, 42.87 |
| α, β, γ (°) | 90.0, 90.0, 120.0 | 90.0, 90.0, 120.0 | 90.0, 90.0, 120.0 | 90.0, 90.0, 120.0 |
| Resolution (Å) | 37.69–1.25 (1.32–1.25) | 33.01–1.40 (1.48–1.40) | 29.03–1.69 (1.79–1.69) | 43.62–1.47 (1.56–1.47) |
| $R_{meas}$ (%) | 4.7 (67.7) | 8.3 (60.5) | 6.7 (66.0) | 4.3 (62.9) |
| I/σ | 28.86 (4.01) | 24.77 (6.16) | 11.22 (2.24) | 37.77 (4.62) |
| Reflections (total) | 72787 | 72322 | 8749 | 114408 |
| Reflections (unique) | 6938 | 5060 | 2709 | 5847 |
| Completeness (%) | 99.7 (99.5) | 99.7 (99.5) | 97.8 (93.8) | 99.8 (98.6) |
| Redundancy | 10.5 (10.2) | 14.3 (14.4) | 3.2 (3.1) | 19.6 (18.2) |
| | Refinement | | | |
| Resolution (Å) | 8.70–1.25 | 19.06–1.40 | 29.03–1.69 | 43.62–1.47 |
| $R_{work}/R_{free}$ (%) | 15.5/22.6 | 17.9/19.8 | 19.3/27.7 | 17.6/24.4 |
| Atoms | 279 | 246 | 259 | 295 |
| Waters | 30 | 18 | 18 | 37 |
| Overall B-factor (Å$^2$) | 13.93 | 14.89 | 29.86 | 26.92 |
| | R.m.s. deviations | | | |
| Bond-lengths (Å) | 0.015 | 0.010 | 0.017 | 0.015 |
| Bond-angles (°) | 1.737 | 2.020 | 2.184 | 1.688 |
| CCDC code | 1030455 | 1030456 | 1030457 | 1030454 |

Values in brackets refer to highest resolution shells.
$R_{work}$: $\Sigma |F_o - F_c|/\Sigma F_o$.
$R_{free}$: R-factor calculated for 5% of the data.
$R_{meas}$: redundancy independent R-factor[15].

Investigating a Self-Assembled Foldamer Helical Bundle as a Tool for Guest Encapsulation.

As discussed above, H1 is an aliphatic oligourea foldamer composed of 11 residues, all bearing proteinogenic side-chains. The folding of this molecule into a canonical 2.5-helix in aqueous conditions distributes the charged and uncharged side-chains such that the resulting helix has a strong global amphiphilic character, with distinct hydrophilic (charged) and hydrophobic regions (FIGS. 36A-36F). The amphiphilic nature of H1 imbues this foldamer with a strong tendency to self-assemble. As shown above, H1 readily self-assembles in aqueous conditions into a discrete, hexameric helical bundle, with a leucine-rich core and a hydrated charged exterior (referred to from hereon as 'H1-bundle') (FIGS. 36A-36F). As discussed above, an X-ray crystal structure revealed the presence of an isolated internal cavity within the hydrophobic core of this foldamer helical bundle, with a volume of approximately 500 Å$^3$. The hexameric helix stoichiometry and innate symmetry of the bundle results in the cavity possessing an unique three-fold symmetry, composed of a roughly spherical central chamber from which three 'tunnels' project at 120° relative to one another (FIG. 36C-36E). As the cavity is located within the core of the helical bundle, it is predominantly hydrophobic in nature, however, there exists two hydrogen bond accepting groups (specifically, the urea carbonyl groups of the Leu$^u{}_6$ residues) at the extremity (relative to the central chamber) of each "tunnel".

The crystal structure of H1 above was determined from crystals grown in the presence of isopropanol. This small secondary alcohol was a logical starting point for investigations into the capability of the H1-bundle cavity to encapsulate guests. Aqueous co-crystallisation trials of H1 in the presence of varying concentrations of isopropanol and at different equilibration rates eventually led to the determination of a high-resolution crystal structure revealing the presence of well-resolved isopropanol molecules localised to the internal cavity of the H1-bundle (FIG. 36F). Three isopropanol molecules are bound within a single internal cavity, with each molecule localised to a separate tunnel, hydrogen bonded to the urea carbonyl groups of Leu$^u{}_6$ residues situated at the extremity of each tunnel. The isopropyl carbons are thus orientated towards the hydrophobic central chamber. However, the majority of the cavity volume is predominantly unoccupied (cavity analysis using SURF-NET (Laskowski, R. A. *J. Mol. Graph.* 1995, 13 (5), 323) indicates the cavity to be 47.7% occupied). Due to their small size, the isopropanol guests are unconstrained and consequently are somewhat mobile in their binding sites. Thus, from this crystal structure it was evident that: 1) aliphatic alcohol groups are suitable moieties for binding to the hydrogen bonding groups present within the cavity, and 2) there was considerable scope for optimisation of the alkyl chain to satisfy the unoccupied volume of the cavity. Next, circular dichroism methods were utilized to screen a range of molecules as potential guest for binding to the H1-bundle in aqueous conditions.

Screening of Alcohol-Based Molecules for Binding to a Foldamer Helical Bundle Cavity by Circular Dichroism.

Figure 37A:
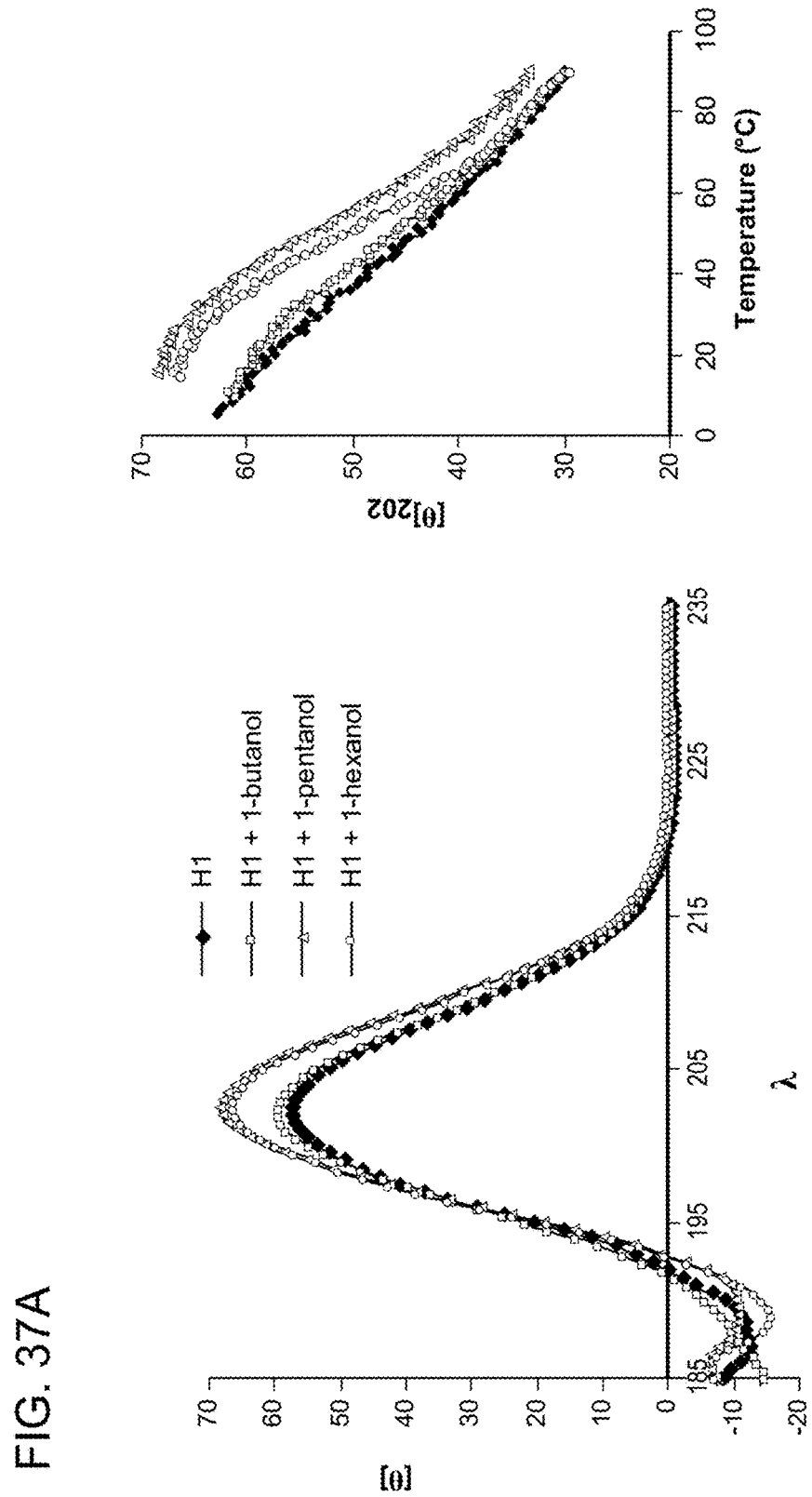
FIGS. 37A and 37B. Circular dichroism studies into the effect of a series of alcohol-based guests on the helicity of H1. Alcohols studied by CD include 1-butanol, 1-pentanol, 1-hexanol (37A) and 2-ethoxyethanol, 2-propoxyethanol, 1,4-butanediol and isopropanol (37B). Full spectrum and thermal melting data were recorded for H1 at 200 μM in pure water plus 1% guest. Full spectra show that the helicity of H1 is not significantly destabilised by any of the guests studied here. Melting data indicate 1-pentanol and 1-hexanol elicit a noticeable stabilising effect on the helicity of H1 in these conditions. Melting profiles were fit to a simple 2-state unfolding model the results of which are shown in Table 1. $[\theta]$: molar elipticity, with units of $deg.cm^2.dmol^{-1}$; $[\theta]_{202}$: molar elipticity at 202 nm. $[\theta]$ and $[\theta]_{202}$ values have been divided by 10,000 for the purposes of visual clarity.
Figure 37B:
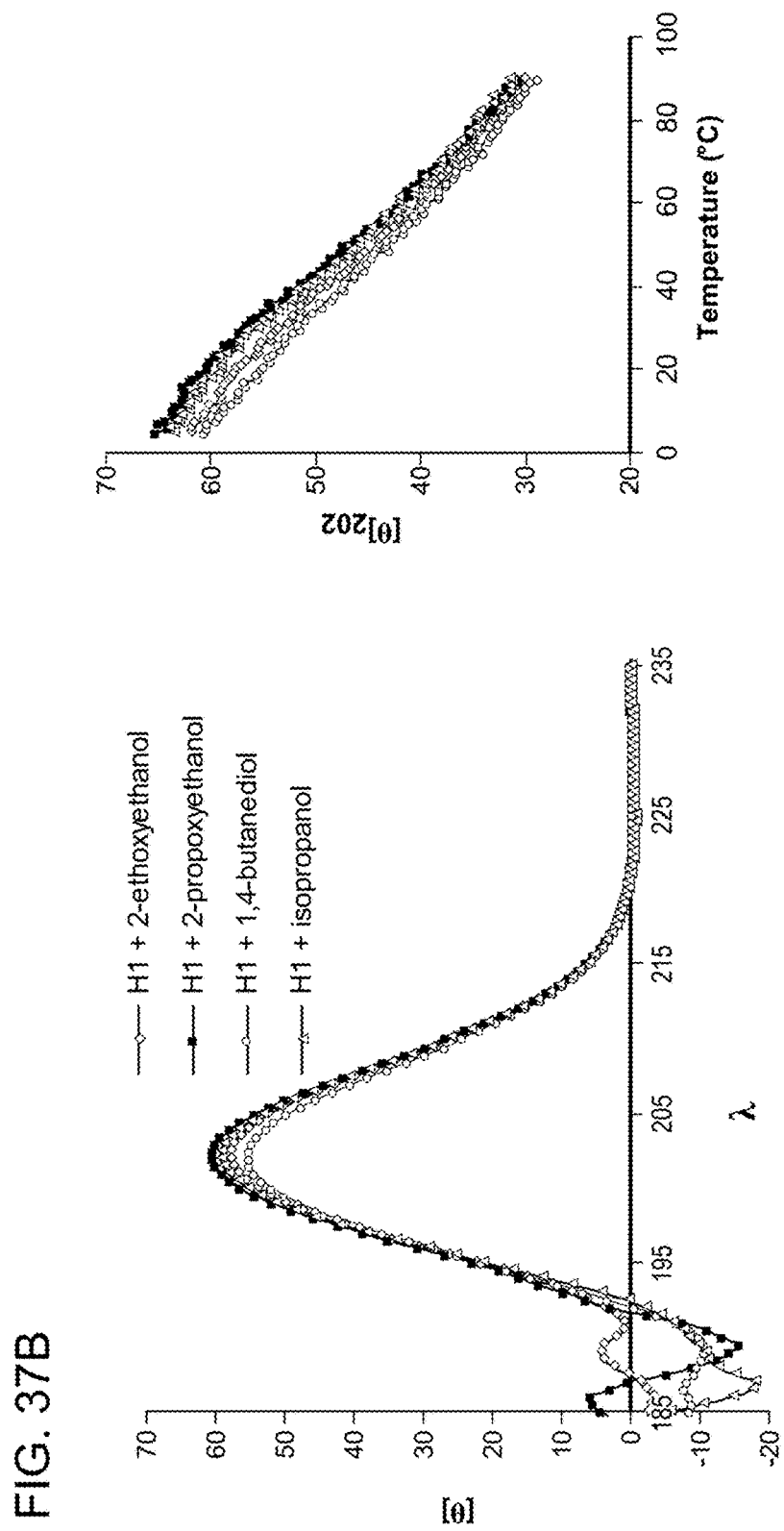

A range of aliphatic compounds differing in chain length and chemical composition yet sharing the common feature of possessing at least one primary alcohol group were chosen as potential guests for binding to the H1-bundle cavity (listed in Table 2). The effect of these compounds on the helicity of H1 in aqueous conditions was investigated by circular dichroism (CD). H1 at a concentration of 200 μM in pure water was supplemented with each guest listed in Table 2 at a concentration of 1% (v/v). Spectra recorded over a wavelength range of 185-250 nm indicated that the helicity of H1 was not perturbed by the addition of any of the guests (FIGS. 37A and 37B). CD-monitored thermal melting data confirmed the observation, and showed that the melting profile of the guest-free H1 is not negatively affected by the presence of the alcohols. Therefore, the quaternary structure of H1 is unperturbed by these potential guests (FIGS. 37A and 37B). Significantly, the melting profiles of H1 in the presence of 1-pentanol and 1-hexanol showed a clear increase in thermal stability, with pronounced melting transitions strongly indicative of quaternary structure unfolding. Thermal melting values determined from these melting profiles demonstrate that 1-pentanol and 1-hexanol (at a concentration of 1% v/v) increase the $T_m$, of H1 by 13.4° C. and 11.5° C., respectively. The clear right-shifting of the alcohol-free H1 melting profile in response to the addition of 1-pentanol and 1-hexanol is a strong indication of potentially interesting host-guest interactions. Next, X-ray crystallographic studies were undertaken as a means to provide atom-scale details of the potential host-guest assemblies.

TABLE 2

CD studies into the effect of various primary and non-primary alcohols (at a concentration of 1% v/v) on the helicity of H1 (at a concentration of 200 μM in pure water).

| Guest[a] | MW | $[\theta]_{202}$ | $T_m$ (° C.) | Adj. R-square | $\Delta T_m$ (° C.)[b] |
|---|---|---|---|---|---|
| no guest | — | 574739 | 41.5 | 0.99875 | — |
| isopropanol | 60.10 | 592003 | 46.4 | 0.99840 | +4.9 |
| 1-butanol | 74.12 | 594610 | 50.8 | 0.99847 | +9.3 |
| 1-pentanol | 88.15 | 680777 | 54.9 | 0.99893 | +13.4 |
| 1-hexanol | 102.17 | 659723 | 53.0 | 0.99918 | +11.5 |
| 2-ethoxyethanol | 90.12 | 579397 | 44.5 | 0.99877 | +3.0 |
| 2-propoxyethanol | 104.15 | 602971 | 47.1 | 0.99877 | +5.6 |
| 1,4-butanediol | 90.12 | 550952 | 43.6 | 0.99881 | +2.1 |

[a]Used at a concentration of 1% (v/v)
[b]'No guest' used as reference

X-Ray Crystallographic Studies of Aqueous H1-Bundle Host-Guest Complexes.

Although it was apparent from the CD data that 1-pentanol and 1-hexanol elicited the greatest stabilising effect on the helicity of H1 in aqueous solution, we endeavoured to co-crystallise H1 in the presence of all guests listed in Table 2, as, importantly, the CD data also indicated that none of the guests studied actively destabilised H1. Crystallisation experiments were performed in standard aqueous hanging drops containing H1 plus 1.5-8% (v/v) of the guests listed in Table 2. Crystals were obtained and structures successfully determined for all H1-guest complexes (structures 2-7, Tables 1 and 2), with resolutions in the range of 1.15-1.62 Å. All six H1-guest complexes are isomorphous, belonging to the same space group as the unbound and isopropanol-bound crystal structures (P6$_3$). Consequently, these crystal structures all reveal highly similar discrete hexameric helical bundles, with structural alignments (using structure 1, corresponding to the H1-isopropanol complex, as a reference) generating RMSD values of <1 Å (Table 3 and FIGS. 38A and 38B). In line with CD data, the H1 molecules of all crystal structures are almost fully helical, although it should be noted that there is evidence of slight helix fraying (in the form of lengthened intra-helical hydrogen bonds) at the N-terminals of the structures determined for crystals grown in conditions containing a combined concentration of precipitant and guest-alcohol of >20%. Importantly, for all structures, alcohol-based guest molecules are well-resolved in electron density, with all guests localising with full occupancy to the three equivalent "tunnel" binding sites of the internal helical bundle cavity (FIGS. 39A-39F and 40A-40C). Thus, all six H1-guest complexes possess a 3:1 guest:bundle ratio (equivalent to a 1:2 guest:helix ratio), with the guests adopting an isomorphous mode of binding to the cavity, involving hydrogen bonding to the carbonyl groups of Leu$^u{}_6$ residues, with the alkyl (or equivalent) tail projecting into the central chamber. Guest binding, however, is not entirely uniform, with differences in cavity occupation, guest orientation and hydrogen bonding correlating surprisingly well with solution CD data, and providing useful clues for the future development of the H1-bundle as a functional capsule/vector.

TABLE 3

Details and analysis of seven crystal structures of H1-bundle-alcohol host-guest complexes.

| | Host | Guest | Res. (Å) | Guest: bundle | B-factor (Å$^2$) Guest | B-factor (Å$^2$) Overall | Ratio$^a$ | RSCC$^b$ | Cavity volume$^c$ (Å$^3$) w/o guest | Cavity volume$^c$ (Å$^3$) w/guest | Cavity volume$^c$ (Å$^3$) % occupied | R.M.S.D.$^d$ (Å) |
|---|---|---|---|---|---|---|---|---|---|---|---|---|
| Structure 1 | H1 | isopropanol | 1.18 | 3:1 | 24.24 | 14.50 | 1.67 | 0.853 | 513.0 | 268.5 | 47.7% | — |
| Structure 2 | H1 | 1-butanol | 1.35 | 3:1 | 27.27 | 26.05 | 1.05 | 0.960 | 517.4 | 139.8 | 73.0% | 0.352 |
| Structure 3 | H1 | 1-pentanol | 1.52 | 3:1 | 21.97 | 24.70 | 0.89 | 0.953 | 526.4 | 48.3 | 90.8% | 0.535 |
| Structure 4 | H1 | 1-hexanol | 1.15 | 3:1 | 24.60 | 19.27 | 1.28 | 0.895 | 543.0 | 62.5 | 88.5% | 0.449 |
| Structure 5 | H1 | 2-ethoxyethanol | 1.45 | 3:1 | 32.35 | 18.46 | 1.75 | 0.797 | 502.9 | 37.1 | 92.6% | 0.884 |
| Structure 6 | H1 | 2-propoxyethanol | 1.62 | 3:1 | 26.43 | 25.22 | 1.05 | 0.949 | 484.8 | 34.6 | 92.9% | 0.864 |
| Structure 7 | H1 | 1,4-butanediol | 1.40 | 3:1 | 43.29 | 29.39 | 1.47 | 0.741 | 500.5 | 24.1 | 95.2% | 0.538 |

$^a$Ratio = guest alcohol B-factor/overall B-factor
$^b$RSCC: real-space correlation coefficient (correlation between 2mF$_{obs}$-DF$_{calc}$ map and F$_{calc}$ map (Afonine, P. V., et al. *J. Appl. Crystallogr.* 2010, 43 (Pt 4), 669)).
$^c$Cavity volumes calculated using SURFNET using a 1.4 Å probe radius (Laskowski, R. A. *J. Mol. Graph.* 1995, 13 (5), 323).
$^d$R.M.S.D.: root-mean square deviation.
Structure 1 used as reference. Alignments performed in PyMOL, with 732 to 732 atoms aligned in all cases. Structural alignment of structures 1-7 is depicted visually in FIG. 38.

Crystal Structures of H1-Bundle Host-Guest Complexes with Primary Alcohols: Structures 2-4.

Figure 38B:
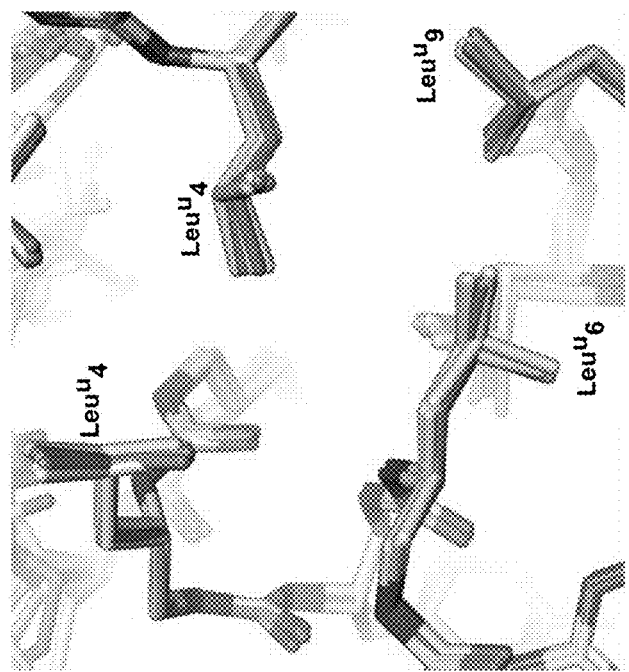
Figure 38A:
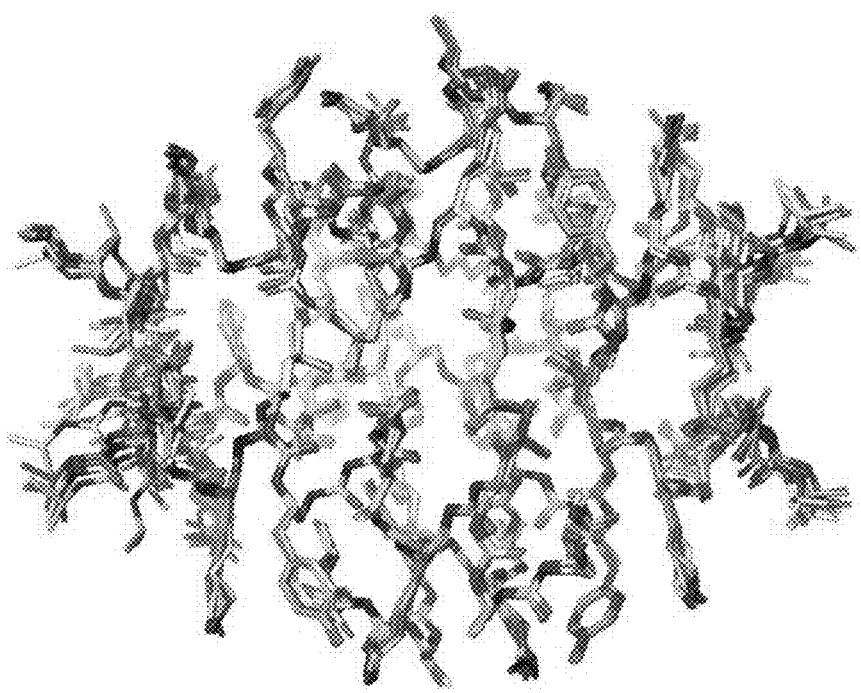
Figure 39C:
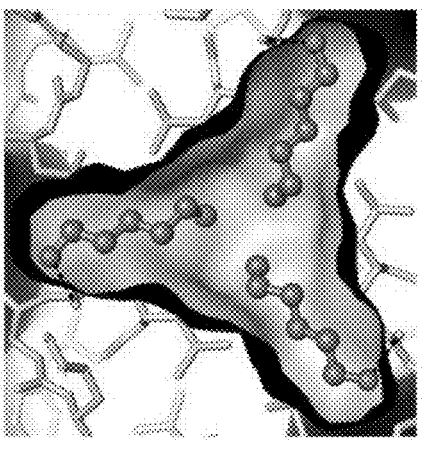
FIGS. 39A, 39B, 39C, 39D, 39E, and 39F. Crystal structures of H1-bundle-alcohol host-guest complexes: 1-butanol (structure 2), 1-pentanol (structure 3), 1-hexanol (structure 4), 2-ethoxyethanol (structure 5), 2-propoxyethanol (structure 6), and 1,4-butanediol (structure 27), respectively. Hydrogen bonds to the carbonyl groups of $Leu^u_6$ residues are shown as black dashes. Additional inter-guest hydrogen bonds are present in (39F).
Figure 39F:
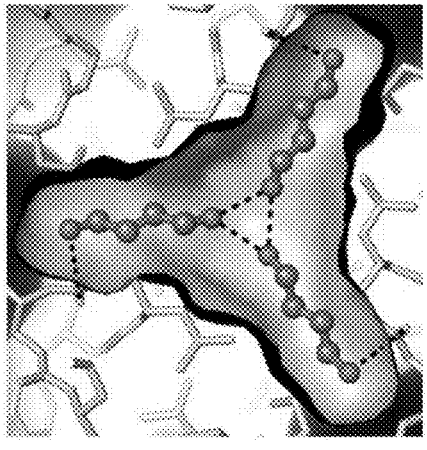
Figure 39B:
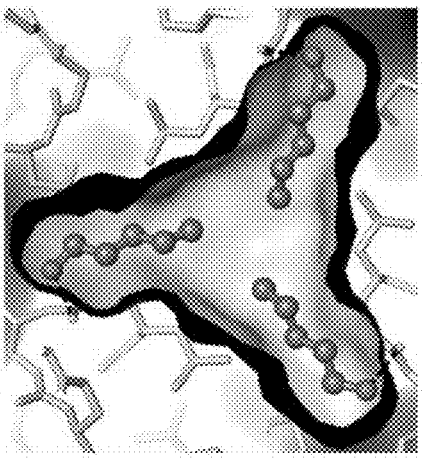
Figure 39E:
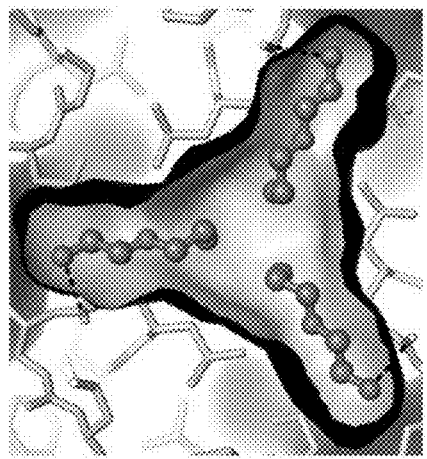
Figure 39A:
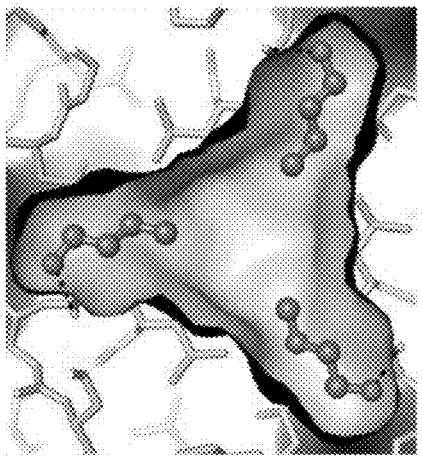

As for all seven host-guest complex co-crystal structures determined in this work, the H1-1-butanol host-guest complex reveals three molecules of 1-butanol bound to equivalent binding sites within the internal cavity of the helical bundle, with the primary alcohol groups hydrogen bonding to the available urea carbonyl groups of the Leu$^u_6$ residues located at the extremity of each 'tunnel' (FIG. 39A). The alkyl chains project into the central cavity, and although cavity occupation is increased significantly compared to the isopropanol-bound complex (from 47.7% to 73.0%), there remains considerable unoccupied cavity volume (FIGS. 41A-41E). As the alkyl chain length is increased to five carbons, in the case of the H1-1-pentanol host-guest complex, the unoccupied space of the cavity is comfortably satisfied, with an increase in cavity volume occupation to 90.8% (FIG. 41D). Based on comparison of B-factor ratios and real-space correlation coefficients (RSCC) (Table 3), crystallographically, 1-pentanol could arguably be considered as the optimal candidate of those studied here for binding to the H1-bundle cavity. Surprisingly, this finding correlates well with solution CD data, which indicate 1-pentanol to elicit the greatest positive effect on the thermal stability of H1 (FIG. 37A). Increasing the alkyl chain length further—in the case of the H1-1-hexanol co-crystal structure—results in an almost paradoxical reduction in cavity occupation: from 90.8% for the 1-pentanol complex to 88.5% for the 1-hexanol complex. Analysis of the total cavity volumes provides the answer: the cavity of the H1-1-hexanol complex is appreciably larger than that of the H1-1-pentanol complex. Indeed, cavity volumes appear to increase in size in direct correlation to increasing guest size. This finding has two implications: 1) the self-assembled H1-bundle is not a rigid entity, but evidently has a significant degree of structural flexibility and, consequently, 2) the self-assembled cavity can, to some degree, adapt to accommodate the binding of sub-optimal guests (such as 1-hexanol). With a higher guest: overall B-factor ratio and a lower RSCC value (compared to the 1-pentanol complex), crystallographically, 1-hexanol is a poorer binder than 1-pentanol. This is supported by solution CD data, which indicate that, while 1-hexanol does indeed exert a stabilising influence on the helicity of H1 in solution, it does so to a slightly less degree than 1-pentanol. Structural alignment of the 1-butanol, 1-pentanol and 1-hexanol co-crystal structures (using the isopropanol structure as a reference) reveals remarkably little difference in the oligourea foldamer component of these complexes, despite the substantial changes in cavity volumes across this series. Therefore, the changes in cavity volume in response to differing guest size is a consequence of local rearrangements of the side-chains directly involved in forming the cavity environment, rather than gross alterations in inter-helix packing. Close analysis of structural alignments supports this conclusion, as moderate variations in orientations of the side-chains of key leucine-type urea residues (Leu$^u_4$, Leu$^u_6$, Leu$^u_9$) are indeed evident (FIGS. 38A and 38B).

Crystal Structures of H1-Bundle Host-Guest Complexes with Chemically Diverse Primary Alcohols: Structures 5-7.

Figure 39D:
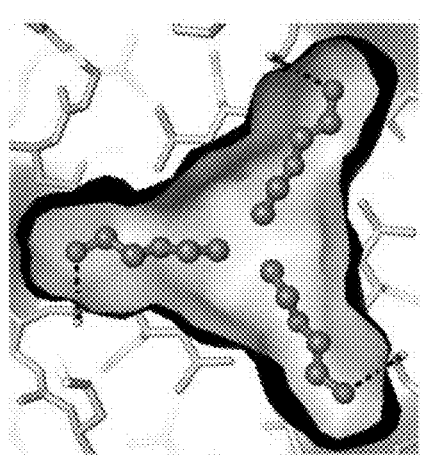
Figure 40A:
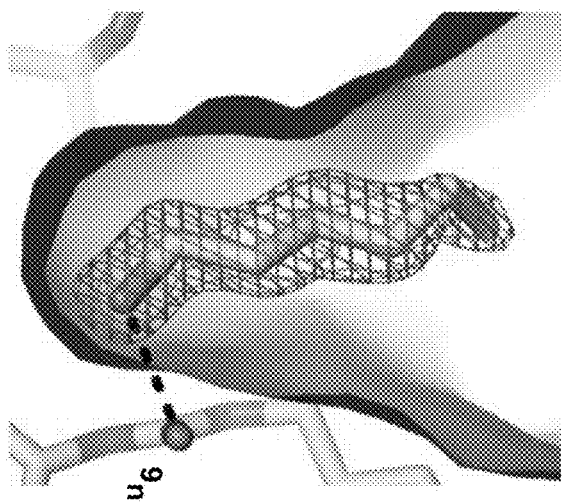
FIGS. 40A, 40B, and 40C. Electron density surrounding 1-butanol (40A), 1-pentanol (40B) and 1-hexanol (4C) guests within H1-bundle cavities. $2F_o-F_c$ maps are shown at sigma levels of 1.2, 1.5 and 1.0 for A-C, respectively. All three hydrogen bond distances (black dashes) are 2.8 Å.
Figure 40B:
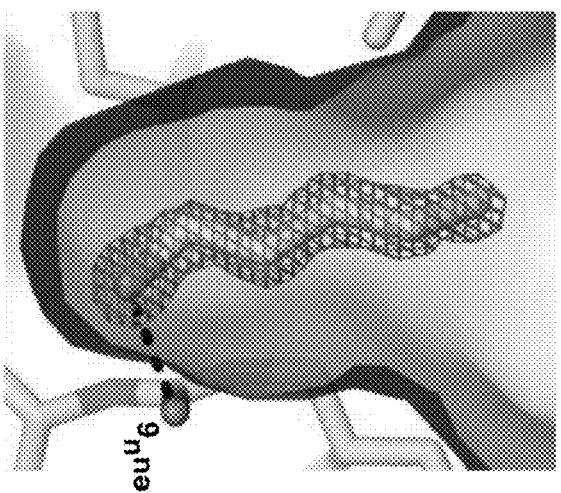
Figure 40C:
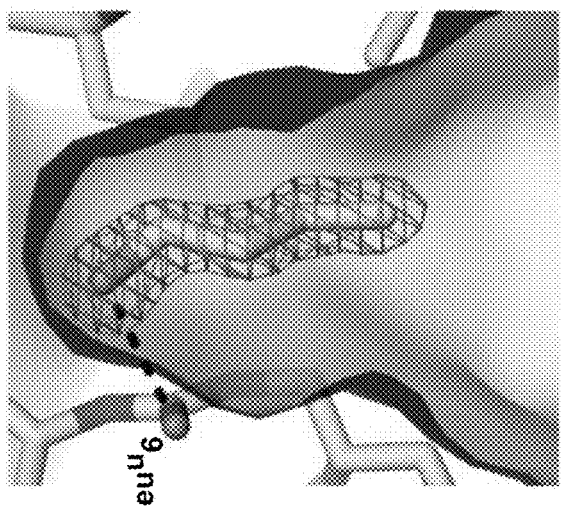

Due to the predominantly hydrophobic nature of the H1-bundle cavity, hydrophobic forces are likely to play a key role in host-guest interactions, forces which the primary alcohol series described above show can be effectively exploited for guest binding. Whether guests bearing polar groups in addition to the alcohol moiety could be encapsulated by the H1-bundle cavity was examined next. CD data indicated that potential guest molecules containing ether groups (2-ethoxyethanol and 2-propoxyethanol) or multiple primary alcohol groups (1,4-butanediol) had little effect on the helicity or thermal stability of H1 in solution (FIG. 37B). High-resolution crystal structures determined of H1-bundle-guest complexes involving each of these three molecules (structures 5-7, Table 3) all reveal an isomorphous mode of host-guest binding as observed for the primary alcohol structures described above (structures 2-4), with the alcohol groups hydrogen bonded to Leu$^u_6$ carbonyls, and the guest "tails" projecting into the central cavity chamber (FIG. 39D-39F). All three structures exhibit variations in cavity volumes, as seen for the primary alcohol series (structures 2-4), indicating further that the H1-bundle cavity has a noticeable degree of structural flexibility. The cavity volumes of the H1-bundles for all three non-primary alcohol guests are all smaller than that of the H1-bundles bound by the pure primary alcohols. This is likely due to the increased hydrophilicity of the diol and alkyl glycol guests. Regardless of the cause of this cavity-shrinking effect, 1,4-butanediol and the alkyl glycol guests occupy the H1-bundle cavities with unexpectedly high occupancies (over 95% in the case of 1,4-butanediol) indicating clearly that the H1-bundle cavity is able to bind guests containing multiple hydrogen bonding groups and that hydrogen bonding groups are tolerated within the highly hydrophobic central chamber of the cavity. In addition, the H1-1,4-butanediol host-guest complex reveals inter-guest hydrogen bonding between all three guest molecules within the heart of the cavity. As such, encapsulation of guests with a higher degree of complexity is possible.

Exploring Guest Encapsulation Through Molecular Dynamics Simulations.

Figure 42:
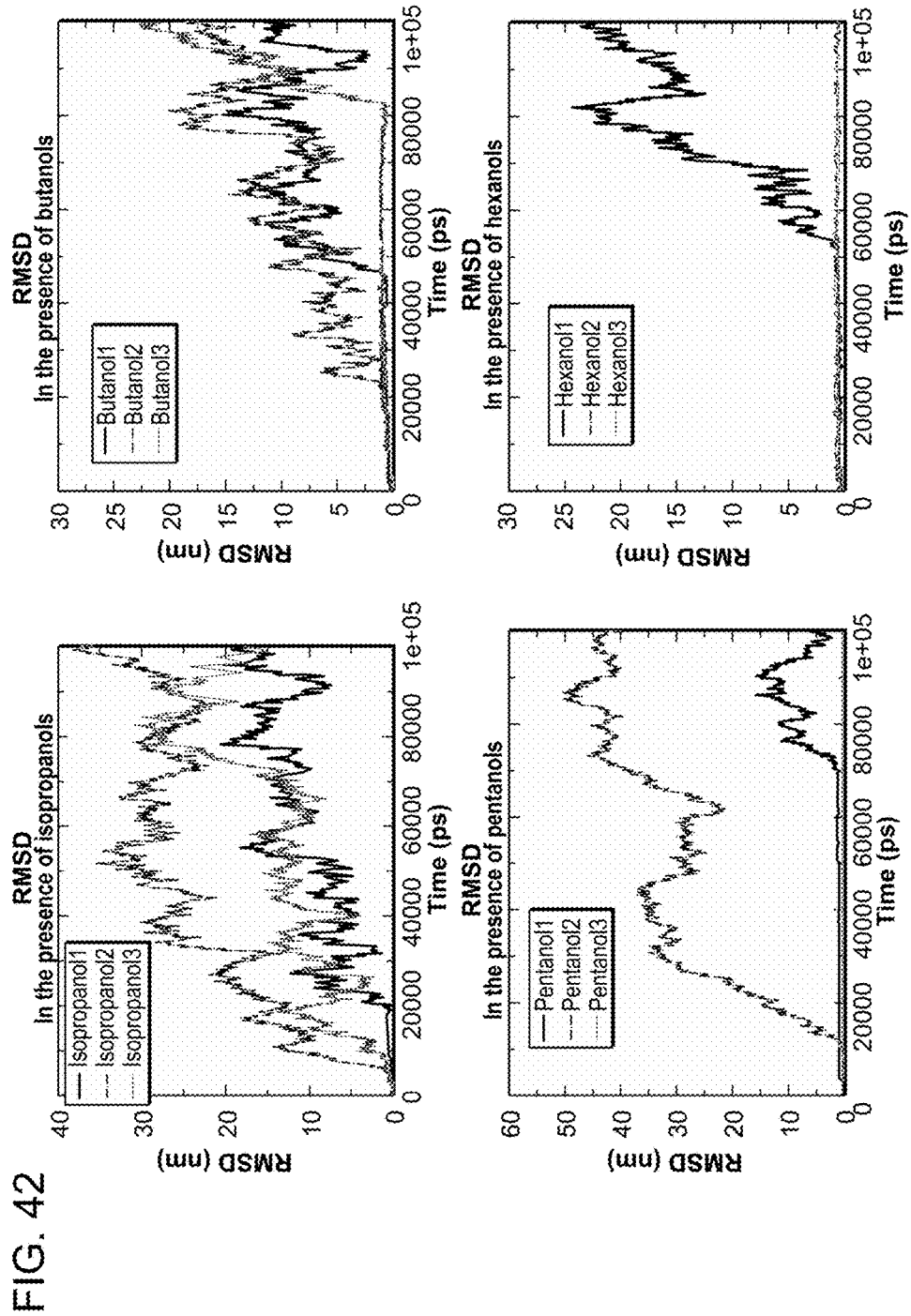
FIG. 42. RMSD profiles of alcohol-based guest molecules located (initially) within the H1-helical bundle cavity over the course of 100 ns molecular dynamics simulations. RMSD values above 0.2 nm indicate ejection of a guest molecule from the cavity of the H1-bundle.

The dynamic aspects of guest encapsulation by the H1-bundle was examined through a series of computational molecular dynamics simulations on H1 in the presence of either: isopropanol, 1-butanol, 1-pentanol or 1-hexanol. For these simulations, the H1-bundle was placed in an 8 nm³ box with explicit water molecules (16,989 waters), with three copies of each guest alcohol placed in the central cavity of the H1-bundle, with their hydroxyl groups orientated towards the carbonyl groups of the Leu$^u_6$ residues. Following an equilibration phase, 100 ns molecular dynamic simulations were then performed for each of the four systems. Analysis of the alcohol RMSD values demonstrate guest retention within the H1-bundle cavity with RMSD values above 0.2 nm indicating the ejection of a single guest molecule from the cavity (FIG. 42). In the case of the H1-bundle-isopropanol simulation, all three isopropanol molecules are rapidly ejected from the H1-bundle cavity (all three guests are ejected within 20 ns), resulting in significant compression of the helical bundle and loss of the internal cavity. Similarly, all three 1-butanol molecules are also ejected from the H1-bundle over the course of the 100 ns simulation, although the overall retention time of the 1-butanol molecules is significantly extended compared to that of isopropanol. Guest retention is extended further in the case of both 1-pentanol and 1-hexanol, with the H1-bundle retaining one 1-pentanol molecule and two 1-hexanol molecules over the course of the 100 ns simulation. In all cases, guest ejection from the H1-bundle cavity involved the H1-bundle rearranging significantly to expose the central cavity (and therefore the entrapped guests) to the bulk solvent, followed by, surprisingly (and unexpectedly), refolding and reformation of the H1-bundle. Although these results appear to suggest that the H1-bundle cavity does not tolerate the presence of these potential guests, it should be noted that: 1) retention of a guest molecule on the multi-nanosecond timescale is significant (as in the case 1-pentanol and 1-hexanol), and 2) as the concentration of alcohol in the bulk solvent surrounding the H1-bundle is zero (a chosen initial simulation condition), re-entry of these guests into the cavity is unlikely. Therefore, encapsulation of alcohol-based guests by the H1-bundle is an energetically feasible yet highly dynamic process, and 1-pentanol and 1-hexanol bind more favourably to the H1-bundle cavity than isopropanol and 1-butanol (FIGS. 37A and 37B and Table 1).

Figure 43:
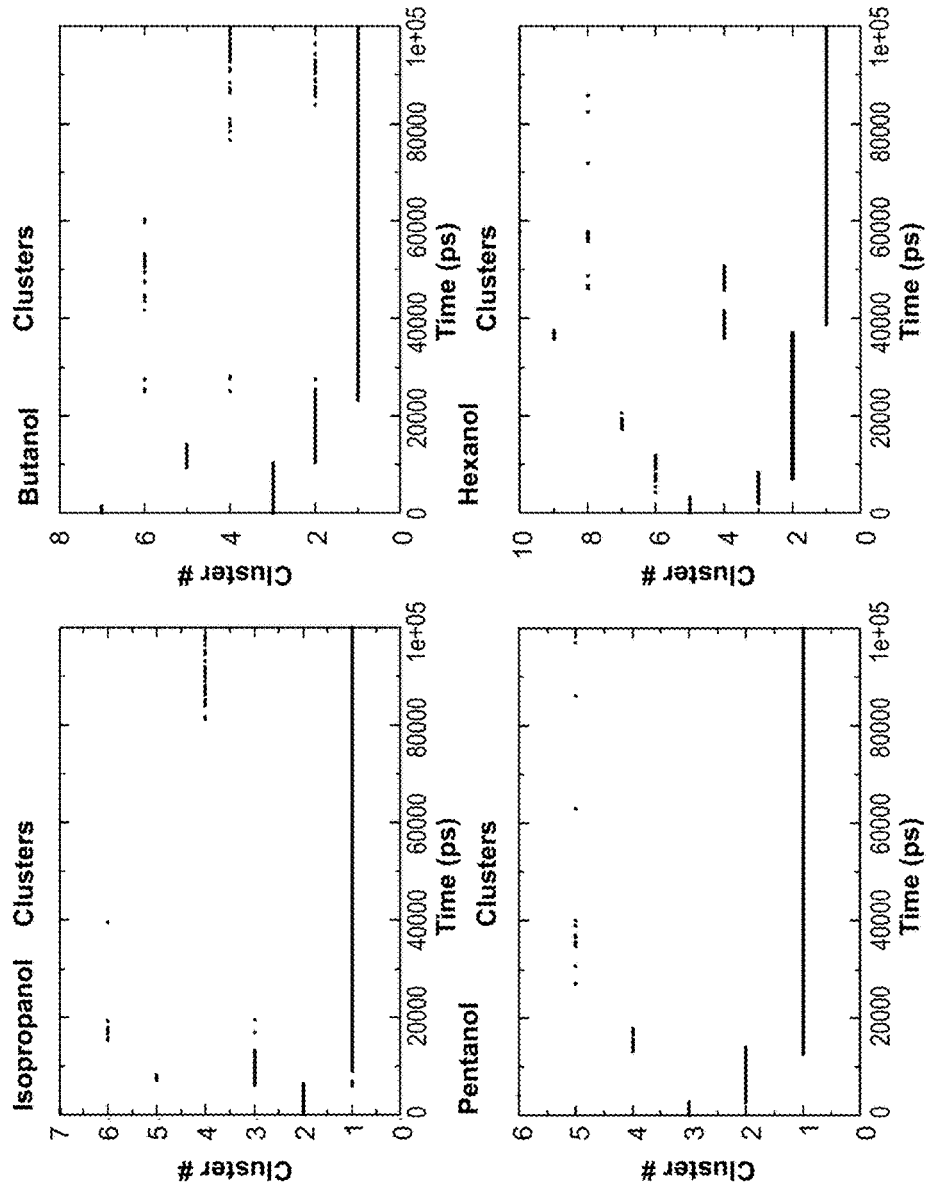
FIG. 43. Cluster analysis of 100 ns H1-bundle-alcohol molecular dynamics simulations.
Figure 44:
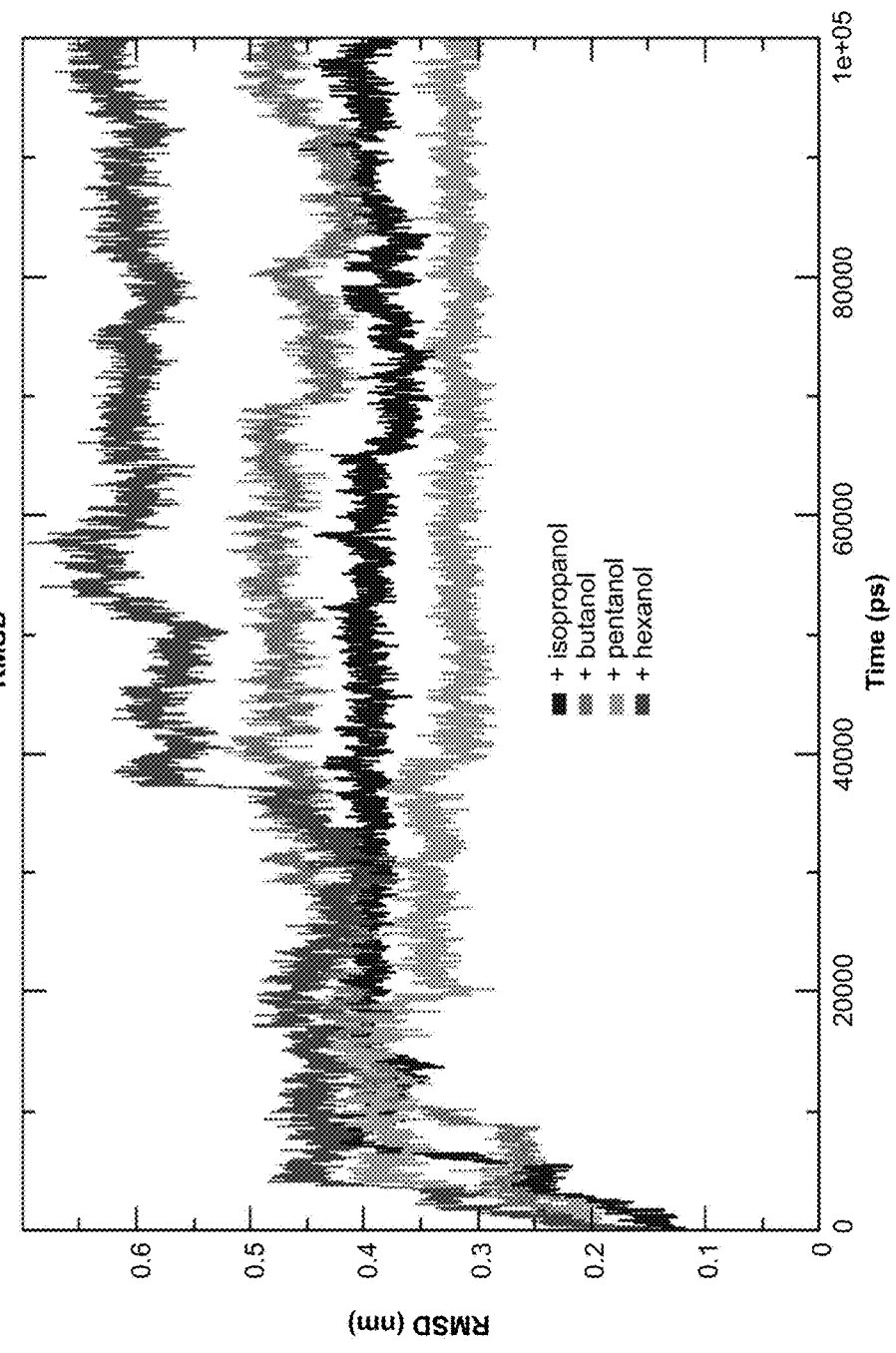
FIG. 44. RMSD analysis of H1-bundles containing three copies of either: isopropanol (black), 1-butanol (red), 1-pentanol (green) or 1-hexanol (blue), over a 100 ns molecular dynamics simulation. RMSD values shown here correspond to the H1-bundles only.

Further details and analyses of these molecular dynamics simulations are shown with regard to FIGS. 43 and 44. The successive ejection of each ligand during the course of the 100 ns simulations (FIG. 42) resulted in significant structural rearrangements of the H1 helical bundles, followed by re-folding and re-formation of the bundles. This temporary unfolding typically led to new conformation states being adopted, depending on the number of ligands remaining in the central cavity. These conformations have been highlighted through a cluster analysis (FIG. 43). RMSD matrices containing the RMSD values between each timestep of a simulation were computed and an analysis was performed with the GROMACS package tool, using a cut-off value of 0.1 nm. A set of new conformations was obtained depending on the ligand and its lifetime inside the cavity. For a given cluster, the H1-bundle conformations are similar enough so as to be considered nearly identical. The RMSD value for one cluster was calculated from the representative structure assigned by the package tool. Numbering of the clusters was automatically assigned, from the most frequently observed to the least. Some conformations were observed for a longer time than others, implying these conformations to be more significant (and arguably more stable) compared to transitory ones (with a shorter time duration). The X axes of the plots correspond to the experiment time at which the cluster was observed. From the number of clusters, one can deduce the structural rearrangement/deformation compared to the equilibrated structure. 1-hexanol results in the greatest number of representative conformations, some with a reasonable lifetime, which can be interpreted as a greater instability of the H1-bundle in the presence of this alcohol. The 1-butanol-filled H1-bundle behaves similarly, b with fewer clusters. Isopropanol and 1-pentanol, however, present a reduced number of clusters, and could thus be considered as more stable. The favourable stability of the H1-bundle-1-pentanol complex indicated by the cluster analysis correlates well with both crystallographic and circular dichroism data, as does, to some degree, the apparent instability of the H1-bundle-1-hexanol complex. Based on the increased cavity volume of the H1-bundle-1-hexanol crystal structure, it appears that 1-hexanol is too large a guest for the H1-bundle cavity, which would be expected to result in greater structural variability, as is indeed shown by the cluster analysis.

For each of the four simulations, the RMSD of the H1-bundle was calculated over time by comparison to the equilibrated structure (FIG. 44). This measure shows that the H1-bundle deformation during the simulations was dependent on the chemical nature of the guest molecules. In the presence of 1-pentanol, the H1-bundle was less deformed than with the others guests, with 1-hexanol eliciting the highest RMSD values for the H1-bundle over the course of the simulation. Isopropanol and 1-butanol provoked intermediate deformations of the H1-bundle compared to 1-pentanol and 1-hexanol. Steric hindrance due to ligand size appears to be of high importance. This does not fully explain the observed effects. It is likely that the observed effects are a result of a balance between (destabilising) steric hindrance and (stabilising) cavity interactions. 1-pentanol reveals the lowest RMSD over the course of the simulation, suggesting that the alkyl chains of this alcohol are of a suitable size to form optimal hydrophobic interactions within the H1-bundle cavity, without causing serious detrimental steric hindrance. Increasing the alkyl chain by one carbon (in the case of 1-hexanol) results in significant destabilisation of the H1-bundle, presumably a result of increased steric clashes within the H1-bundle hydrophobic cavity. The intermediate influence of isopropanol and 1-butanol on the structural stability of the H1-bundle in these simulations could be a result of sub-optimal cavity occupation (due to the small guest size), which is insufficiently compensated for by a reduction in (or absence of) steric hindrance. The RMSD analysis of the H1-bundle simulations described here thus correlates well with the circular dichroism (CD) studies and crystallographic data, as well as with the cluster analysis described above (FIG. 44).

Methods for H1-H5 Self-assembly Studies

Data Deposition. Atomic coordinates and structure factors have been deposited in the Cambridge Crystallographic Data Centre with accession codes: 1030455, 1030456, 1030457 and 1030454, for structures H1, H2, H4 and H5, respectively, and can be obtained free of charge upon request (www.ccdc.cam.ac.uk/data_request/).

Chemistry.

Oligoureas H1, H3, H4 and H5 were synthesized on solid support using azide-protected succinimidyl carbamate building blocks following previously reported procedures (Douat-Casassus, C., et al. Microwave-enhanced solid-phase synthesis of N,N'-linked aliphatic oligoureas and related hybrids. *Org. Lett.* 14, 3130-3133 (2012)). H2 was assembled in solution using Boc-protected succinimidyl carbamate building blocks and a fragment condensation approach (Fremaux, J., et al. Condensation approach to aliphatic oligourea foldamers: helices with N-(pyrrolidin-2-ylmethyl)ureido junctions. *Angew. Chem. Int. Ed Engl.* 50, 11382-11385 (2011)). Full details of chemical synthesis and purification can be found in the supplementary information.

Circular Dichroism.

Circular dichroism (CD) experiments were performed on a Jasco J-815 spectrometer. Variable concentration experiments were performed on oligoureas H1-5 in double-distilled $H_2O$ ($ddH_2O$) as well as buffered conditions (20 mM sodium acetate at pH 4.0 for H1 and H3 and 20 mM sodium phosphate at pH 7.4 for H2) starting from oligourea concentrations of 200 μM followed by serial two-fold dilutions. Data were recorded at 20° C. between wavelengths of 180 and 250 nm at 0.5 nm intervals at a speed of 50 nm/min with an integration time of 2 seconds. CD-monitored thermal melting experiments were performed on oligoureas H1-5 in pure water (and H1 in 20 mM sodium acetate at pH 4.0) at a concentration of 200 μM. For these experiments, oligourea samples were heated from 5° C. to 90° C. using a gradient of 1° C.min$^{-1}$. The CD signal at 202 nm was monitored for these experiments. The $T_m$ value for H1 (in pure water) was determined by fitting CD-monitored thermal melting data to a simple two-state Boltzmann unfolding model using Origin 8.6 (adjusted R-square of fit: 0.99943).

X-Ray Crystallography.

For crystallisation trials, lyophilized powders of oligoureas H1-H5 were dissolved to final concentrations of 10 mg/ml in $ddH_2O$. Crystallisation trials were performed at 20° C. in standard aqueous hanging drops composed of 0.5 μL of oligourea solution plus 0.5 μL of crystallisation reagent. Crystals were obtained for all oligourea molecules except H3. X-ray diffraction data were collected at the European Synchrotron Radiation Facility (ESRF) on beam lines ID23-2 (H1 and H2) and ID29 (H5) and at the SOLEIL synchrotron on beam line PROXIMA-1 (H4). Data were processed using XDS (Kabsch, W. XDS. *Acta Crystallogr. D Biol. Crystallogr.* 66, 125-132 (2010)) and CCP4 (Winn, M. D. et al. Overview of the CCP4 suite and current developments. *Acta Crystallogr. D Biol. Crystallogr.* 67, 235-242 (2011)). The structures were solved by molecular replacement using previously reported oligourea crystal structures as search models (Fischer, L. et al. The canonical helix of urea oligomers at atomic resolution: insights into folding-induced axial organization. *Angew. Chem. Int. Ed Engl.* 49, 1067-1070 (2010); and Fremaux, J., Fischer, L., Arbogast, T., Kauffmann, B. & Guichard, G. Condensation approach to aliphatic oligourea foldamers: helices with N-(pyrrolidin-2-ylmethyl)ureido junctions. *Angew. Chem. Int. Ed Engl.* 50, 11382-11385 (2011)) using Phaser (McCoy, A. J. et al. Phaser crystallographic software. *J. Appl. Crystallogr.* 40, 658-674 (2007)) from the CCP4 suite (Winn, M. D. et al. Overview of the CCP4 suite and current developments. *Acta Crystallogr. D Biol. Crystallogr.* 67, 235-242 (2011)). Model building and restrained refinement were performed in Coot (Emsley, P., Lohkamp, B., Scott, W. G. & Cowtan, K. Features and development of Coot. *Acta Crystallogr. D Biol. Crystallogr.* 66, 486-501 (2010)) and Refmac5 (Murshudov, G. N. et al. REFMAC5 for the refinement of macromolecular crystal structures. *Acta Crystallogr. D Biol. Crystallogr.* 67, 355-367 (2011)), respectively. Resolutions and $R_{work}$/$R_{free}$ factors of final refined models are: 1.25 Å, 15.5/22.6% (H1), 1.40 Å, 17.9/19.8% (H2), 1.69 Å, 19.3/27.7% (H4) and 1.47 Å, 17.6/24.4% (H5). Additional crystallisation, data collection and refinement details can be found in the supplementary information.

For crystallisation trials, lyophilized powders of oligoureas H1-H5 were dissolved to final concentrations of 10 mg/ml in double-distilled $H_2O$ ($ddH_2O$). Crystallisation trials were performed at 20° C. in standard aqueous hanging drops composed of 0.5 μL of oligourea solution plus 0.5 μL of crystallisation reagent. Crystals were obtained for all oligourea molecules except H3. Data collection and refinement statistics for crystal structures of oligoureas H1, H2, H4 and H5 can be found in Table S1. Further details of crystallisation, data collection and refinement are given below.

Crystals of oligourea H1 were grown using a crystallisation reagent composed of 20% isopropanol, 200 mM calcium chloride and 100 mM sodium acetate buffer (pH 4.6). For data collection, a single crystal was cryo-protected in a solution composed of 25% glycerol, 13.3% isopropanol, 133 mM calcium chloride and 67 mM sodium acetate (pH 4.6) and flash frozen in liquid nitrogen. X-ray diffraction data were collected on beam line ID23-2 at the European Synchrotron Radiation Facility (ESRF), and processed using XDS (Kabsch, W. XDS. *Acta Crystallogr. D Biol. Crystallogr.* 66, 125-132 (2010)) and CCP4 (Winn, M. D. et al. Overview of the CCP4 suite and current developments. *Acta Crystallogr. D Biol. Crystallogr.* 67, 235-242 (2011)). The structure was solved by molecular replacement using a previously reported oligourea crystal structure as a search model (CCDC code: 750017; Fischer, L. et al. The canonical helix of urea oligomers at atomic resolution: insights into folding-induced axial organization. *Angew. Chem. Int. Ed Engl.* 49, 1067-1070 (2010)), using Phaser (McCoy, A. J. et al. Phaser crystallographic software. *J. Appl. Crystallogr.* 40, 658-674 (2007)) from the CCP4 suite (Winn, M. D. et al. Overview of the CCP4 suite and current developments. *Acta Crystallogr. D Biol. Crystallogr.* 67, 235-242 (2011)). Geometric restraints for maximum likelihood restrained refinement were generated using the PRODRG server (Schüttelkopf, A. W. & van Aalten, D. M. F. PRODRG: a tool for high-throughput crystallography of protein-ligand complexes. *Acta Crystallogr. D Biol. Crystallogr.* 60, 1355-1363 (2004)). Model building and restrained refinement were performed in Coot (Emsley, P., Lohkamp, B., Scott, W. G. & Cowtan, K. Features and development of Coot. *Acta Crystallogr. D Biol. Crystallogr.* 66, 486-501 (2010)) and Refmac5 (Murshudov, G. N. et al. REFMAC5 for the refinement of macromolecular crystal structures. *Acta Crystallogr. D Biol. Crystallogr.* 67, 355-367 (2011)), respectively. Twinning was detected using Xtriage from the Phenix software suite (Adams, P. D. et al. PHENIX: a comprehensive Python-based system for macromolecular structure solution. *Acta Crystallogr. D Biol. Crystallogr.* 66, 213-221 (2010)), and was subsequently accounted for during the refinement process. The data are hemihedrally twinned, with relative twin fractions of 0.508 and 0.492 for domains defined by operators H, K, L and K, H, -L, respectively. The final model was refined (including anisotropic displacement parameters) to a resolution of 1.25 Å, with $R_{work}$ and $R_{free}$ factors of 15.5% and 22.6% respectively.

Oligourea H2 crystallized in a surprisingly large number of different crystallisation conditions—many of which differed considerably in pH, precipitant and ion content—yet all crystals obtained of H2 were isomorphous (i.e. they were all of the same space group and unit cell). The structure reported here was solved from diffraction data collected on a crystal grown from a crystallisation reagent composed of 30% 2-methyl-2,4-pentanediol, 200 mM sodium chloride and 100 mM sodium acetate buffer (pH 4.6). This crystal/dataset was selected purely on the basis of resolution. The crystal was flash frozen directly in liquid nitrogen and diffraction data collected on beam line ID23-2 at the ESRF. Diffraction data were processed as above. The structure was solved by molecular replacement using a previously reported pyrrolidine-containing oligourea crystal structure as a search model (CCDC code: 836811; Fremaux, J., Fischer, L., Arbogast, T., Kauffmann, B. & Guichard, G. Condensation approach to aliphatic oligourea foldamers: helices with N-(pyrrolidin-2-ylmethyl)ureido junctions. *Angew. Chem. Int. Ed Engl.* 50, 11382-11385 (2011)) using Phaser (McCoy, A. J. et al. Phaser crystallographic software. *J. Appl. Crystallogr.* 40, 658-674 (2007)) from the CCP4 suite (Winn, M. D. et al. Overview of the CCP4 suite and current developments. *Acta Crystallogr. D Biol. Crystallogr.* 67, 235-242 (2011)). Model building and restrained refinement were performed in Coot (Emsley, P., Lohkamp, B., Scott, W. G. & Cowtan, K. Features and development of Coot. *Acta Crystallogr. D Biol. Crystallogr.* 66, 486-501 (2010)) and Refmac5 (Murshudov, G. N. et al. REFMAC5 for the refinement of macromolecular crystal structures. *Acta Crystallogr. D Biol. Crystallogr.* 67, 355-367 (2011)), respectively. The final model was refined (including anisotropic displacement parameters) to a resolution of 1.40 Å, with $R_{work}$ and $R_{free}$ factors of 17.9% and 19.8%, respectively.

Crystals of oligourea H4 were grown using a crystallisation reagent composed of 15% isopropanol, 1 M sodium chloride, 200 mM calcium chloride and 100 mM sodium acetate buffer (pH 4.6). Data were collected on beam line PROXIMA 1 at SOLEIL Synchrotron and diffraction data processed in XDS and CCP4. The structure was solved by molecular replacement using a truncated version of a single helix from the crystal structure of H1 as a search model (using Phaser; McCoy, A. J. et al. Phaser crystallographic software. *J. Appl. Crystallogr.* 40, 658-674 (2007)). Model building and restrained refinement were performed as described for H1. Twinning was detected using Xtriage from the Phenix software suite (Adams, P. D. et al. PHENIX: a comprehensive Python-based system for macromolecular structure solution. *Acta Crystallogr. D Biol. Crystallogr.* 66, 213-221 (2010)), and was subsequently accounted for during the refinement process. The data are hemihedrally twinned, with relative twin fractions of 0.513 and 0.487 for domains defined by operators H, K, L and K, H, -L, respectively. The final model was refined (including isotropic displacement parameters) to a resolution of 1.69 Å, with $R_{work}$ and $R_{free}$ factors of 19.3 and 27.7, respectively.

Crystals of oligourea H5 were grown using a crystallisation reagent composed of 20% Jeffamine M600 and 100 mM sodium HEPES buffer (pH 7.5). Crystals were cryo-protected in a solution composed of 25% glycerol, 13.3% Jeffamine M600 plus 67 mM sodium HEPES buffer (pH 7.5) and flash frozen in liquid nitrogen. Diffraction data were collected on beam line ID29 at the ESRF, and processed as above. The structure was solved by molecular replacement using a single modified helix from the crystal structure of H1 as a search model, using Phaser (McCoy, A. J. et al. Phaser crystallographic software. *J. Appl. Crystallogr.* 40, 658-674 (2007).) from the CCP4 suite (Winn, M. D. et al. Overview of the CCP4 suite and current developments. *Acta Crystallogr. D Biol. Crystallogr.* 67, 235-242 (2011)). Model building and restrained refinement were performed as described for oligoureas H1, H2 and H4. The final model was refined (including anisotropic displacement parameters) to a resolution of 1.47 Å, with $R_{work}$ and $R_{free}$ factors of 17.6% and 24.4%, respectively.

Atomic coordinates and structure factors for all four crystal structures have been deposited in the Cambridge Crystallographic Data Centre (CCDC) with accession codes 1030455, 1030456, 1030457 and 1030454 for structures H1, H2, H4 and H5, respectively (see Table S1). These data are available free of charge upon request (www.ccdc.cam.ac.uk/).

Cavity analysis for structures H1 and H4 was performed using SURFNET (Laskowski, R. A. SURFNET: a program for visualizing molecular surfaces, cavities, and intermolecular interactions. *J. Mol. Graph.* 13, 323-330 (1995)), using a 1.4 Å probe radius. All figures were prepared using PyMOL (DeLano, W. L. *The PyMOL Molecular Graphics System.* (DeLano Scientific, San Carlos, Calif., USA, 2002)).

Native Electrospray Ionization Mass Spectrometry.

Native electrospray ionization mass spectrometry (ESI-MS) experiments were performed on an Agilent 6560 DTIMS-Q-TOF spectrometer (Agilent Technologies, Santa Clara, Calif.), with the dual-ESI source operated in positive ion mode. Oligoureas H1-H5 were analyzed at a concentration 100 µM in 20 mM ammonium acetate, with a syringe pump flow rate of 180 µL/h. The trapping funnel RF amplitude was set to 150 V to improve softness. The data were analyzed using the Agilent MassHunter software (version B.07).

NMR Spectroscopy.

Spectra were recorded on a Bruker Avance 700 MHz or 800 MHz spectrometer equipped with a standard or cryogenic triple resonance gradient probe, respectively. Samples were measured at a concentration of 200 µM in 450 uL water with 10% or 100% $D_2O$, at both pH 4.0 and 5.5, and in 98% $D_2O$ plus 20 mM sodium acetate at pH 4.0, at a temperature of 293 K. 1D spectra used a 3-9-19 WATERGATE sequence for suppression of the water signal. Assignment of proton chemical shifts used 2D 1H,1H-TOCSY spectra collected in $D_2O$ with and without 20 mM sodium acetate (pH 4.0) with a mixing time of 80 ms and a sweepwidth of 8000 Hz in both dimensions with 1024×180 complex points, and centered on the water signal. Side-chain assignments were supported by natural abundance 2D 1H,13C-HSQC spectra collected with 512×128 complex points using a 13C sweepwidth of 16000 Hz centered on 40 ppm. Structure characterization used 2D 1H,1H-NOESY spectra with a mixing time of 200 ms and a sweepwidth of 8000 Hz in both dimensions centered on the water signal, and using 1024×256, 1024×160 or 1024×128 complex points. NMR spectra were collected with the software Topspin 2.1 or 3.2 and processed with NMRPipe/Draw[47]. Chemical shift assignment and figure preparation used Sparky 3 (T. D. Goddard & D. G. Kneller, University of California, San Francisco, USA). Further details of experimental NMR conditions can be found in the appropriate figure legends.

Electron Microscopy Imaging.

For negative staining electron microscopy (EM) studies, a 5 µl sample of H2 at a concentration of 200 µM (in 50 mM sodium HEPES buffer, pH 7.5) was deposited for 2 minutes on carbon copper grids submitted to a glow discharge (Elmo, Cordouan technologies). After a brief wash using distilled water, they were stained with 2% uranyl acetate and dried with filter paper. Grids were observed with a FEI Tecnai F20 electron microscope. For cryo-EM studies, the sample was deposited onto a lacey carbon glow discharged copper grids.

After removing the excess of solution with filter paper, grids were rapidly plunged into a liquid ethane bath cooled with liquid nitrogen using EM GP (Leica). Specimens were observed at −170° C. using a cryo holder (Gatan, USA), with a FEI Tecnai F20 electron microscope operating at 200 kV under low-dose conditions. Images were acquired with a USC1000 2k×2k Gatan camera.

Methods for Helical Bundle-Guest Encapsulation Studies

X-Ray Crystallography.

For crystallisation experiments, oligourea H1 was used at a concentration of 10 mg/ml in double-distilled water (ddH$_2$O). Crystallisation trials were performed at 20° C. in standard aqueous hanging drops composed of 0.6-0.7 µL of oligourea H1 plus an equal volume of crystallisation reagent. The compositions of the crystallisation reagents used to obtain crystals of structures 1-7 were as follows: 15% isopropanol (structure 1); 8% 1-butanol plus 15% 1,4-dioxane (structure 2); 2.5% 1-pentanol plus 10% 1,4-dioxane (structure 3); 1.5% 1-hexanol plus 25% 1,4-dioxane (structure 4); 5% 2-ethoxyethanol plus 20% 1,4-dioxane (structure 5); 5% 2-propoxyethanol plus 15% 1,4-dioxane (structure 6); 5% 1,4-butanediol plus 20% 1,4-dioxane (structure 7). In addition, all crystallisation conditions contained 100 mM sodium acetate buffer (pH 4.6) and 200 mM calcium chloride. All crystals were cryo-protected in a solution composed of 67% of the concentration of crystallisation reagent plus 25% glycerol before flash freezing in liquid nitrogen. X-ray diffraction data were collected at the European Synchrotron Radiation Facility (beam lines ID23-2 and ID29) and SOLEIL synchrotron (beam line PROXIMA 1). Crystals diffracted in the range of 1.15 to 1.62 Å. Diffraction data were processed using XDS (Kabsch, W. *Acta Crystallogr. D Biol. Crystallogr.* 2010, 66 (Pt 2), 125) and Scala (Evans, P. *Acta Crystallogr. D Biol. Crystallogr.* 2006, 62 (Pt 1), 72) from the CCP4 suite (Winn, M. D., et al. *Acta Crystallogr. D Biol. Crystallogr.* 2011, 67 (Pt 4), 235). All diffraction data collected for H1 crystals grown in the presence of the above primary alcohols belong to space group P6$_3$ with almost identical unit cell dimensions (specific details of unit cell values are provided in Table 4).

All structures were solved by molecular replacement using Phaser (McCoy, A. J., et al. *J. Appl. Crystallogr.* 2007, 40 (Pt 4), 658) using the crystal structure of H1 from the self-assembly studies above as a search model (with sidechains, terminal residues and water molecules removed). Model building and restrained refinement were performed in Coot (Emsley, P., et al. *Acta Crystallogr. D Biol. Crystallogr.* 2010, 66 (Pt 4), 486) and REFMAC5 (Murshudov, G. N., et al. *Acta Crystallogr. D Biol. Crystallogr.* 2011, 67 (Pt 4), 355), respectively, with geometric restraints generated using the PRODRG server (Schüttelkopf, A. W., et al. *Acta Crystallogr. D Biol. Crystallogr.* 2004, 60 (Pt 8), 1355). Following completion of oligourea and water model building, the relevant alcohol molecules were modelled into appropriate residual electron density (from F$_o$-F$_c$ and 2F$_o$-F$_c$ maps) evident within the hydrophobic cavities of all structures. The asymmetric units of all crystal structures reported here contain two oligourea H1 molecules and one guest molecule, resulting in a total of three crystallographically identical guest molecules bound per hexameric helical bundle. Final refinement details can be found in Table 4. Cavity analysis was performed using SURFNET (Laskowski, R. A. *J. Mol. Graph.* 1995, 13 (5), 323) (using a 1.4 Å probe radius) and PyMOL (DeLano, W. L. *The PyMOL Molecular Graphics System*; DeLano Scientific, San Carlos, Calif., USA, 2002). Structure validation (including RSCC calculation) was performed in Phenix (Adams, P. D., et al. *Acta Crystallogr. D Biol. Crystallogr.* 2010, 66 (Pt 2), 213). Atomic coordinates and structure factors for structures 1-7 have been deposited in the Cambridge Crystallographic Data Centre with accession codes: 1057608-1057614.

Circular Dichroism.

Circular dichroism experiments were performed on a Jasco J-815 spectrometer. Oligourea H1 was analysed at a concentration of 200 µM in ddH$_2$O supplemented with 1% of one of the seven primary alcohols listed in Table 2. Single temperature spectra were recorded at 20° C. over a wavelength range of 185 to 235 nm. For CD-monitored thermal melting experiments, samples were heated from 5° C. to 90° C. using a gradient of 1° C.min$^{-1}$. The CD signal at 202 nm was monitored for these experiments. Thermal melting (T$_m$) values were estimated by fitting CD-monitored thermal melting data to a simple two-state Boltzmann unfolding model using Origin 8.6. Accuracy of the fits (reduced R-square values) are indicated in Table 2.

Molecular Dynamics Simulations.

All simulations were performed using the GROMACS simulation package version 4.6 (Pronk, S., et al. *Bioinformatics* 2013, 29 (7), 845), using the gromos53a6 forcefield and the SPC (single point charge) water model (Oostenbrink, C., et al. *J. Comput. Chem.* 2004, 25 (13), 1656). Simulations were performed using periodic boundary conditions with an integration timestep of 0.002 ps. The temperature and pressure were kept constant at 300 K and 1 atm with Berendsen coupling baths in equilibration steps. During production a velocity rescale temperature coupling and a Parrinello-Rahman pressure coupling were applied. Two separate groups were created to couple to each temperature bath; one for the oligourea helices with the three associated alcohol ligands and a second one for the solvent. The pressure coupling constant was 2.0 ps and the temperature coupling constant was 0.1 ps. Electrostatic interactions were treated with a fast smooth particle mesh Ewald and a cut-off distance of 0.9 nm. The Van Der Waals interactions were considered between 0.9 nm and 1.4 nm. The neighbour lists were updated every 10 steps. All bonds were constrained with the LINCS algorithm and a force constant of 1000 kJ mol$^{-1}$ nm$^{-1}$ was applied for all the distance restraints defined along the helix backbones. A first steepest descent minimization of 5000 steps was performed. Then an NVT (number of molecules, volume and temperature) equilibration was performed with position restraints of 1000 kJ mol$^{-1}$ nm$^{-1}$ on the helix backbones and all the ligand atoms. Finally, an NPT (number of molecules, pressure and temperature) equilibration was carried out without positional restraints on the ligands (while they were still applied to the helix backbones). All simulations were run for 100 ns.

The starting H1-bundle model was built by providing a single helix from the H1 crystal structure described with regard to the self-assembly study above to the ATB server (Automated Topology Builder) (Koziara, K. B., et al. *J. Comput. Aided Mol. Des.* 2014, 28 (3), 221), in order to generate a topology in the chosen forcefield. Helix backbones were defined by analogy to peptidic structures, with amide bonds replaced by urea linkages. A set of distance restraints between each atom of the helix backbone within a cut-off of 0.9 nm was applied in order to maintain the helical structure observed crystallographically. Topologies for the isopropanol, 1-butanol, 1-pentanol and 1-hexanol ligands were also generated using the ATB server.

Four systems, one for each ligand, were simulated with identical key characteristics. In each case, the ligand was placed in the central cavity of the H1-bundle with the hydroxyl functional group directed toward the 'exterior', at 0.4 nm between the urea carbonyl groups of two Leu"$_6$ residues. Each system was placed in a cubic box of 8 nm$^3$ and solvated with 16,989 water molecules. The initial velocities randomly generated during the NVT equilibration were reapplied for the subsequent simulations.

Synthesis of Exemplary Oligoureas

Two different strategies have been adopted to synthesize the oligoureas studied in this work: compound H2 was assembled in solution, using Boc-protected succinimidyl carbamate building blocks and a fragment condensation approach (Fremaux, J., et al. Condensation approach to aliphatic oligourea foldamers: helices with N-(pyrrolidin-2-ylmethyl)ureido junctions. Angew. Chem. Int. Ed Engl. 50, 11382-11385 (2011)); whereas compounds H1, H3, H4 and H5 were prepared by microwave assisted solid phase synthesis, starting from N$_3$-protected succinimidyl carbamate building blocks (Douat-Casassus, C., et al. Microwave-enhanced solid-phase synthesis of N,N'-linked aliphatic oligoureas and related hybrids. Org. Lett. 14, 3130-3133 (2012)).

Boc-Protected Building Block Synthesis for Oligourea Synthesis in Solution

The building blocks containing Ala- (1), Leu- (2) and Lys-type (3) side chains were synthesized as previously reported (Fremaux, J., et al. Condensation approach to aliphatic oligourea foldamers: helices with N-(pyrrolidin-2-ylmethyl)ureido junctions. Angew. Chem. Int. Ed Engl. 50, 11382-11385 (2011)). The characterization of the Lys-type building block obtained starting from Boc-L-Lys(2-ClZ)-OH is reported here as an example. Furthermore, the strategy followed to obtain the Glu-type building block (4) is also described.

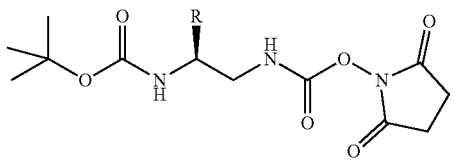

(1): R = Me
(2): R = i-Bu
(3): R = (CH$_2$)$_4$NH(2-Cl-Z)
(4): R = (CH$_2$)$_2$CO$_2$(Bzl)

Boc-Lys: 5-tert-Butoxycarbonylamino-6-(2,5-dioxo-pyrrolidin-1-yloxycarbonylamino)-hexyl]-carbamic Acid 2-chloro-benzyl Ester (3)

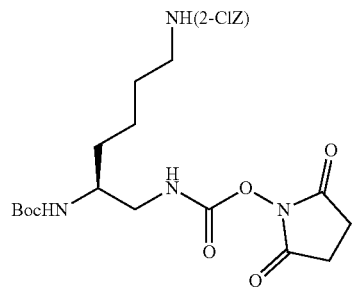

Figure 17:
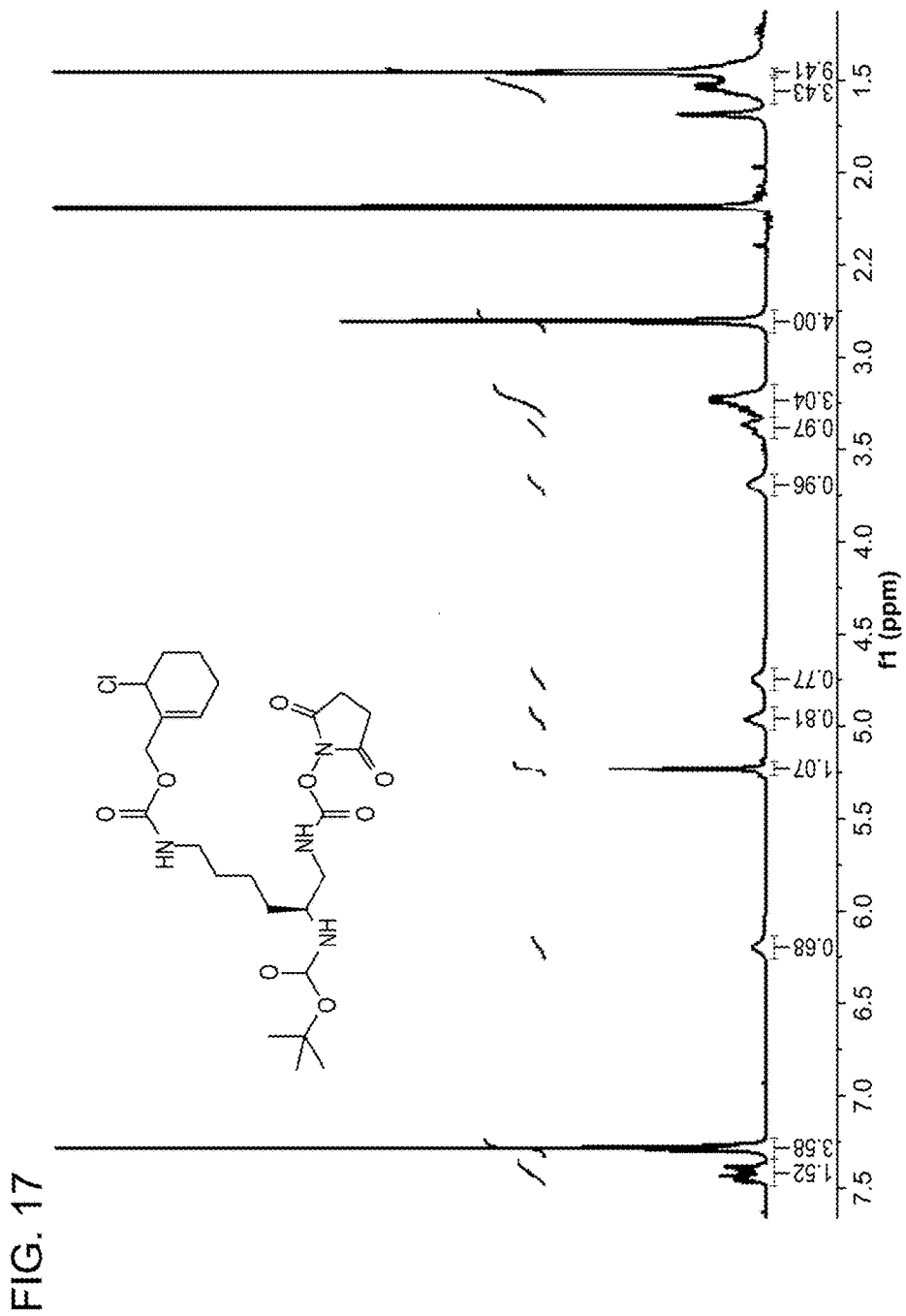
FIG. 17. $^1$H NMR (300 MHz) of compound (3).

Boc-L-Lys(2-ClZ)-OH (5 g, 20.06 mmol) was transformed according to a procedure previously described (Fremaux, J., et al. Condensation approach to aliphatic oligourea foldamers: helices with N-(pyrrolidin-2-ylmethyl)ureido junctions. Angew. Chem. Int. Ed Engl. 50, 11382-11385 (2011)). The product (3) was obtained as a white solid after recrystallization from EtOAc with cyclohexane, with an overall yield of 38% after 4 steps. $^1$H NMR (CDCl$_3$, 300 MHz) δ: 7.48-7.34 (m, 4H), 6.18 (s, 1H), 5.22 (s, 2H), 4.96 (s, 1H), 4.73 (s, 1H), 3.69 (s, 1H), 3.46-3.15 (m, 4H), 2.80 (s, 4H), 1.64-1.47 (m, 6H) 1.46 (s, 9H); $^{13}$C NMR (75 MHz, CDCl$_3$) δ: 170.10, 156.48, 152.23, 132.18, 132.05, 129.73, 129.45, 129.32, 128.65, 128.48, 126.90, 63.81, 50.42, 40.38, 31.54, 29.48, 28.35, 25.46, 22.64; ESI-MS (ESI+) m/z: 563.19 [M+Na]$^+$ (FIGS. 17 and 18).

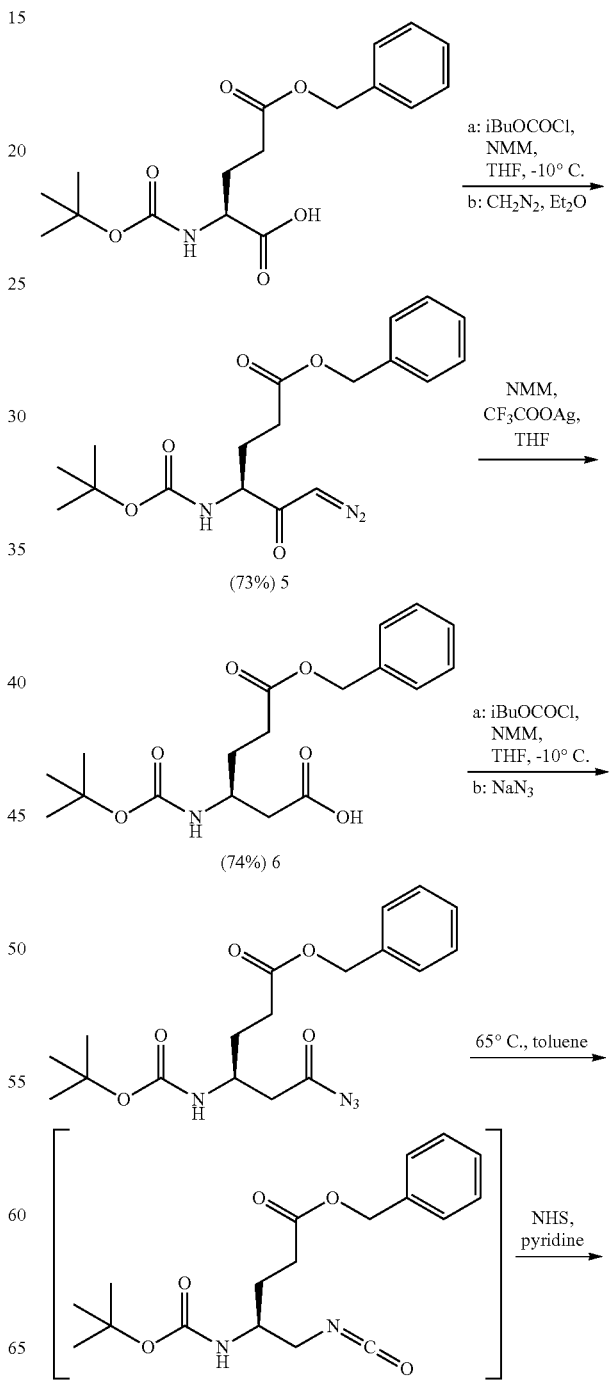

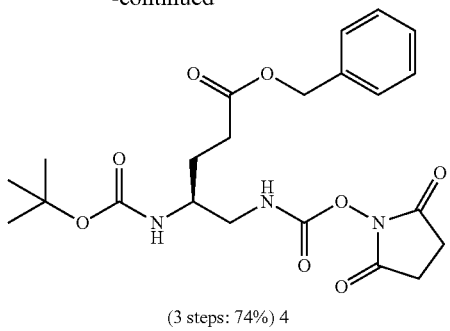

(3 steps: 74%) 4

4-tert-Butoxycarbonylamino-6-diazo-5-oxo-hexanoic Acid Benzyl Ester (5)

Boc-Glu(OBn)-OH (5.06 g, 15.00 mmol) was dissolved in anhydrous THF (80 mL) under an atmosphere of $N_2$, and cooled to −10° C. NMM (2.14 ml, 19.50 mmol) was added, followed by IBCF (2.95 ml, 22.50 mmol). The reaction was stirred at −10° C. for 1 h. The white precipitate formed was eliminated by filtration. The filtrate was cooled to 0° C. and freshly prepared diazomethane in diethyl ether was added (2 eq, prepared from Diazald and KOH). The mixture was warmed up to room temperature and stirred overnight. The reaction was then quenched with the addition of acetic acid (1 ml), and the mixture was vigorously stirred (750 rpm) for two hours. An excess of acetic acid was then added (1 ml), and the mixture was then neutralised with a saturated aqueous $NaHCO_3$ solution (70 ml) and stirred until the effervescence disappeared. The organic phase was separated and washed with 1 N $KHSO_4$ (aq) (60 ml), brine (60 ml), dried over $MgSO_4$, and the solvents were evaporated in vacuo. The crude obtained was purified by flash chromatography on silica gel (gradient cyclohexane-30% ethyl acetate), to afford the pure product as a yellow solid (3.94 g, 73%). $^1$H NMR (CDCl$_3$, 300 MHz) δ: 7.46-7.29 (m, 5H), 5.47 (s, 1H), 5.25 (m, 1H), 5.14 (s, 2H), 4.26 (m, 1H), 2.60-2.38 (m, 2H), 2.23-2.10 (m, 1H), 1.93-1.77 (m, 1H), 1.45 (s, 9H).

3-tert-Butoxycarbonylamino-hexanedioic Acid 6-benzyl Ester (6)

The diazoketone (5) (3.00 g, 8.30 mmol), was dissolved in a mixture 5:1 of THF/$H_2O$ (60 ml), and cooled in an ice bath in a flask covered with aluminium foil to protect from the light. Silver trifluoroacetate (0.37 g, 1.66 mmol) was then added, followed by a drop-wise addition of NMM (2.28 ml, 20.75 mmol). The reaction mixture was stirred for 4.5 hrs and warmed to room temperature. After completion was reached, THF was evaporated, 1N $KHSO_4$ (aq) (40 ml) was added, and the precipitate observed was removed by filtration. The aqueous solution was extracted with ethyl acetate, and the organic phase was washed with 1N $KHSO_4$ (aq) (twice), dried over $MgSO_4$, and the solvents were evaporated in vacuo. Trituration of the yellow crude oil with diethyl ether gave the desired compound as a white solid (2.17 g, 74%). $^1$H NMR (CDCl$_3$, 300 MHz) δ: 7.42-7.31 (m, 5H), 5.13 (s, 2H), 4.00 (m, 1H), 4.03-3.90 (m, 1H), 2.70-2.56 (m, 2H), 2.54-2.40 (m, 2H), 1.98-1.85 (m, 2H), 1.45 (s, 9H).

Boc-Glu: 4-tert-Butoxycarbonylamino-5-(2,5-dioxo-pyrrolidin-1-yloxycarbonylamino)-pentanoic Acid Benzyl Ester (4)

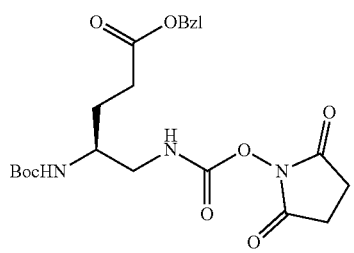

Figure 19:
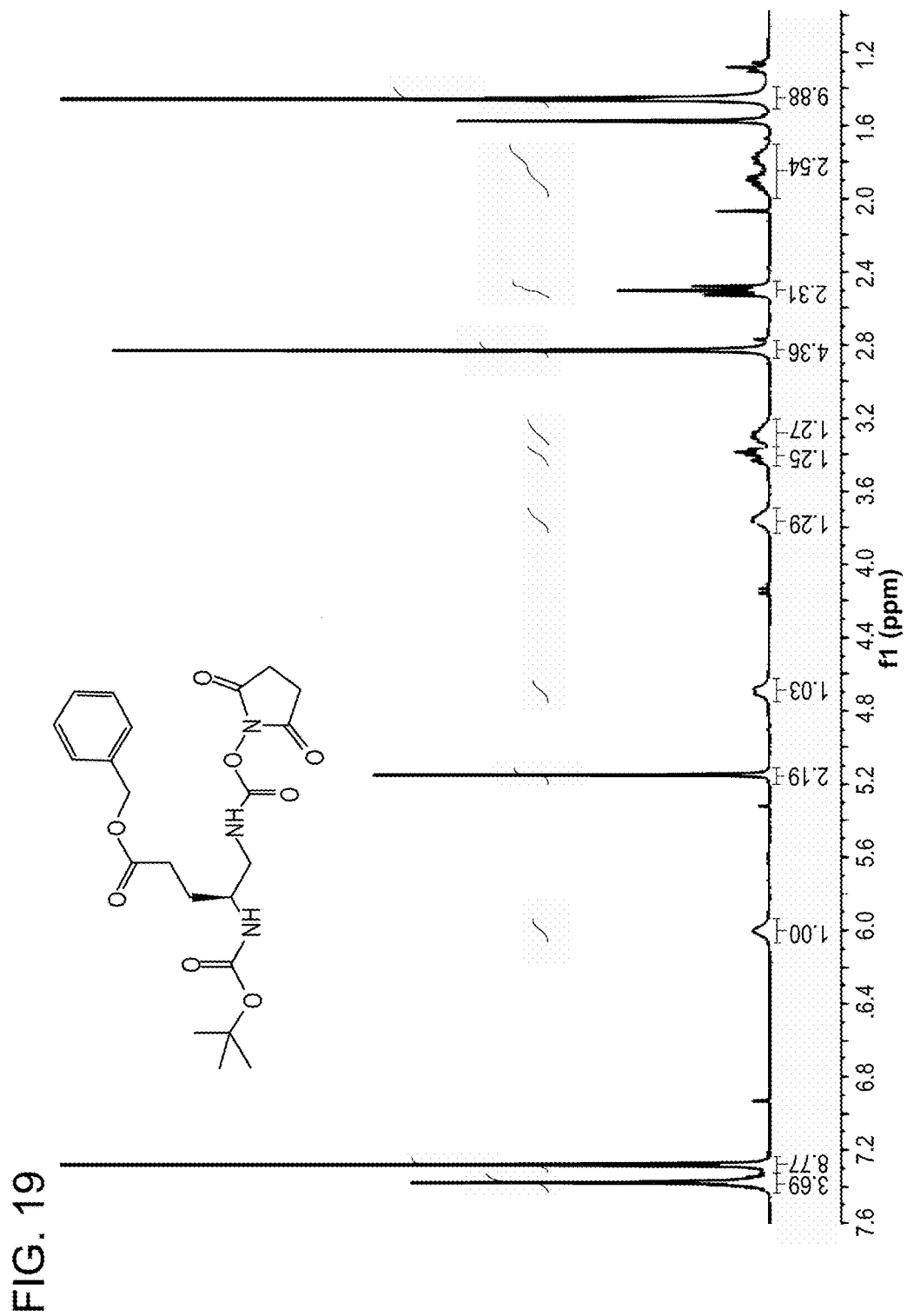
FIG. 19. $^1$H NMR (300 MHz) of compound (4).
Figure 20:
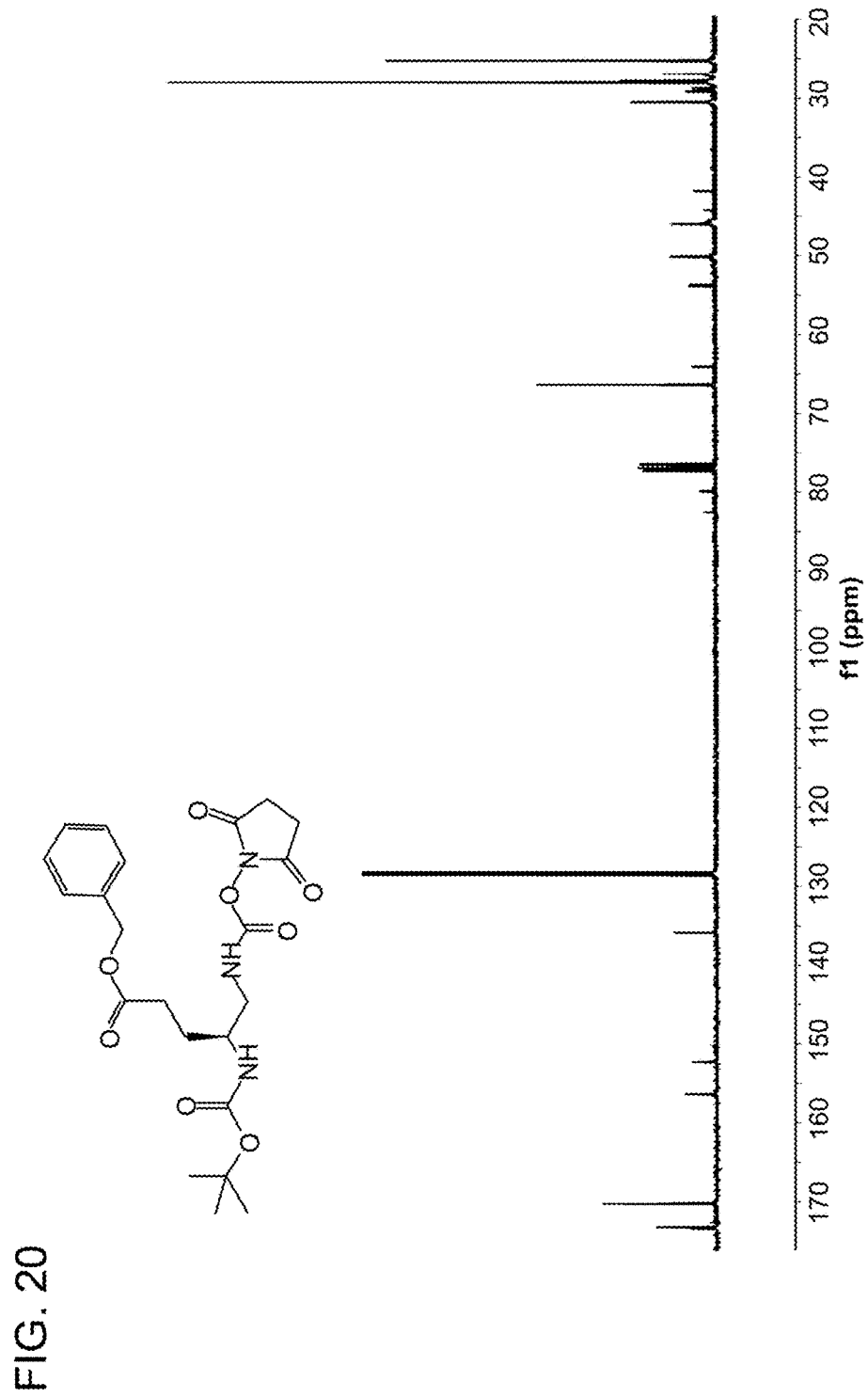
FIG. 20. $^{13}$C NMR (75 MHz) of compound (4).

The acid (6) (0.64 g, 1.82 mmol) was reacted as previously reported (Fischer, L. et al. Succinimidyl Carbamate Derivatives from N-Protected α-Amino Acids and Dipeptides—Synthesis of Ureidopeptides and Oligourea/Peptide Hybrids. *Eur. J. Org. Chem.* 2007, 2511-2525 (2007)). The desired product (4) was obtained as a white solid after precipitation from EtOAc with hexane (0.63 g, 74%). $^1$H NMR (CDCl$_3$, 300 MHz) δ: 7.45-7.33 (m, 5H, CHAr), 6.08 (s, 1H, NH), 5.14 (s, 2H, CH$_2$Ar), 4.74 (m, 1H, NH), 3.82-3.68 (m, 1H, CHN), 3.45-3.22 (m, 2H, CH$_2$N), 2.83 (s, 4H, CH$_2$), 2.55-2.44 (m, 2H, CH$_2$), 1.98-1.69 (m, 2H, CH$_2$), 1.45 (s, 9H, Boc). $^{13}$C NMR (CDCl$_3$, 75 MHz) δ: 173.07, 170.17, 156.41, 152.27, 135.80, 128.59, 128.27, 128.22, 80.00, 66.51, 50.26, 46.27, 30.73, 28.30, 27.17, 25.48; ESI-MS (ESI+) m/z: 486.20 [M+Na]$^+$ (FIGS. 19 and 20).

Synthesis of Oligourea H2

The couplings of Boc-protected OSu activated building blocks were performed according to the general procedure previously reported (Fremaux, J., Fischer, L., Arbogast, T., Kauffmann, B. & Guichard, G. Condensation approach to aliphatic oligourea foldamers: helices with N-(pyrrolidin-2-ylmethyl)ureido junctions. *Angew. Chem. Int. Ed Engl.* 50, 11382-11385 (2011)). The characterization of each intermediate and a scheme of the synthetic strategy adopted are described herein.

FRAGMENT 1

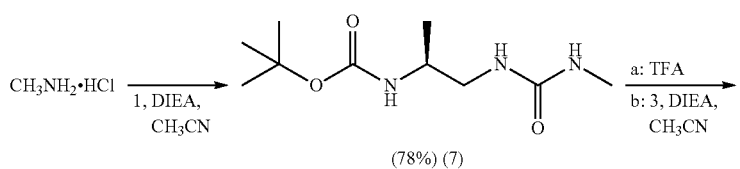

(78%) (7)

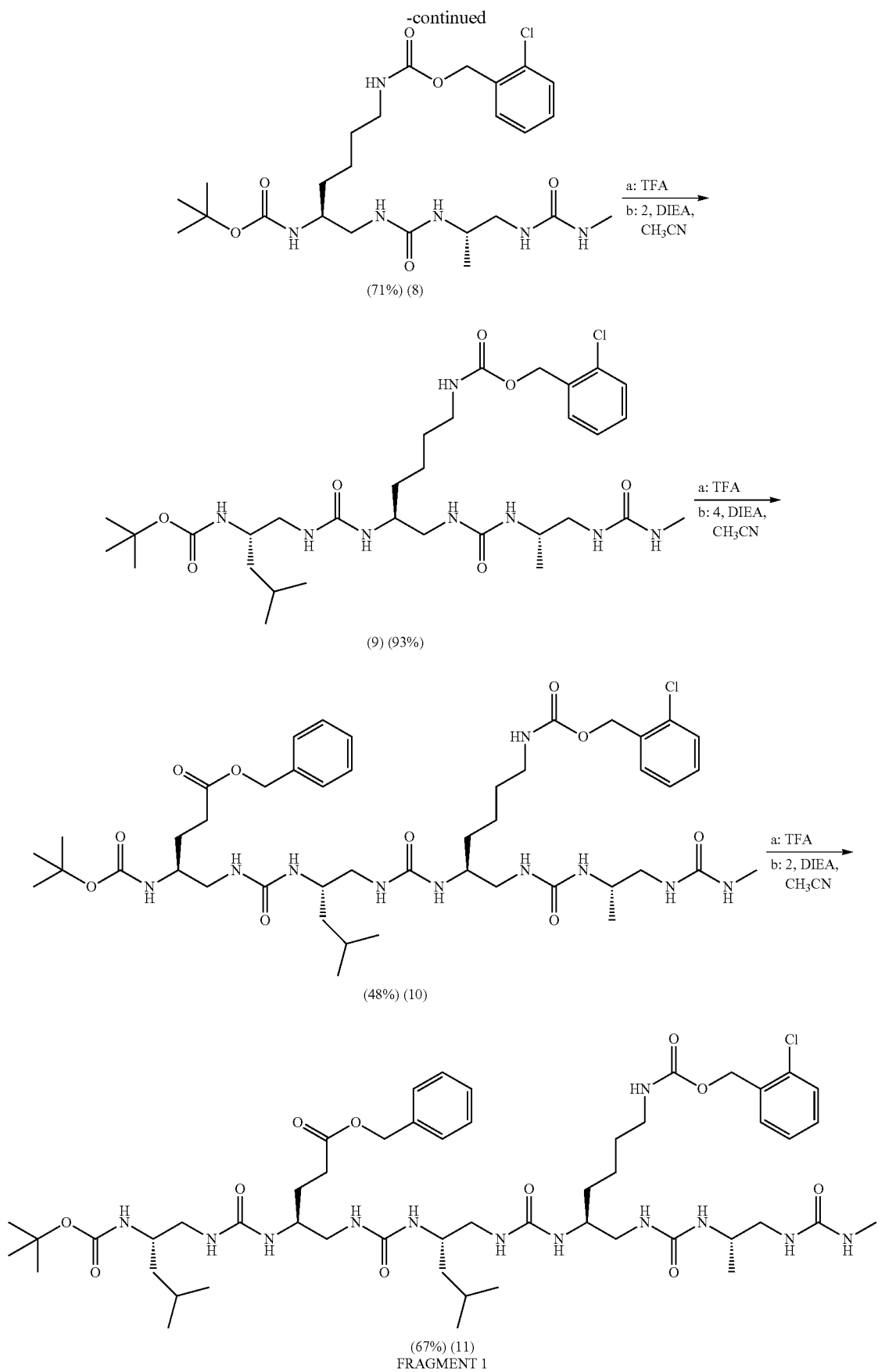

Boc-Ala$^u$-NHMe (7)

The compound was prepared as previously reported (Fischer, L. et al. The canonical helix of urea oligomers at atomic resolution: insights into folding-induced axial organization. *Angew. Chem. Int. Ed Engl.* 49, 1067-1070 (2010)) from the Boc-Ala type building block (1) (0.260 g, 3.81 mmol), to afford compound (7) as a white solid (0.531 g, crude yield 90%) after aqueous work up. $^1$H NMR (DMSO d6, 300 MHz) δ: 6.65 (m, 1H, NH), 5.88 (m, 1H, NH), 5.80 (m, 1H, NH), 3.46-3.35 (m, 1H, CHN), 3.05-2.84 (m, 2H, CHN), 2.53 (d, 3H, CH$_3$N), 1.37 (s, 9H, Boc), 0.95 (d, J=6.6 Hz, 3H, CH$_3$).

Boc-Lys(2ClZ)$^u$-Ala$^u$-NHMe (8)

Compound (8) was prepared from (3) (1.38 g, 2.54 mmol) and (7) (0.620 g, 2.68 mmol), as described in the general procedure previously reported (Fremaux, J., Fischer, L., Arbogast, T., Kauffmann, B. & Guichard, G. Condensation approach to aliphatic oligourea foldamers: helices with N-(pyrrolidin-2-ylmethyl)ureido junctions. *Angew. Chem. Int. Ed Engl.* 50, 11382-11385 (2011)). Oligourea (8) was obtained as a white solid (1.06 g, 71%) after purification by silica gel flash chromatography (DCM 9:MeOH 1). $^1$H NMR (CD$_3$CN, 300 MHz) δ: 7.51-7.32 (m, 4H, CH$_{Ar}$), 5.83 (m, 1H, NH), 5.60 (m, 1H, NH), 5.38-5.25 (m, 2H, NH), 5.18 (s, 2H, CH$_2$OCO), 5.12-5.02 (m, 2H, NH), 3.74-3.63 (m, 1H, CHN), 3.61-3.50 (m, 1H, CHN), 3.25-3.07 (m, 4H, CH$_2$N), 3.06-2.91 (m, 2H, CH$_2$N), 2.66 (d, J=4.7 Hz, 3H, CH$_3$N), 1.58-1.46 (m, 2H, CH$_2$), 1.45 (s, 9H, Boc), 1.42-1.29 (m, 4H, CH$_2$), 1.07 (d, J=6.7 Hz, 3H, CH$_3$); ESI-MS (ESI+) m/z: 579.27 [M+Na]$^+$, 1134.8 [2M+Na]$^+$.

Boc-Leu$^u$-Lys(2ClZ)$^u$-Ala$^u$-NHMe (9)

Compound (9) was prepared from (2) (0.64 g, 1.80 mmol) and (8) (1.00 g, 1.80 mmol) as described in the general procedure previously reported (Fremaux, J., et al. Condensation approach to aliphatic oligourea foldamers: helices with N-(pyrrolidin-2-ylmethyl)ureido junctions. *Angew. Chem. Int. Ed Engl.* 50, 11382-11385 (2011)). Oligourea (9) was obtained as a white solid (1.25 g, 93%) after purification by silica gel flash chromatography (DCM 9:MeOH 1). $^1$H NMR (CD$_3$OH, 300 MHz) δ: 7.49-7.29 (m, 4H, CH$_{Ar}$), 7.12 (m, 1H, NH), 6.53 (d, J=9.6 Hz, 1H, NH), 6.04 (m, 1H, NH), 5.94 (m, 1H, NH), 5.89 (m, 1H, NH), 5.81 (m, 1H, NH), 5.19 (s, 2H, CH$_2$OCO), 3.92-3.72 (m, 3H, CHN), 3.57-3.40 (m, 2H, CH$_2$N), 3.20-3.11 (m, 2H, CH$_2$N), 2.90-2.79 (m, 2H, CH$_2$N), 2.72 (d, J=3.9 Hz, 3H, CH$_3$N), 2.68-2.44 (m, 2H, CH$_2$N), 1.76-1.61 (m, 1H, CH), 1.60-1.51 (m, 2H, CH$_2$), 1.47 (s, 9H, Boc), 1.44-1.15 (m, 6H, CH$_2$), 1.08 (d, J=6.7 Hz, 3H, CH$_3$), 0.99-0.87 (m, 6H, CH$_3$); ESI-MS (ESI+) m/z: 699.2 [M+Na]$^+$, 721.3 [M+Na]$^+$.

Boc-Glu(OBn)$^u$-Leu$^u$-Lys(2ClZ)$^u$-Ala$^u$-NHMe (10)

Compound (10) was prepared from (4) (0.86 g, 1.86 mmol) and (9) (1.30 g, 1.86 mmol) as described in the general procedure previously reported (Fremaux, J., et al. Condensation approach to aliphatic oligourea foldamers: helices with N-(pyrrolidin-2-ylmethyl)ureido junctions. *Angew. Chem. Int. Ed Engl.* 50, 11382-11385 (2011)). Oligourea (10) was obtained as a white solid (0.86 g, 48%) after purification by silica gel flash chromatography (DCM 9:MeOH 1). $^1$H NMR (CD$_3$OH, 300 MHz) δ: 7.51-7.28 (m, 9H, CH$_{Ar}$), 7.10 (m, 1H, NH), 6.66 (d, J=9.7 Hz, 1H, NH), 6.40 (m, 1H, NH), 6.28 (m, 1H, NH), 6.20 (m, 1H, NH), 6.08-5.99 (m, 2H, NH), 5.93 (m, 1H, NH), 5.82-5.75 (m, 2H, NH), 5.19 (s, 2H, CH$_2$OCO), 5.13 (s, 2H, CH$_2$OCO), 4.01-3.66 (m, 4H, CHN), 3.60-3.42 (m, 4H, CH$_2$N), 3.16-3.07 (m, 2H, CH$_2$N), 2.86-2.75 (m, 1H, CH$_2$N), 2.73 (d, J=3.9 Hz, 3H, CH$_3$N), 2.68-2.51 (m, 2H, CH$_2$N), 2.49-2.40 (m, 2H, CH$_2$COO), 2.40-2.32 (m, 1H, CH$_2$N), 1.91-1.78 (m, 1H, CH), 1.76-1.51 (m, 4H, CH$_2$), 1.47 (s, 9H, Boc), 1.42-1.16 (m, 6H, CH$_2$), 1.08 (d, J=6.7 Hz, 3H, CH$_3$), 0.96-0.88 (m, 6H, CH$_3$); ESI-MS (ESI+) m/z: 947.3 [M+H]$^+$, 969.4 [M+Na]$^+$.\

Boc-Leu$^u$-Glu(OBz)$^u$-Leu$^u$-Lys(2ClZ)$^u$-Ala$^u$-NHMe (11)

Figure 21:
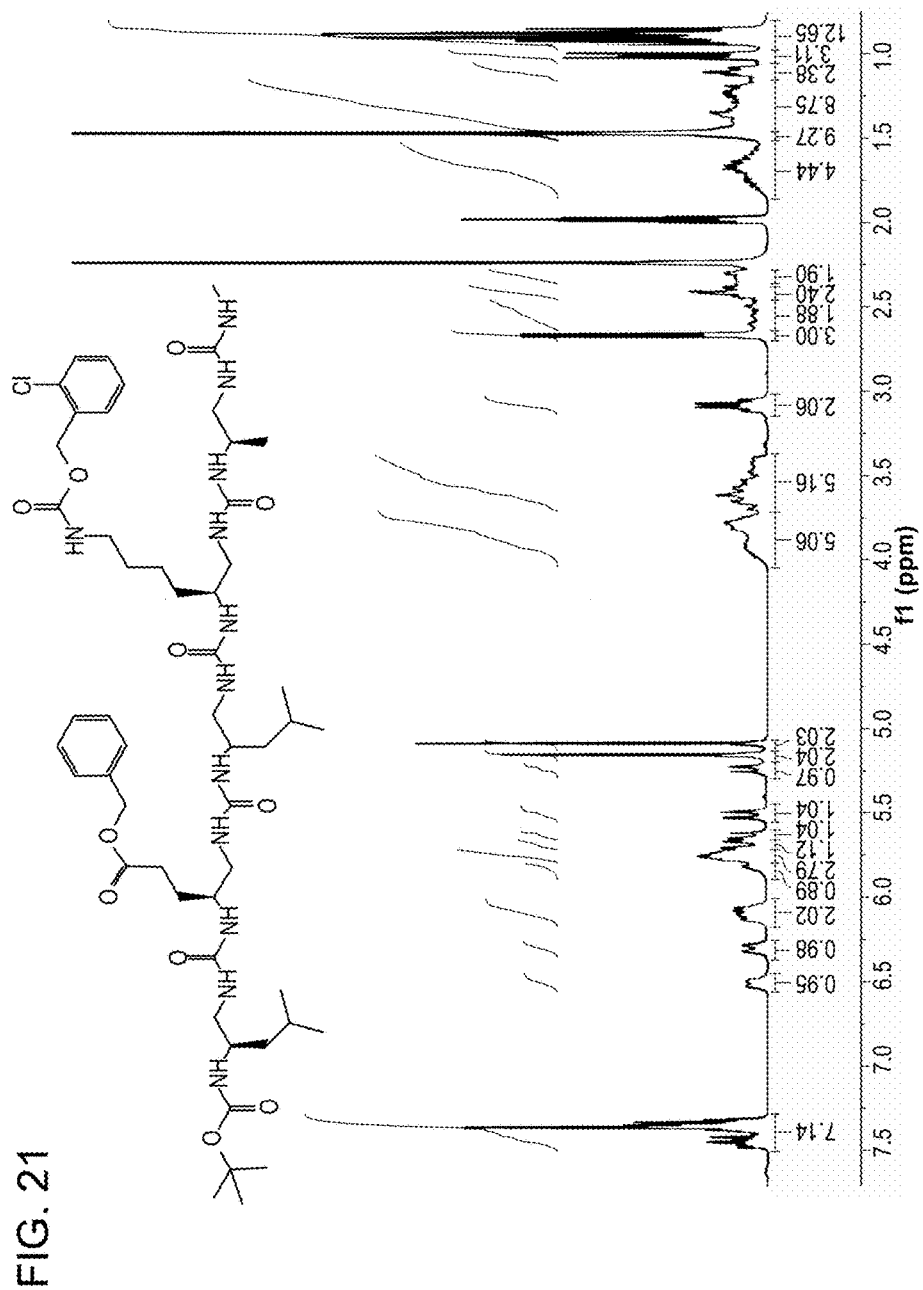
FIG. 21. $^1$H NMR (300 MHz) of compound (11).

Compound (11) was prepared from (2) (0.113 g, 0.317 mmol) and (10) (0.300 g, 0.317 mmol) as previously described (Fremaux, J., et al. Condensation approach to aliphatic oligourea foldamers: helices with N-(pyrrolidin-2-ylmethyl)ureido junctions. *Angew. Chem. Int. Ed Engl.* 50, 11382-11385 (2011)). Oligourea (11) was obtained as a white solid (0.23 g, 67%) after purification by silica gel flash chromatography (DCM 9:MeOH 1). $^1$H NMR (CD$_3$OH, 300 MHz) δ: 7.51-7.32 (m, 9H, CH$_{Ar}$), 6.51 (m, 1H, NH), 6.30 (m, 1H, NH), 6.12 (m, 1H, NH), 6.07 (m, 1H, NH), 5.82 (m, 1H, NH), 5.80-5.72 (m, 3H, NH), 5.69 (d, J=10.6 Hz, 1H, NH), 5.64 (d, J=10.4 Hz, 1H, NH), 5.52 (d, J=9.9 Hz, 1H, NH), 5.24 (d, J=10.1 Hz, 1H, NH), 5.16 (s, 2H, CH$_2$OCO), 5.09 (s, 2H, CH$_2$OCO), 4.04-3.72 (m, 5H, CHN), 3.70-3.38 (m, 5H, CH$_2$N), 3.13-3.05 (m, 2H, CH$_2$N), 2.67 (d, J=4.7 Hz, 3H, CH$_3$N), 2.65-2.46 (m, 2H, CH$_2$N), 2.45-2.37 (m, 2H, CH$_2$COO), 2.37-2.28 (m, 3H, CH$_2$N), 1.83-1.53 (m, 4H, CH—CH$_2$), 1.46 (s, 9H, Boc), 1.44-1.16 (m, 8H, CH$_2$), 1.15-1.07 (m, 2H, CH$_2$), 1.01 (d, J=6.7 Hz, 3H, CH$_3$), 0.95-0.84 (m, 12H, CH$_3$); ESI-MS (ESI+) m/z: 1089.5 [M+H]$^+$, 1111.5 [M+Na]$^+$ (FIG. 21).

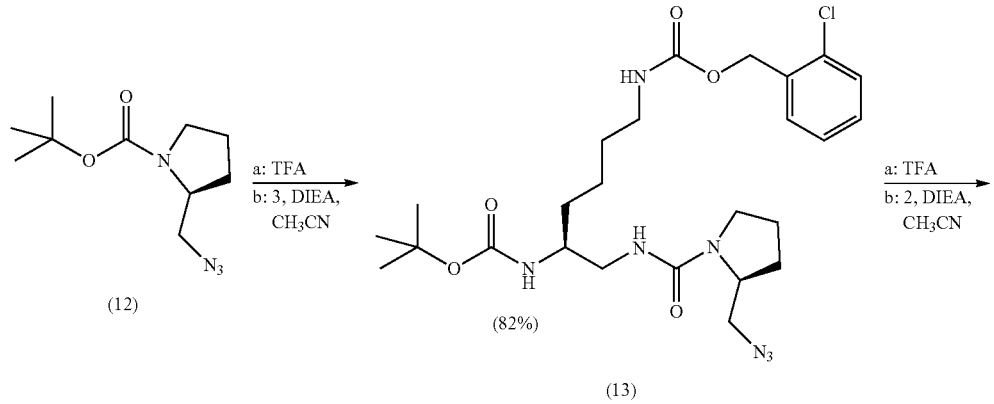

FRAGMENT 2

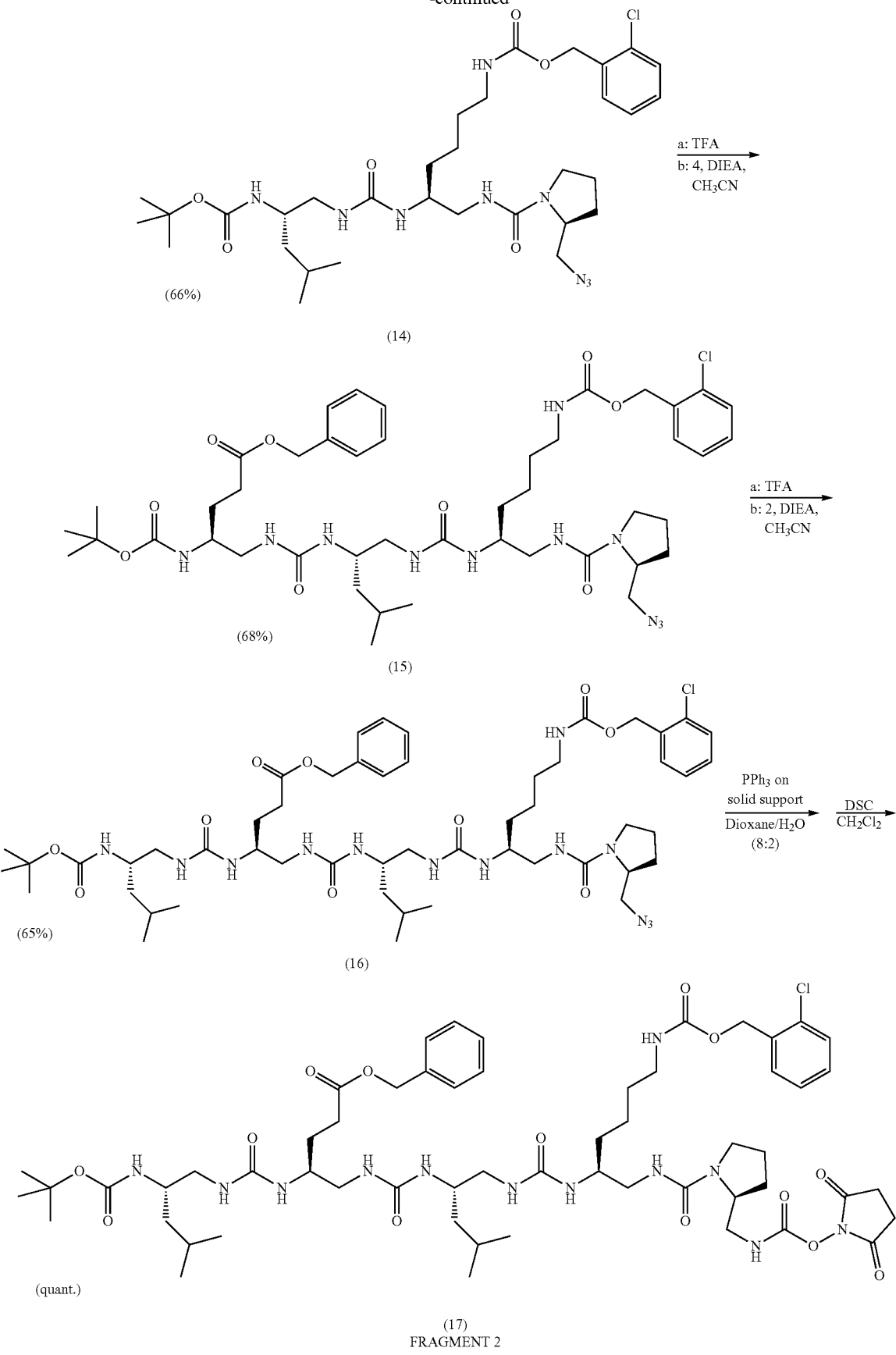

Boc Lys(2ClZ)$^u$-Pro$^u$-N$_3$ (13)

Compound (13) was prepared from (3) (0.43 g, 2.65 mmol) and (12) (0.600 g, 2.65 mmol) as previously described (Fremaux, J., et al. Condensation approach to aliphatic oligourea foldamers: helices with N-(pyrrolidin-2-ylmethyl)ureido junctions. *Angew. Chem. Int. Ed Engl.* 50, 11382-11385 (2011)). Oligourea (13) was obtained as a white solid (1.2 g, 82%) after purification by silica gel flash chromatography (DCM 9: MeOH 1). The synthesis of compound (12) was also previously reported (Fremaux, J., et al. Condensation approach to aliphatic oligourea foldamers: helices with N-(pyrrolidin-2-ylmethyl)ureido junctions. *Angew. Chem. Int. Ed Engl.* 50, 11382-11385 (2011)). $^1$H NMR (CD$_3$CN, 300 MHz) δ: 7.74-7.33 (m, 4H, CH$_{Ar}$), 5.82 (m, 1H, NH), 5.51 (s, 1H, NH), 5.32 (m, 1H, NH), 5.17 (s, 2H, CH$_2$OCO), 4.04-3.97 (m, 1H, CHN), 3.59-3.52 (m, 1H, CHN), 3.48 (dd, J=12.1, 6.5 Hz, 1H, CH$_2$N), 3.37 (dd, J=12.1, 3.8 Hz, 1H, CH$_2$N), 3.33-3.23 (m, 2H, CH$_2$N), 3.21-3.09 (m, 4H, CH$_2$N), 2.03-1.78 (m, 4H, CH$_2$), 1.56-1.45 (m, 3H, CH$_2$), 1.43 (s, 9H, Boc), 1.41-1.30 (m, 3H, CH$_2$); ESI-MS (ESI+) m/z: 279.09 [M+2H]$^{2+}$, 574.25 [M+Na]$^+$.

Boc Leu-Lys(2ClZ)$^u$-Pro$^u$-N$_3$ (14)

Compound (14) was prepared from (2) (0.77 g, 2.17 mmol) and (13) (1.20 g, 2.17 mmol) as previously described (Fremaux, J., et al. Condensation approach to aliphatic oligourea foldamers: helices with N-(pyrrolidin-2-ylmethyl)ureido junctions. *Angew. Chem. Int. Ed Engl.* 50, 11382-11385 (2011)). Oligourea (14) was obtained as a white solid (1.00 g, 66%) after purification by silica gel flash chromatography (DCM 9:MeOH 1). $^1$H NMR (CD$_3$CN, 300 MHz) δ: 7.53-7.35 (m, 4H, CH$_{Ar}$), 5.87 (m, 1H, NH), 5.68-5.53 (m, 2H, NH), 5.39 (m, 1H, NH), 5.18 (s, 2H, CH$_2$OCO), 5.12 (m, 1H, NH), 4.07-3.98 (m, 1H, CHN), 3.70-3.56 (m, 2H, CHN), 3.48 (dd, J=12.1, 6.6 Hz, 1H, CH$_2$N), 3.38 (dd, J=12.1, 3.8 Hz, 1H, CH$_2$N), 3.34-3.26 (m, 2H, CH$_2$N), 3.21-2.99 (m, 6H, CH$_2$N), 1.96-1.77 (m, 4H, CH$_2$), 1.72-1.47 (m, 4H, CH$_2$), 1.43 (s, 9H, Boc), 1.40-1.20 (m, 5H, CH$_2$), 0.95-0.88 (m, 6H, CH$_3$); ESI-MS (ESI+) m/z: 694.38 [M+H]$^+$, 716.36 [M+Na]$^+$.

Boc Lys(2ClZ)$^u$-Leu-Lys(2ClZ)$^u$-Pro$^u$-N$_3$ (15)

Compound (15) was prepared from (4) (0.63 g, 1.36 mmol) and (14) (0.95 g, 1.36 mmol) as previously described (Fremaux, J., et al. Condensation approach to aliphatic oligourea foldamers: helices with N-(pyrrolidin-2-ylmethyl)ureido junctions. *Angew. Chem. Int. Ed Engl.* 50, 11382-11385 (2011)). Oligourea (15) was obtained as a white solid (0.88 g, 68%) after purification by silica gel flash chromatography (DCM 9:MeOH 1). $^1$H NMR (CD$_3$CN, 300 MHz) δ: 7.51-7.32 (m, 9H, CH$_{Ar}$), 6.00-5.88 (m, 2H, NH), 5.67 (m, 1H, NH), 5.54-5.38 (m, 3H, NH), 5.16 (s, 2H, CH$_2$OCO), 5.11 (s, 2H, CH$_2$OCO), 4.06-4.00 (m, 1H, CHN), 3.86-3.61 (m, 3H, CHN), 3.51-3.24 (m, 7H, CH$_2$N), 3.15-3.07 (m, 2H, CH$_2$N), 2.96-2.80 (m, 2H, CH$_2$N), 2.72-2.57 (m, 1H, CH$_2$N), 2.45-2.38 (m, 2H, CH$_2$COO), 1.95-1.73 (m, 4H, CH$_2$), 1.73-1.59 (m, 2H, CH$_2$), 1.52-1.45 (m, 3H, CH—CH$_2$), 1.44 (s, 9H, Boc), 1.39-1.29 (m, 4H, CH$_2$), 1.28-1.17 (m, 2H, CH$_2$), 0.96-0.85 (m, 6H, CH$_3$); ESI-MS (ESI+) m/z: 942.49 [M+H]$^+$, 980.45 [M+Na]$^+$.

Boc Leu-Lys(2ClZ)$^u$-Leu-Lys(2ClZ)$^u$-Pro$^u$-N$_3$ (16)

Compound (16) was prepared from (2) (0.32 g, 0.90 mmol) and (15) (0.85 g, 0.90 mmol as previously described (Fremaux, J., et al. Condensation approach to aliphatic oligourea foldamers: helices with N-(pyrrolidin-2-ylmethyl) ureido junctions. *Angew. Chem. Int. Ed Engl.* 50, 11382-11385 (2011)). Oligourea (16) was obtained as a white solid (0.64 g, 65%) after purification by silica gel flash chromatography (DCM 9:MeOH 1). $^1$H NMR (CD$_3$CN, 300 MHz) δ: 7.50-7.33 (m, 9H, CH$_{Ar}$), 6.12 (m, 1H, NH), 5.99-5.87 (m, 2H, NH), 5.75 (d, J=8.7 Hz, 1H, NH), 5.57-5.48 (m, 2H, NH), 5.43-5.37 (m, 2H, NH), 5.17 (s, 2H, CH$_2$OCO), 5.10 (s, 2H, CH$_2$OCO), 4.97 (d, J=10.3 Hz, 1H, NH), 4.08-4.02 (m, 1H, CHN), 3.95-3.74 (m, 3H, CHN), 3.73-3.50 (m, 4H, CHN—CH$_2$N), 3.49-3.29 (m, 5H, CH$_2$N), 3.14-3.06 (m, 2H, CH$_2$N), 2.85-2.75 (m, 1H, CH$_2$N), 2.58-2.45 (m, 1H, CH$_2$N), 2.44-2.36 (m, 2H, CH$_2$COO), 2.37-2.28 (m, 2H, CH$_2$N), 1.93-1.53 (m, 8H, CH—CH$_2$), 1.45 (s, 9H, Boc), 1.43-1.10 (m, 10H, CH$_2$), 0.95-0.86 (m, 12H, CH$_3$); ESI-MS (ESI+) m/z: 1084.4 [M+H]$^+$, 1106.5 [M+Na]$^+$.

Boc Leu$^u$-Glu(OBn)$^u$-Leu$^u$-Lys(2ClZ)$^u$-Pro$^u$-NHOSu (17)

Figure 22:
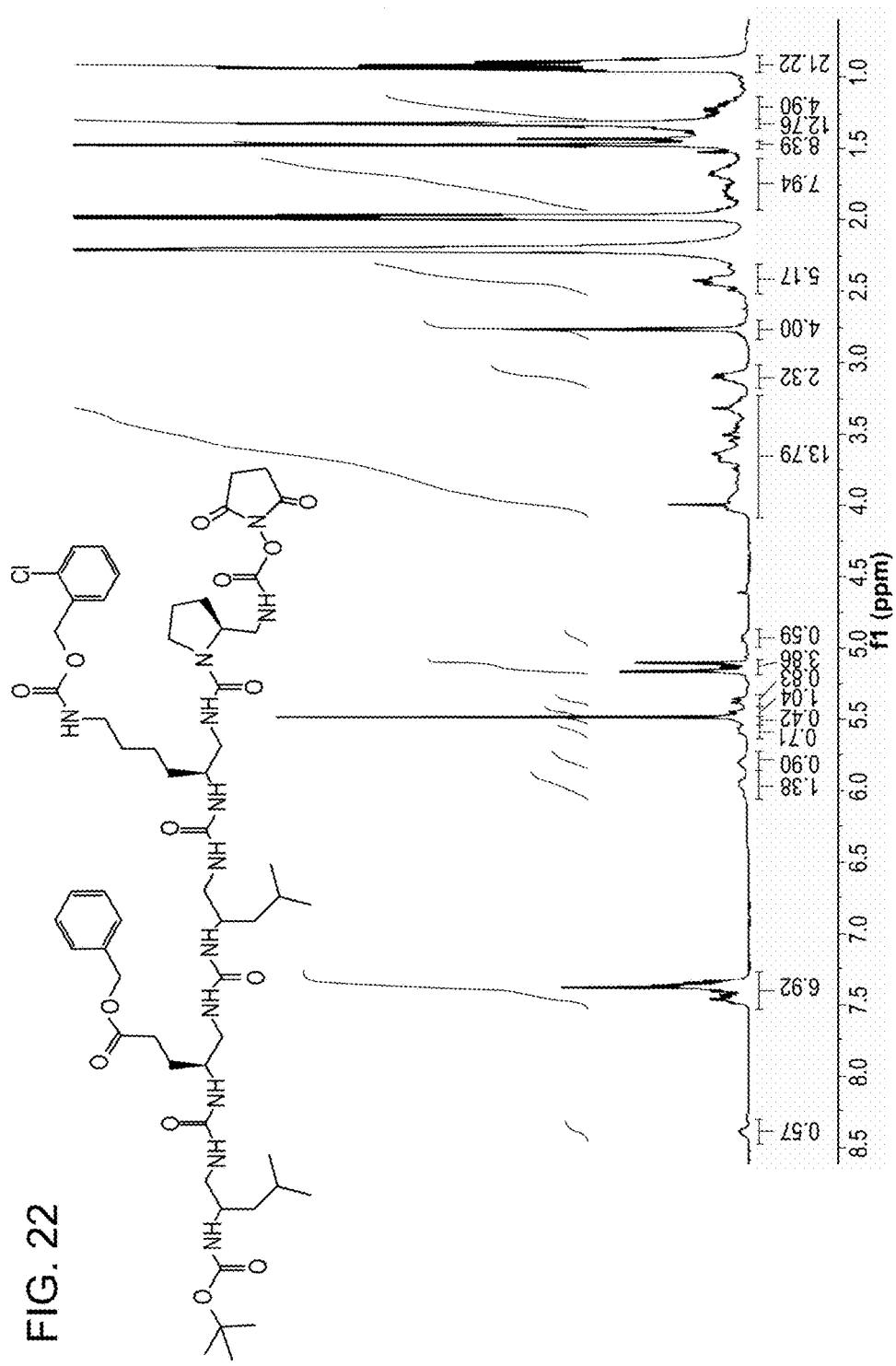
FIG. 22. $^1$H NMR (300 MHz) of compound (17).

Compound (17) (0.30 g, 0.260 mmol) was dissolved in a mixture 8:2 dioxane/H$_2$O (8 ml). PL-TPP resin (1.5 mmol/g, 0.200 g) was added and the mixture was stirred under microwave irradiation (50 W, 50° C., CEM Discover) for 2 h. After completion, the resin was removed by filtration, washed with dioxane and H$_2$O, and the filtrate was evaporated in vacuo. The amine obtained was used without further purification. Disuccinimidyl carbonate (0.080 g, 0.31 mmol) was suspended in dry DCM (10 mL) and a DCM solution of the amine was added portion wise. The reaction mixture was stirred at room temperature under a N$_2$ atmosphere for 4 hr. After that time, the white precipitate was eliminated by filtration and washed with DCM. The filtrate was washed with 1N KHSO$_4$ (aq), water, dried over Na$_2$SO$_4$, and concentrated under reduced pressure. The pure product (17) was precipitated from concentrated DCM solution as a white solid by adding Et$_2$O (0.340 g, quantitative). $^1$H NMR (CD$_3$CN, 300 MHz) δ: 8.40 (s, 1H, NHOSu), 7.51-7.31 (m, 9H, CH$_{Ar}$), 6.09-5.89 (m, 2H, NH), 5.80 (m, 1H, NH), 5.57 (m, 1H, NH), 5.46 (m, 1H, NH), 5.37 (d, J=10.2 Hz, 1H, NH) 5.16 (s, 2H, CH$_2$OCO), 5.11 (s, 2H, CH$_2$OCO), 4.93 (m, 1H, NH), 4.07-3.21 (m, 14H, CHN—CH$_2$N), 3.18-3.04 (m, 2H, CH$_2$N), 2.76 (s, 4H, CH$_2$), 2.55-2.27 (m, 6H, CH$_2$N), 1.95-1.50 (m, 8H, CH—CH$_2$), 1.46 (s, 9H, Boc), 1.42-1.11 (m, 10H, CH$_2$), 0.98-0.83 (m, 12H, CH$_3$); ESI-MS (ESI+) m/z: 1199.4 [M+H]$^+$, 1221.6 [M+Na]$^+$ (FIG. 22).

FRAGMENT 1 (11) →  a: TFA
b: FRAGMENT 2 (17), DIEA, CH$_3$CN

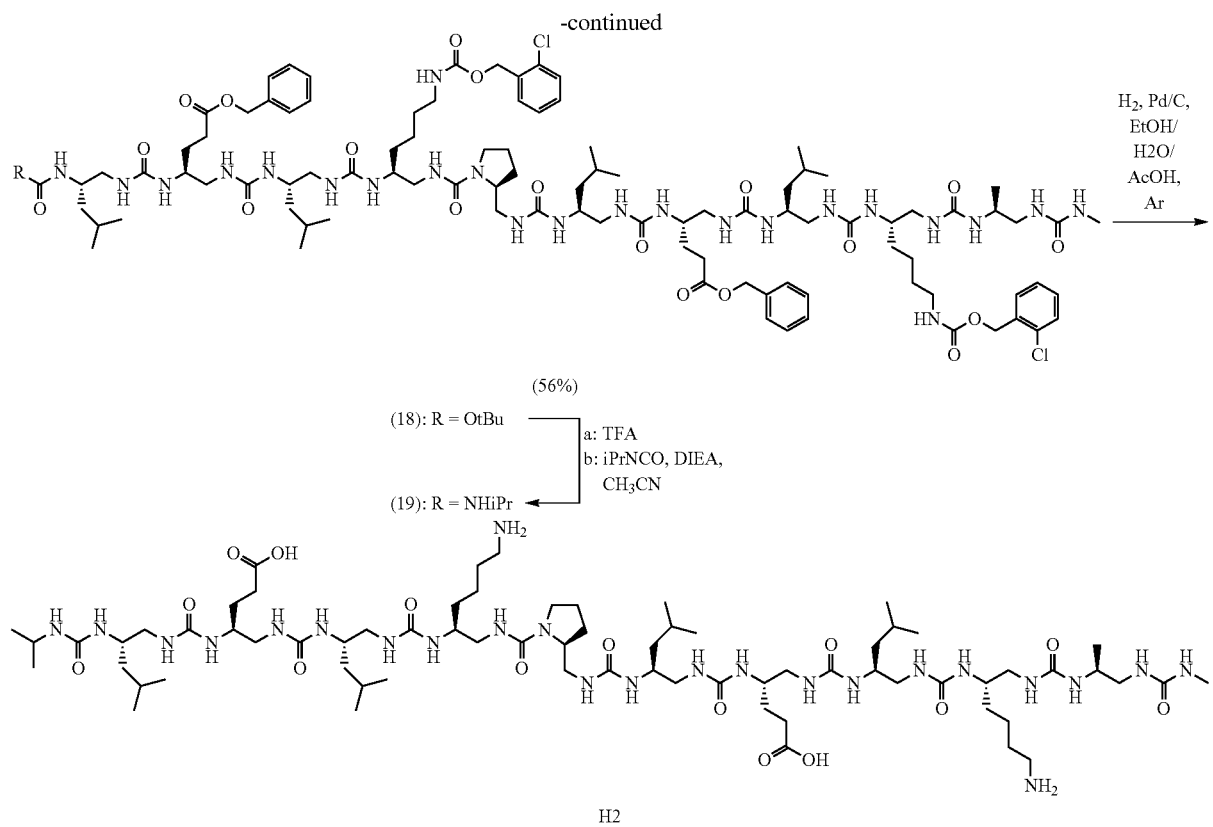

(18): R = OtBu
(19): R = NHiPr a: TFA
b: iPrNCO, DIEA, CH₃CN

H2

Boc-Leu$^u$-Glu(OBn)$^u$-Leu$^u$-Lys(2ClZ)$^u$-Pro$^u$-Leu$^u$-Glu(OBn)$^u$-Leu$^u$-Lys(2ClZ)$^u$-Ala$^u$-NHMe (18)

Compound (11) (0.130 g, 0.119 mmol) was dissolved in TFA (3 ml) and stirred for 45 min at room temperature. After Boc deprotection was completed, the mixture was concentrated under reduced pressure, co-evaporated with cyclohexane. The crude product was then dissolved in DMF (3 ml), then DIEA (0.06 ml, 0.36 mmol) and (17) (0.143 g, 0.119 mmol) were added, and the reaction mixture was then stirred under microwave irradiation (50° C., 25 W) for 3 hrs. After completion, the solvent was evaporated in vacuo, the crude was dissolved in EtOAc and washed with saturated aqueous NaHCO₃, 1N KHSO₄ (aq) and brine. The organic layer was then dried over Na₂SO₄ and the solvents were evaporated in vacuo. The crude product was purified by silica gel flash chromatography (DCM 9:MeOH 1) to afford compound (18) as a white solid (0.140 g, 56%). ¹H NMR (CD₃CN, 300 MHz) δ: 7.50-7.31 (m, 18H, CH$_{Ar}$), 7.13 (m, 1H, NH), 6.90 (m, 1H, NH), 6.76 (m, 1H, NH), 6.62 (m, 1H, NH), 6.48-6.30 (m, 3H, NH), 6.10-5.84 (m, 8H, NH), 5.80-5.70 (m, 2H, NH), 5.68-5.58 (m, 2H, NH), 5.54-5.51 (m, 1H, NH), 5.37 (d, J=10.0 Hz, 1H, NH), 5.16 (s, 2H, CH₂OCO), 5.14 (s, 2H, CH₂OCO), 5.10 (s, 2H, CH₂OCO), 5.9 (s, 2H, CH₂OCO), 4.93 (d, J=10.3 Hz, 1H, NH), 4.33-4.24 (m, 1H, CHN), 4.09-3.40 (m, 19H, CHN—CH₂N), 3.30-3.19 (m, 2H, CH₂N), 3.13-2.92 (m, 4H, CH₂N), 2.84-2.71 (m, 1H, CH₂N), 2.67 (d, J=4.6 Hz, 3H, CH₃N), 2.65-2.53 (m, 2H, CH₂N), 2.52-2.20 (m, 12H, CH₂N—CH₂COO), 1.95-1.50 (m, 16H, CH—CH₂), 1.48 (s, 9H, Boc), 1.43-1.05 (m, 16H, CH₂), 1.01 (d, J=6.7 Hz, 3H, CH₃), 0.95-0.82 (m, 24H, CH₃); ESI-MS (ESI+) m/z: 1060.4 [M+2Na]²⁺.

iPr-NHCO-Leu$^u$-Glu(OBn)$^u$-Leu$^u$-Lys(2ClZ)$^u$-Pro$^u$-Leu$^u$-Glu(OBn)$^u$-Leu$^u$-Lys(2ClZ)$^u$-Ala$^u$-NHMe (19)

Boc-protected oligourea (18) (0.065 g, 0.031 mmol) was dissolved in TFA (3 ml) and stirred for 45 min. After Boc deprotection was completed, the mixture was concentrated under reduced pressure, and TFA was co-evaporated with cyclohexane. The crude product was then dissolved in a CH₃CN/DMF mixture (4:1, 2.5 ml), then DIEA (0.016 ml, 0.094 mmol) and isopropyl isocyanate (0.005 ml, 0.05 mmol) were added, and the mixture was stirred under microwave irradiation (50° C., 25 W) for 3 hrs. After completion, the solvents were evaporated in vacuo, the crude product was dissolved in EtOAc and treated with saturated aqueous NaHCO₃, 1N KHSO₄ (aq) and brine. The organic layer was then dried over Na₂SO₄ and the solvents were evaporated in vacuo. Crude compound (19) was used as such in the next step. ESI-MS (ESI+) m/z: 1049.4 [M+2Na]²⁺.

iPr-NHCO-Leu$^u$-Glu$^u$-Leu$^u$-Lys$^u$-Pro$^u$-Leu$^u$-Glu$^u$-Leu$^u$-Lys$^u$-Ala$^u$-NHMe (H2)

Compound (19) (0.065 g, 0.031 mmol) was dissolved in a mixture 5:2:1 of EtOH/H₂O/Acetic acid and stirred under an atmosphere of Ar. Pd/C 10% (0.006 g) was added, Ar was replaced by H₂ and the mixture was stirred at room temperature for 24 hrs. The Pd/C was then removed by filtration on Millipore paper and washed with the solvent mixture used for the reaction. EtOH was completely evaporated in vacuo, the crude product was freeze-dried and purified by semi-preparative HPLC (25-70% CH₃CN 0.1% TFA in H₂O 0.1% TFA, 20 min; Macherey-Nagel Nucleodur 100-16 C18 ec, 10×250). Pure H2 was freeze-dried and TFA was exchanged with HCl by repeated lyophilisations in 0.1 N HCl. ESI-MS (ESI+) m/z: 771.6 [M+2H]$^{2+}$, 1541.9 [M+H]$^{+}$; HPLC: R$_f$=8.04 min (0-100% CH$_3$CN 0.1% TFA in H$_2$O 0.1% TFA, 10 min, Macherey-Nagel, Nucleodur cc 70/4 100-3 C18 ec, 4.6×100, 1 ml/min) (FIG. 23).

Azido Building Block Synthesis for Oligourea Synthesis on Solid Support

The building blocks containing Ser-, Glu- and Lys-type side chains were synthesized as previously reported (Douat-Casassus, C., et al. Microwave-enhanced solid-phase synthesis of N,N'-linked aliphatic oligoureas and related hybrids. *Org. Lett.* 14, 3130-3133 (2012)), following path A, starting from the N-Cbz protected (L) amino acid. The Asn type building block was synthesized following path B described in the same report (Douat-Casassus, C., et al. Microwave-enhanced solid-phase synthesis of N,N'-linked aliphatic oligoureas and related hybrids. *Org. Lett.* 14, 3130-3133 (2012)), starting from the N-Fmoc protected amino acid. Fmoc deprotection was performed using DBU, as previously described (Zhang, Z. & Fan, E. Solid-phase and solution-phase syntheses of oligomeric guanidines bearing peptide side chains. *J. Org. Chem.* 70, 8801-8810 (2005)).

N$_3$-Ser: (R)-2,5-dioxopyrrolidin-1-yl (2-azido-3-(tert-butoxy)propyl)carbamate (20)

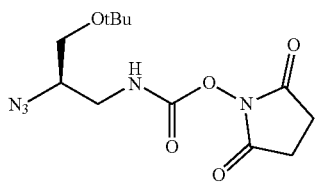 [SMILES: CC(C)(C)OC[C@@H](CNC(=O)ON1C(=O)CCC1=O)N=[N+]=[N-]]

Figure 24:
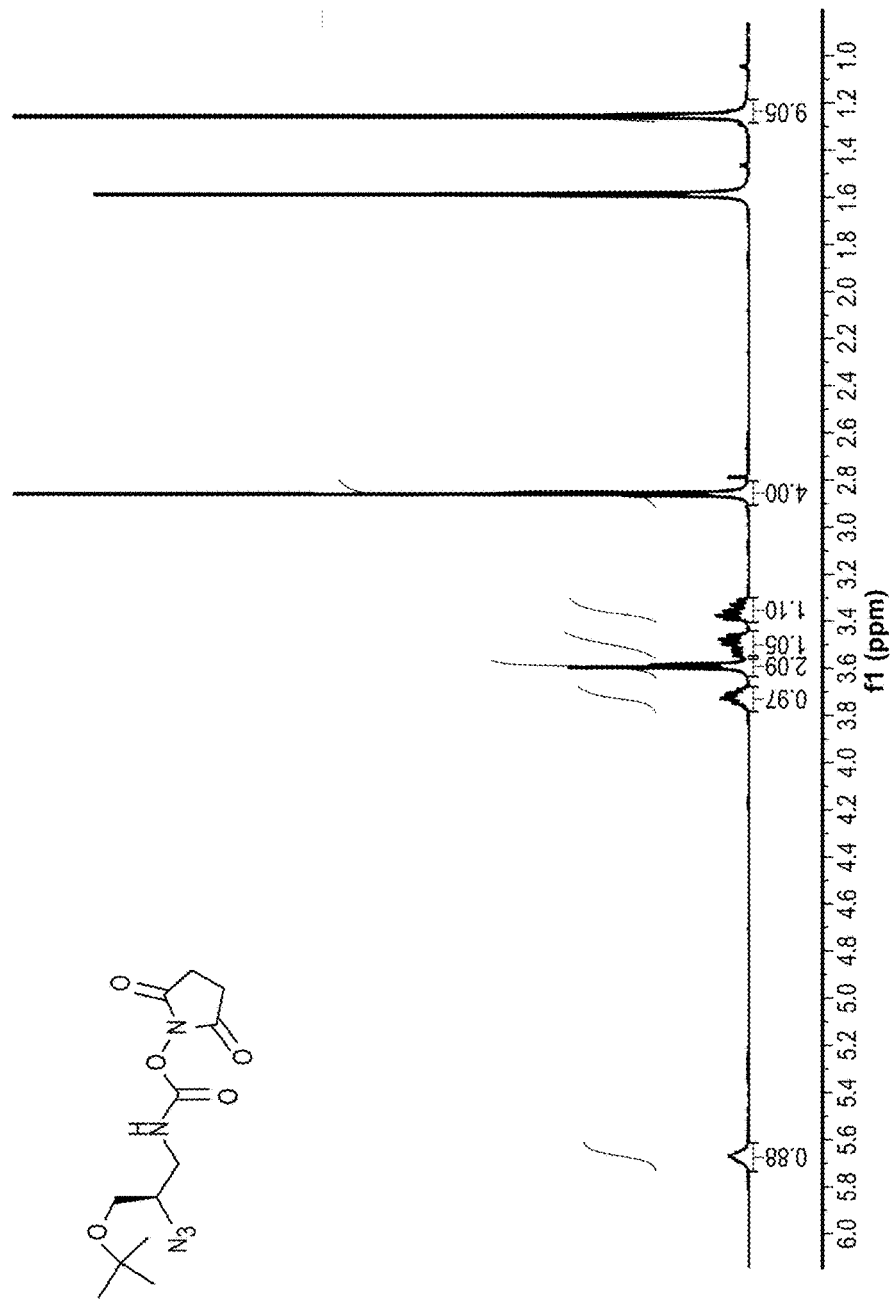
FIG. 24. $^1$H NMR (300 MHz) of compound (20).
Figure 25:
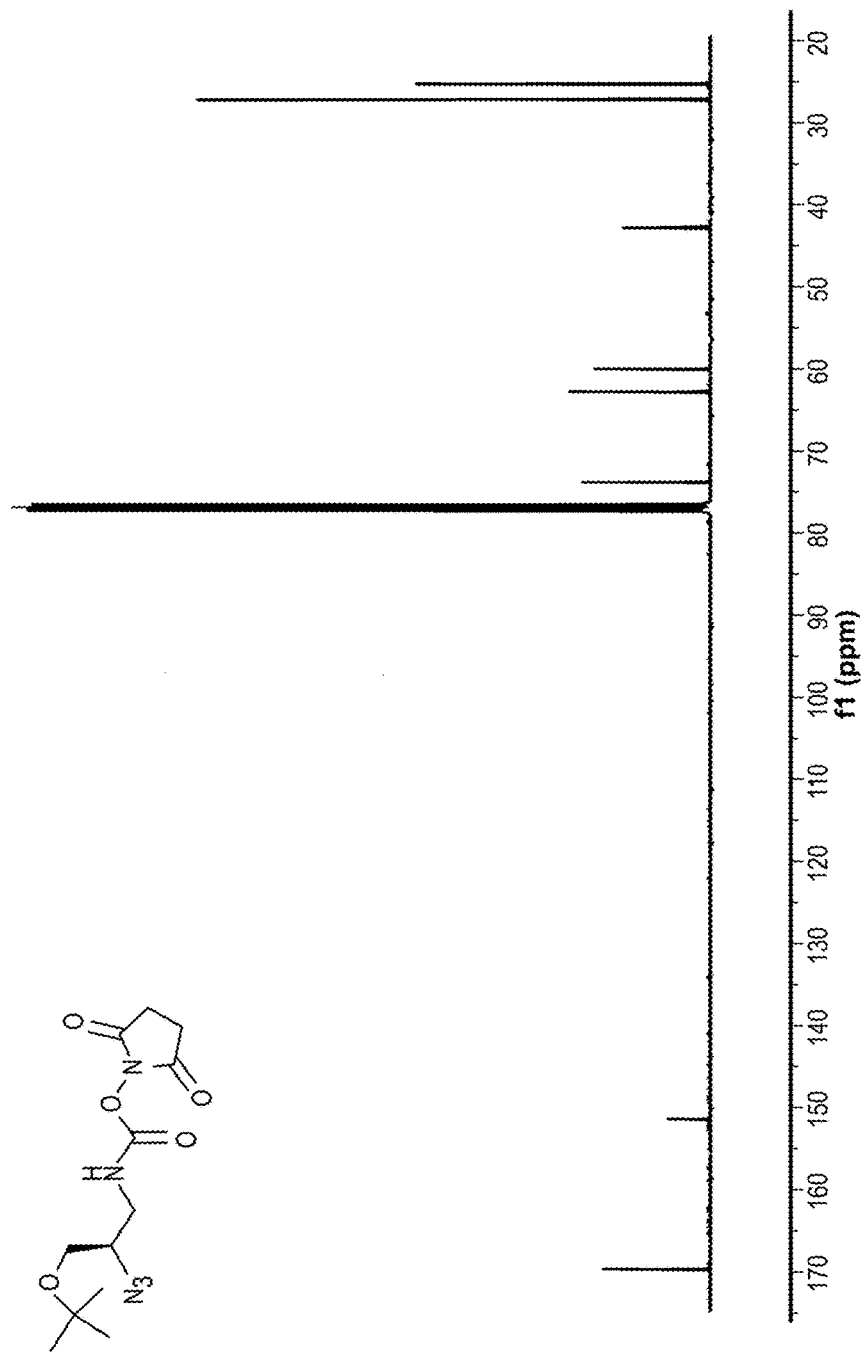
FIG. 25. $^{13}$C NMR (75 MHz) of compound (20).

The pure product was obtained as a pale yellow solid, with an overall yield of 41% after 6 steps. $^1$H NMR (CDCl$_3$, 300 MHz) δ: 5.67 (bs, 1H), 3.67-3.69 (m, 1H), 3.59 (d, J=5.1 Hz, 2H), 3.50 (ddd, J=13.8, 6.2, 4.9 Hz, 1H), 3.42-3.29 (m, 1H), 2.86 (s, 4H), 1.26 (s, 9H); $^{13}$C NMR (CDCl$_3$, 75 MHz) δ: 169.73, 151.54, 74.06, 62.81, 60.21, 43.00, 27.27, 25.48; HRMS (ESI+) m/z: calcd for C$_{12}$H$_{19}$N$_5$O$_5$Na [M+H]$^+$ 336.1278, found 336.1285 (FIGS. 24 and 25).

N$_3$-Glu: (S)-tert-butyl 4-azido-5-((((2,5-dioxopyrrolidin-1-yl)oxy)carbonyl)amino) Pentanoate (21)

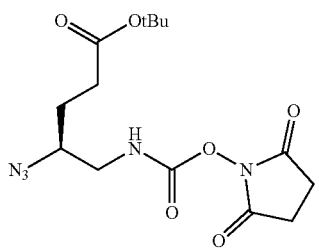 [SMILES: CC(C)(C)OC(=O)CC[C@@H](CNC(=O)ON1C(=O)CCC1=O)N=[N+]=[N-]]

Figure 26:
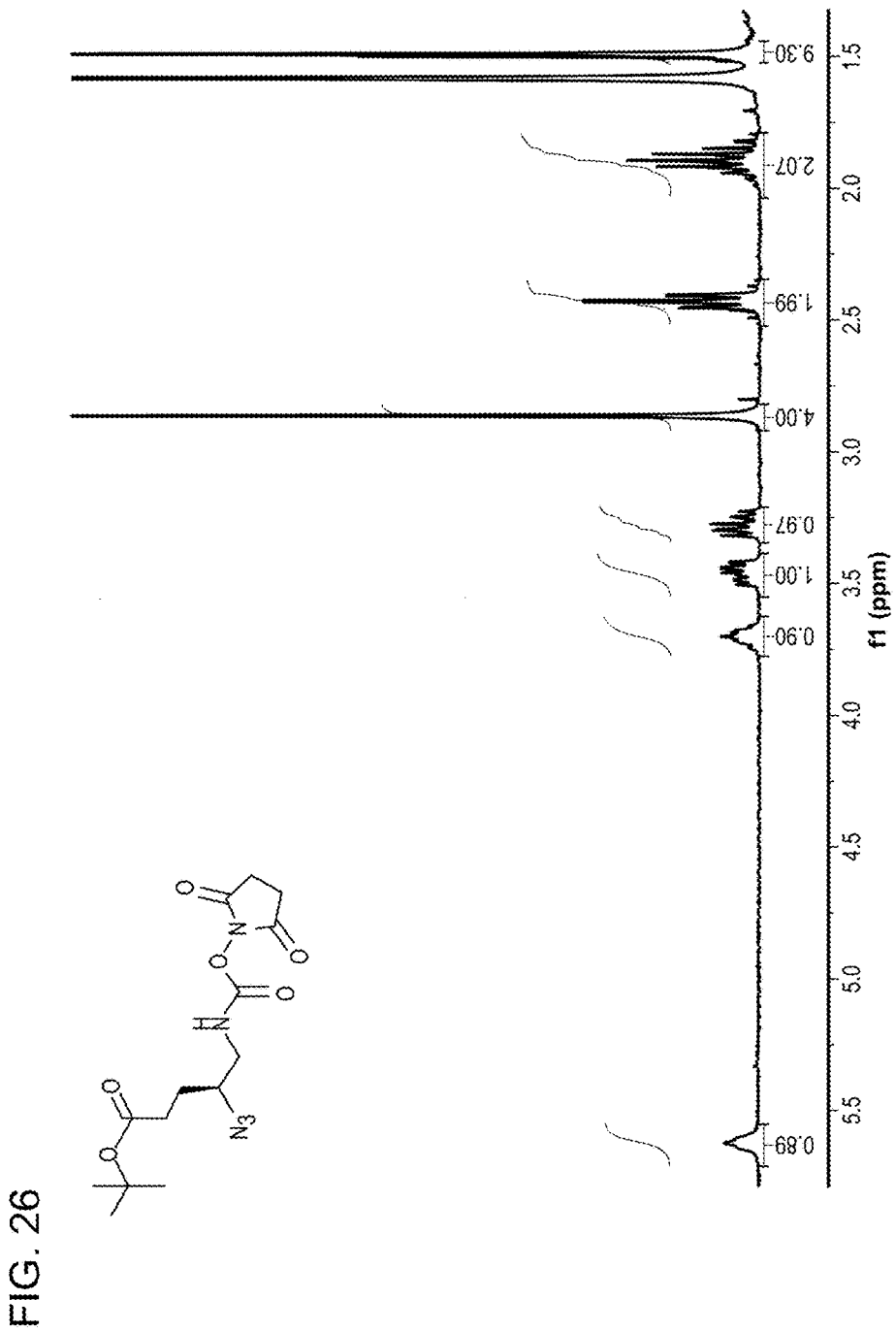
FIG. 26. $^1$H NMR (300 MHz) of compound (21).
Figure 27:
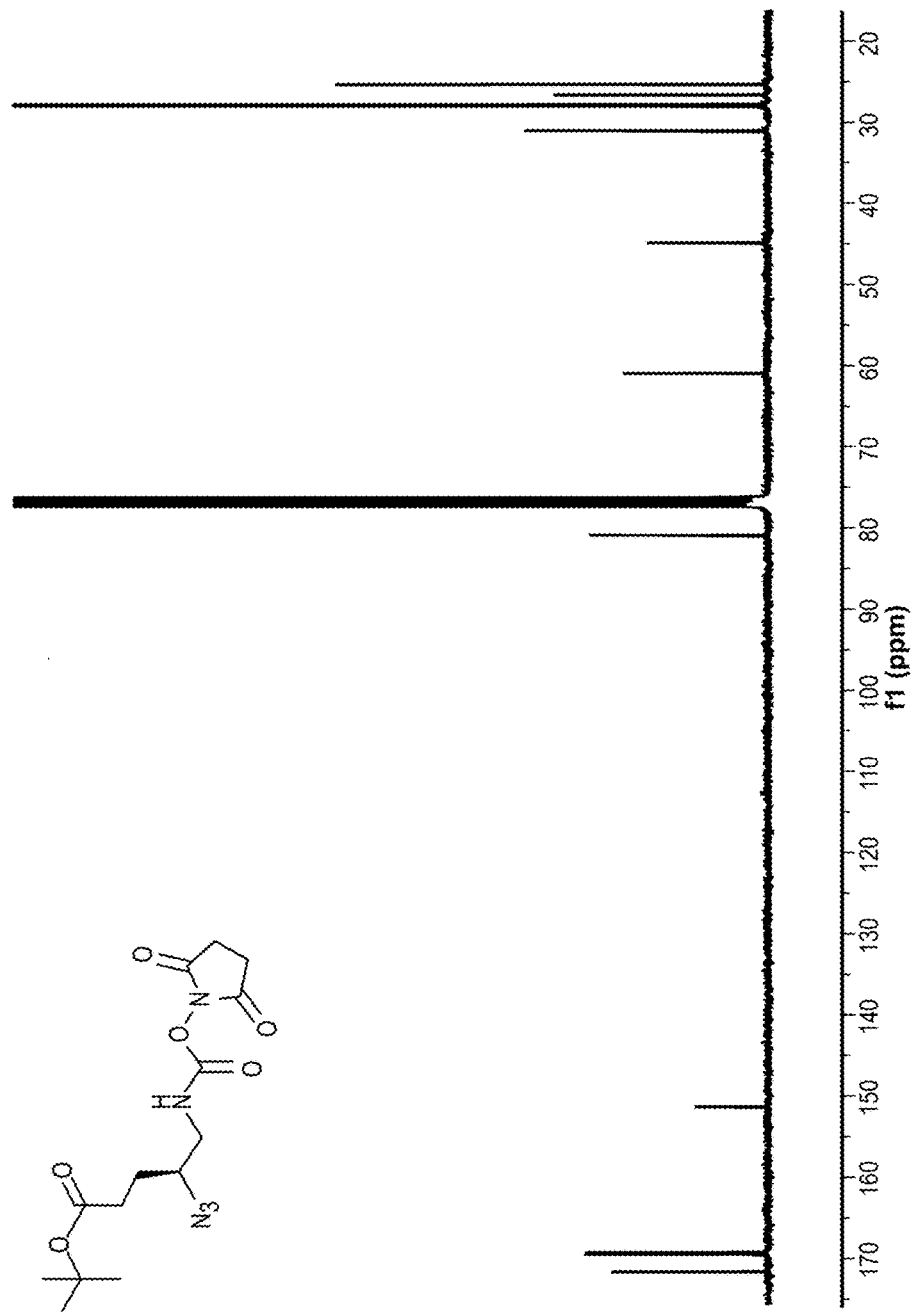
FIG. 27. $^{13}$C NMR (75 MHz) of compound (21).

The pure product was obtained as an off white solid, with an overall yield of 38% after 6 steps. $^1$H NMR (CDCl$_3$, 300 MHz) δ: 5.63 (bs, 1H), 3.74-3.66 (m, 1H), 3.46 (ddd, J=14.2, 6.5, 4.5 Hz, 1H), 3.34-3.21 (m, 1H), 2.86 (s, 4H), 2.43 (td, J=7.1, 1.9 Hz, 2H), 2.01-1.78 (m, 2H), 1.49 (s, 9H), 1.23 (d, J=6.2 Hz, 3H); $^{13}$C NMR (CDCl$_3$, 75 MHz) δ: 171.97, 169.73, 151.67, 81.08, 61.06, 45.02, 31.27, 28.08, 26.84, 25.48; HRMS (ESI+) m/z: calcd for C$_{14}$H$_{22}$N$_5$O$_6$ [M+H]$^+$ 356.1572, found 356.1572 (FIGS. 26 and 27).

N$_3$-Lys: (S)-2,5-dioxopyrrolidin-1-yl (2-azido-5-N-tert-butoxycarbonylaminohexyl) Carbamate (22)

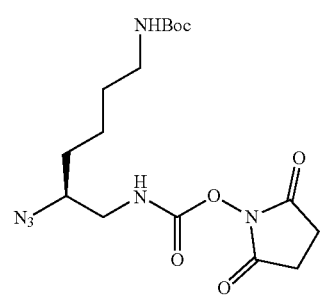 [SMILES: CC(C)(C)OC(=O)NCCCC[C@@H](CNC(=O)ON1C(=O)CCC1=O)N=[N+]=[N-]]

Figure 28:
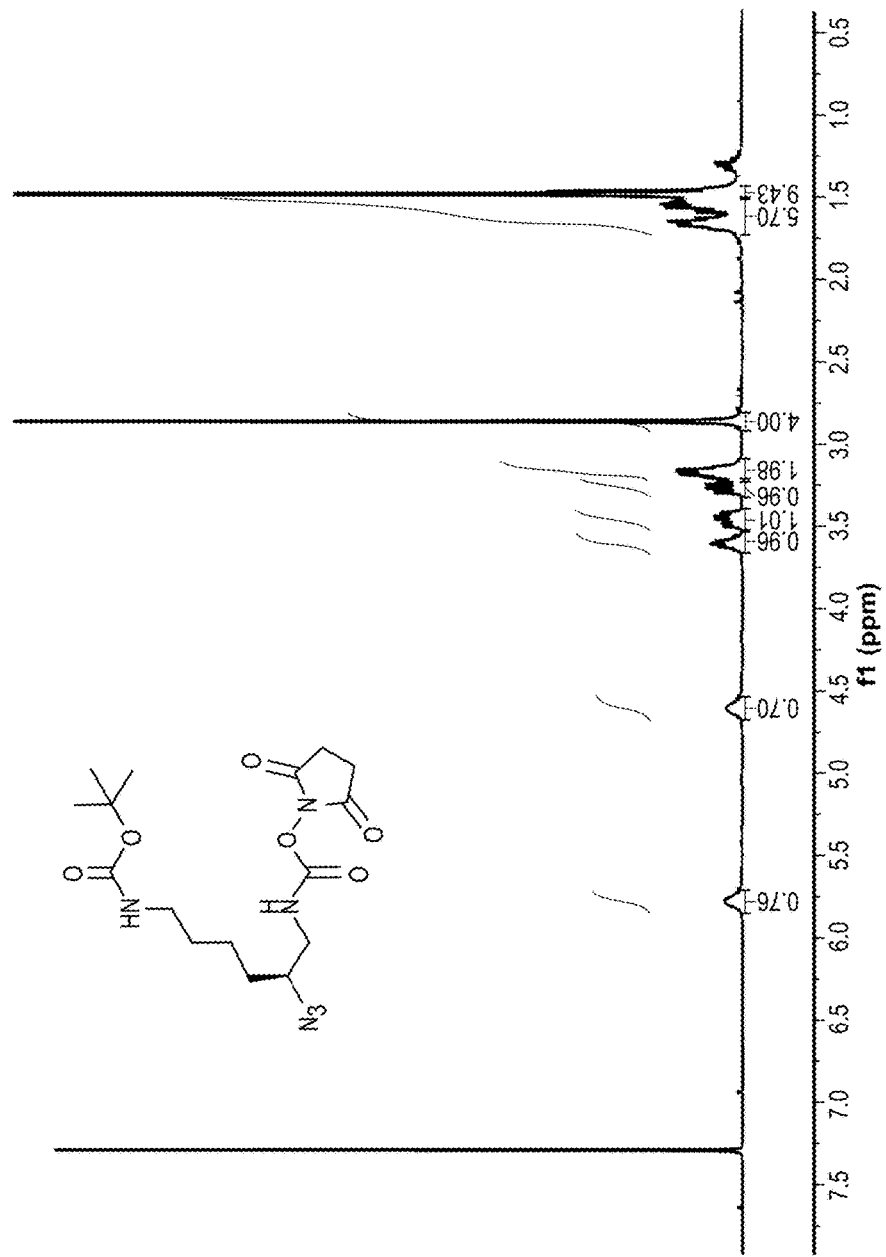
FIG. 28. $^1$H NMR (300 MHz) of compound (22).
Figure 29:
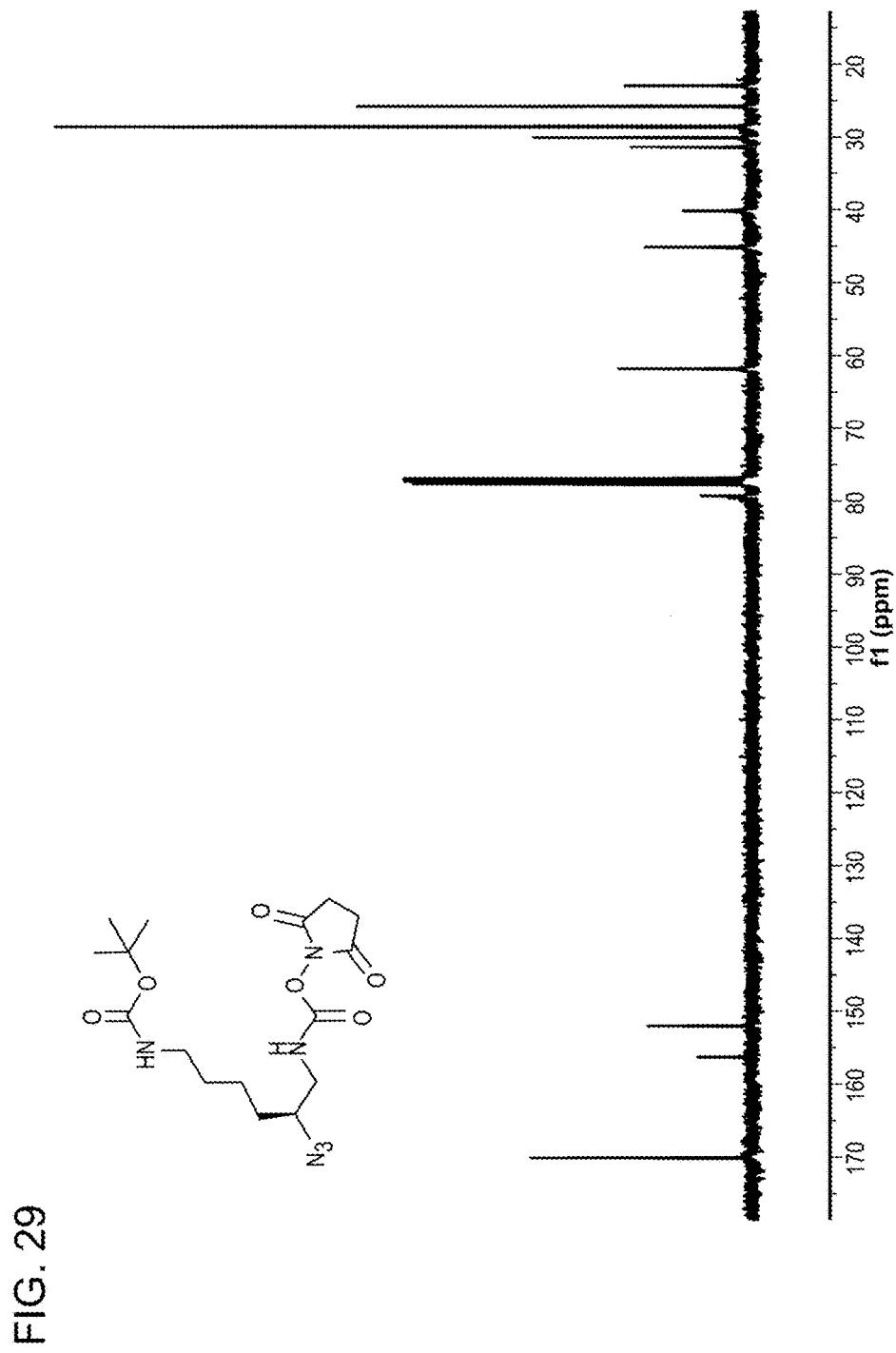
FIG. 29. $^{13}$C NMR (75 MHz) of compound (22).

The pure product was obtained as an off white solid, with an overall yield of 35% after 6 steps. $^1$H NMR (CDCl$_3$, 300 MHz) δ: 5.78 (bs, 1H), 4.61 (bs, 1H), 3.67-3.54 (m, 1H), 3.46 (ddd, J=13.9, 6.5, 4.4 Hz, 1H), 3.32-3.21 (m, 1H), 3.17 (dd, J=12.2, 6.1 Hz, 2H), 2.83 (s, 4H), 1.69-1.45 (m, 6H), 1.48 (s, 9H); $^{13}$C NMR (CDCl$_3$, 75 MHz) δ: 170.10, 156.19, 151.92, 79.24, 61.66, 45.01, 40.00, 31.17, 29.78, 28.42, 25.48, 22.71; HRMS (ESI+) m/z: calcd for C$_{16}$H$_{27}$N$_6$O$_6$ [M+H]$^+$399.1994, found 399.1993 (FIGS. 28 and 29).

N$_3$-Asn: (S)-2,5-dioxopyrrolidin-1-yl (2-azido-4-oxo-4-(tritylamino)butyl)carbamate (23)

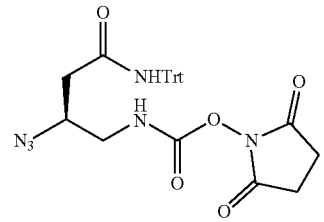

Figure 30:
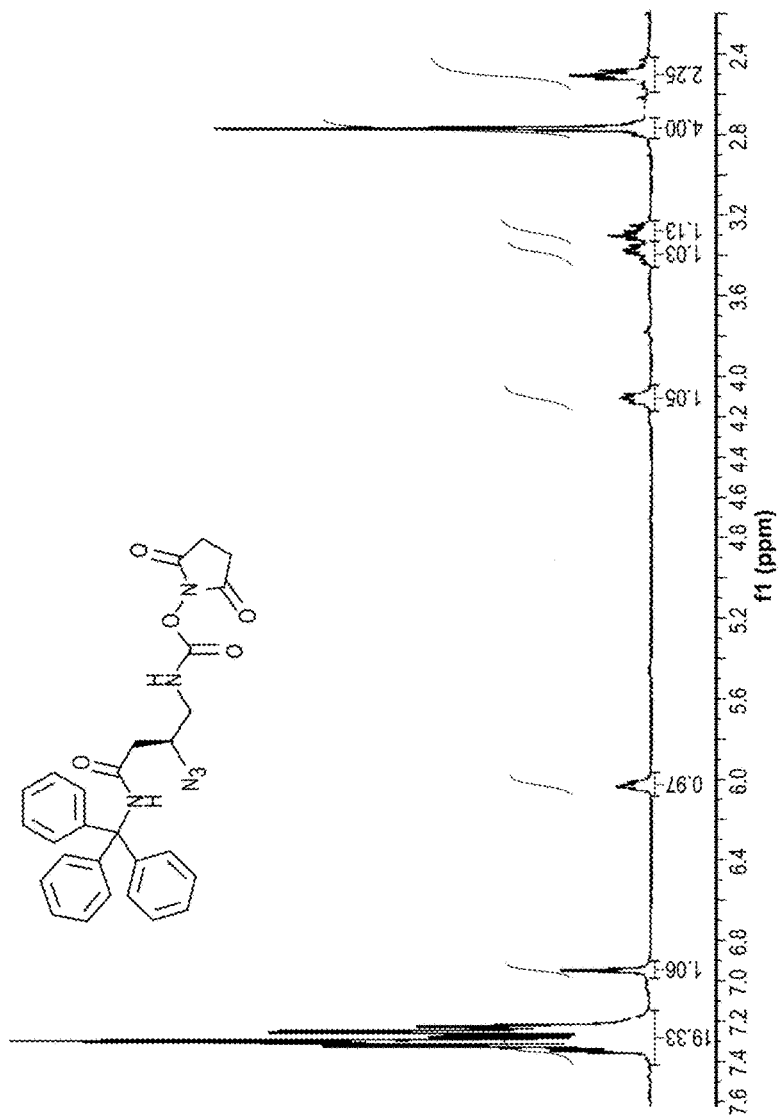
FIG. 30. $^1$H NMR (300 MHz) of compound (23).
Figure 31:
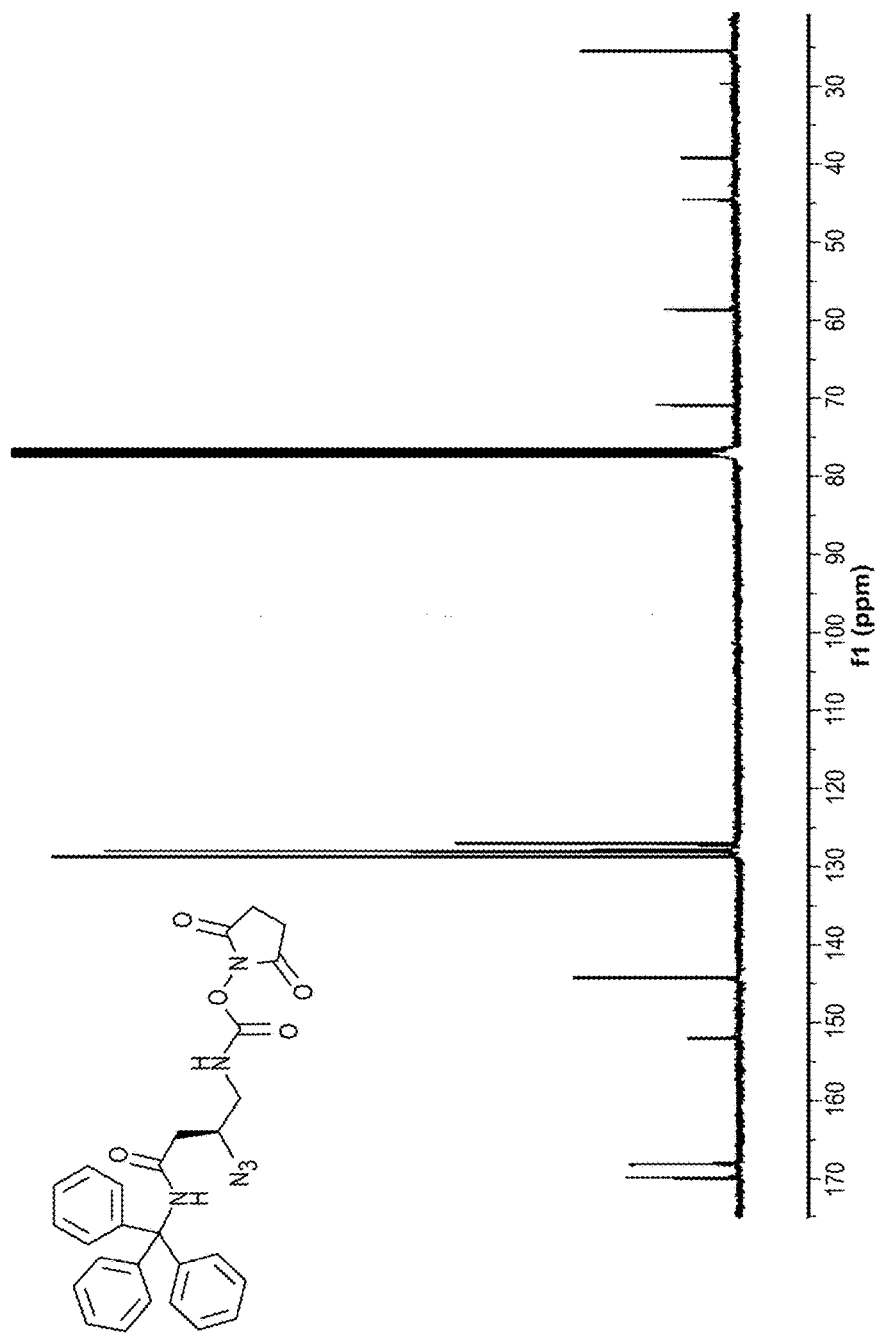
FIG. 31. $^{13}$C NMR (75 MHz) of compound (23).

The pure product was obtained as a pale yellow solid, with an overall yield of 27% after 6 steps. $^1$H NMR (CDCl$_3$, 300 MHz) δ: 7.36-7.23 (m, 15H), 6.95 (s, 1H), 6.04 (t, J=6.2 Hz, 1H), 4.16-4.08 (m, 1H), 3.40 (ddd, J=12.5, 7.1, 5.3 Hz, 1H), 3.29 (dt, J=14.2, 5.2 Hz, 1H), 2.78 (s, 4H), 2.59-2.42 (m, 2H); $^{13}$C NMR (CDCl$_3$, 75 MHz) δ: 169.84, 168.18, 152.04, 144.30, 128.70, 128.04, 127.16, 70.94, 58.53, 44.64, 39.24, 25.45. HRMS (ESI+) m/z: calcd for C$_{28}$H$_{27}$N$_6$O$_5$ [M+H]$^+$527.2045, found 527.2037 (FIGS. 30 and 31).

Solid Phase Synthesis of Oligoureas H1, H3, H4 and H5

Compounds H1, H3, H4 and H5 were assembled following previously reported procedures (Douat-Casassus, C., et al. Microwave-enhanced solid-phase synthesis of N,N'-linked aliphatic oligoureas and related hybrids. *Org. Lett.* 14, 3130-3133 (2012)) in a polypropylene SPE tube (CEM) using microwave assisted solid phase synthesis (CEM DiscoveryBio) on NovaPeg Rink Amide resin (Novabiochem) using variable scales (0.02-0.1 mmol). The syntheses were monitored using the chloranil test. Unless stated otherwise, the reagents were purchased from Sigma Aldrich. Coupling: $N_3$-OSu activated building blocks (3 eq) were dissolved in DMF (Carlo Erba Reagents) in the presence of DIEA (6 eq) and reacted with the resin at 50 W, 50° C. for 40 min. Azide reduction: the resin was swelled using a mixture of 7/3 1,4-dioxane/$H_2O$ and reacted with a solution of $Me_3P$ 1M in THF (10 eq) at 50 W, 50° C. for 15 min under an atmosphere of $N_2$. This procedure was repeated two to four times, until a positive chloranil test was observed. N-terminus isopropylation: the final isopropyl protection was performed by reacting the resin with isopropyl isocyanate (3 eq) in the presence of DIEA (6 eq) in DMF at 50 W, 50° C. for 10 min. This procedure was repeated if necessary. Resin cleavage and purification: the dried resin was treated with a mixture of 95:2.5:2.5 TFA: $H_2O$:TIS and shaken at room temperature for 2.5 hrs (or overnight in the case of oligoureas containing Ser(tBu) side chains). The crude products were precipitated as TFA salts with $Et_2O$ and purified with the appropriate gradient by semipreparative HPLC (Dionex Ultimate 3000, column Macherey-Nagel Nucleodur 100-16 C18 ec, 10×250, solvents acetonitrile/water 0.1% TFA, 4 ml/min). Analytic HPLC characterizations were performed on Macherey-Nagel column, Nucleodur cc 70/4 100-3 C18 ec, 4.6×100, 1 ml/min, solvents acetonitrile/water 0.1% TFA, 1 ml/min. The compounds were freeze-dried and TFA was exchanged with HCl by repeated lyophilisations in 0.1 N HCl.

iPr-NHCO-Leu$^u$-Glu$^u$-Lys$^u$-Leu$^u$-Tyr$^u$-Leu$^u$-Glu$^u$-Lys$^u$-Leu$^u$-Ala$^u$-Leu$^u$-$NH_2$ (H1)

ESI-MS (ESI+) m/z: 579.67 $[M+3H]^{3+}$, 869.07 $[M+2H]^{2+}$, 1737.07 $[M+H]^+$; HPLC: $R_t$=7.87 min (10-100% $CH_3CN$ 0.1% TFA in $H_2O$ 0.1% TFA, 10 min, C18) (FIG. 32).

iPr-NHCO-Leu$^u$-Glu$^u$-Lys$^u$-Leu$^u$-Tyr$^u$-Asn$^u$-Glu$^u$-Lys$^u$-Leu$^u$-Ala$^u$-Leu$^u$-$NH_2$ (H3)

ESI-MS (ESI+) m/z: 580.00 $[M+3H]^{3+}$, 870.40 $[M+2H]^{2+}$, 1738.13 $[M+H]^+$; HPLC: $R_t$=7.93 min (30-39 5 min 39-40 7.5 min $CH_3CN$ 0.1% TFA in $H_2O$ 0.1% TFA, C18) (FIG. 33).

iPr-NHCO-Ser$^u$-Glu$^u$-Lys$^u$-Leu$^u$-Tyr$^u$-Leu$^u$-Glu$^u$-Lys$^u$-Leu$^u$-Ala$^u$-Leu$^u$-$NH_2$ (H4)

ESI-MS (ESI+) m/z: 570.73 $[M+3H]^{3+}$, 855.60 $[M+2H]^{2+}$, 1710.93 $[M+H]^+$; HPLC: $R_t$=6.98 min (10-100% $CH_3CN$ 0.1% TFA in $H_2O$ 0.1% TFA, 10 min, C18) (FIG. 34).

iPr-NHCO-Ala$^u$-Leu$^u$-Lys$^u$-Leu$^u$-Glu$^u$-Tyr$^u$-Leu$^u$-Glu$^u$-Leu$^u$-Lys$^u$-Ala$^u$-Leu$^u$-$NH_2$ (H5)

ESI-MS (ESI+) m/z: 919.13 $[M+2H]^{2+}$, 1836.87 $[M+H]^+$; HPLC: $R_t$=11.13 min (10-100% $CH_3CN$ 0.1% TFA in $H_2O$ 0.1% TFA, 15 min, C18) (FIG. 35).

Thus, the experimental results demonstrate that peptide-oligourea chimeric foldamers (compounds having a polypeptide portion contiguous with or linked to oligomers of amino acids having an N,N'-linked urea bridging unit) demonstrate enhanced or improved properties relative to the parental or cognate "natural" peptide. Oligoureas can be derived from building blocks with any desired amino acid side chain. In particular, the chimeric compounds as described herein demonstrate regular and persistent helical conformations and improved helix stability. Because the chimeric foldamers as described herein can adopt desired secondary structures similar to native peptides, including, e.g., linear, cyclic or helicoidal structures, they can serve as, for example, receptor ligands, effector molecules, agonists, antagonists, modulators of protein-protein interactions, organocatalysts or enzymes.

While preferred embodiments of the disclosure have been shown and described herein, it will be understood that such embodiments are provided by way of example only. Numerous variations, changes and substitutions will occur to those skilled in the art without departing from the spirit of the disclosure. Accordingly, it is intended that the appended claims cover all such variations as fall within the spirit and scope of the disclosure.

The contents of all references, patents, pending patent applications and published patents, cited throughout this application are hereby expressly incorporated by reference.

Those skilled in the art will recognize, or be able to ascertain using no more than routine experimentation, many equivalents to the specific embodiments of the disclosure described herein. Such equivalents are intended to be encompassed by the following claims. It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

The invention claimed is:

1. A compound comprising
   multiple non-peptide oligourea helical foldamers having a structure of at least one of:
   an aliphatic non-peptide oligourea helical foldamer;
   a short amphiphilic α-helicomimetic foldamer with proteinaceous side-chains; and a non-peptide oligourea peptidomimetic residue sequence selected from the group consisting of:

(i)   Leu" Glu" Lys" Leu" Tyr" Leu"
         Glu" Lys" Leu" Ala" Leu" (H1);
   (ii)  Leu" Glu" Leu" Lys" Pro" Leu" Glu"
         Leu" Lys" Ala" (H2);
   (iii) Leu" Glu" Lys" Leu" Tyr" Asn" Glu"
         Lys" Leu" Ala" Leu" (H3);
   (iv)  Ser" Glu" Lys" Leu" Tyr" Leu" Glu"
         Lys" Leu" Ala" Leu" (H4);
   and
   (v)   Ala" Leu" Lys" Leu" Glu" Tyr" Leu" Glu"
         Leu" Lys" Ala" Leu" (H5), wherein the oligourea helical foldamers self-assemble to form at least one of an internal cavity, a pH-responsive water-filled channel with controllable pore diameter, a pH-responsive superhelical water-filled channel within a hydrophobic core, or a combination thereof.

2. The compound of claim 1, wherein the agent has an atomic mass less than about 1500 Da.

3. The compound of claim 1, wherein the oligourea helical foldamers self-assemble into their three-dimensional nanostructure in aqueous conditions.

4. The compound of claim 1, wherein at least one of:
   the compound has a secondary structure similar to a native peptide;
   the compound is biologically active;
   the compound further comprises a peptide that is fused to, contiguous with, or conjugated to the oligourea helical foldamer; or
   a combination thereof.

5. The compound of claim 4, wherein the secondary structure acts as a receptor ligand, an effector molecule, an agonist, an antagonist, a modulator of protein-protein interactions, an organocatalyst, or an enzyme.

6. The compound of claim 5, wherein the peptide segment comprises an amino acid sequence corresponding to a biologically active peptide or a fragment thereof.

7. The compound of claim 6, wherein the peptide is a peptide a-helix.

8. The compound of claim 7, wherein the peptide a-helix includes an epitope that recognizes another compound.

9. The compound of claim 8, wherein the epitope acts as a receptor ligand, an effector molecule, an agonist, an antagonist, a modulator of protein-protein interactions, an organocatalyst, or an enzyme.

10. The compound of claim 1, wherein at least one of:
    the oligourea helical foldamer encapsulates a drug or substrate;
    the oligourea helical foldamer transfers substances across a membrane;
    the oligourea helical foldamer has an internal cavity with a volume in a range of about 400-600 Å$^3$; or
    a combination thereof.

11. A composition comprising:
    an oligourea helical bundle comprising a non-peptide oligourea helical foldamer; and
    an agent at least partially encapsulated by the oligourea helical bundle.

12. The composition of claim 11, wherein the agent has an atomic mass less than about 600 Da.

13. A therapeutic composition comprising an effective amount of the compound of claim 1 and a pharmaceutically acceptable carrier or excipient.

14. A peptide-oligourea chimeric compound, comprising:
    a peptide; and
    an oligourea helical bundle comprising a non-peptide oligourea helical foldamer that is at least partially encapsulating an agent.

15. The peptide-oligourea chimeric compound of claim 14, wherein the agent has an atomic mass less than about 600 Da.

16. The compound of claim 14, wherein the oligourea helical foldamer self-assembles into its three-dimensional nanostructure under aqueous conditions.

17. The compound of claim 14, wherein the peptide is a peptide a-helix.

18. The compound of claim 14, wherein at least one of:
    the non-peptide oligourea helical foldamer includes aliphatic oligoureas;
    the non-peptide oligourea helical foldamer is a short amphiphilic a-helicomimetic foldamer with proteinaceous side-chains;
    the oligourea helical bundle has a non-peptide oligourea peptidomimetic residue sequence selected from the group consisting of:

Leu" Glu" Lys" Leu" Tyr" Leu" Glu" Lys" Leu" Ala" Leu" (H1);

Leu" Glu" Leu" Lys" Pro" Leu" Glu" Leu" Lys" Ala" (H2);

Leu" Glu" Lys" Leu" Tyr" Asn" Glu" Lys" Leu" Ala" Leu" (H3)

Ser" Glu" Lys" Leu" Tyr" Leu" Glu" Lys" Leu" Ala" Leu" (H4);
and

Ala" Leu" Lys" Leu" Glu" Tyr" Leu" Glu" Leu" Lys" Ala" Leu" (H5);

the non-peptide oligourea helical foldamer has a non-peptide oligourea peptidomimetic residue sequence selected from the group consisting of:

Leu" Glu" Lys" Leu" Tyr" Leu" Glu" Lys" Leu" Ala" Leu" (H1);

Leu" Glu" Leu" Lys" Pro" Leu" Glu" Leu" Lys" Ala" (H2);

Leu" Glu" Lys" Leu" Tyr" Asn" Glu" Lys" Leu" Ala" Leu" (H3)

Ser" Glu" Lys" Leu" Tyr" Leu" Glu" Lys" Leu" Ala" Leu" (H4); and

Ala" Leu" Lys" Leu" Glu" Tyr" Leu" Glu" Leu" Lys" Ala" Leu" (H5);

and
the oligourea helical bundle has an isolated cavity, a pH-responsive water-filled channels with controllable pore diameters or a pH-responsive superhelical channel with water-filled pores within the hydrophobic core of the bundle; or
a combination thereof.

19. The compound of claim 14, wherein the oligourea helical bundle has an internal cavity with a volume in a range of about 400-600 Å³.

20. A method of delivering an agent for the treatment or prevention of a disease or disorder, the method comprising administering to an individual in need thereof an effective amount of the composition of claim 11, wherein the agent is a therapeutic agent effective in ameliorating the disease or disorder.

21. A therapeutic composition comprising an effective amount of the compound of claim 1 and a pharmaceutically acceptable carrier or excipient.

22. A method of synthesizing a oligourea compound comprising the steps of:
fabricating under aqueous conditions, a oligourea helical bundle with a non-peptide oligourea peptidomimetic residue sequence selected from the group consisting of:
a helical pentad repeat (a, b, c, d, e):
oligourea peptidomimetic residues with a hydrophobic side chain in positions a and d (e.g., Leu");
oligourea peptidomimetic residues with a charged residue in position b and c (e.g. Glu" and Lys", respectively); and
Tyr" and Ala" in position e;
a helical pentad repeat (a, b, c, d, e):
oligourea peptidomimetic residues with a hydrophobic side chain in positions a and c (e.g. Leu");
oligourea peptidomimetic residues with a hydrophobic side chain in position e (e.g., Ala" and Pro" residues at the e position); and
oligourea peptidomimetic residues with a charged side chain in positions b and d (e.g., Glu" and Lys", respectively);

Leu" Glu" Lys" Leu" Tyr" Leu" Glu" Lys" Leu" Ala" Leu" (H1);

Leu" Glu" Leu" Lys" Pro" Leu" Glu" Leu" Lys" Ala" (H2);

Leu" Glu" Lys" Leu" Tyr" Asn" Glu" Lys" Leu" Ala" Leu" (H3)

Ser" Glu" Lys" Leu" Tyr" Leu" Glu" Lys" Leu" Ala" Leu" (H4); or

Ala" Leu" Lys" Leu" Glu" Tyr" Leu" Glu" Leu" Lys" Ala" Leu" (H5);

and
providing an agent while the oligourea helical bundle is self-assembling.

23. The method of claim 22, wherein the agent has an atomic mass less than about 600 Da.

24. The compound of claim 11, wherein:
the non-peptide oligourea helical foldamer includes aliphatic oligoureas; the non-peptide oligourea helical foldamer is a short amphiphilic a-helicomimetic foldamer with proteinaceous side-chains;
the oligourea helical bundle has a non-peptide oligourea peptidomimetic residue sequence selected from the group consisting of:

(i) Leu" Glu" Lvs" Leu" Tvr" Leu" Glu" Lvs" Leu" Ala" Leu" (H1);

(ii) Leu" Glu" Leu" Lvs" Pro" Leu" Glu" Leu" Lvs" Ala" (H2);

(iii) Leu" Glu" Lvs" Leu" Tvr" Asn" Glu" Lvs" Leu" Ala" Leu" (H3);

(iv) Ser" Glu" Lvs" Leu" Tvr" Leu" Glu" Lvs" Leu" Ala" Leu" (H4); and (v) Ala" Leu" Lvs" Leu" Glu" Tvr" Leu" Glu" Leu" Lvs" Ala" Leu" (H5), the non-peptide oligourea helical foldamer has a non-peptide oligourea peptidomimetic residue sequence selected from the group consisting of:

(i) Leu" Glu" Lvs" Leu" Tvr" Leu" Glu" Lvs" Leu" Ala" Leu" (H1);

(ii) Leu" Glu" Leu" Lvs" Pro" Leu" Glu" Leu" Lvs" Ala" (H2);

(iii) Leu" Glu" Lvs" Leu" Tvr" Asn" Glu" Lvs" Leu" Ala" Leu" (H3);

-continued (iv) Ser" Glu" Lys" Leu" Tyr" Leu" Glu" Lys" Leu" Ala" Leu" (H4);

and (v) Ala" Leu" Lys" Leu" Glu" Tyr" Leu" Glu" Leu" Lys" Ala" Leu" (H5), and the oligourea helical bundle has an isolated cavity, a pH-responsive water-filled channels with controllable pore diameters or a pH-responsive superhelical channel with water-filled pores within the hydrophobic core of the bundle.

* * * * *